US011141322B2

(12) United States Patent
Schneider et al.

(10) Patent No.: US 11,141,322 B2
(45) Date of Patent: Oct. 12, 2021

(54) METHODS AND APPARATUSES FOR MAKING ELASTOMERIC LAMINATES

(71) Applicant: The Procter & Gamble Company, Cincinnati, OH (US)

(72) Inventors: Uwe Schneider, Cincinnati, OH (US); Joseph Allen Eckstein, Sunman, IN (US); Kazuaki Tameishi, Kobe (JP)

(73) Assignee: The Procter & Gamble Company, Cincinnati, OH (US)

( * ) Notice: Subject to any disclaimer, the term of this patent is extended or adjusted under 35 U.S.C. 154(b) by 149 days.

(21) Appl. No.: 15/839,896

(22) Filed: Dec. 13, 2017

(65) Prior Publication Data

US 2018/0168879 A1     Jun. 21, 2018

Related U.S. Application Data

(60) Provisional application No. 62/581,278, filed on Nov. 3, 2017, provisional application No. 62/436,589, filed on
(Continued)

(51) Int. Cl.
*A61F 13/15*     (2006.01)
*A61F 13/49*     (2006.01)
(Continued)

(52) U.S. Cl.
CPC .... *A61F 13/15593* (2013.01); *A61F 13/4902* (2013.01); *A61F 13/49061* (2013.01);
(Continued)

(58) Field of Classification Search
CPC .......... A61F 13/15593; A61F 13/15601; A61F 13/15699; A61F 13/49011; A61F 13/49012; A61F 13/49014; A61F 13/49015; A61F 13/49017; A61F 13/49019; A61F 13/49061; A61F 13/51464; A61F 13/4902; A61F 2013/15422; A61F 2013/15439; A61F 2013/49025;
(Continued)

(56) References Cited

U.S. PATENT DOCUMENTS 3,113,225 A    12/1963    Kleesattel et al.
3,434,189 A    3/1969    Buck et al.
(Continued)

FOREIGN PATENT DOCUMENTS

CA    2158790    3/1996
CN    1276196 A    6/1999
(Continued)

OTHER PUBLICATIONS

Machine translation of JP 2008104853 date unknown.*
(Continued)

*Primary Examiner* — John L Goff, II
(74) *Attorney, Agent, or Firm* — Charles R. Matson

(57) ABSTRACT

The present disclosure relates to methods for making elastomeric laminates that may be used as components of absorbent articles. Aspects of the methods for assembling elastomeric laminates may utilize elastic strands supplied from beams that may be joined with first and second substrates, and may be configured to carry out various types of operations, such as bonding and splicing operations.

9 Claims, 82 Drawing Sheets

Related U.S. Application Data on Dec. 20, 2016, provisional application No. 62/483,965, filed on Apr. 11, 2017, provisional application No. 62/553,149, filed on Sep. 1, 2017, provisional application No. 62/553,171, filed on Sep. 1, 2017, provisional application No. 62/553,538, filed on Sep. 1, 2017.

(51) Int. Cl.

| | | |
|---|---|---|
| B32B 27/12 | (2006.01) | |
| D01F 6/04 | (2006.01) | |
| A61F 13/53 | (2006.01) | |
| D01D 5/08 | (2006.01) | |
| B29C 65/08 | (2006.01) | |
| B29C 65/48 | (2006.01) | |
| B29L 31/48 | (2006.01) | |
| B05C 1/08 | (2006.01) | |
| B32B 37/14 | (2006.01) | |
| B65H 39/16 | (2006.01) | |
| B65H 51/30 | (2006.01) | |
| B29C 65/00 | (2006.01) | |
| B29C 65/74 | (2006.01) | |
| B29K 701/12 | (2006.01) | |
| A61F 13/64 | (2006.01) | |
| A61F 13/84 | (2006.01) | |
| B32B 5/04 | (2006.01) | |
| B32B 37/00 | (2006.01) | |
| B32B 37/12 | (2006.01) | |
| D04H 3/12 | (2006.01) | |
| A61F 13/56 | (2006.01) | |
| B32B 37/22 | (2006.01) | |
| A61F 13/513 | (2006.01) | |

(52) U.S. Cl.
CPC ... *A61F 13/15601* (2013.01); *A61F 13/15699* (2013.01); *A61F 13/15739* (2013.01); *A61F 13/15764* (2013.01); *A61F 13/49012* (2013.01); *A61F 13/49015* (2013.01); *A61F 13/49017* (2013.01); *A61F 13/49019* (2013.01); *A61F 13/53* (2013.01); *A61F 13/5622* (2013.01); *A61F 13/64* (2013.01); *A61F 2013/1552* (2013.01); *A61F 2013/1591* (2013.01); *A61F 2013/15292* (2013.01); *A61F 2013/15373* (2013.01); *A61F 2013/15406* (2013.01); *A61F 2013/15447* (2013.01); *A61F 2013/15552* (2013.01); *A61F 2013/15869* (2013.01); *A61F 2013/15918* (2013.01); *A61F 2013/15959* (2013.01); *A61F 2013/49022* (2013.01); *A61F 2013/49025* (2013.01); *A61F 2013/49026* (2013.01); *A61F 2013/49074* (2013.01); *A61F 2013/49092* (2013.01); *A61F 2013/49093* (2013.01); *A61F 2013/51322* (2013.01); *A61F 2013/53043* (2013.01); *A61F 2013/530343* (2013.01); *A61F 2013/8497* (2013.01); *B05C 1/0808* (2013.01); *B29C 65/08* (2013.01); *B29C 65/086* (2013.01); *B29C 65/48* (2013.01); *B29C 65/74* (2013.01); *B29C 66/01* (2013.01); *B29C 66/344* (2013.01); *B29C 66/8141* (2013.01); *B29C 66/83411* (2013.01); *B29K 2701/12* (2013.01); *B29K 2995/0046* (2013.01); *B29L 2031/4878* (2013.01); *B32B 5/04* (2013.01); *B32B 27/12* (2013.01); *B32B 37/0053* (2013.01); *B32B 37/12* (2013.01); *B32B 37/144* (2013.01); *B32B 37/22* (2013.01); *B32B 2305/20* (2013.01); *B32B 2307/51* (2013.01); *B32B 2307/726* (2013.01); *B32B 2555/02* (2013.01); *B65H 39/16* (2013.01); *B65H 51/30* (2013.01); *C08J 2300/26* (2013.01); *D01D 5/08* (2013.01); *D01F 6/04* (2013.01); *D04H 3/12* (2013.01)

(58) Field of Classification Search
CPC .. A61F 2013/49026; A61F 2013/49028; A61F 13/1591; A61F 13/15918; A61F 13/15959; A61F 13/15869; A61F 13/15739; A61F 13/15764; A61F 2013/15861; A61F 2013/15886; A61F 13/49009; A61F 2013/49031; A61F 2013/49033; A61F 2013/49034; A61F 2013/49036; A61F 2013/49038; A61F 2013/49039; B29C 65/08; B29C 65/083; B29C 65/087; B29C 65/085; B29C 65/086; B29C 65/088; B29C 65/74; B29C 66/344; B29C 65/48; B29C 66/01; B29L 2031/4878; B32B 37/144; B32B 38/1825; B32B 38/1875; B32B 2038/0028; B32B 2555/02
USPC ............... 156/160, 161, 176, 178, 179, 229
See application file for complete search history.

(56) References Cited

U.S. PATENT DOCUMENTS

| | | |
|---|---|---|
| 3,508,722 A | 4/1970 | Kohl |
| 3,562,041 A | 2/1971 | Robertson |
| 3,575,782 A * | 4/1971 | Hansen ............... A61F 13/0273 442/329 |
| 3,733,238 A | 5/1973 | Long et al. |
| 3,860,003 A | 1/1975 | Buell |
| 3,871,378 A | 3/1975 | Duncan et al. |
| 4,251,587 A | 2/1981 | Mimura et al. |
| 4,333,979 A | 6/1982 | Sciaraffa et al. |
| 4,525,905 A | 7/1985 | Bogucki-Land |
| 4,610,678 A | 9/1986 | Weisman et al. |
| 4,640,859 A | 2/1987 | Hansen et al. |
| 4,657,539 A | 4/1987 | Hasse |
| 4,673,402 A | 6/1987 | Weisman et al. |
| 4,695,278 A | 9/1987 | Lawson |
| 4,704,115 A | 11/1987 | Buell |
| 4,741,941 A | 5/1988 | Englebert et al. |
| 4,776,911 A | 10/1988 | Uda et al. |
| 4,795,454 A | 1/1989 | Dragoo |
| 4,834,735 A | 5/1989 | Alemany et al. |
| 4,854,984 A | 8/1989 | Ball et al. |
| 4,888,231 A | 12/1989 | Angstadt |
| 4,909,803 A | 3/1990 | Aziz et al. |
| 4,940,464 A | 7/1990 | Van Gompel et al. |
| 4,984,584 A | 1/1991 | Hansen et al. |
| 5,003,676 A | 4/1991 | McFalls |
| 5,060,881 A | 10/1991 | Bogucki-Land |
| 5,092,861 A | 3/1992 | Nomura et al. |
| 5,110,403 A | 5/1992 | Ehlert |
| 5,167,897 A | 12/1992 | Weber et al. |
| 5,246,433 A | 9/1993 | Hasse et al. |
| 5,334,289 A | 8/1994 | Trokhan et al. |
| 5,342,341 A | 8/1994 | Igaue et al. |
| 5,360,420 A | 11/1994 | Cook et al. |
| 5,393,360 A | 2/1995 | Bridges et al. |
| 5,413,849 A | 5/1995 | Austin et al. |
| 5,514,523 A | 5/1996 | Trokhan et al. |
| 5,531,729 A | 7/1996 | Coles et al. |
| 5,558,658 A | 9/1996 | Menard et al. |
| 5,562,646 A | 10/1996 | Goldman et al. |
| 5,569,234 A | 10/1996 | Buell et al. |
| 5,575,874 A | 11/1996 | Griesbach, III et al. |
| 5,599,335 A | 2/1997 | Goldman et al. |
| 5,599,420 A | 2/1997 | Yeo et al. |
| 5,628,097 A | 5/1997 | Benson et al. |
| 5,643,588 A | 7/1997 | Roe et al. |

(56) References Cited

U.S. PATENT DOCUMENTS

| | | |
|---|---|---|
| 5,643,653 A | 7/1997 | Griesbach, III et al. |
| 5,669,894 A | 9/1997 | Goldman et al. |
| 5,674,216 A | 10/1997 | Buell et al. |
| 5,702,551 A | 12/1997 | Huber et al. |
| 5,775,380 A | 7/1998 | Roelstraete et al. |
| 5,827,259 A | 10/1998 | Laux et al. |
| 5,858,504 A | 1/1999 | Steven |
| 5,887,322 A | 3/1999 | Hartzheim et al. |
| 5,895,623 A | 4/1999 | Trokhan et al. |
| 5,897,545 A | 4/1999 | Kline et al. |
| 5,916,661 A | 6/1999 | Benson et al. |
| 5,957,908 A | 9/1999 | Kline et al. |
| 5,968,025 A | 10/1999 | Roe et al. |
| 5,993,433 A | 11/1999 | St. Louis et al. |
| 5,997,521 A | 12/1999 | Robles et al. |
| 6,036,796 A | 3/2000 | Halbert et al. |
| 6,043,168 A | 3/2000 | Colman et al. |
| 6,107,537 A | 8/2000 | Elder et al. |
| 6,107,539 A | 8/2000 | Palumbo et al. |
| 6,118,041 A | 9/2000 | Roe et al. |
| 6,120,487 A | 9/2000 | Ashton |
| 6,120,489 A | 9/2000 | Johnson et al. |
| 6,139,941 A | 10/2000 | Jankevics et al. |
| 6,153,209 A | 11/2000 | Vega et al. |
| 6,248,195 B1 | 6/2001 | Schmitz |
| 6,248,197 B1 | 6/2001 | Nakanishi et al. |
| 6,291,039 B1 | 9/2001 | Combe et al. |
| 6,319,239 B1 | 11/2001 | Daniels et al. |
| 6,361,638 B2 | 3/2002 | Takai et al. |
| 6,383,431 B1 | 5/2002 | Dobrin et al. |
| 6,395,957 B1 | 5/2002 | Chen et al. |
| 6,410,129 B2 | 6/2002 | Zhang et al. |
| 6,426,444 B2 | 7/2002 | Roe et al. |
| 6,475,600 B1 | 11/2002 | Morman et al. |
| 6,478,785 B1 | 11/2002 | Ashton et al. |
| 6,482,191 B1 | 11/2002 | Roe et al. |
| 6,508,641 B1 | 1/2003 | Kubik |
| 6,545,197 B1 | 4/2003 | Muller et al. |
| 6,554,815 B1 | 4/2003 | Umebayashi |
| 6,586,652 B1 | 7/2003 | Roe et al. |
| 6,617,016 B2 | 9/2003 | Zhang et al. |
| 6,627,787 B1 | 9/2003 | Roe et al. |
| 6,632,504 B1 | 10/2003 | Gillespie et al. |
| 6,645,330 B2 | 11/2003 | Pargass et al. |
| 6,673,418 B1 | 1/2004 | DeOlivera et al. |
| 6,676,054 B2 | 1/2004 | Heaney et al. |
| 6,702,798 B2 | 3/2004 | Christoffel et al. |
| 6,790,798 B1 | 9/2004 | Suzuki et al. |
| 6,821,301 B2 | 11/2004 | Azuse et al. |
| 6,825,393 B2 | 11/2004 | Roe et al. |
| 6,861,571 B1 | 3/2005 | Roe et al. |
| 7,008,685 B2 | 3/2006 | Groitzsch et al. |
| 7,118,558 B2 | 10/2006 | Wu et al. |
| 7,465,367 B2 | 12/2008 | Day |
| 7,569,039 B2 | 8/2009 | Matsuda et al. |
| 7,582,348 B2 | 9/2009 | Ando et al. |
| 7,585,348 B2 | 9/2009 | Nyberg et al. |
| 7,642,398 B2 | 1/2010 | Järpenberg et al. |
| 7,708,849 B2 | 5/2010 | McCabe |
| 7,777,094 B2 | 8/2010 | Mori et al. |
| 7,861,756 B2 | 1/2011 | Jenquin et al. |
| 7,878,447 B2 | 2/2011 | Hartzheim |
| 7,901,393 B2 | 3/2011 | Matsuda et al. |
| 7,905,446 B2 | 3/2011 | Hartzheim |
| 7,954,213 B2 | 6/2011 | Mizutani |
| 8,093,161 B2 | 1/2012 | Bansal et al. |
| 8,143,177 B2 | 3/2012 | Noda et al. |
| 8,186,296 B2 | 5/2012 | Brown et al. |
| 8,226,625 B2 | 7/2012 | Turner et al. |
| 8,308,706 B2 | 11/2012 | Fukae |
| 8,377,554 B2 | 2/2013 | Martin et al. |
| 8,388,594 B2 | 3/2013 | Turner et al. |
| 8,440,043 B1 | 5/2013 | Schneider et al. |
| 8,585,666 B2 | 11/2013 | Weisman et al. |
| 8,647,319 B2 | 2/2014 | Een et al. |
| 8,729,332 B2 | 5/2014 | Takahashi et al. |
| 8,778,127 B2 | 7/2014 | Schneider et al. |
| 8,853,108 B2 | 10/2014 | Ahoniemi et al. |
| 8,906,275 B2 | 12/2014 | Davis et al. |
| 8,939,957 B2 | 1/2015 | Raycheck et al. |
| 9,005,392 B2 | 4/2015 | Schneider et al. |
| 9,039,855 B2 | 5/2015 | Schneider et al. |
| 9,050,213 B2 | 6/2015 | LaVon et al. |
| 9,156,648 B2 | 10/2015 | Yamamoto |
| 9,168,182 B2 | 10/2015 | Hargett et al. |
| 9,198,804 B2 | 12/2015 | Nakamura et al. |
| 9,226,861 B2 | 1/2016 | LaVon et al. |
| 9,248,054 B2 | 2/2016 | Brown et al. |
| 9,265,672 B2 | 2/2016 | Brown et al. |
| 9,295,590 B2 | 3/2016 | Brown et al. |
| 9,370,775 B2 | 6/2016 | Harvey et al. |
| 9,440,043 B2 | 9/2016 | Schneider et al. |
| 9,453,303 B2 | 9/2016 | Aberg et al. |
| 9,539,735 B2 | 1/2017 | Ferguson et al. |
| 9,732,454 B2 | 8/2017 | Davis et al. |
| 9,758,339 B2 | 9/2017 | Yanez, Jr. et al. |
| 9,795,520 B2 | 10/2017 | Kaneko et al. |
| 9,877,876 B2 | 1/2018 | Huang et al. |
| 1,019,024 A1 | 1/2019 | Ashraf et al. |
| 10,596,045 B2 | 3/2020 | Koshijima et al. |
| 10,792,194 B2 | 10/2020 | Hohm et al. |
| 2001/0030014 A1 | 10/2001 | Kwok |
| 2002/0026660 A1 | 3/2002 | Goda |
| 2002/0046802 A1 | 4/2002 | Tachibana et al. |
| 2002/0072723 A1 | 6/2002 | Ronn et al. |
| 2002/0099347 A1 | 7/2002 | Chen et al. |
| 2002/0103469 A1 | 8/2002 | Chen et al. |
| 2002/0134067 A1 | 9/2002 | Heaney et al. |
| 2002/0153271 A1 | 10/2002 | McManus et al. |
| 2002/0177829 A1 | 11/2002 | Fell et al. |
| 2003/0044585 A1 | 3/2003 | Taylor et al. |
| 2003/0070780 A1 | 4/2003 | Chen et al. |
| 2003/0087056 A1 | 5/2003 | Ducker et al. |
| 2003/0093045 A1 | 5/2003 | Jensen |
| 2003/0119404 A1 | 6/2003 | Belau et al. |
| 2003/0125687 A1 | 7/2003 | Gubernick et al. |
| 2003/0144643 A1 | 7/2003 | Järpenberg et al. |
| 2003/0203162 A1 | 10/2003 | Christopher et al. |
| 2003/0233082 A1 | 12/2003 | Kline et al. |
| 2004/0006323 A1 | 1/2004 | Hall et al. |
| 2004/0030317 A1 | 2/2004 | Torigoshi |
| 2004/0059309 A1 | 3/2004 | Nortman |
| 2004/0097895 A1 | 5/2004 | Busam et al. |
| 2004/0127881 A1 | 7/2004 | Stevens et al. |
| 2004/0133180 A1 | 7/2004 | Mori et al. |
| 2004/0158212 A1 | 8/2004 | Ponomarenko et al. |
| 2004/0158217 A1 | 8/2004 | Wu et al. |
| 2004/0219854 A1 | 11/2004 | Groitzsch et al. |
| 2004/0230171 A1 | 11/2004 | Ando et al. |
| 2005/0013975 A1 | 1/2005 | Brock et al. |
| 2005/0107764 A1 | 5/2005 | Matsuda et al. |
| 2005/0148971 A1 | 7/2005 | Kuroda et al. |
| 2005/0230037 A1 | 10/2005 | Jenquin et al. |
| 2005/0244640 A1 | 11/2005 | Riswick et al. |
| 2005/0267431 A1 | 12/2005 | Sasaki et al. |
| 2006/0032578 A1 | 2/2006 | Schneider |
| 2006/0047260 A1 | 3/2006 | Ashton et al. |
| 2006/0069373 A1 | 3/2006 | Schlinz et al. |
| 2006/0087053 A1 | 4/2006 | O'Donnell et al. |
| 2006/0105075 A1 | 5/2006 | Otsubo |
| 2006/0189954 A1 | 8/2006 | Kudo et al. |
| 2006/0228969 A1 | 10/2006 | Erdman |
| 2006/0270302 A1 | 11/2006 | Ando et al. |
| 2007/0026753 A1 | 2/2007 | Neely et al. |
| 2007/0045143 A1 | 3/2007 | Clough et al. |
| 2007/0045144 A1 | 3/2007 | Wheeler et al. |
| 2007/0131335 A1 | 6/2007 | Zhou et al. |
| 2007/0141311 A1 | 6/2007 | Mleziva et al. |
| 2007/0179466 A1 | 8/2007 | Tremblay et al. |
| 2007/0196650 A1 | 8/2007 | Yamamoto et al. |
| 2008/0134487 A1 | 6/2008 | Hartono |
| 2008/0149292 A1 | 6/2008 | Scherb |
| 2008/0161768 A1 | 7/2008 | Baba et al. |
| 2008/0287897 A1 | 11/2008 | Guzman et al. |

(56) References Cited

U.S. PATENT DOCUMENTS

| | | |
|---|---|---|
| 2009/0177176 A1 | 7/2009 | Saito |
| 2009/0204093 A1 | 8/2009 | Vasic et al. |
| 2009/0312730 A1 | 12/2009 | LaVon et al. |
| 2010/0022151 A1 | 1/2010 | Malowaniec |
| 2010/0036346 A1 | 2/2010 | Hammons |
| 2010/0048072 A1 | 2/2010 | Kauschke |
| 2010/0075103 A1 | 3/2010 | Miyamoto |
| 2010/0076394 A1* | 3/2010 | Hayase ............ A61F 13/15593 604/385.29 |
| 2010/0248575 A1 | 9/2010 | Malz |
| 2010/0307668 A1 | 12/2010 | Lange et al. |
| 2011/0092943 A1 | 4/2011 | Bishop et al. |
| 2011/0118689 A1 | 5/2011 | Een et al. |
| 2011/0120897 A1 | 5/2011 | Takahashi |
| 2011/0250378 A1 | 10/2011 | Eaton et al. |
| 2012/0004633 A1 | 1/2012 | Marcelo et al. |
| 2012/0061015 A1 | 3/2012 | LaVon et al. |
| 2012/0061016 A1 | 3/2012 | LaVon et al. |
| 2012/0071852 A1 | 3/2012 | Tsang et al. |
| 2012/0095429 A1 | 4/2012 | Kobayashi et al. |
| 2012/0271267 A1 | 10/2012 | Love et al. |
| 2012/0277713 A1 | 11/2012 | Raycheck et al. |
| 2012/0323206 A1 | 12/2012 | McMorrow et al. |
| 2013/0032656 A1 | 2/2013 | Yamamoto et al. |
| 2013/0072887 A1 | 3/2013 | LaVon et al. |
| 2013/0102982 A1 | 4/2013 | Nakano et al. |
| 2013/0112584 A1 | 5/2013 | Gaspari et al. |
| 2013/0139960 A1 | 6/2013 | Maruyama et al. |
| 2013/0171421 A1 | 7/2013 | Weisman et al. |
| 2013/0199696 A1 | 8/2013 | Schneider et al. |
| 2013/0199707 A1 | 8/2013 | Schneider |
| 2013/0211356 A1 | 8/2013 | Nishikawa et al. |
| 2013/0211363 A1 | 8/2013 | LaVon et al. |
| 2013/0255861 A1 | 10/2013 | Schneider |
| 2013/0255862 A1 | 10/2013 | Schneider et al. |
| 2013/0255863 A1 | 10/2013 | LaVon et al. |
| 2013/0255864 A1 | 10/2013 | Schneider et al. |
| 2013/0255865 A1 | 10/2013 | Brown et al. |
| 2013/0261589 A1 | 10/2013 | Fujkawa et al. |
| 2013/0306226 A1 | 11/2013 | Zink et al. |
| 2014/0000794 A1 | 1/2014 | Hamilton et al. |
| 2014/0005621 A1 | 1/2014 | Roe et al. |
| 2014/0018759 A1 | 1/2014 | Jayasinghe et al. |
| 2014/0041797 A1 | 2/2014 | Schneider |
| 2014/0107605 A1 | 4/2014 | Schroer, Jr. et al. |
| 2014/0127460 A1 | 5/2014 | Xu et al. |
| 2014/0136893 A1 | 5/2014 | Xie et al. |
| 2014/0148773 A1 | 5/2014 | Brown et al. |
| 2014/0234575 A1 | 8/2014 | Mitsuno et al. |
| 2014/0235127 A1 | 8/2014 | DeJesus et al. |
| 2014/0257231 A1* | 9/2014 | Wang ................... A61F 13/514 604/394 |
| 2014/0276517 A1 | 9/2014 | Chester et al. |
| 2014/0288521 A1 | 9/2014 | Wade et al. |
| 2014/0296815 A1 | 10/2014 | Takken et al. |
| 2014/0302286 A1 | 10/2014 | Okuda et al. |
| 2014/0305570 A1 | 10/2014 | Matsunaga et al. |
| 2014/0324009 A1 | 10/2014 | Lee et al. |
| 2014/0343525 A1 | 11/2014 | Roh et al. |
| 2014/0377506 A1 | 12/2014 | Eckstein et al. |
| 2014/0377513 A1 | 12/2014 | Galie et al. |
| 2015/0083309 A1 | 3/2015 | Long et al. |
| 2015/0126956 A1 | 5/2015 | Raycheck et al. |
| 2015/0136893 A1 | 5/2015 | Koskol |
| 2015/0164708 A1 | 6/2015 | Hashimoto et al. |
| 2015/0167207 A1 | 6/2015 | Bongartz et al. |
| 2015/0173967 A1 | 6/2015 | Kreuzer et al. |
| 2015/0230995 A1 | 8/2015 | Kaneko et al. |
| 2015/0245958 A1 | 9/2015 | Chmielewski et al. |
| 2015/0257941 A1 | 9/2015 | Eckstein et al. |
| 2015/0282999 A1 | 10/2015 | Arizti et al. |
| 2015/0320612 A1 | 11/2015 | Seitz et al. |
| 2015/0320613 A1 | 11/2015 | Seitz et al. |
| 2015/0320619 A1 | 11/2015 | Seitz et al. |
| 2015/0320620 A1 | 11/2015 | Seitz et al. |
| 2015/0320622 A1 | 11/2015 | Seitz et al. |
| 2015/0328056 A1 | 11/2015 | Een et al. |
| 2015/0351972 A1 | 12/2015 | Bing-Wo |
| 2016/0058624 A1 | 3/2016 | Hohm et al. |
| 2016/0058627 A1 | 3/2016 | Barnes et al. |
| 2016/0067119 A1 | 3/2016 | Weisman et al. |
| 2016/0100989 A1 | 4/2016 | Seitz et al. |
| 2016/0100997 A1 | 4/2016 | Seitz et al. |
| 2016/0106633 A1 | 4/2016 | Nagata et al. |
| 2016/0129661 A1 | 5/2016 | Arora et al. |
| 2016/0136009 A1 | 5/2016 | Weisman et al. |
| 2016/0228305 A1 | 8/2016 | Gualtieri et al. |
| 2016/0270977 A1 | 9/2016 | Surushi et al. |
| 2016/0331600 A1 | 11/2016 | Polidori et al. |
| 2017/0014281 A1 | 1/2017 | Xie et al. |
| 2017/0027774 A1 | 2/2017 | Ashraf et al. |
| 2017/0029993 A1 | 2/2017 | Ashraf et al. |
| 2017/0029994 A1 | 2/2017 | Ashraf et al. |
| 2017/0056256 A1 | 3/2017 | Smith et al. |
| 2017/0065461 A1 | 3/2017 | Schneider |
| 2017/0079852 A1 | 3/2017 | Fujima et al. |
| 2017/0119595 A1 | 5/2017 | Carla et al. |
| 2017/0191198 A1 | 7/2017 | Ashraf et al. |
| 2017/0258650 A1 | 9/2017 | Rosati et al. |
| 2017/0281417 A1 | 10/2017 | Ishikawa |
| 2017/0319403 A1 | 11/2017 | Bewick-Sonntag et al. |
| 2017/0348163 A1 | 12/2017 | Lakso et al. |
| 2018/0092784 A1 | 4/2018 | Wade et al. |
| 2018/0140473 A1 | 5/2018 | Koshijima et al. |
| 2018/0168874 A1 | 6/2018 | LaVon et al. |
| 2018/0168875 A1 | 6/2018 | LaVon et al. |
| 2018/0168876 A1 | 6/2018 | LaVon et al. |
| 2018/0168877 A1 | 6/2018 | Schneider et al. |
| 2018/0168878 A1 | 6/2018 | Schneider et al. |
| 2018/0168880 A1 | 6/2018 | Schneider et al. |
| 2018/0168885 A1 | 6/2018 | Zink, II et al. |
| 2018/0168887 A1 | 6/2018 | LaVon et al. |
| 2018/0168888 A1 | 6/2018 | Zink, II et al. |
| 2018/0168889 A1 | 6/2018 | LaVon et al. |
| 2018/0168890 A1 | 6/2018 | LaVon et al. |
| 2018/0168891 A1 | 6/2018 | Wise et al. |
| 2018/0168892 A1 | 6/2018 | LaVon et al. |
| 2018/0168893 A1 | 6/2018 | Ashraf et al. |
| 2018/0169964 A1 | 6/2018 | Schneider et al. |
| 2018/0170026 A1 | 6/2018 | Schneider et al. |
| 2018/0170027 A1 | 6/2018 | Schneider et al. |
| 2018/0214318 A1 | 8/2018 | Ashraf et al. |
| 2018/0214321 A1 | 8/2018 | Ashraf et al. |
| 2018/0216269 A1 | 8/2018 | Ashraf et al. |
| 2018/0216270 A1 | 8/2018 | Ashraf et al. |
| 2018/0216271 A1 | 8/2018 | Ashraf et al. |
| 2018/0333311 A1 | 11/2018 | Maki et al. |
| 2019/0003079 A1 | 1/2019 | Ashraf et al. |
| 2019/0003080 A1 | 1/2019 | Ashraf et al. |
| 2019/0070041 A1 | 3/2019 | Schneider et al. |
| 2019/0070042 A1 | 3/2019 | LaVon et al. |
| 2019/0112737 A1 | 4/2019 | Ashraf et al. |
| 2019/0254881 A1 | 8/2019 | Ishikawa et al. |
| 2019/0298586 A1 | 10/2019 | Ashraf et al. |
| 2019/0298587 A1 | 10/2019 | Ashraf et al. |
| 2019/0246196 A1 | 12/2019 | Han et al. |
| 2019/0374392 A1 | 12/2019 | Ninomiya et al. |
| 2019/0374404 A1 | 12/2019 | Ninomiya et al. |
| 2020/0155370 A1 | 5/2020 | Ohtsubo et al. |
| 2020/0155371 A1 | 5/2020 | Ohtsubo et al. |
| 2020/0206040 A1 | 7/2020 | Andrews et al. |
| 2020/0214901 A1 | 7/2020 | Andrews et al. |
| 2020/0298545 A1 | 9/2020 | Andrews et al. |

FOREIGN PATENT DOCUMENTS

| | | |
|---|---|---|
| CN | 1685099 | 10/2005 |
| CN | 1756659 A | 4/2006 |
| CN | 1849187 A | 10/2006 |
| CN | 101746057 A | 6/2010 |
| CN | 103635167 A | 3/2014 |
| CN | 104470710 A | 3/2015 |
| CN | 105147456 A | 12/2015 |
| CN | 105997351 A | 10/2016 |

(56) References Cited

FOREIGN PATENT DOCUMENTS

| | | |
|---|---|---|
| CN | 106913422 A | 7/2017 |
| CN | 107072825 A | 8/2017 |
| CN | 107106362 A | 8/2017 |
| EP | 0989218 A1 | 3/2000 |
| EP | 1305248 B1 | 5/2003 |
| EP | 1452157 A1 | 9/2004 |
| EP | 1473148 A1 | 11/2004 |
| EP | 1393701 B1 | 7/2013 |
| EP | 3056176 A1 | 8/2016 |
| EP | 3 092 997 B1 | 8/2017 |
| EP | 3251642 A1 | 12/2017 |
| EP | 3257488 A1 | 12/2017 |
| EP | 3563817 A1 | 11/2019 |
| JP | 3213543 A | 9/1991 |
| JP | H03213543 A | 9/1991 |
| JP | H0430847 A | 2/1992 |
| JP | H06254117 | 9/1994 |
| JP | 8071107 A | 3/1996 |
| JP | H08071107 A | 3/1996 |
| JP | H08132576 A | 5/1996 |
| JP | 2000026015 A | 1/2000 |
| JP | 2000160460 | 6/2000 |
| JP | 3086141 B2 | 9/2000 |
| JP | 2002035029 A | 2/2002 |
| JP | 2002178428 A | 6/2002 |
| JP | 2002248127 A | 9/2002 |
| JP | 2003521949 | 7/2003 |
| JP | 2004500169 A | 1/2004 |
| JP | 2004081365 | 3/2004 |
| JP | 2004229857 A | 8/2004 |
| JP | 2004237410 A | 8/2004 |
| JP | 2004254862 A | 9/2004 |
| JP | 2004298362 A | 10/2004 |
| JP | 2005509096 A | 4/2005 |
| JP | 2005320636 A | 11/2005 |
| JP | 2006137147 A | 6/2006 |
| JP | 2006149747 A | 6/2006 |
| JP | 2006149749 A | 6/2006 |
| JP | 2006204673 A | 12/2006 |
| JP | 2007190397 A | 8/2007 |
| JP | 2008029749 A | 2/2008 |
| JP | 2008055198 A | 3/2008 |
| JP | 2008104853 A * | 5/2008 ......... B29C 66/1122 |
| JP | 2008105425 A | 5/2008 |
| JP | 2008154998 | 5/2008 |
| JP | 2008148942 A | 7/2008 |
| JP | 2008179128 A | 8/2008 |
| JP | 2008194493 A | 8/2008 |
| JP | 2008229006 A | 10/2008 |
| JP | 2008229007 A | 10/2008 |
| JP | 2008253290 | 10/2008 |
| JP | 2008260131 A | 10/2008 |
| JP | 2014188042 | 10/2008 |
| JP | 2008264480 A | 11/2008 |
| JP | 2008272250 A | 11/2008 |
| JP | 2008272253 A | 11/2008 |
| JP | 2008296585 A | 12/2008 |
| JP | 2009000161 A | 1/2009 |
| JP | 2009039341 A | 2/2009 |
| JP | 2009056156 A | 3/2009 |
| JP | 2009106667 | 5/2009 |
| JP | 2009172231 A | 8/2009 |
| JP | 2009240804 A | 10/2009 |
| JP | 2009241607 A | 10/2009 |
| JP | 2010131833 A | 6/2010 |
| JP | 2011015707 | 1/2011 |
| JP | 2011111165 | 6/2011 |
| JP | 2011178124 A | 9/2011 |
| JP | 2011225000 A | 11/2011 |
| JP | 2012050882 A | 3/2012 |
| JP | 2012050883 A | 3/2012 |
| JP | 2012115358 A | 6/2012 |
| JP | 2012516203 A | 7/2012 |
| JP | 2012521498 | 9/2012 |
| JP | 5124187 B2 | 11/2012 |
| JP | 5124188 B2 | 11/2012 |
| JP | 2013515871 A1 | 5/2013 |
| JP | 2013138795 A | 7/2013 |
| JP | 2014111222 | 6/2014 |
| JP | 2014097257 | 10/2014 |
| JP | 2015510831 | 4/2015 |
| JP | 2015521499 | 7/2015 |
| JP | 2016013687 A | 1/2016 |
| JP | 2016016536 A | 2/2016 |
| JP | 5942819 B2 | 6/2016 |
| JP | 2016193199 A | 11/2016 |
| JP | 6149635 B2 | 6/2017 |
| JP | 2020054741 A | 4/2018 |
| JP | 2020054742 A | 4/2018 |
| JP | 2020054744 A | 4/2018 |
| JP | 2020054745 A | 4/2018 |
| JP | 2019081304 | 5/2019 |
| JP | 2019166804 A * | 10/2019 |
| JP | 2019181807 | 10/2019 |
| WO | WO2017105997 | 3/1996 |
| WO | WO 9925296 | 5/1999 |
| WO | WO 20030059603 | 7/2003 |
| WO | WO2008123348 | 2/2013 |
| WO | WO2003015681 | 6/2013 |
| WO | WO2014084168 A1 | 6/2014 |
| WO | WO2013084977 | 11/2014 |
| WO | WO 2015165927 A1 | 11/2015 |
| WO | WO 2016047320 | 3/2016 |
| WO | WO2016056092 A1 | 4/2016 |
| WO | WO2016056093 A1 | 4/2016 |
| WO | WO2016063346 A1 | 4/2016 |
| WO | WO2016067387 A1 | 5/2016 |
| WO | WO2016071981 A1 | 5/2016 |
| WO | WO2016075974 A1 | 5/2016 |
| WO | WO2016098416 A1 | 6/2016 |
| WO | WO2016104412 A1 | 6/2016 |
| WO | WO2016104422 A1 | 6/2016 |
| WO | WO2016158499 A1 | 10/2016 |
| WO | WO2016158746 A1 | 10/2016 |
| WO | WO2016208502 A1 | 12/2016 |
| WO | WO2016208513 A1 | 12/2016 |
| WO | WO2014196669 | 6/2017 |
| WO | WO 2018061288 | 4/2018 |
| WO | WO 2018084145 | 5/2018 |
| WO | WO 2018154680 A1 | 8/2018 |
| WO | WO 2018154682 A1 | 8/2018 |
| WO | WO 2018167836 A1 | 8/2018 |
| WO | WO 2019046363 | 3/2019 |
| WO | WO 2019111203 | 6/2019 |
| WO | WO 2019150802 A1 | 8/2019 |
| WO | WO 2020006996 | 1/2020 |

OTHER PUBLICATIONS

All Office Actions, U.S. Appl. No. 15/831,448.
All Office Actions, U.S. Appl. No. 15/831,464.
All Office Actions, U.S. Appl. No. 15/832,929.
All Office Actions, U.S. Appl. No. 15/833,057.
All Office Actions, U.S. Appl. No. 15/838,405.
All Office Actions, U.S. Appl. No. 15/846,382.
All Office Actions, U.S. Appl. No. 16/115,617.
3D Nonwovens Developments for textured nonwovens; Detlef Frey; http://web.archive.org/web/20170919080326/https://www.reicofil.com/en/pages/3d_nonwovens, Sep. 19, 2017.
15039 PCT International Search Report, dated Mar. 13, 2018, 13 pages.
American Cancer Society—What Cancer Patients Their Families and Caregivers Need to Know About COVID 19—Is Impacting Our Patient Services.
ASTM—Standard Tables of Body Measurements for Adult Females Misses Figure Type Size Range 00-20.
ASTM—Standard Tables of Body Measurements for Children Infant Size—Preemie to 24 Months.

* cited by examiner

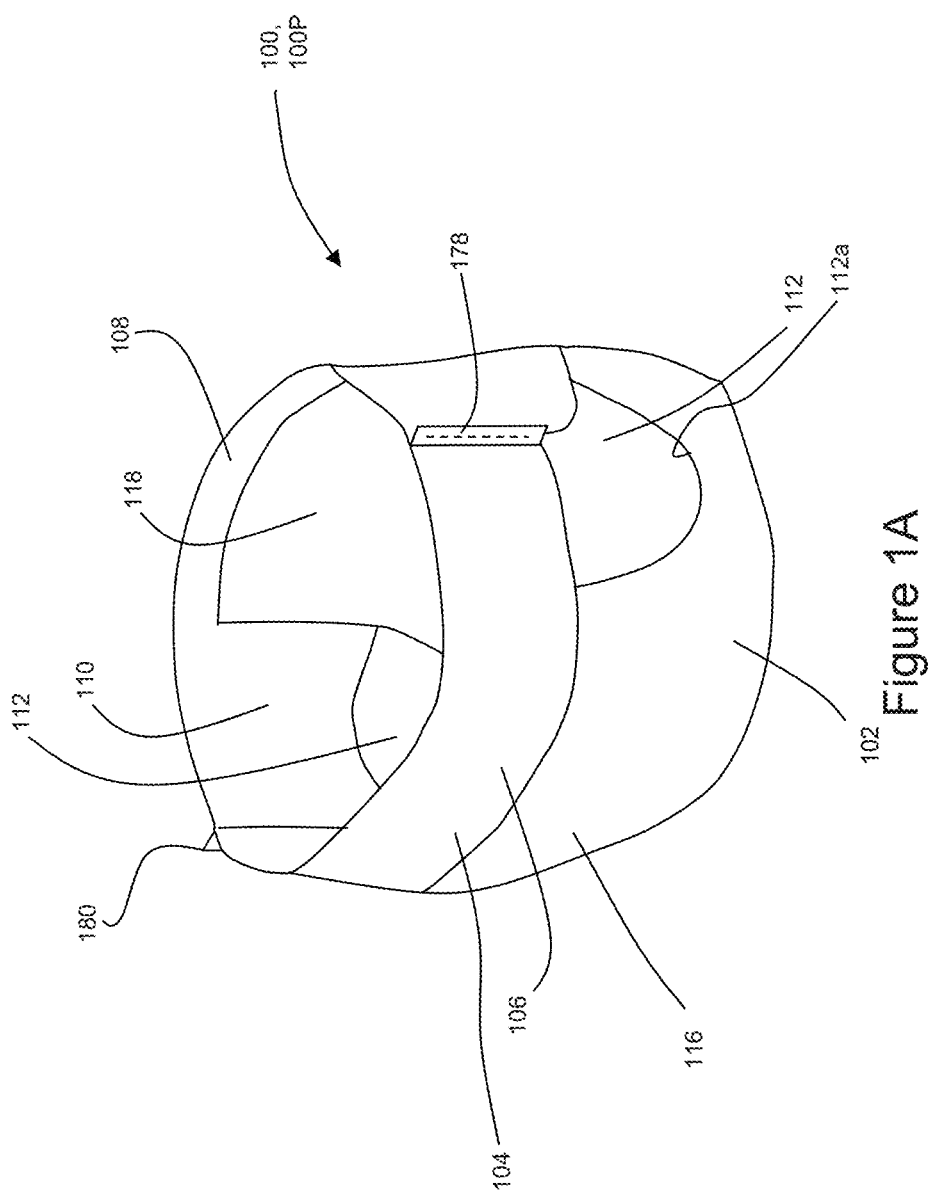

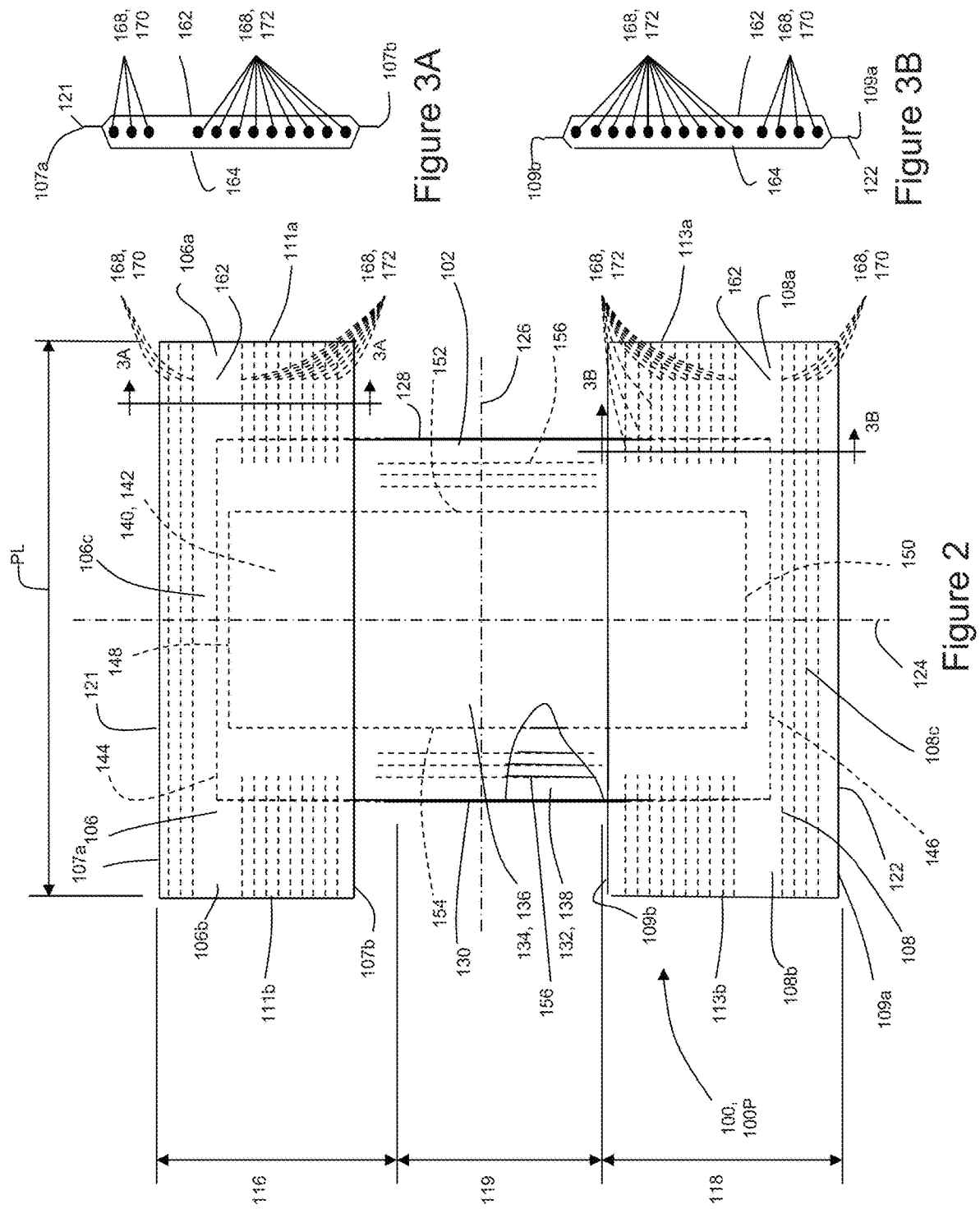

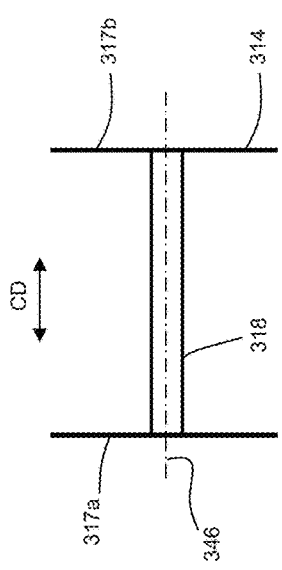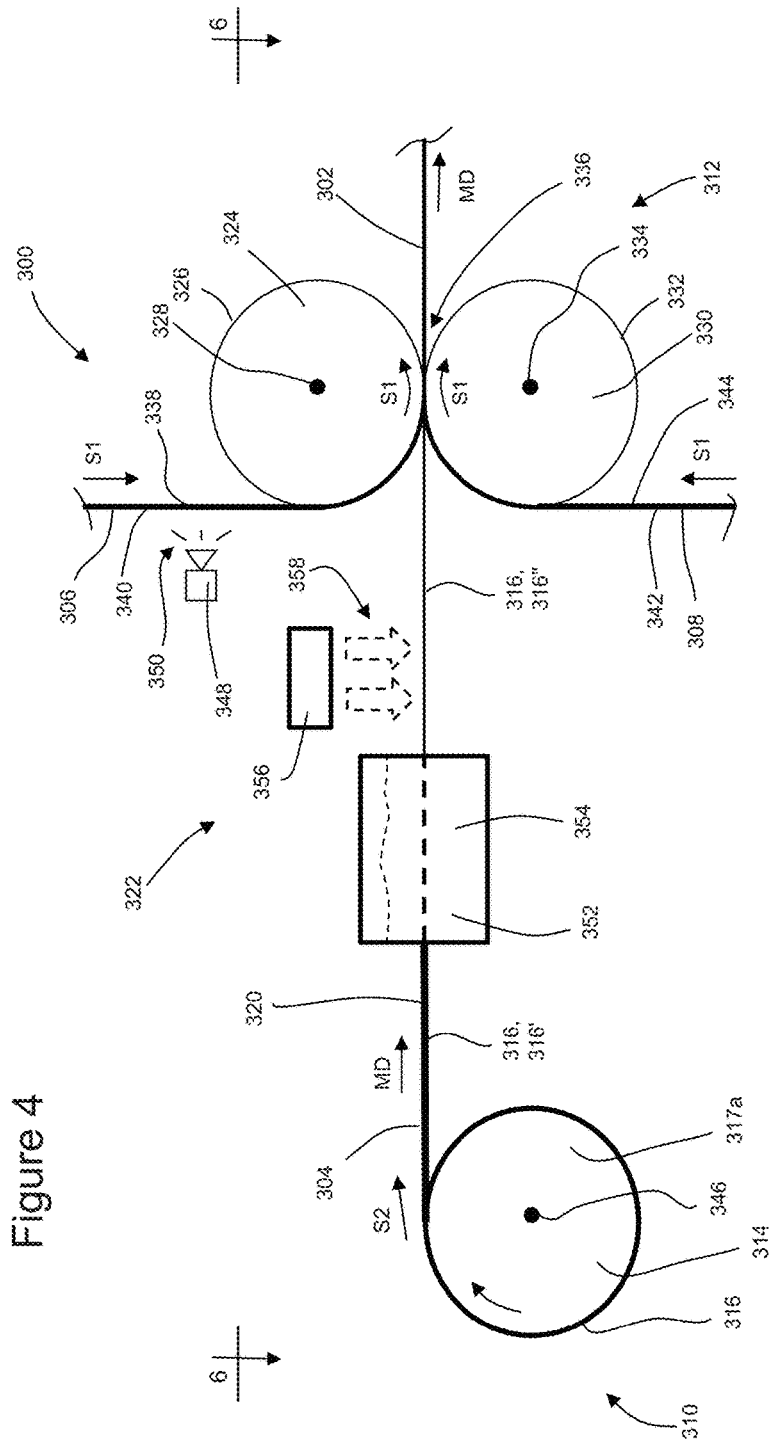

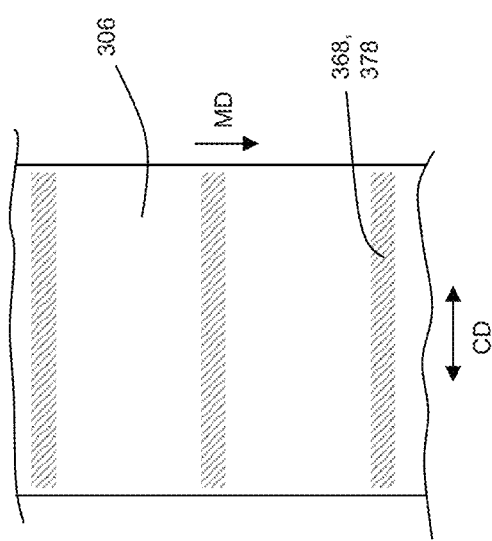
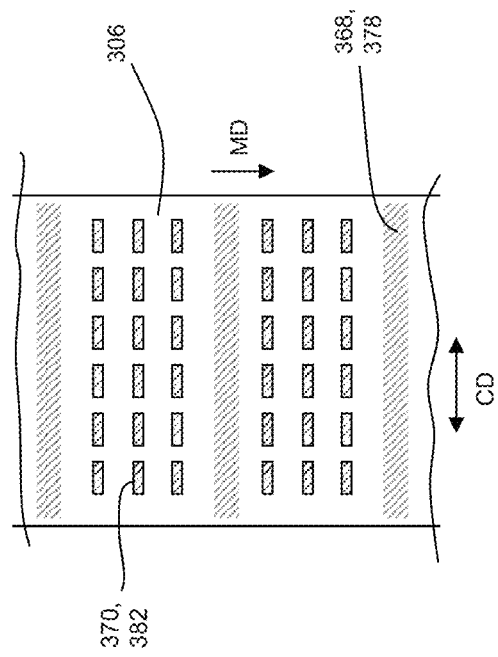

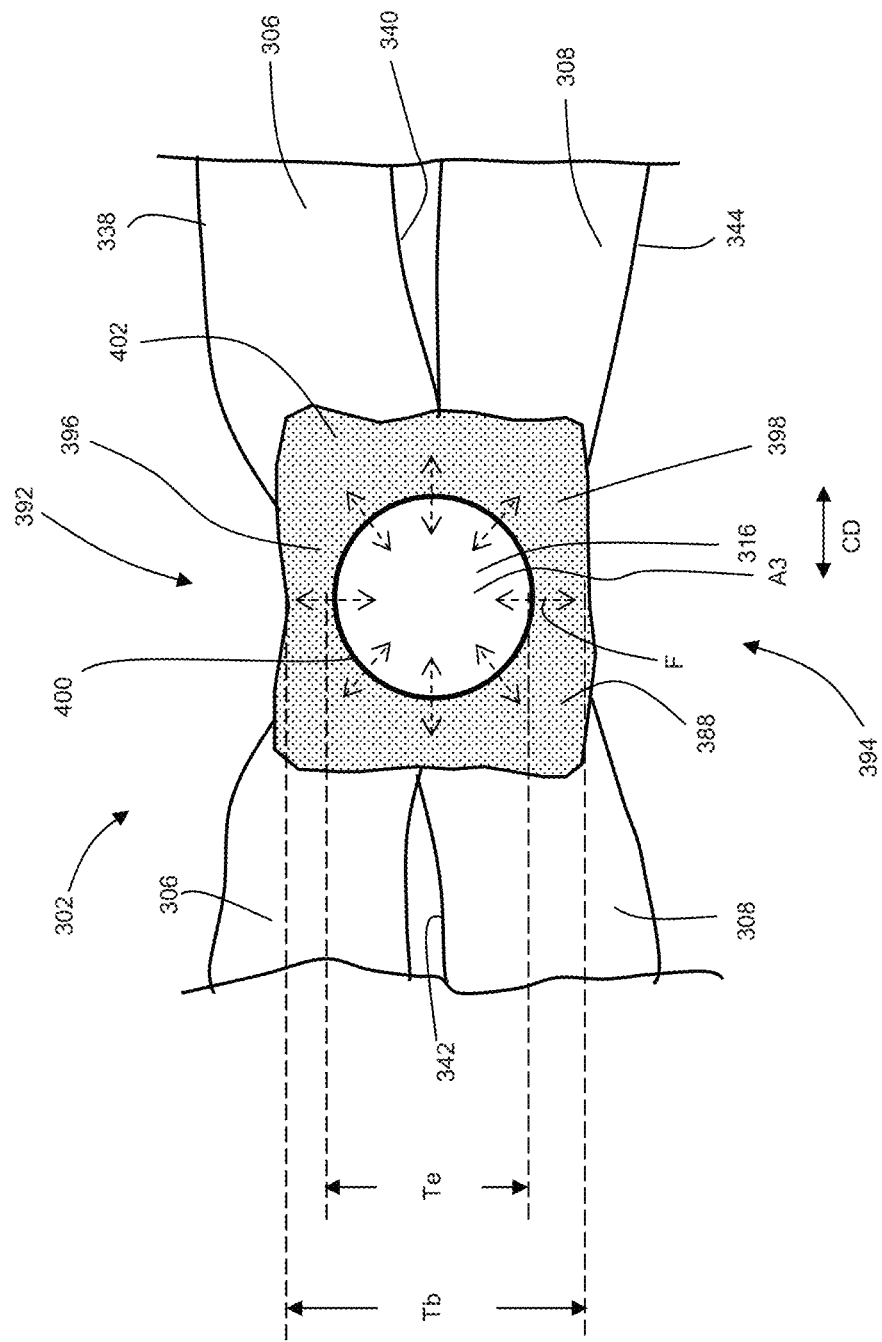

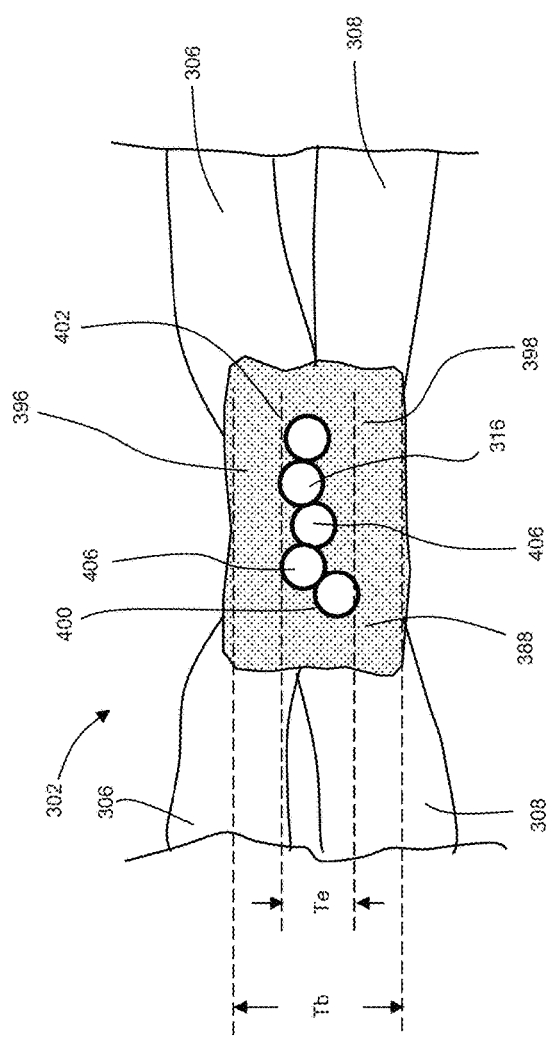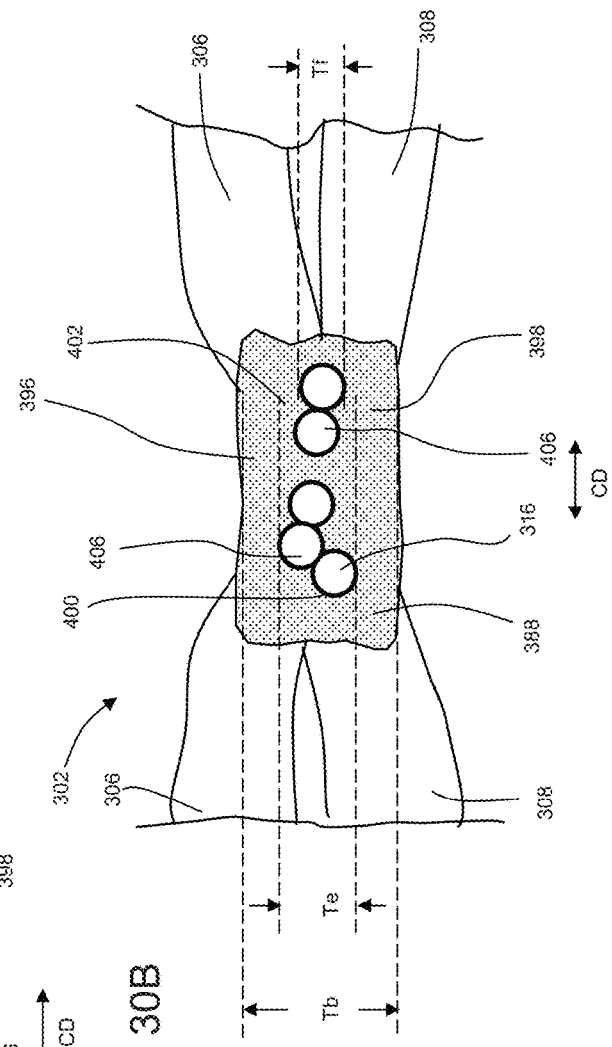

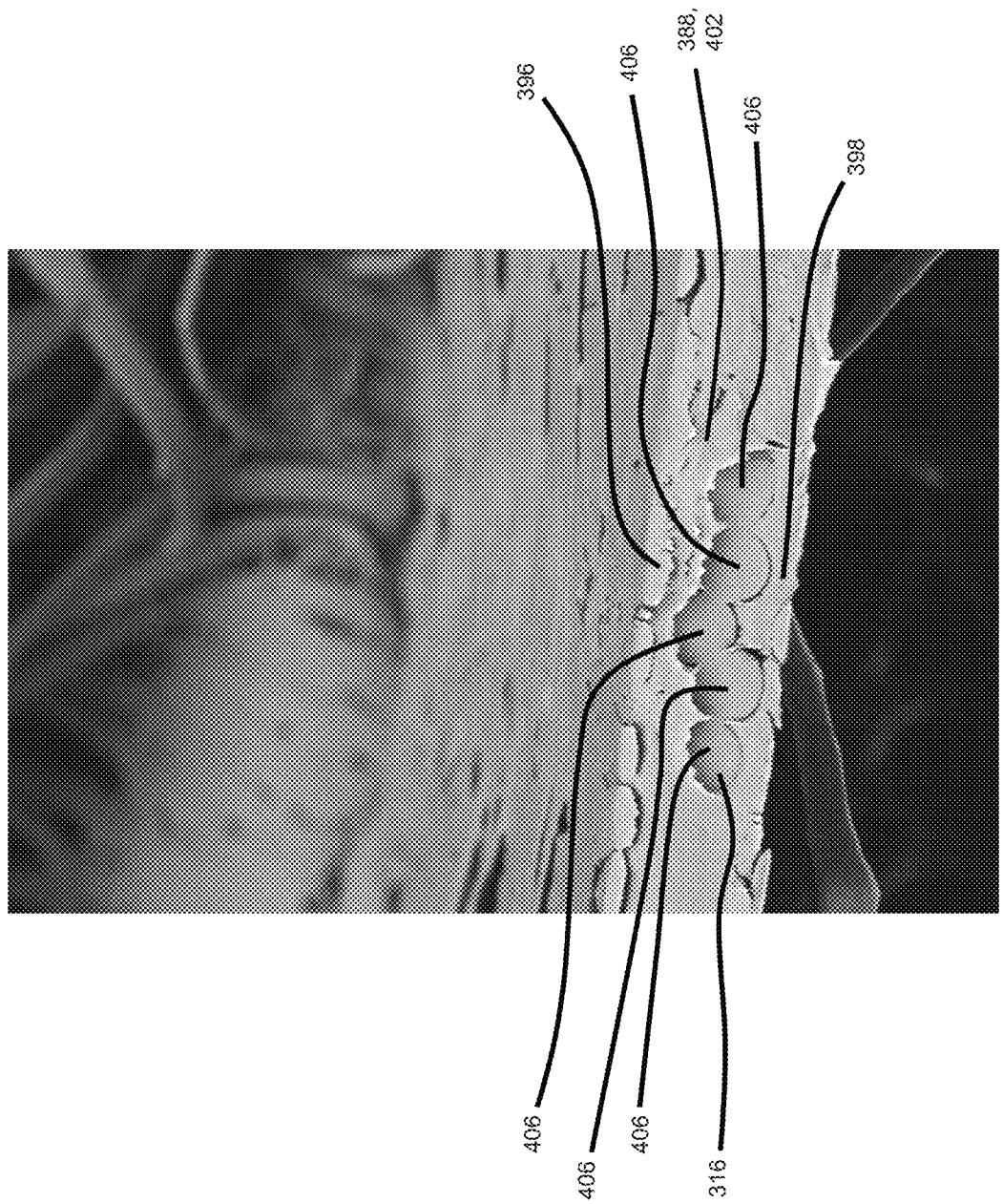

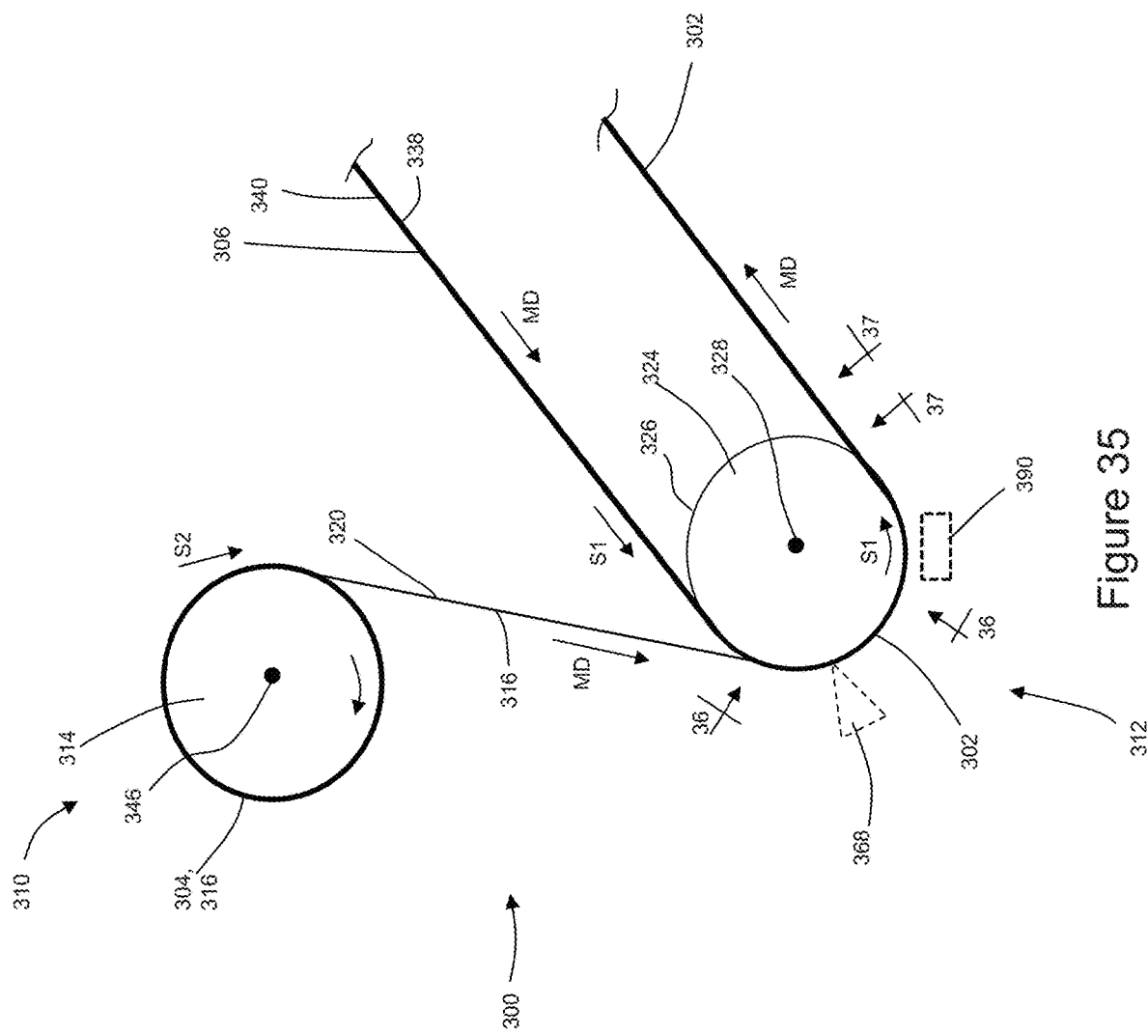

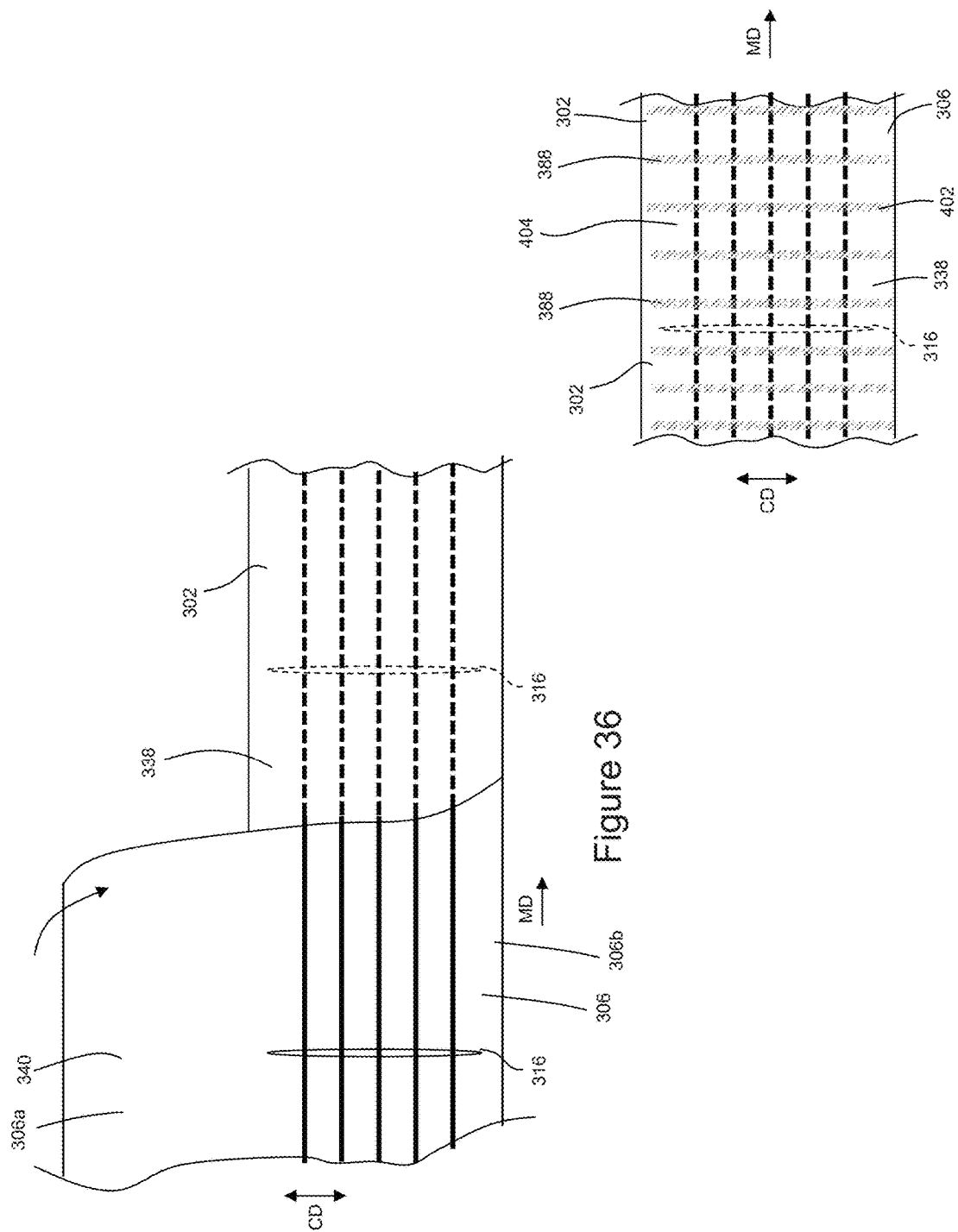

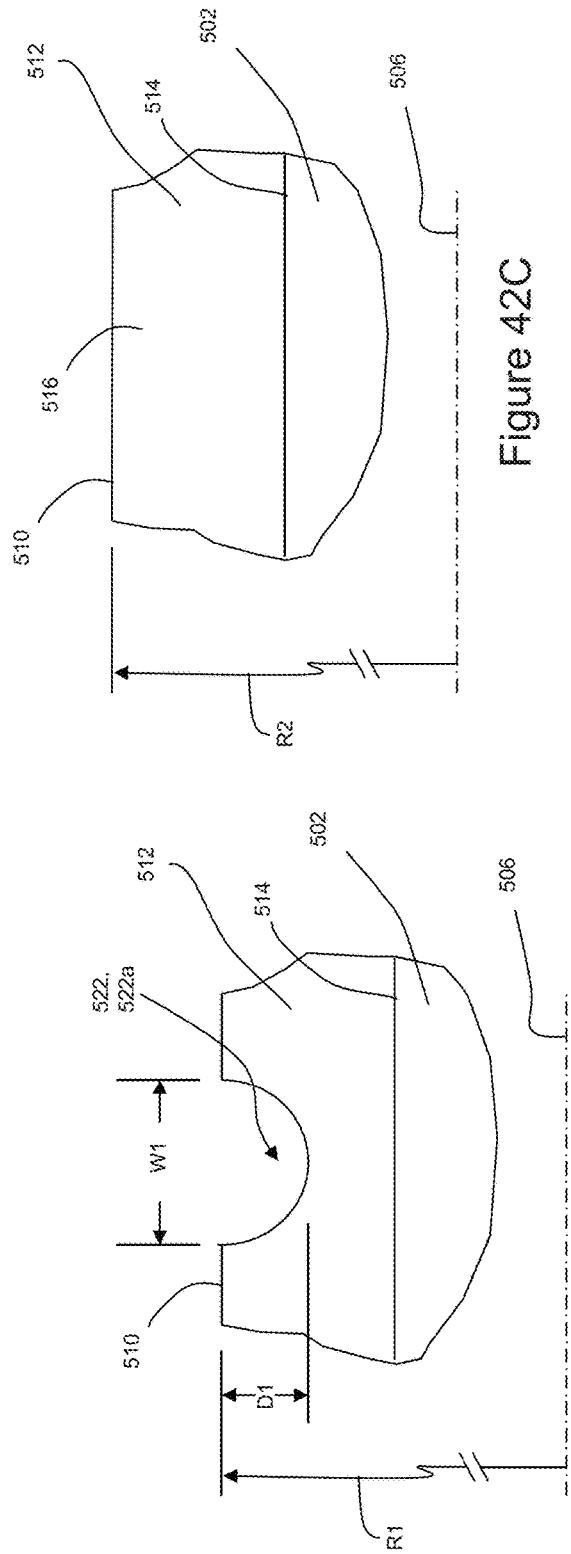
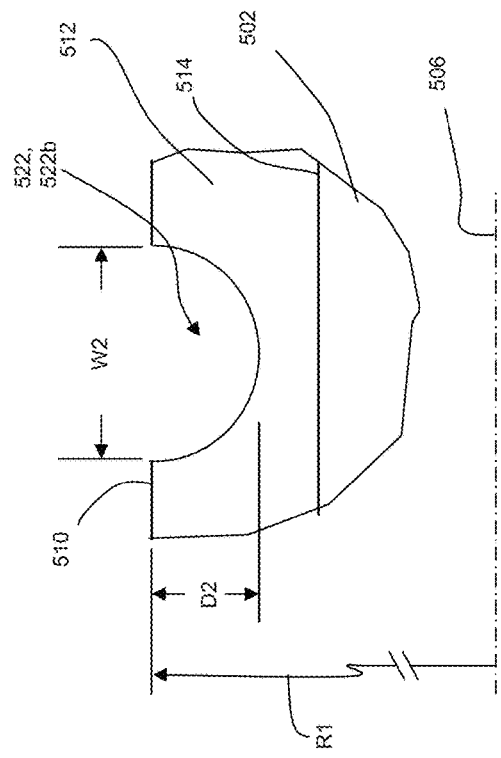
Figure 42A
Figure 42B
Figure 42C

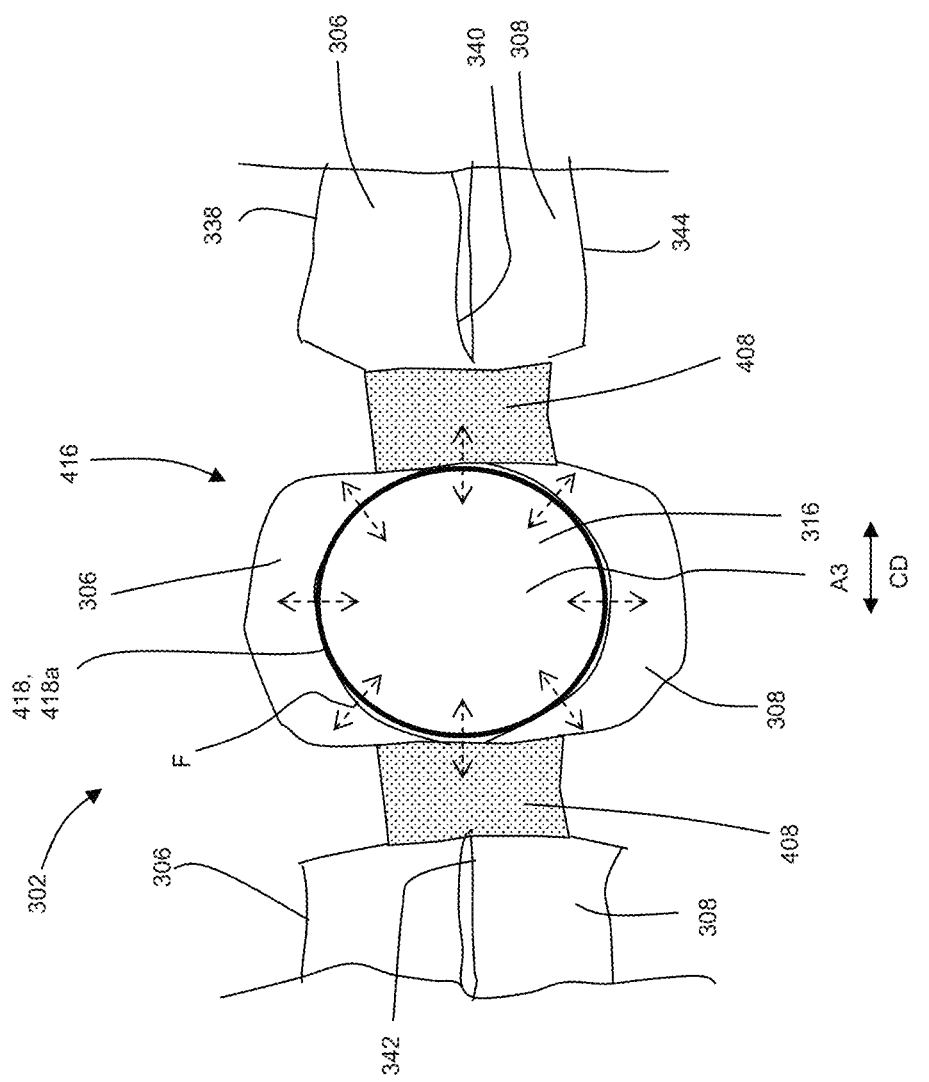

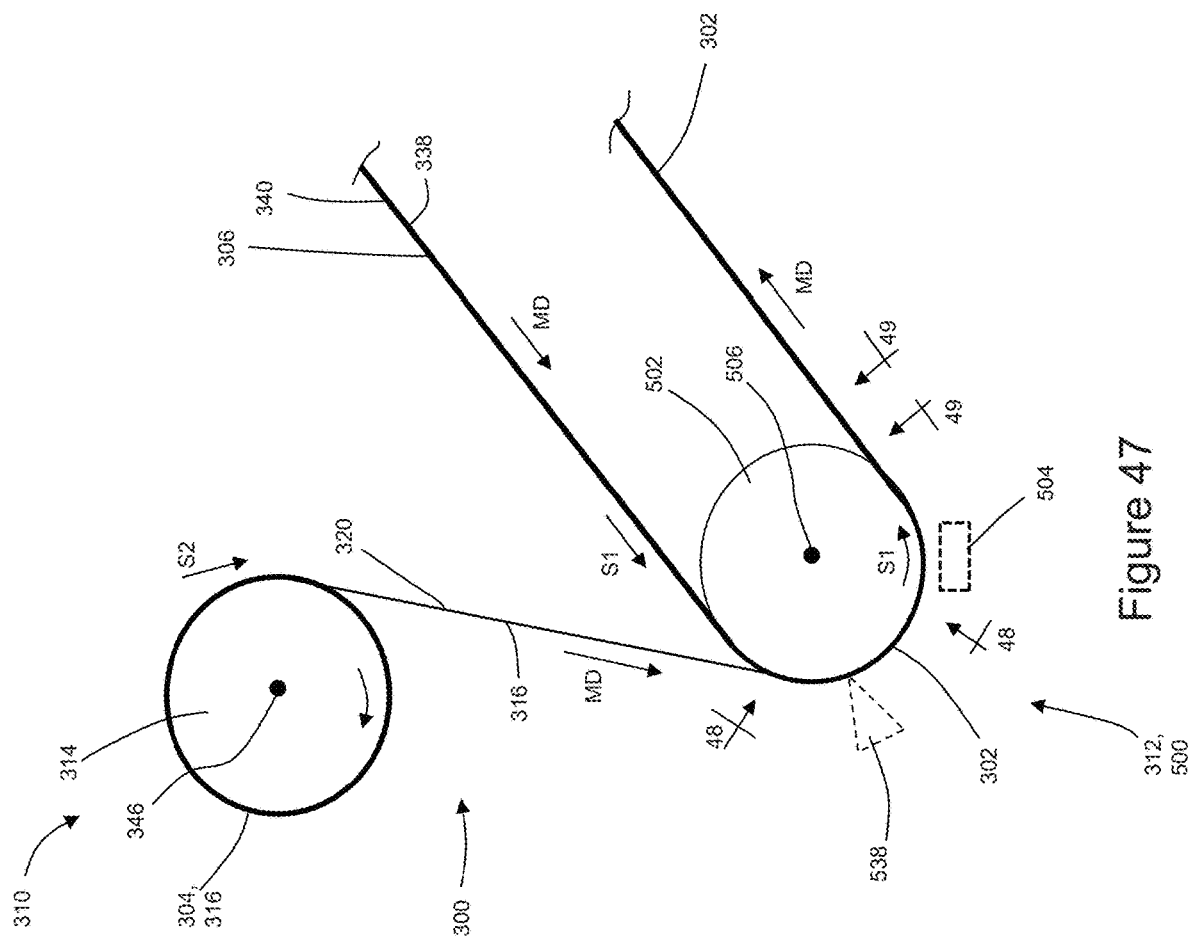

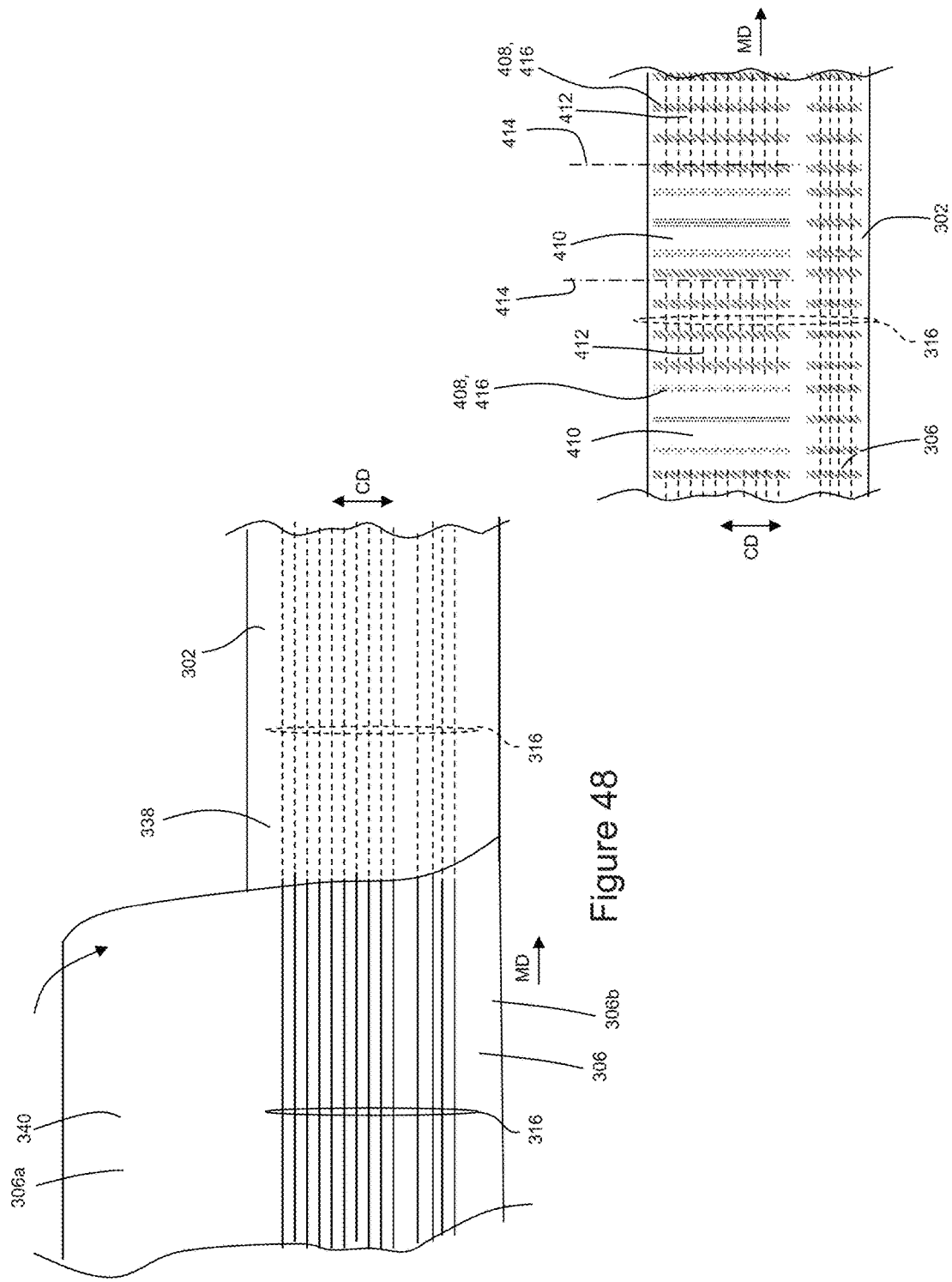

METHODS AND APPARATUSES FOR MAKING ELASTOMERIC LAMINATES

This application claims the benefit of U.S. Provisional Application No. 62/436,589, filed on Dec. 20, 2016; 62/483,965, filed on Apr. 11, 2017; 62/553,538, filed on Sep. 1, 2017; 62/553,149, filed on Sep. 1, 2017; 62/553,171, filed on Sep. 1, 2017; and 62/581,278, filed on Nov. 3, 2017, the entireties of which are all incorporated by reference herein.

FIELD OF THE INVENTION

The present disclosure relates to methods for manufacturing absorbent articles, and more particularly, to apparatuses and methods for making elastomeric laminates that may be used as components of absorbent articles.

BACKGROUND OF THE INVENTION

Along an assembly line, various types of articles, such as for example, diapers and other absorbent articles, may be assembled by adding components to and/or otherwise modifying an advancing, continuous web of material. For example, in some processes, advancing webs of material are combined with other advancing webs of material. In other examples, individual components created from advancing webs of material are combined with advancing webs of material, which in turn, are then combined with other advancing webs of material. In some cases, individual components created from an advancing web or webs are combined with other individual components created from other advancing webs. Webs of material and component parts used to manufacture diapers may include: backsheets, topsheets, leg cuffs, waist bands, absorbent core components, front and/or back ears, fastening components, and various types of elastic webs and components such as leg elastics, barrier leg cuff elastics, stretch side panels, and waist elastics. Once the desired component parts are assembled, the advancing web(s) and component parts are subjected to a final knife cut to separate the web(s) into discrete diapers or other absorbent articles.

Some absorbent articles have components that include elastomeric laminates. Such elastomeric laminates may include an elastic material bonded to one or more nonwovens. The elastic material may include an elastic film and/or elastic strands. In some laminates, a plurality of elastic strands are joined to a nonwoven while the plurality of strands are in a stretched condition so that when the elastic strands relax, the nonwoven gathers between the locations where the nonwoven is bonded to the elastic strands, and in turn, forms corrugations. The resulting elastomeric laminate is stretchable to the extent that the corrugations allow the elastic strands to elongate.

In some assembly processes, stretched elastic strands may be advanced in a machine direction and may be adhered between two advancing substrates, wherein the stretched elastic strands are spaced apart from each other in a cross direction. Some assembly processes are also configured with several elastic strands that are very closely spaced apart from each other in the cross direction. In some configurations, close cross directional spacing between elastic strands can be achieved by drawing elastic strands from windings that have been stacked in the cross direction on a beam. For example, various textile manufacturers may utilize beam elastics and associated handling equipment, such as available from Karl Mayer Corporation. However, problems can be encountered in manufacturing processes when drawing elastic strands stacked on a beam.

For example, relatively low decitex elastic strands supplied on a beam may include a coating, sometimes referred to as a yarn finish or spin finish, to help prevent the elastics strands from adhering to themselves, each other, and/or downstream handling equipment. When constructing absorbent articles, hot melt adhesives are sometimes used to adhere stretched elastic stands to advancing substrates to create elastic laminates. However, hot melt adhesives used to adhere stretched elastic strands to substrates when constructing absorbent articles may not adhere well to strands having a spin finish. As such, increased amounts of adhesive may be required to adequately adhere the stretched elastic strands to the substrates than would otherwise be required for elastic stands without a spin finish. In turn, relatively larger amounts of adhesives required to bond the elastic strands to the substrates may have a negative impact on aspects of the resulting product, such as with respect to costs, functionality, and aesthetics.

Consequently, it may be beneficial to provide methods and apparatuses for producing elastomeric laminates by removing or substantially removing the spin finish from elastic strands unwound from beams before adhering the elastic strands to advancing substrates. It may also be beneficial to provide methods and apparatuses for producing elastomeric laminates by bonding elastic strands with a spin finish to substrates without having to apply relatively large amounts of adhesive along the entire lengths of the elastic strands.

In an attempt to overcome the aforementioned problems associated with adhesives, some assembly processes may be configured to apply mechanical bonds with heat and pressure to trap the stretched elastic strands between two substrates. Such mechanical bonds may be created, for example, by advancing the substrates and elastic strands between an ultrasonic horn and anvil. However, the heat and pressure from the anvil and horn may also sever the elastic strands. As such, grooves may be provided in the horn or anvil for the elastic strands to nest in and to shield the elastic strands from pressure and prevent severing through the bonding process, such as disclosed in U.S. Pat. No. 6,291,039 and European Patent Publication No. EP 3 092 997 B1. However, positioning hundreds of elastic strands drawn from a beam in nesting grooves on an ultrasonic horn and/or anvil may add complexity to the assembly process.

Consequently, it would be beneficial to provide methods and apparatuses for producing elastomeric laminates by mechanically bonding elastic strands between substrates without severing the elastics strands, and/or without the need for having to guide elastic strands into designated nesting grooves in a mechanical bonding device.

In some absorbent article assembly operations, the elasticity of regions of an elastomeric laminate may be removed or deactivated by cutting elastic strands in the regions. For example, some diaper pant embodiments are configured with an absorbent chassis connected with front and back elastic belts, wherein opposing end regions of the front and back belts are connected with each other at side seams. In some configurations, diaper pants may include graphics in certain regions of the belts connect with the absorbent chassis, and the absence of elasticity in such regions may allow for reduced distortion of graphics located in those regions. As such, the elasticity of the front and back belts may be removed in regions where the absorbent chassis connects with the belts. Thus, in some converting configurations adapted to assemble such diaper pants, stretched elastic strands are bonded between two continuous nonwoven webs to form an elastomeric laminate. Regions of the elastic strands may then be intermittently deactivated along the length of the elastomeric laminate by cutting the elastic strands. Subsequent to deactivating the elastic strands, the elastomeric laminate may be subjected to additional handling and converting operations.

As previously mentioned, in some manufacturing configurations, hot melt adhesives are used to adhere stretched elastic stands to advancing substrates to create elastomeric laminates. However, in attempts to eliminate and reduce the costs and complexities associated with the use of adhesives, some assembly processes may be configured to apply mechanical bonds with heat and pressure to trap the stretched elastic strands between two substrates.

However, utilizing mechanical bonding techniques to create elastomeric laminates with unbonded regions and subsequently cutting stretched elastic strands in the unbonded regions to create deactivated regions in the elastomeric laminates may present certain challenges. For example, the ends of the cut elastic stands may snap back in an uncontrolled fashion and consequently may end up in undesired locations within the elastomeric laminate. In some instances, ends of cut elastic strands may form of a lump of elastic material within the elastomeric laminate, which may negatively impact comfort and appearance of an assembled product.

Consequently, it may be beneficial to provide methods and apparatuses that are configured to assemble elastomeric laminates in such a way to maximize the aesthetic appearance of such laminates when placed in an assembled product and/or reduce handling of the elastomeric laminates after mechanically bonding the elastics therein.

Other problems can be encountered in manufacturing processes when drawing elastic strands stacked on a beam. For example, when elastic strands are completely drawn from the beam, a new beam of elastics will be needed to replace the empty beam. As such, in some configurations, an entire manufacturing line may need to be temporarily stopped while the empty beam is replaced. Manufacturing lines in the textile industry often operate at relatively slow speeds, and as such, these textile manufacturing lines can be temporarily stopped to replace an empty beam and may not result in a major disruption to production. However, some manufacturing lines, such as disposable absorbent article manufacturing lines, may operate at high speeds and/or would require depleted beams of elastics to be replaced relatively often. As such, it can be inefficient and/or cost prohibitive to frequently stop and restart high speed manufacturing operations to replace empty beams.

Consequently, it may be beneficial to provide a method and apparatus for producing elastomeric laminates with beams of elastic strands that can be replaced without having to stop the assembly process.

SUMMARY OF THE INVENTION

In one form, a method for making absorbent articles comprises: providing elastic strands wound onto a beam; rotating the beam to unwind the elastic strands from the beam; advancing the elastic strands from the rotating beam; stretching the elastic strands; and bonding the stretched elastic strands between a first substrate and a second substrate to form an elastomeric laminate.

In another form, a method for making an elastomeric laminate comprises: providing first elastic strands wound onto a first beam, wherein at least one of the first elastic strands comprises a spin finish; providing second elastic strands; unwinding the first elastic strands from the first beam; advancing a first substrate and a second substrate in a machine direction; stretching the first and second elastic strands; and bonding the stretched first elastic strands and the second elastic strands with and between the first substrate and the second substrate to form an elastomeric laminate, wherein the elastomeric laminate comprises a first region having a first stretch characteristic defined by the first elastic strands and a second region having a second stretch characteristic defined by the second elastic strands, wherein the first stretch characteristic is different from the second stretch characteristic.

In yet another form, a method for making an elastomeric laminate comprises: providing elastic strands wound onto a beam, wherein the elastic strands comprise a spin finish; rotating the beam to unwind the elastic strands from the beam; advancing the elastic strands from the rotating beam; stretching the elastic strands; bonding discrete lengths of the stretched elastic strands with and between a first substrate and a second substrate with discrete first bonds arranged intermittently along a machine direction; and applying second bonds extending in the machine direction between consecutive first bonds to bond the first and second substrates directly to each other.

BRIEF DESCRIPTION OF THE DRAWINGS

FIG. 1A is a front perspective view of a diaper pant.

FIG. 2 is a partially cut away plan view of the diaper pant shown in FIGS. 1A and 1B in a flat, uncontracted state.

FIG. 3A is a cross-sectional view of the diaper pant of FIG. 2 taken along line 3A-3A.

FIG. 3B is a cross-sectional view of the diaper pant of FIG. 2 taken along line 3B-3B.

FIG. 4 shows an example of an empty beam having two side plates connected with opposing end portions of a mandrel core and illustrates a view of the converting apparatus of FIG. 57 taken along line 4-4.

FIG. 5 is a schematic side view of a converting apparatus including a detergent bath adapted to remove a spin finish from a plurality of elastic strands before being adhered between a first substrate and a second substrate.

FIG. 14 is a view of the first substrate of FIGS. 12, 18, and 21 taken along line 14-14.

FIG. 15 is a view of the first substrate of FIG. 12 taken along line 15-15.

FIG. 29C is a sectional view of the elastic strand in an unbonded region of FIG. 28B taken along line 29C-29C, wherein the elastic strand is in a relaxed state.

FIG. 30B is a sectional view of an elastic strand, bond, first substrate, and second substrate of FIG. 28A taken along line 29A-29A, wherein a plurality of filaments of the elastic strand are bonded in a second configuration.

FIG. 30C is a sectional view of an elastic strand, bond, first substrate, and second substrate of FIG. 28A taken along line 29A-29A, wherein a plurality of filaments of the elastic strand are bonded in a third configuration.

FIG. 30D is a scanning electron microscope ("SEM") photograph of a cross sectional view of an elastic strand including five filaments in a bonded region and surrounded by hardened first and second materials.

FIG. 35 is a schematic side view of another configuration of a converting apparatus adapted to manufacture an elastomeric laminate.

FIG. 36 is a view of the converting apparatus of FIG. 35 taken along line 36-36.

FIG. 37 is a view of the converting apparatus of FIG. 44 taken along line 37-37.

FIG. 42A is a sectional view of a first channel on the pattern roll of FIG. 41 taken along line 42A-42A.

FIG. 42B is a sectional view of a second channel on the pattern roll of FIG. 41 taken along line 42B-42B.

FIG. 42C is a sectional view of a protuberance on the pattern roll of FIG. 41 taken along line 42C-42C.

FIG. 44B is a sectional view of the elastic strand, bonds, first substrate, and second substrate of FIG. 43B taken along line 44B-44B.

FIG. 47 is a schematic side view of an additional configuration of a converting apparatus adapted to manufacture an elastomeric laminate.

FIG. 48 is a view of the converting apparatus of FIG. 47 taken along line 48-48.

FIG. 49 is a view of the converting apparatus of FIG. 47 taken along line 48-48.

DETAILED DESCRIPTION OF THE INVENTION

Figure 1B:
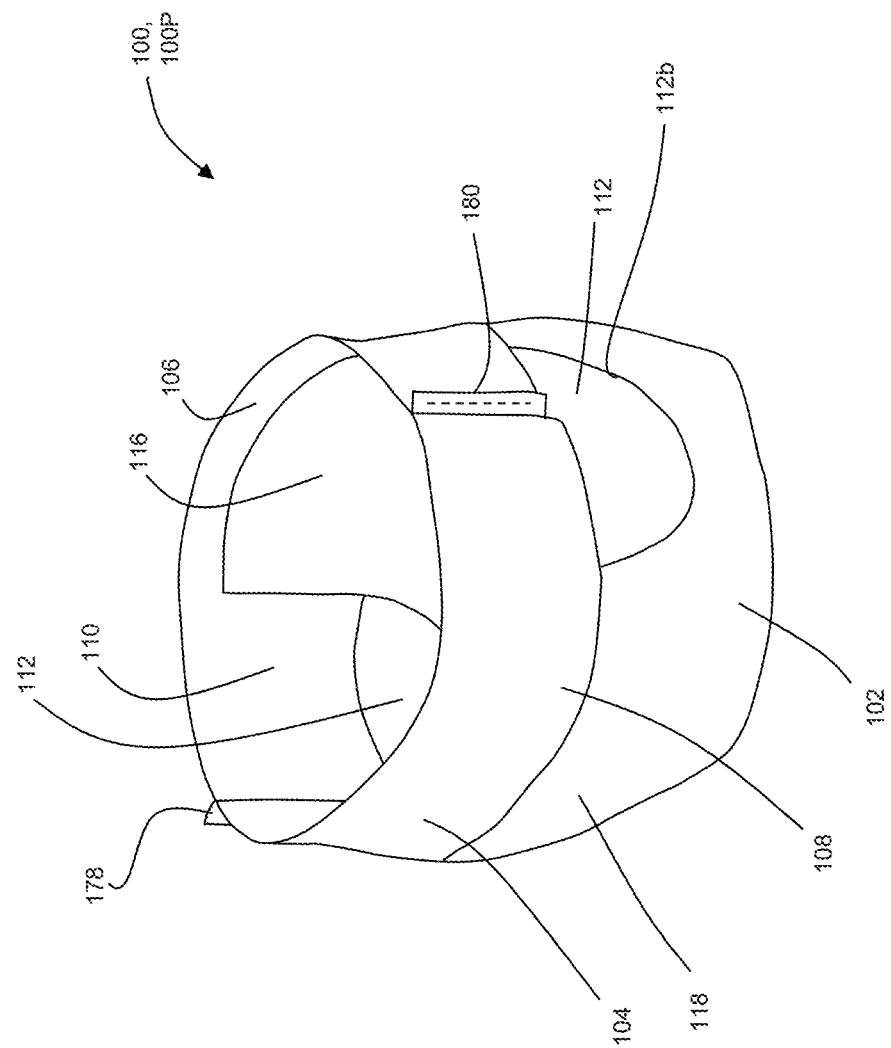
FIG. 1B is a rear perspective view of a diaper pant.

The following term explanations may be useful in understanding the present disclosure:

"Absorbent article" is used herein to refer to consumer products whose primary function is to absorb and retain soils and wastes. Absorbent articles can comprise sanitary napkins, tampons, panty liners, interlabial devices, wound dressings, wipes, disposable diapers including taped diapers and diaper pants, inserts for diapers with a reusable outer cover, adult incontinent diapers, adult incontinent pads, and adult incontinent pants. The term "disposable" is used herein to describe absorbent articles which generally are not intended to be laundered or otherwise restored or reused as an absorbent article (e.g., they are intended to be discarded after a single use and may also be configured to be recycled, composted or otherwise disposed of in an environmentally compatible manner).

An "elastic," "elastomer" or "elastomeric" refers to materials exhibiting elastic properties, which include any material that upon application of a force to its relaxed, initial length can stretch or elongate to an elongated length more than 10% greater than its initial length and will substantially recover back to about its initial length upon release of the applied force.

As used herein, the term "joined" encompasses configurations whereby an element is directly secured to another element by affixing the element directly to the other element, and configurations whereby an element is indirectly secured to another element by affixing the element to intermediate member(s) which in turn are affixed to the other element.

The term "substrate" is used herein to describe a material which is primarily two-dimensional (i.e. in an XY plane) and whose thickness (in a Z direction) is relatively small (i.e. 1/10 or less) in comparison to its length (in an X direction) and width (in a Y direction). Non-limiting examples of substrates include a web, layer or layers or fibrous materials, nonwovens, films and foils such as polymeric films or metallic foils. These materials may be used alone or may comprise two or more layers laminated together. As such, a web is a substrate.

The term "nonwoven" refers herein to a material made from continuous (long) filaments (fibers) and/or discontinuous (short) filaments (fibers) by processes such as spunbonding, meltblowing, carding, and the like. Nonwovens do not have a woven or knitted filament pattern.

The term "machine direction" (MD) is used herein to refer to the direction of material flow through a process. In addition, relative placement and movement of material can be described as flowing in the machine direction through a process from upstream in the process to downstream in the process.

The term "cross direction" (CD) is used herein to refer to a direction that is generally perpendicular to the machine direction.

The term "taped diaper" (also referred to as "open diaper") refers to disposable absorbent articles having an initial front waist region and an initial back waist region that are not fastened, pre-fastened, or connected to each other as packaged, prior to being applied to the wearer. A taped diaper may be folded about the lateral centerline with the interior of one waist region in surface to surface contact with the interior of the opposing waist region without fastening or joining the waist regions together. Example taped diapers are disclosed in various suitable configurations U.S. Pat. Nos. 5,167,897, 5,360,420, 5,599,335, 5,643,588, 5,674, 216, 5,702,551, 5,968,025, 6,107,537, 6,118,041, 6,153,209, 6,410,129, 6,426,444, 6,586,652, 6,627,787, 6,617,016, 6,825,393, and 6,861,571; and U.S. Patent Publication Nos. 2013/0072887 A1; 2013/0211356 A1; and 2013/0306226 A1, all of which are incorporated by reference herein.

The term "pant" (also referred to as "training pant", "pre-closed diaper", "diaper pant", "pant diaper", and "pull-on diaper") refers herein to disposable absorbent articles having a continuous perimeter waist opening and continuous perimeter leg openings designed for infant or adult wearers. A pant can be configured with a continuous or closed waist opening and at least one continuous, closed, leg opening prior to the article being applied to the wearer. A pant can be preformed or pre-fastened by various techniques including, but not limited to, joining together portions of the article using any refastenable and/or permanent closure member (e.g., seams, heat bonds, pressure welds, adhesives, cohesive bonds, mechanical fasteners, etc.). A pant can be preformed anywhere along the circumference of the article in the waist region (e.g., side fastened or seamed, front waist fastened or seamed, rear waist fastened or seamed). Example diaper pants in various configurations are disclosed in U.S. Pat. Nos. 4,940,464; 5,092,861; 5,246,433; 5,569,234; 5,897, 545; 5,957,908; 6,120,487; 6,120,489; 7,569,039 and U.S. Patent Publication Nos. 2003/0233082 A1; 2005/0107764 A1, 2012/0061016 A1, 2012/0061015 A1; 2013/0255861 A1; 2013/0255862 A1; 2013/0255863 A1; 2013/0255864 A1; and 2013/0255865 A1, all of which are incorporated by reference herein.

The present disclosure relates to methods for manufacturing absorbent articles, and in particular, to methods for making elastomeric laminates that may be used as components of absorbent articles. The elastomeric laminates may include a first substrate, a second substrate, and an elastic material located between the first substrate and second substrate. During the process of making the elastomeric laminate, the elastic material may be advanced and stretched in a machine direction and may be joined with either or both the first and second substrates advancing in the machine direction. The elastomeric laminates made according to the processes and apparatuses discussed herein may be used to construct various types of components used in the manufacture of different types of absorbent articles, such as diaper pants and taped diapers, such as for example disclosed in U.S. Patent Application No. 62/553,538, filed on Sep. 1, 2017. To help provide additional context to the subsequent discussion of the process embodiments, the following provides a general description of absorbent articles in the form of diapers that include components including the elastomeric laminates that may be produced with the methods and apparatuses disclosed herein.

FIGS. 1A, 1B, and 2 show an example of an absorbent article 100 in the form of a diaper pant 100P that may include components constructed from elastomeric laminates assembled in accordance with the apparatuses and methods disclosed herein. In particular, FIGS. 1A and 1B show perspective views of a diaper pant 100P in a pre-fastened configuration, and FIG. 2 shows a plan view of the diaper pant 100P with the portion of the diaper that faces away from a wearer oriented toward the viewer. The diaper pant 100P includes a chassis 102 and a ring-like elastic belt 104. As discussed below in more detail, a first elastic belt 106 and a second elastic belt 108 are bonded together to form the ring-like elastic belt 104.

With continued reference to FIG. 2, the diaper pant 100P and the chassis 102 each include a first waist region 116, a second waist region 118, and a crotch region 119 disposed intermediate the first and second waist regions. The first waist region 116 may be configured as a front waist region, and the second waist region 118 may be configured as back waist region. The diaper 100P may also include a laterally extending front waist edge 121 in the front waist region 116 and a longitudinally opposing and laterally extending back waist edge 122 in the back waist region 118. To provide a frame of reference for the present discussion, the diaper 100P and chassis 102 of FIG. 2 are shown with a longitudinal axis 124 and a lateral axis 126. In some embodiments, the longitudinal axis 124 may extend through the front waist edge 121 and through the back waist edge 122. And the lateral axis 126 may extend through a first longitudinal or right side edge 128 and through a midpoint of a second longitudinal or left side edge 130 of the chassis 102.

As shown in FIGS. 1A, 1B, and 2, the diaper pant 100P may include an inner, body facing surface 132, and an outer, garment facing surface 134. The chassis 102 may include a backsheet 136 and a topsheet 138. The chassis 102 may also include an absorbent assembly 140, including an absorbent core 142, disposed between a portion of the topsheet 138 and the backsheet 136. As discussed in more detail below, the diaper 100P may also include other features, such as leg elastics and/or leg cuffs to enhance the fit around the legs of the wearer.

As shown in FIG. 2, the periphery of the chassis 102 may be defined by the first longitudinal side edge 128, a second longitudinal side edge 130, a first laterally extending end edge 144 disposed in the first waist region 116, and a second laterally extending end edge 146 disposed in the second waist region 118. Both side edges 128 and 130 extend longitudinally between the first end edge 144 and the second end edge 146. As shown in FIG. 2, the laterally extending end edges 144 and 146 are located longitudinally inward from the laterally extending front waist edge 121 in the front waist region 116 and the laterally extending back waist edge 122 in the back waist region 118. When the diaper pant 100P is worn on the lower torso of a wearer, the front waist edge 121 and the back waist edge 122 may encircle a portion of the waist of the wearer. At the same time, the side edges 128 and 130 may encircle at least a portion of the legs of the wearer. And the crotch region 119 may be generally positioned between the legs of the wearer with the absorbent core 142 extending from the front waist region 116 through the crotch region 119 to the back waist region 118.

As previously mentioned, the diaper pant 100P may include a backsheet 136. The backsheet 136 may also define the outer surface 134 of the chassis 102. The backsheet 136 may also comprise a woven or nonwoven material, polymeric films such as thermoplastic films of polyethylene or polypropylene, and/or a multi-layer or composite materials comprising a film and a nonwoven material. The backsheet may also comprise an elastomeric film. An example backsheet 136 may be a polyethylene film having a thickness of from about 0.012 mm (0.5 mils) to about 0.051 mm (2.0 mils). Further, the backsheet 136 may permit vapors to escape from the absorbent core (i.e., the backsheet is breathable) while still preventing exudates from passing through the backsheet 136.

Also described above, the diaper pant 100P may include a topsheet 138. The topsheet 138 may also define all or part of the inner surface 132 of the chassis 102. The topsheet 138 may be liquid pervious, permitting liquids (e.g., menses, urine, and/or runny feces) to penetrate through its thickness. A topsheet 138 may be manufactured from a wide range of materials such as woven and nonwoven materials; apertured or hydroformed thermoplastic films; apertured nonwovens, porous foams; reticulated foams; reticulated thermoplastic films; and thermoplastic scrims. Woven and nonwoven materials may comprise natural fibers such as wood or cotton fibers; synthetic fibers such as polyester, polypropylene, or polyethylene fibers; or combinations thereof. If the topsheet 138 includes fibers, the fibers may be spunbond, carded, wet-laid, meltblown, hydroentangled, or otherwise processed as is known in the art. Topsheets 138 may be selected from high loft nonwoven topsheets, apertured film topsheets and apertured nonwoven topsheets. Exemplary apertured films may include those described in U.S. Pat. Nos. 5,628,097; 5,916,661; 6,545,197; and 6,107,539.

As mentioned above, the diaper pant 100P may also include an absorbent assembly 140 that is joined to the chassis 102. As shown in FIG. 2, the absorbent assembly 140 may have a laterally extending front edge 148 in the front waist region 116 and may have a longitudinally opposing and laterally extending back edge 150 in the back waist region 118. The absorbent assembly may have a longitudinally extending right side edge 152 and may have a laterally opposing and longitudinally extending left side edge 154, both absorbent assembly side edges 152 and 154 may extend longitudinally between the front edge 148 and the back edge 150. The absorbent assembly 140 may additionally include one or more absorbent cores 142 or absorbent core layers. The absorbent core 142 may be at least partially disposed between the topsheet 138 and the backsheet 136 and may be formed in various sizes and shapes that are compatible with the diaper. Exemplary absorbent structures for use as the absorbent core of the present disclosure are described in U.S. Pat. Nos. 4,610,678; 4,673,402; 4,888,231; and 4,834,735.

Some absorbent core embodiments may comprise fluid storage cores that contain reduced amounts of cellulosic airfelt material. For instance, such cores may comprise less than about 40%, 30%, 20%, 10%, 5%, or even 1% of cellulosic airfelt material. Such a core may comprise primarily absorbent gelling material in amounts of at least about 60%, 70%, 80%, 85%, 90%, 95%, or even about 100%, where the remainder of the core comprises a microfiber glue (if applicable). Such cores, microfiber glues, and absorbent gelling materials are described in U.S. Pat. Nos. 5,599,335; 5,562,646; 5,669,894; and 6,790,798 as well as U.S. Patent Publication Nos. 2004/0158212 A1 and 2004/0097895 A1.

As previously mentioned, the diaper 100P may also include elasticized leg cuffs 156. It is to be appreciated that the leg cuffs 156 can be and are sometimes also referred to as leg bands, side flaps, barrier cuffs, elastic cuffs or gasketing cuffs. The elasticized leg cuffs 156 may be configured in various ways to help reduce the leakage of body exudates in the leg regions. Example leg cuffs 156 may include those described in U.S. Pat. Nos. 3,860,003; 4,909,803; 4,695,278; 4,795,454; 4,704,115; 4,909,803; and U.S. Patent Publication No. 2009/0312730 A1.

As mentioned above, diaper pants may be manufactured with a ring-like elastic belt 104 and provided to consumers in a configuration wherein the front waist region 116 and the back waist region 118 are connected to each other as packaged, prior to being applied to the wearer. As such, diaper pants may have a continuous perimeter waist opening 110 and continuous perimeter leg openings 112 such as shown in FIGS. 1A and 1B. The ring-like elastic belt may be formed by joining a first elastic belt to a second elastic belt with a permanent side seam or with an openable and reclosable fastening system disposed at or adjacent the laterally opposing sides of the belts.

As previously mentioned, the ring-like elastic belt 104 may be defined by a first elastic belt 106 connected with a second elastic belt 108. As shown in FIG. 2, the first elastic belt 106 extends between a first longitudinal side edge 111*a* and a second longitudinal side edge 111*b* and defines first and second opposing end regions 106*a*, 106*b* and a central region 106*c*. And the second elastic 108 belt extends between a first longitudinal side edge 113*a* and a second longitudinal side edge 113*b* and defines first and second opposing end regions 108*a*, 108*b* and a central region 108*c*. The distance between the first longitudinal side edge 111*a* and the second longitudinal side edge 111*b* defines the pitch length, PL, of the first elastic belt 106, and the distance between the first longitudinal side edge 113*a* and the second longitudinal side edge 113*b* defines the pitch length, PL, of the second elastic belt 108. The central region 106*c* of the first elastic belt is connected with the first waist region 116 of the chassis 102, and the central region 108*c* of the second elastic belt 108 is connected with the second waist region 118 of the chassis 102. As shown in FIGS. 1A and 1B, the first end region 106*a* of the first elastic belt 106 is connected with the first end region 108*a* of the second elastic belt 108 at first side seam 178, and the second end region 106*b* of the first elastic belt 106 is connected with the second end region 108*b* of the second elastic belt 108 at second side seam 180 to define the ring-like elastic belt 104 as well as the waist opening 110 and leg openings 112.

As shown in FIGS. 2, 3A, and 3B, the first elastic belt 106 also defines an outer laterally extending edge 107*a* and an inner laterally extending edge 107*b*, and the second elastic belt 108 defines an outer laterally extending edge 109*a* and an inner laterally extending edge 109*b*. As such, a perimeter edge 112*a* of one leg opening may be defined by portions of the inner laterally extending edge 107*b* of the first elastic belt 106, the inner laterally extending edge 109*b* of the second elastic belt 108, and the first longitudinal or right side edge 128 of the chassis 102. And a perimeter edge 112*b* of the other leg opening may be defined by portions of the inner laterally extending edge 107*b*, the inner laterally extending edge 109*b*, and the second longitudinal or left side edge 130 of the chassis 102. The outer laterally extending edges 107*a*, 109*a* may also define the front waist edge 121 and the laterally extending back waist edge 122 of the diaper pant 100P. The first elastic belt and the second elastic belt may also each include an outer, garment facing layer 162 and an inner, wearer facing layer 164. It is to be appreciated that the first elastic belt 106 and the second elastic belt 108 may comprise the same materials and/or may have the same structure. In some embodiments, the first elastic belt 106 and the second elastic belt may comprise different materials and/or may have different structures. It should also be appreciated that the first elastic belt 106 and the second elastic belt 108 may be constructed from various materials. For example, the first and second belts may be manufactured from materials such as plastic films; apertured plastic films; woven or nonwoven webs of natural materials (e.g., wood or cotton fibers), synthetic fibers (e.g., polyolefins, polyamides, polyester, polyethylene, or polypropylene fibers) or a combination of natural and/or synthetic fibers; or coated woven or nonwoven webs. In some embodiments, the first and second elastic belts include a nonwoven web of synthetic fibers, and may include a stretchable nonwoven. In other embodiments, the first and second elastic belts include an inner hydrophobic, non-stretchable nonwoven material and an outer hydrophobic, non-stretchable nonwoven material.

The first and second elastic belts 106, 108 may also each include belt elastic material interposed between the outer substrate layer 162 and the inner substrate layer 164. The belt elastic material may include one or more elastic elements such as strands, ribbons, films, or panels extending along the lengths of the elastic belts. As shown in FIGS. 2, 3A, and 3B, the belt elastic material may include a plurality of elastic strands 168 which may be referred to herein as outer, waist elastics 170 and inner, waist elastics 172. Elastic strands 168, such as the outer waist elastics 170, may continuously extend laterally between the first and second opposing end regions 106*a*, 106*b* of the first elastic belt 106 and between the first and second opposing end regions 108*a*, 108*b* of the second elastic belt 108. In some embodiments, some elastic strands 168, such as the inner waist elastics 172, may be configured with discontinuities in areas, such as for example, where the first and second elastic belts 106, 108 overlap the absorbent assembly 140. In some embodiments, the elastic strands 168 may be disposed at a constant interval in the longitudinal direction. In other embodiments, the elastic strands 168 may be disposed at different intervals in the longitudinal direction. The belt elastic material in a stretched condition may be interposed and joined between the uncontracted outer layer and the uncontracted inner layer. When the belt elastic material is relaxed, the belt elastic material returns to an unstretched condition and contracts the outer layer and the inner layer. The belt elastic material may provide a desired variation of contraction force in the area of the ring-like elastic belt. It is to be appreciated that the chassis 102 and elastic belts 106, 108 may be configured in different ways other than as depicted in FIG. 2. The belt elastic material may be joined to the outer and/or inner layers continuously or intermittently along the interface between the belt elastic material and the inner and/or outer belt layers.

In some configurations, the first elastic belt 106 and/or second elastic belt 108 may define curved contours. For example, the inner lateral edges 107*b*, 109*b* of the first and/or second elastic belts 106, 108 may include non-linear or curved portions in the first and second opposing end regions. Such curved contours may help define desired shapes to leg opening 112, such as for example, relatively rounded leg openings. In addition to having curved contours, the elastic belts 106, 108 may include elastic strands 168, 172 that extend along non-linear or curved paths that may correspond with the curved contours of the inner lateral edges 107*b*, 109*b*.

It is to be appreciated that the apparatuses and methods of assembly of elastomeric laminates and absorbent articles described herein and illustrated in the accompanying drawings are non-limiting example configurations. The features illustrated or described in connection with one non-limiting configuration may be combined with the features of other non-limiting configurations. Such modifications and variations are intended to be included within the scope of the present disclosure.

Some configurations of the methods and apparatuses according to the present disclosure may utilize a plurality of elastic strands wound onto a beam, wherein one or more elastic strands comprises a spin finish. During assembly of an elastomeric laminate, the beam is rotated to unwind the elastic strands from the beam. The elastic strands may be stretched while advancing in a machine direction. A portion of the spin finish may be removed from the advancing elastic strand with a spin finish removal apparatus. As discussed below, the spin finish removal apparatus may treat the advancing elastic strand to remove some or all the spin finish from the elastic strand. The spin finish removal apparatus may be configured to apply detergent to an advancing elastic strand and may also wipe and/or dry the advancing elastic strand. The treated stretched elastic strand may then be connected between a first substrate and a second substrate. In some configurations, adhesive may be applied to the treated the elastic strand, the first substrate, and/or the second substrate. As such, the methods and apparatuses are adapted to utilize elastic strands having a spin finish that are unwound from beams to produce elastomeric laminates. By removing the spin finish from the elastics strands, relatively less adhesive may be utilized to adhere the strands between the substrates.

As previously mentioned, apparatuses and methods according to the present disclosure may be utilized to produce elastomeric laminates that may be used to construct various components of diapers, such as elastic belts, leg cuffs, and the like. For example, FIGS. 4-11 show schematic views of converting apparatuses 300 adapted to manufacture elastomeric laminates 302. As described in more detail below, the converting apparatuses 300 shown in FIGS. 4-11 operate to advance a continuous length of elastic material 304, a continuous length of a first substrate 306, and a continuous length of a second substrate 308 along a machine direction MD. It is also to be appreciated that in some configurations, the first substrate 306 and second substrate 308 herein may be defined by two discrete substrates or may be defined by folded portions of a single substrate. The apparatus 300 stretches the elastic material 304 and joins the stretched elastic material 304 with the first and second substrates 306, 308 to produce an elastomeric laminate 302. Although the elastic material 304 is illustrated and referred to herein as strands, it is to be appreciated that elastic material 304 may include one or more continuous lengths of elastic strands, ribbons, and/or films.

It is to be appreciated that the elastomeric laminates 302 can be used to construct various types of absorbent article components. It also to be appreciated that the methods and apparatuses herein may be adapted to operate with various types of absorbent article assembly processes, such as disclosed for example in U.S. Patent Publication Nos. 2013/0255861 A1; 2013/0255862 A1; 2013/0255863 A1; 2013/0255864 A1; and 2013/0255865 A1. For example, the elastomeric laminates 302 may be used as a continuous length of elastomeric belt material that may be converted into the first and second elastic belts 106, 108 discussed above with reference to FIGS. 1-3B. As such, the elastic material 304 may correspond with the belt elastic material 168 interposed between the outer layer 162 and the inner layer 164, which in turn, may correspond with either the first and/or second substrates 306, 308. In other examples, the elastomeric laminates may be used to construct waistbands and/or side panels in taped diaper configurations. In yet other examples, the elastomeric laminates may be used to construct various types of leg cuff and/or topsheet configurations.

As discussed in more detail below, the converting apparatuses 300 may include metering devices arranged along a process machine direction MD, wherein the metering devices may be configured to stretch the advancing elastic material and/or join stretch elastic material with one or more advancing substrates. In some configurations, a metering device may comprise a beam of elastic strands wound thereon. During operation, elastic material may advance in a machine direction from a rotating beam to a downstream metering device to be joined with one or more advancing substrates. The elastic material advancing from the rotating beam may include a spin finish, and as such, the apparatuses herein may be configured to remove some or all the spin finish before joining the elastic material with the substrates.

Figure 6:
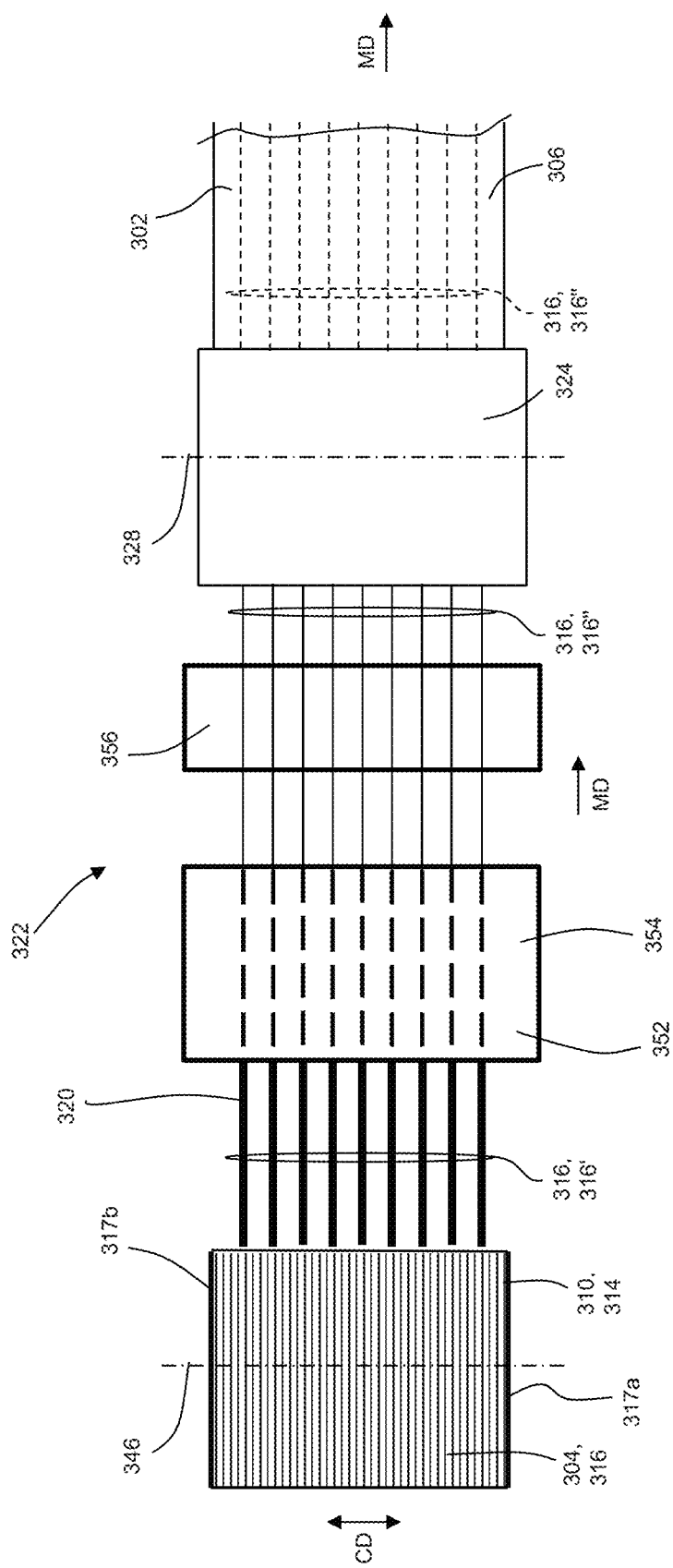
FIG. 6 is a view of the converting apparatus of FIG. 5 taken along line 6-6.

As shown in FIGS. 4-6, a converting apparatus 300 for producing an elastomeric laminate 302 may include a first metering device 310 and a second metering device 312. The first metering device may be configured as a beam 314 with a plurality of elastic strands 316 wound thereon. FIG. 4 shows an example of an empty beam 314 that includes two side plates 317*a*, 317*b* that may be connected with opposing end portions of a mandrel core 318, wherein elastic strands may be wound onto the mandrel core 318. It is to be appreciated that beams of various sizes and technical specifications may be utilized in accordance with the methods and apparatuses herein, such as for example, beams that are available from ALUCOLOR Textilmaschinen, GmbH. It is to be appreciated that various methods and apparatuses may be used to assemble elastic strands and/or beams and to wind elastic strands on beams. For example, in some configurations, the tension of elastic strands may be controlled to desired levels when winding elastic strands onto a beam. During the beam winding process, reeds used to separate elastic strands may be oscillated back and forth and/or the beam may be oscillated back and forth to help ensure uniform winding of the elastic strands on the beams.

During operation, the plurality of elastic strands 316 advance in the machine direction MD from the beam 314 to the second metering device 312. In addition, the plurality of elastic strands 316 may be stretched along the machine direction MD between the beam 314 and the second metering device 312. The stretched elastic strands 316 are also joined with a first substrate 306 and a second substrate 308 at the second metering device 312 to produce an elastomeric laminate 302. As discussed in more detail below, one or more of the elastic strands 316' advancing from the beam 314 may include a spin finish 320 located on outer surfaces of the elastics strands. In turn, all or some of the spin finish 320 may be removed from the advancing elastic strands 316' with a spin finish removal apparatus 322. In turn, treated stretched elastic strands 316" may then be connected between the first substrate 306 and the second substrate 308.

It is to be appreciated the elastic strands 316 may include various types of spin finish 320, also referred herein as yarn finish, configured as coating on the elastic strands 316 that may be intended to help prevent the elastics strands from adhering to themselves, each other, and/or downstream handling equipment. In some configurations, a spin finish may include various types of oils and other components, such as disclosed for example in U.S. Pat. Nos. 8,377,554; 8,093,161; and 6,821,301. In some configurations, a spin finish may include various types of silicone oils, such as for example, polydimethylsiloxane. In some configurations, a spin finish may include various types of mineral oils, including hydrogenated paraffinic and napthenic oils. In some configurations, the molecular weight of an oil may be adjusted to optimize adhesion properties of the elastic strands depending on the process configuration in which the elastic strands may be used. In some configurations, a spin finish may include various types of fatty amides, erucamide, behenamide, and oleamide. It is also to be appreciated that the amount of spin finish applied to elastic strands may be optimized depending on the process configuration in which the elastic strands may be used. For example, in process configurations wherein elastic strands have limited contact or do not contact downstream handling equipment, such as idlers, the amount of spin finish may be selected to help prevent the elastics strands from adhering to themselves and/or each other while wound on a beam without regard to whether elastic strands would adhere to downstream handling equipment. As such, it is to be appreciated that the elastic strands herein may include various amounts of spin finish that may be expressed in various ways. For example, a quantity of 10 grams of spin finish per 1 kilogram of elastic strand may be expressed as 1% spin finish. In some configurations, an elastic strand may include about 0.1% spin finish. In some configurations, a strand may include from about 0.01% to about 10% spin finish, specifically reciting all 0.01% increments within the above-recited range and all ranges formed therein or thereby.

As shown in FIGS. 5 and 6, the second metering device 312 may include: a first roller 324 having an outer circumferential surface 326 and that rotates about a first axis of rotation 328, and a second roller 330 having an outer circumferential surface 332 and that rotates about a second axis of rotation 334. The first roller 324 and the second roller 330 rotate in opposite directions, and the first roller 324 is adjacent the second roller 330 to define a nip 336 between the first roller 324 and the second roller 330. The first roller 324 rotates such that the outer circumferential surface 326 has a surface speed S1, and the second roller 330 may rotate such that the outer circumferential surface 332 has the same, or substantially the same, surface speed S1.

With continued reference to FIGS. 5 and 6, the first substrate 306 includes a first surface 338 and an opposing second surface 340, and the first substrate 306 advances to the first roller 324. In particular, the first substrate 306 advances at speed S1 to the first roller 324 where the first substrate 306 partially wraps around the outer circumferential surface 326 of the first roller 324 and advances through the nip 336. As such, the first surface 338 of the first substrate 306 travels in the same direction as and in contact with the outer circumferential surface 326 of the first roller 324. In addition, the second substrate 308 includes a first surface 342 and an opposing second surface 344, and the second substrate 308 advances to the second roller 330. In particular, the second substrate 308 advances at speed S1 to the second roller 330 where the second substrate 308 partially wraps around the outer circumferential surface 332 of the second roller 330 and advances through the nip 336. As such, the second surface 344 of the second substrate 308 travels in the same direction as and in contact with the outer circumferential surface 332 of the second roller 330.

Still referring to FIGS. 5 and 6, the beam 314 includes elastic strands 316 wound thereon, and the beam 314 is rotatable about a beam rotation axis 346. In some configurations, the beam rotation axis 346 may extend in the cross direction CD. As the beam 314 rotates, the elastic strands 316 advance from the beam 314 at a speed S2 with the elastic strands 316 being spaced apart from each other in the cross direction CD. From the beam 314, the elastic strands 316 advance in the machine direction MD to the nip 336. In some configurations, the speed S2 is less than the speed S1, and as such, the elastic strands 316 are stretched in the machine direction MD. In turn, the stretched elastic strands 316 advance through the nip 336 between the first and second substrates 306, 308 such that the elastic strands 316 are joined with the second surface 340 of the first substrate 306 and the first surface 342 of the second substrate 308 to produce a continuous length of elastomeric laminate 302.

As discussed above, one or more of the elastic strands 316' advancing from the beam 314 may include a spin finish 320. In turn, the advancing elastic strands 316' may be treated with the spin finish removal apparatus 322 that may remove some or all the spin finish 320. As such, the treated elastic strands 316" having some or all the spin finish 320 removed may advance from the spin finish removal apparatus 322 to be joined with the first substrate 306 and the second substrate 308 to form the elastomeric laminate 302. As shown in FIG. 5, the first substrate 306 may advance past an adhesive applicator device 348 that applies adhesive 350 to the second surface 340 of the first substrate 306 before advancing to the nip 336. It is to be appreciated that the adhesive 350 may be applied to the first substrate 306 upstream of the first roller 324 and/or while the first substrate 306 is partially wrapped around the outer circumferential surface 326 of the first roller 324. It is to be appreciated that adhesive may be applied to the treated elastic strands 316" before and/or while being joined with first substrate 306 and second substrate 308. In addition, it is to be appreciated that adhesive may be applied to the first surface 342 of the second substrate 308 before or while being joined with the treated elastic strands 316" and the first substrate 306. It is also to be appreciated that untreated 316' and/or treated elastic strands 316" may be bonded with the first substrate 306 and/or second substrate 308 with the various methods and apparatuses described herein and combinations thereof.

As shown in FIGS. 5 and 6, the spin finish removal apparatus 322 may be configured to include a bath 352 containing a detergent 354. As such the elastic strands 316' having a spin finish 320 advance from the beam 314 to the bath 352, wherein the elastic strands 316' advance through the detergent 354 adapted to remove some or all the spin finish 320 from the elastic strands 316. As shown in FIGS. 5 and 6, the spin finish removal apparatus 322 may also be configured to include a drying apparatus 356 to remove the detergent 354 from the elastic strands 316. It is to be appreciated that the drying apparatus 356 may be configured in various ways, such as a fan, a blower, a heater, and/or combinations thereof. In some configurations, the drying apparatus 356 may move air or some other gas 358 relative to the elastic strands 316 to evaporate the detergent from the elastic strands 316. As such, the treated elastic strands 316" may advance from the bath 352 to the drying apparatus 356 to remove some or all the detergent from the treated elastic strands 316". In turn, the treated elastic strands 316" may advance from the drying apparatus 356 to be combined with the first substrate 306 and the second substrate 308. Although FIG. 6 shows nine elastic strands 316 advancing from the beam 314, it is to be appreciated that the apparatuses herein may be configured such that more or less than nine elastic strands 316 advance from the beam 314.

It is to be appreciated that various configurations of detergent 354 may be used to remove spin finish 320 from the elastic strands 316. For example, in some configurations, a detergent may include various different ingredients, such as those included for example in TISSOCYL RC available from Zschimmer & Schwarz GmbH.

It is to be appreciated that different components may be used to construct the elastomeric laminates 302 in accordance with the methods and apparatuses herein. For example, the first and/or second substrates 306, 308 may include nonwovens and/or films and may be constructed from various types of materials, such as plastic films; apertured plastic films; woven or nonwoven webs of natural materials, such as wood or cotton fibers; synthetic fibers, such as polyolefins, polyamides, polyester, polyethylene, or polypropylene fibers or a combination of natural and/or synthetic fibers; or coated woven or nonwoven webs; polymeric films such as thermoplastic films of polyethylene or polypropylene, and/or a multi-layer or composite materials comprising a film and a nonwoven material. In addition, the elastic strands 316 herein may be configured in various ways and having various decitex values. In some configurations, the elastic strands 316 may be configured with decitex values ranging from about 10 decitex to about 500 decitex, specifically reciting all 1 decitex increments within the above-recited range and all ranges formed therein or thereby.

It is also to be appreciated the beams 314 herein may be configured in various ways and with various quantities of elastic strands. Example beams, also referred to as warp beams, that may be used with the apparatus and methods herein are disclosed in U.S. Pat. Nos. 4,525,905; 5,060,881; and 5,775,380; and U.S. Patent Publication No. 2004/0219854 A1. In some configurations, the elastic strands 316 advancing from the beam 314 may include from about 100 to about 2000 strands, specifically reciting all 1 strand increments within the above-recited range and all ranges formed therein or thereby. In some configurations, the elastic strands 316 may be separated from each other by about 0.5 mm to about 4 mm in the cross direction, specifically reciting all 0.1 mm increments within the above-recited range and all ranges formed therein or thereby. As discussed herein, the elastics in the plurality of elastic strands may be pre-strained prior to joining the elastic strand to the first or second substrate layers 306, 308. In some configurations, the elastic may be pre-strained from about 75% to about 300%, specifically reciting all 1% increments within the above-recited range and all ranges formed therein or thereby. Pre-strain refers to the strain imposed on an elastic or elastomeric material prior to combining it with another element of the elastomeric laminate or the absorbent article. Pre-strain is determined by the following equation: Pre-strain=((extended length of the elastic-relaxed length of the elastic)/relaxed length of the elastic)*100. It is also to be appreciated that one or more beams of elastics may be arranged along the cross direction CD of a converting process and/or arranged along a machine direction MD in various different portions of a converting process. It is also to be appreciated that the beam 314 can be connected with one or more motors, such as servo motors, to drive and control the rotation of the beam 314. It is to be appreciated that in some configurations, the elastic strands 316 may be supplied on the beam 314 in a stretched state, and as such, may not require additional stretching (or may require relatively less additional stretching) before being combined with the first substrate 306 and/or the second substrate 308. In some configurations, an elastic strand 316 may be drawn from a single roll utilizing a rolling unwind, such as for example, available from Overend Technologies, Inc.

It is to be appreciated that the apparatuses 300 herein may be configured in various ways with various features described herein to assemble elastomeric laminates 302 having various stretch characteristics. For example, the apparatus 300 may be configured to assemble elastomeric laminates 302 with elastic strands 316 unwound from more than one beam and/or in combination with elastic strands supplied from an overend unwinder.

The elastic strands 316 may be joined with the first and second substrates 306, 308 such that the elastomeric laminate 302 may have different stretch characteristics in different regions along the cross direction CD. For example, when the elastomeric laminate 302 is elongated, some elastic strands may exert contraction forces in the machine direction MD that are different from contraction forces exerted by other elastic strands. Such differential stretch characteristics can be achieved by stretching some elastic strands more or less than other elastic strands before joining the elastic strands with the first and second substrates 306, 308. It is also to be appreciated that the elastic strands may have various different material constructions and/or decitex values to create elastomeric laminates 302 having different stretch characteristics in different regions. In some configurations, the elastomeric laminate may have regions where the elastic strands are spaced relatively close to one another in the cross direction CD and other regions where the elastic strands are spaced relatively farther apart from each other in the cross direction CD to create different stretch characteristics in different regions. In some configurations, the elastic strands 316 may be supplied on the beam in a stretched state, and as such, may not require additional stretching (or may require relatively less additional stretching) before being combined with the first substrate 306 and/or the second substrate 308.

Figure 7:
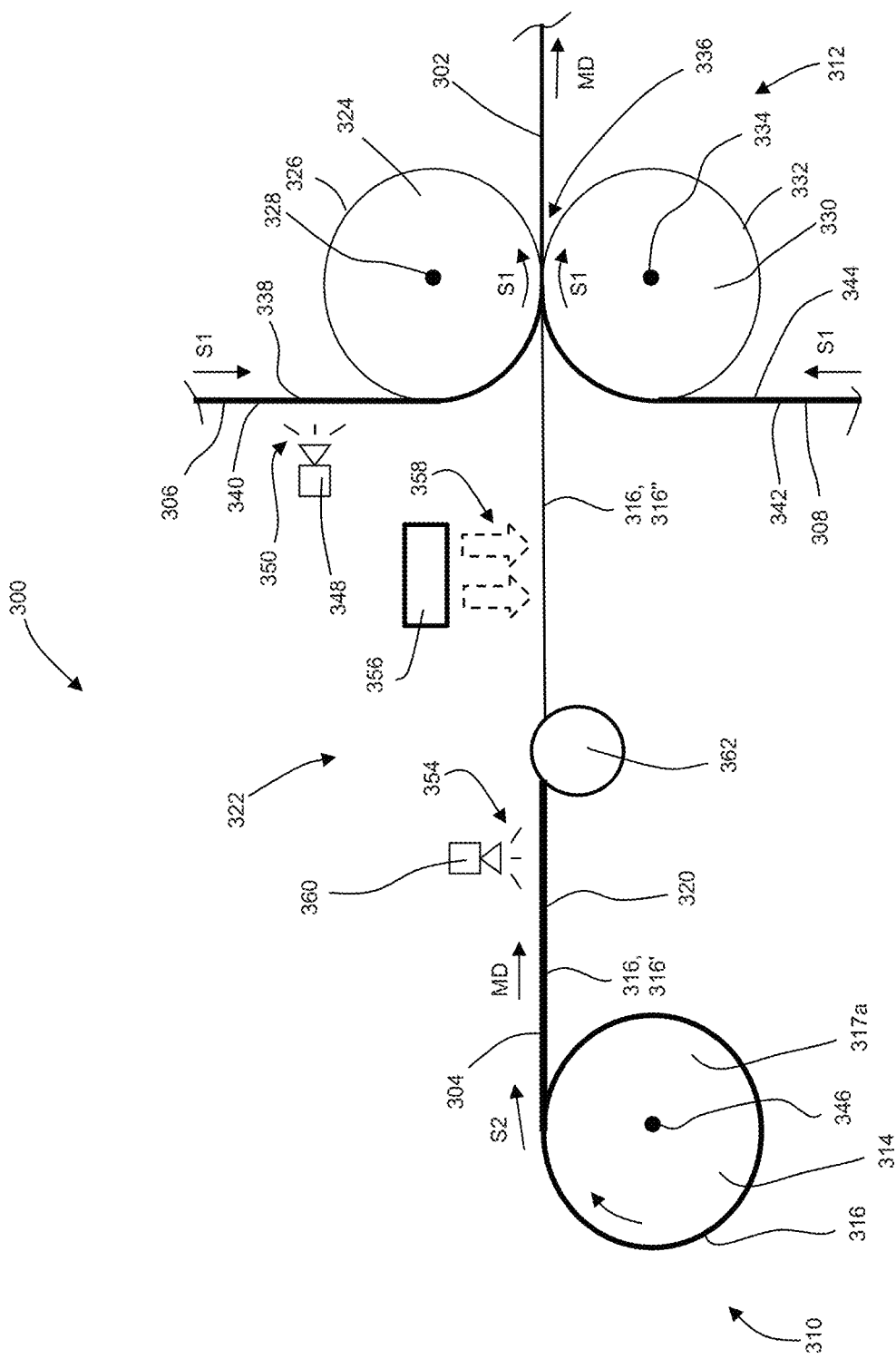
FIG. 7 is a schematic side view of a converting apparatus including a detergent spray and wiper adapted to remove a spin finish from a plurality of elastic strands before being adhered between a first substrate and a second substrate.

It is to be appreciated that the spin finish removal apparatus 322 may be configured in various ways. For example as shown in FIG. 7, the spin finish removal apparatus 322 may include one or more detergent applicator devices 360, such as a nozzle, that sprays detergent 354 onto the spin finish 320 of advancing elastic strands 316'. With continued reference to FIG. 7, the spin finish removal apparatus 322 may also include a wiper 362 downstream of the detergent applicator device 360 that is configured to wipe detergent 354 and/or spin finish 320 from the elastic strands 316. The elastic strands 316 may then advance from the wiper 362 to the drying apparatus 356 such as described above. It is to be appreciated that the wiper 362 may be in direct contact with the elastic strands and may be configured as a static device or may be configured to move relative to the elastic strands 316. For example, the wiper 362 may be configured with an outer surface in contact with the elastic strands 316 that rotates in a direction opposite of the machine direction MD of the advancing elastic strands 316. In some configurations, the wiper 362 may be configured with an outer surface in contact with the elastic strands 316 that rotates in a same direction as the machine direction MD of the advancing elastic strands 316 wherein the outer surface may move faster or slower than the speed of the elastic strands 316.

Figure 8:
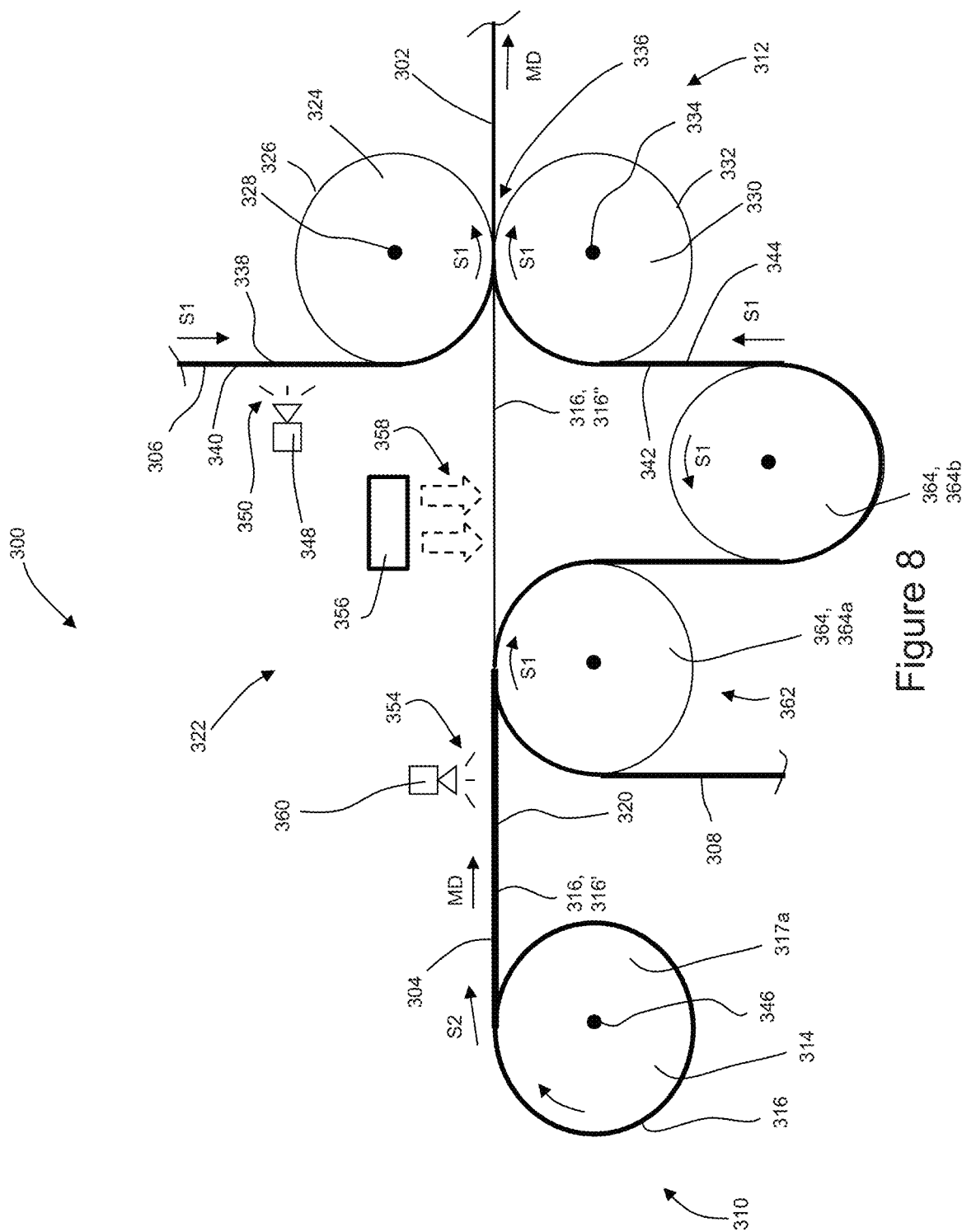
FIG. 8 is a schematic side view of a converting apparatus wherein a first substrate is configured to wipe a spin finish from a plurality of elastic strands before being adhered between the first substrate and a second substrate.

In some configurations, the first and/or second substrates 306, 308 may be used in conjunction with a wiper 362 to remove detergent 354 and/or spin finish 320 from the elastic strands 316. For example, FIG. 8 shows a configuration wherein the advancement path of second substrate 308 is configured such that the second substrate 308 contacts the elastic strands 316 to remove detergent 354 and/or spin finish 320. As shown in FIG. 8, the spin finish removal apparatus 322 may include one or more rotating drums 364 arranged such that before the second substrate 308 is combined with the elastic strands 316 and the first substrate 306, the second substrate 308 contacts the elastic strands 316. For example, the second substrate 308 may advance onto a first drum 364a wherein the second substrate 308 advances at a first speed S. The first drum 364a rotates and brings first surface 342 of the second substrate 308 into contact with the elastic strands 316 advancing at a second speed S2, wherein S1 is not equal S2. As such, the second substrate 308 and the elastic strands 316 move relative to each other when in contact. In turn, the relative movement between the second substrate 308 and the elastic strands 316 may wipe detergent 354 and/or spin finish 320 from the elastic strands 316. From the first drum 364a, the second substrate 308 may advance to a second drum 364b before being combined with the elastic strands 316 and the first substrate 306 to form the elastomeric laminate 302.

It is to be appreciated that the advancement path of either or both the first substrate 306 and the second substrate 308 may be configured such that either or both the first substrate 306 and the second substrate 308 may advance and contact to the elastic strands 316 to wipe detergent 354 and/or spin finish 320 from the elastic strands 316. It is also to be appreciated that that the first surface 338 and/or the second surface 340 of the first substrate 306 and/or the first surface 342 and/or the second surface 344 of the second substrate 308 may be used to contact the elastic strands 316 and wipe detergent 354 and/or spin finish 320 from the elastic strands 316. In some configurations, the advancement path of the assembled elastic laminate 302 may be configured such that the either or both the first substrate 306 and the second substrate 308 of the elastic laminate 302 may contact the elastic strands 316 and wipe detergent 354 and/or spin finish 320 from the elastic strands 316 before the elastic strands 316 are joined with the first substrate 306 and the second substrate 308. In some configurations, the spin finish 320 and/or detergent 354 may be wiped onto one surface of either or both the first and second substrates 306, 308 and wherein the elastic strands 316 are bonded to the opposing surface of either or both the first and second substrates 306, 308 to help improve adhesion of the elastic strands 316 to the first substrate 306 and/or the second substrate 308.

Figure 9:
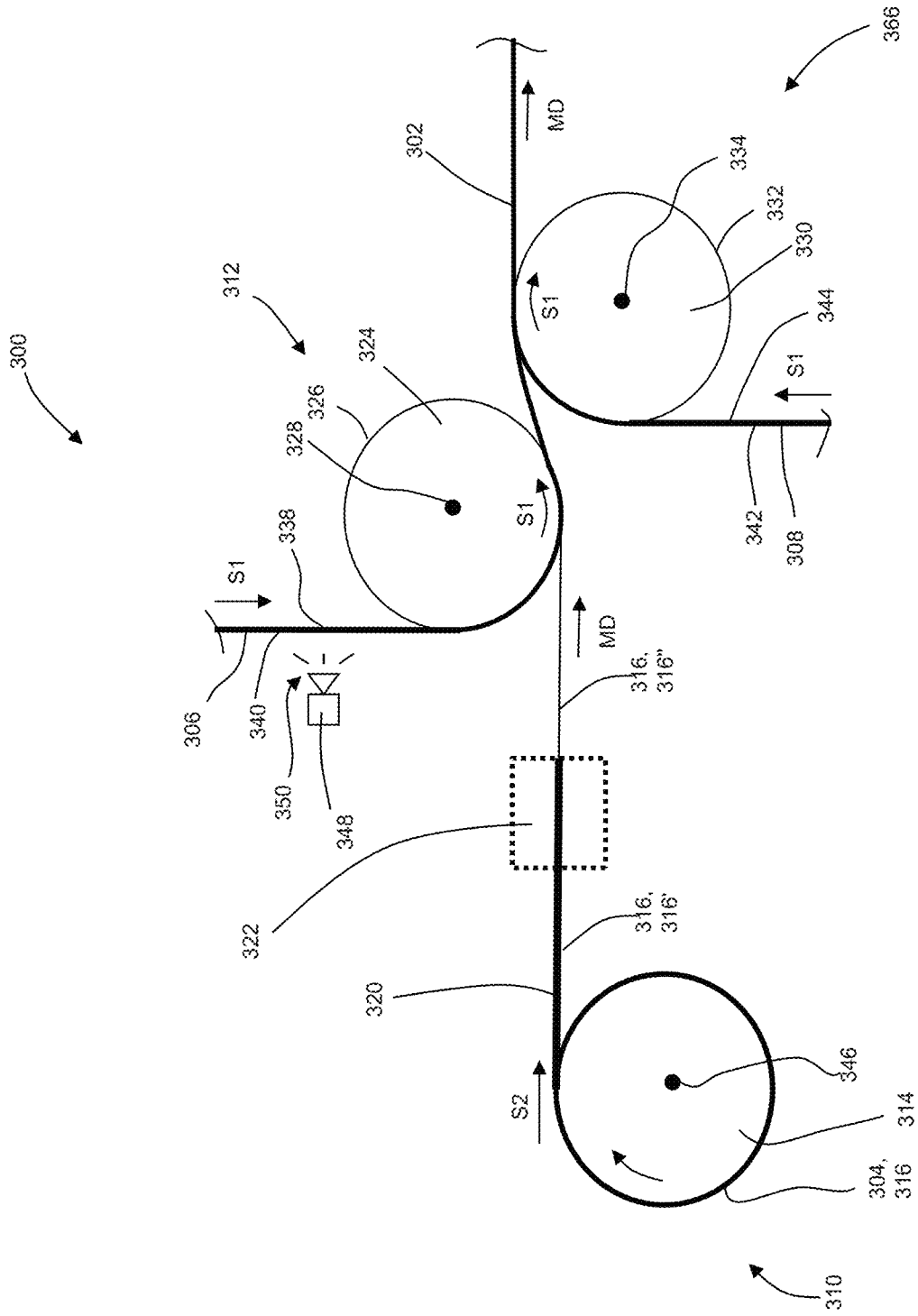
FIG. 9 is a schematic side view of another configuration of a converting apparatus adapted to manufacture an elastomeric laminate including a spin finish removal apparatus.

It is to be appreciated that the apparatuses 300 herein may be configured in various ways with various features of the spin finish removal apparatuses 322 described herein to assemble elastomeric laminates 302. For example, in another configuration of the apparatus 300 shown in FIG. 9, the second roller 330 may be positioned downstream from the first roller 324. As such, the first roller 324 may be configured as the second metering device 312 and the second roller 330 may be configured as a third metering device 366. As shown in FIG. 9, the first substrate 306 advances at speed S1 to the first roller 324 where the first substrate 306 partially wraps around the outer circumferential surface 326 of the first roller 324 and advances from the first roller to the second roller 330 to be combined with second substrate 308. As the beam 314 rotates, the elastic strands 316 advance from the beam 314 at a speed S2 with the elastic strands 316 being spaced apart from each other in the cross direction CD. From the beam 314, elastic strands 316' having a spin finish 320 advance to a spin finish removal apparatus 322 generically illustrated by a dashed-line rectangle. It is to be appreciated that the spin finish removal apparatus 322 may be configured with various combinations of features of the spin finish removal apparatus 322 described herein. In turn, all or some of the spin finish 320 may be removed from the advancing elastic strands 316' with the spin finish removal apparatus 322. As such, the treated elastic strands 316" having some or all the spin finish 320 removed may advance from the spin finish removal apparatus 322 to the first roller 324 and are positioned on the second surface 340 of the first substrate 306. In some configurations, the speed S2 is less than the speed S1, and as such, the elastic strands 316 are stretched in the machine direction MD.

With continued reference to FIG. 9, the first substrate 306 and the elastic strands 316 advance from the outer circumferential surface 326 of the first roller 324 to the second roller 330. In addition, the second substrate 308 advances at speed S1 to the second roller 330 where the second substrate 308 partially wraps around the outer circumferential surface 332 of the second roller 330. In turn, the combined first substrate 306 and the stretched elastic strands 316, 316" advance from first roller 324 to the second roller 330 and are combined with the second substrate 308 such that the elastic strands 316, 316" are joined with the second surface 340 of the first substrate 306 and the first surface 342 of the second substrate 308 to produce a continuous length of elastomeric laminate 302. As discussed above, the first substrate 306 may advance past an adhesive applicator device 348 that applies adhesive 350 to the second surface 340 of the first substrate 306 while advancing to the first roller 324. It is to be appreciated that the adhesive 350 may be applied to the first substrate 306 while the first substrate 306 is partially wrapped around the outer circumferential surface 326 of the first roller 324. It is to be appreciated that adhesive may also be applied to the elastic strands 316, 316" before and/or while being joined with first substrate 306 and second substrate 308. In addition, it is to be appreciated that adhesive may be applied to the first surface 342 of the second substrate 308 before or while being joined with the elastic strands 316 and first substrate 306.

Figure 10:
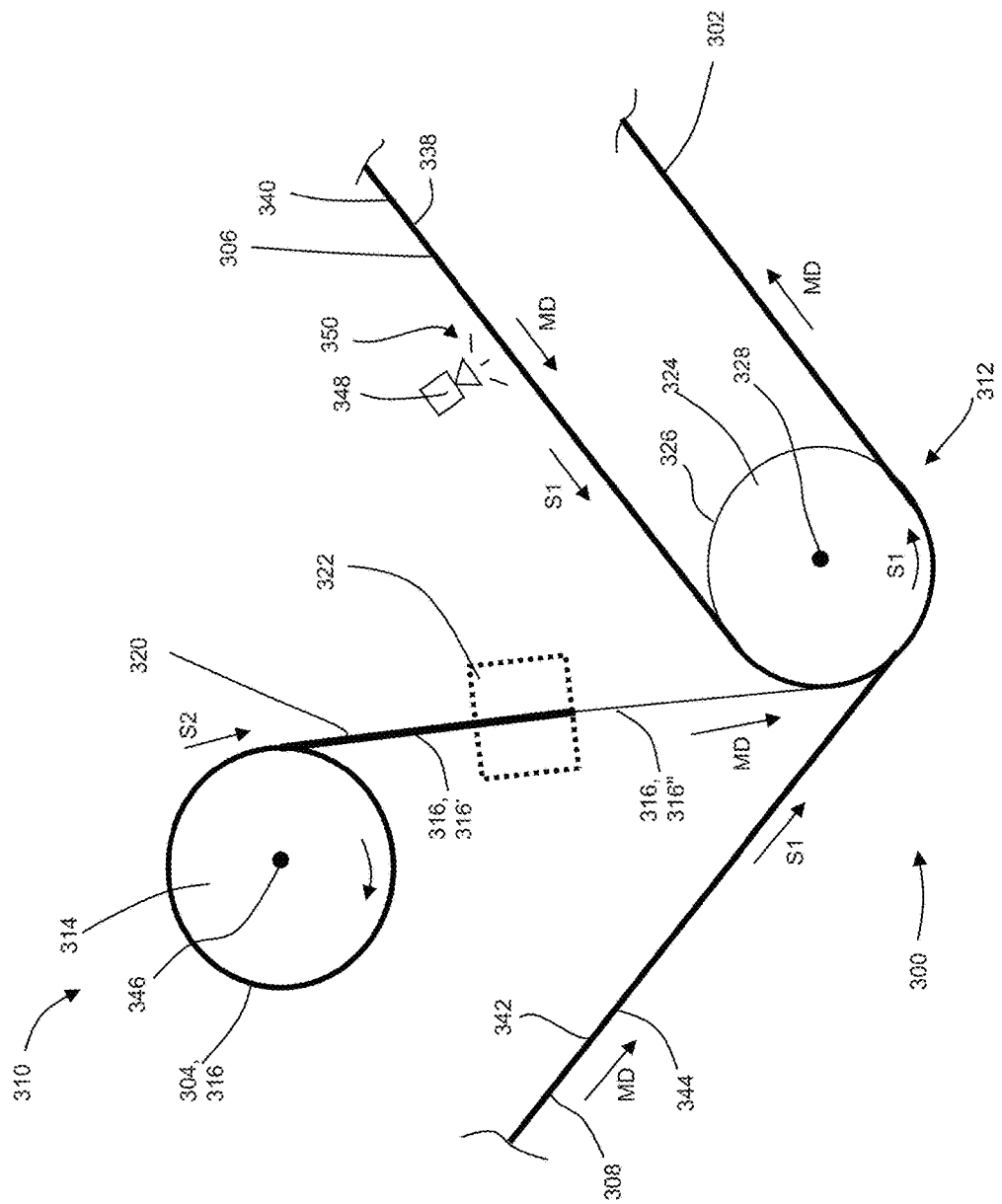
FIG. 10 is a schematic side view of another configuration of a converting apparatus adapted to manufacture an elastomeric laminate including a spin finish removal apparatus.

In another configuration shown in FIG. 10, the apparatus 300 may be configured with only the first roller 324 and without a second roller 330. As such, the first roller 324 may be configured as the second metering device 312. As shown in FIG. 10, the first substrate 306 advances at speed S1 to the first roller 324 where the first substrate 306 partially wraps around the outer circumferential surface 326 of the first roller 324. While partially wrapped around the outer circumferential surface 326 of the first roller 324, the first substrate 306 is combined with the elastic strands 316, 316" and the second substrate 308. As the beam 314 rotates, the elastic strands 316 advance from the beam 314 at a speed S2 with the elastic strands 316 being spaced apart from each other in the cross direction CD. From the beam 314, elastic strands 316' having a spin finish 320 advance to a spin finish removal apparatus 322 generically illustrated by a dashed-line rectangle. As discussed above, it is to be appreciated that the spin finish removal apparatus 322 may be configured with various combinations of features of the spin finish removal apparatus 322 described herein. In turn, all or some of the spin finish 320 may be removed from the advancing elastic strands 316' with the spin finish removal apparatus 322. As such, the treated elastic strands 316" having some or all the spin finish 320 removed may advance from the spin finish removal apparatus 322 to the first roller 324 and are positioned on the second surface 340 of the first substrate 306. In some configurations, the speed S2 is less than the speed S1, and as such, the elastic strands 316 are stretched in the machine direction MD.

With continued reference to FIG. 10, the second substrate 308 advances at speed S1 to the first roller 324 and partially wraps around the outer circumferential surface 326 of the first roller 324. In turn, the second substrate 308 is combined with the first substrate 306 and the stretched elastic strands 316 while on the first roller 324 such that the elastic strands 316 are joined with the second surface 340 of the first substrate 306 and the first surface 342 of the second substrate 308 to produce a continuous length of elastomeric laminate 302. As discussed above, the first substrate 306 may advance past an adhesive applicator device 348 that applies adhesive 350 to the second surface 340 of the first substrate 306 while advancing to the first roller 324. It is to be appreciated that the adhesive 350 may be applied to the first substrate 306 while the first substrate 306 is partially wrapped around the outer circumferential surface 326 of the first roller 324. It is to be appreciated that adhesive may also be applied to the elastic strands 316 before and/or while being joined with first substrate 306 and second substrate 308. In addition, it is to be appreciated that adhesive may be applied to the first surface 342 of the second substrate 308 before or while being joined with the elastic strands 316 and first substrate 306.

Figure 11:
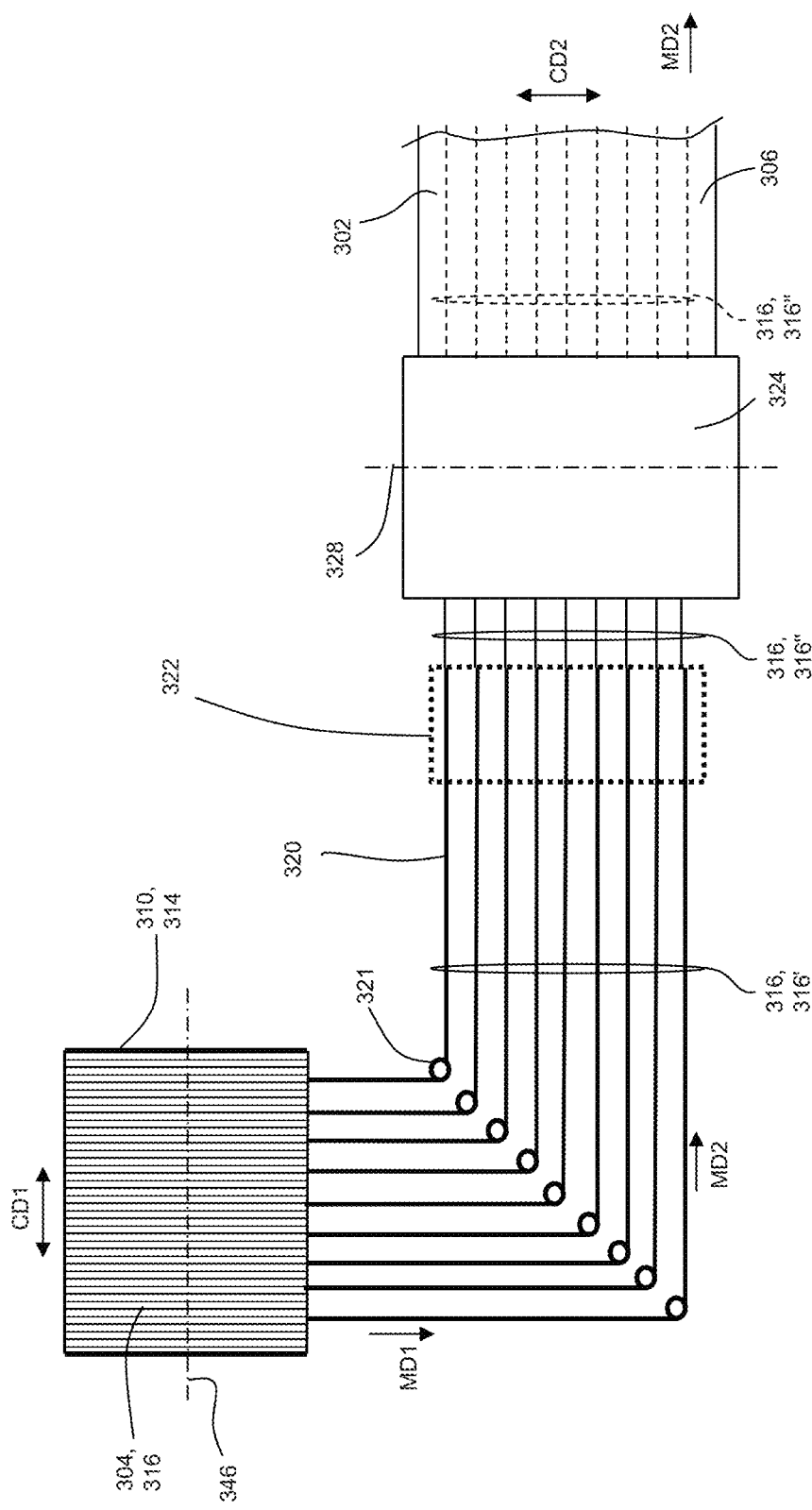
FIG. 11 is a schematic side view of another configuration of a converting apparatus adapted to manufacture an elastomeric laminate including a spin finish removal apparatus.

As illustrated herein, the apparatuses and processes may be configured such that elastic strands may be advanced from the beams and directly to the assembly process without having to touch additional machine components, such as for example, guide rollers. It is also to be appreciated that in some configurations, elastic strands may be advanced from beams and may be redirected and/or otherwise touched by and/or redirected before advancing to the assembly process. For example, FIG. 11 shows a configuration where the beam rotation axis 346 may extend in a first cross direction CD1. As the beam 314 rotates, the elastic strands 316 advance from the beam 314 in a first machine direction MD1 with the elastic strands 316 being spaced apart from each other in the first cross direction CD1. The elastic strands 316 may then be redirected by rollers 321 from the first machine direction MD1 to a second machine direction MD2, wherein the elastic strands 316 may remain separated from each other in a second cross direction CD2. From the rollers 321, the elastic strands 316 may advance in the second machine direction MD2 to be combined with the first and second substrates 306, 308 to form the elastomeric laminate 302. Thus, it is to be appreciated that the beam 314 may be arranged and/or oriented such that the beam rotation axis 346 may be parallel, perpendicular, or otherwise angularly offset with respect to the machine direction advancement of the elastomeric laminate 302 and/or the substrates 306, 308. It is also to be appreciated that the elastic laminate 302 may be assembled and advanced in a machine direction that is parallel with a machine direction of another assembly process, such as an absorbent article assembly process that incorporates the advancing elastic laminate 302. In some configurations, the elastic laminate 302 may be assembled and advanced in a machine direction that is perpendicular or otherwise angularly offset with respect to a machine direction of another assembly process, such as an absorbent article assembly process that incorporates the advancing elastic laminate 302. As such, the elastic laminate 302 may advance over a turn bar, web twist, or other similar device to change the machine direction of the advancing elastic laminate 302 as needed for incorporation into another assembly process.

The apparatus shown in FIG. 11 also includes a spin finish removal apparatus 322 generically illustrated by a dashed-line rectangle, which may be configured with various combinations of features of the spin finish removal apparatus 322 described herein. As discussed above, the spin finish removal apparatus 322 is configured to remove all or some of the spin finish 320 from the advancing elastic strands 316'. And in turn, the treated elastic strands 316" having some or all the spin finish 320 removed may advance downstream to be joined with the first substrate 306 and the second substrate 308. It is to be appreciated that the spin finish removal apparatus 322 may be positioned in various locations along the advancement path of the elastic strands 316. For example, the spin finish removal apparatus 322 may be positioned upstream or downstream of the rollers 321 shown in FIG. 11.

As discussed above, the methods and apparatuses according to the present disclosure may be configured with a plurality of elastic strands wound onto a beam, wherein one or more elastic strands comprises a spin finish. During assembly of an elastomeric laminate, the beam is rotated to unwind the elastic strands from the beam. The elastic strands may be stretched while advancing in a machine direction. In some configurations discussed below, first bonds may be applied to bond discrete lengths of the spin finish on the stretched elastic strands with and between the first substrate and the second substrate, wherein the discrete first bonds are arranged intermittently along the machine direction. In addition, second bonds may be applied between consecutive first bonds to bond the first and second substrates directly to each other, wherein the second bonds extend in the machine direction and are separated from each other in a cross direction by at least one elastic strand. As discussed in more detail below, adhesive may be used to create the first bonds and second bonds. And in some configurations, the first bonds and/or the second bonds may be in the form of mechanical bonds, such as for example, heat, pressure, and/or ultrasonic bonds. Thus, the methods and apparatuses are adapted to utilize elastic strands having a spin finish that are unwound from beams to produce elastomeric laminates. By utilizing the disclosed arrangements of first and second bonds, relatively less adhesive may be utilized to adhere the strands between the substrates without having to remove the spin finish from the elastic strands.

As previously mentioned, apparatuses and methods according to the present disclosure may be utilized to produce elastomeric laminates that may be used to construct various components of diapers, such as elastic belts, leg cuffs, and the like. For example, FIGS. 12-25 show various aspects of converting apparatuses 300 adapted to manufacture elastomeric laminates 302. As described in more detail below, the converting apparatuses 300 operate to advance a continuous length of elastic material 304, a continuous length of a first substrate 306, and a continuous length of a second substrate 308 along a machine direction MD. The apparatus 300 stretches the elastic material 304 and joins the stretched elastic material 304 with the first and second substrates 306, 308 to produce an elastomeric laminate 302. Although the elastic material 304 is illustrated and referred to herein as strands, it is to be appreciated that elastic material 304 may include one or more continuous lengths of elastic strands, ribbons, and/or films. It is also to be appreciated that in some configurations, the first substrate and second substrate 306, 308 herein may be defined by two discrete substrates or may be defined by folded portions of a single substrate.

As discussed in more detail below, the converting apparatuses 300 may include metering devices arranged along a process machine direction MD, wherein the metering devices may be configured to stretch the advancing elastic material and/or join stretch elastic material with one or more advancing substrates. In some configurations, a metering device may comprise a beam of elastic strands wound thereon. During operation, elastic material may advance in a machine direction from a rotating beam to a downstream metering device to be joined with one or more advancing substrates. The elastic material advancing from the rotating beam may include a spin finish, and as such, the apparatuses herein may be configured to bond the elastic material with the substrates without having to remove the spin finish before joining the elastic material with the substrates. First bonds are applied to bond discrete lengths of the spin finish on the stretched elastic strands with and between the first substrate and the second substrate, and second bonds are applied between consecutive first bonds to bond the first and second substrates directly to each other. The discrete first bonds are arranged intermittently along the machine direction, the second bonds extend in the machine direction and are separated from each other in a cross direction by at least one elastic strand. It is to be appreciated that the apparatuses and methods of assembly of elastomeric laminates and absorbent articles described herein and illustrated in the accompanying drawings are non-limiting example configurations. The features illustrated or described in connection with one non-limiting configuration may be combined with the features of other non-limiting configurations. Such modifications and variations are intended to be included within the scope of the present disclosure.

As shown in FIGS. 12-24, a converting apparatus 300 for producing an elastomeric laminate 302 may include a first metering device 310 and a second metering device 312. The first metering device may be configured as a beam 314 with a plurality of elastic strands 316 wound thereon. During operation, the plurality of elastic strands 316 advance in the machine direction MD from the beam 314 to the second metering device 312. In addition, the plurality of elastic strands 316 may be stretched along the machine direction MD between the beam 314 and the second metering device 312. The stretched elastic strands 316 are also joined with a first substrate 306 and a second substrate 308 at the second metering device 312 to produce an elastomeric laminate 302. As discussed in more detail below, one or more of the elastic strands 316 advancing from the beam 314 may include a spin finish 320 located on outer surfaces of the elastics strands. In turn, stretched elastic strands 316 may be connected between the first substrate 306 and the second substrate 308 with first bonds 368 and second bonds 370. The first bonds 368 may be configured to anchor and bond discrete lengths of the stretched elastic strands 316 with spin finish 320 thereon with and between the first substrate 306 and the second substrate 308, and second bonds 370 may be configured to bond the first and second substrates 306, 308 directly to each other, wherein the second bonds 370 are separated from each other in a cross direction by at least one elastic strand 316, and as such, the elastic strands 316 may be trapped between the second bonds 370.

Figure 12:
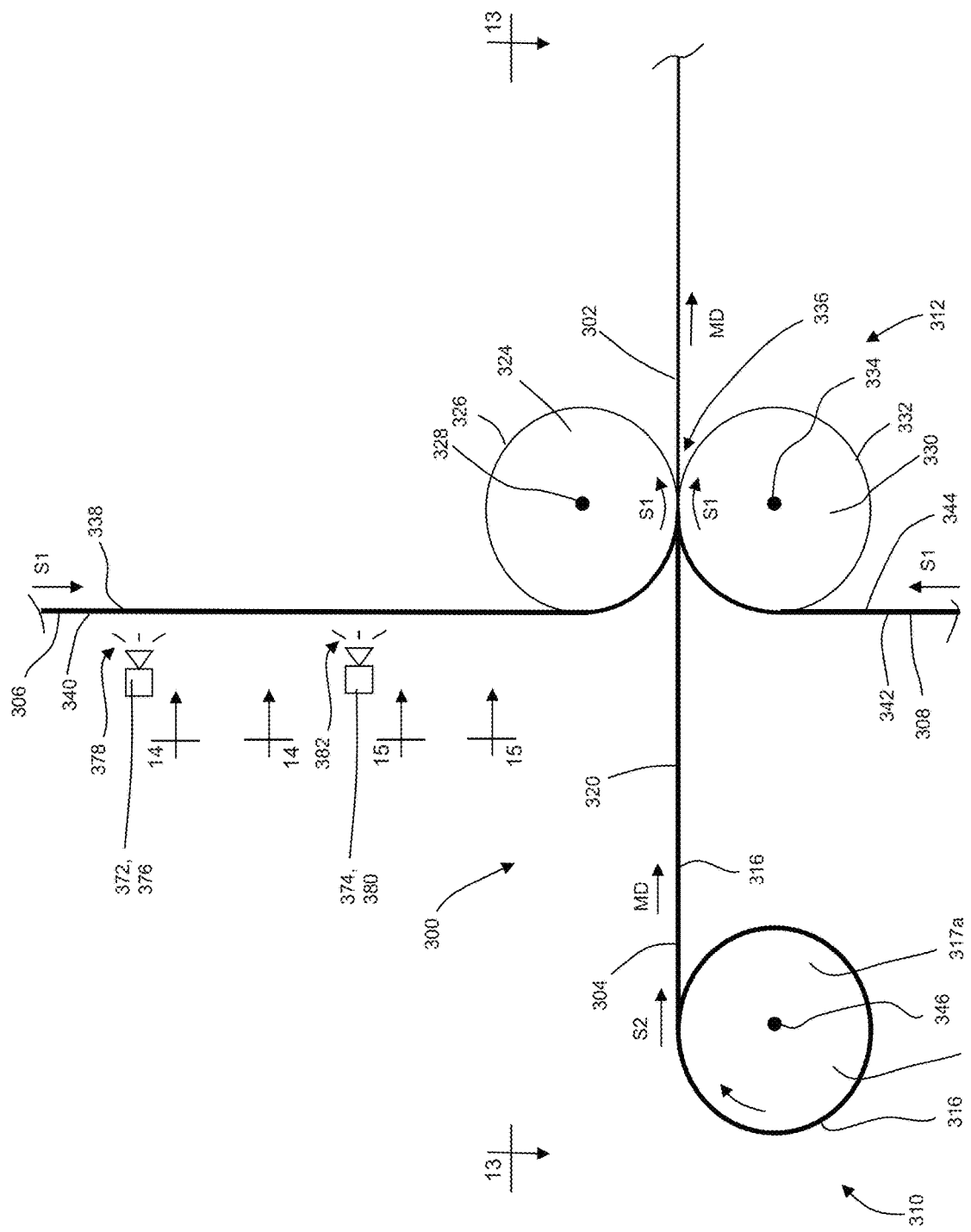
FIG. 12 is a schematic side view of a converting apparatus joining stretched elastic strands having a spin finish between a first substrate and a second substrate, wherein first and second bonds are applied to the first substrate before joining the first and second substrates with the elastics strands.
Figure 13:
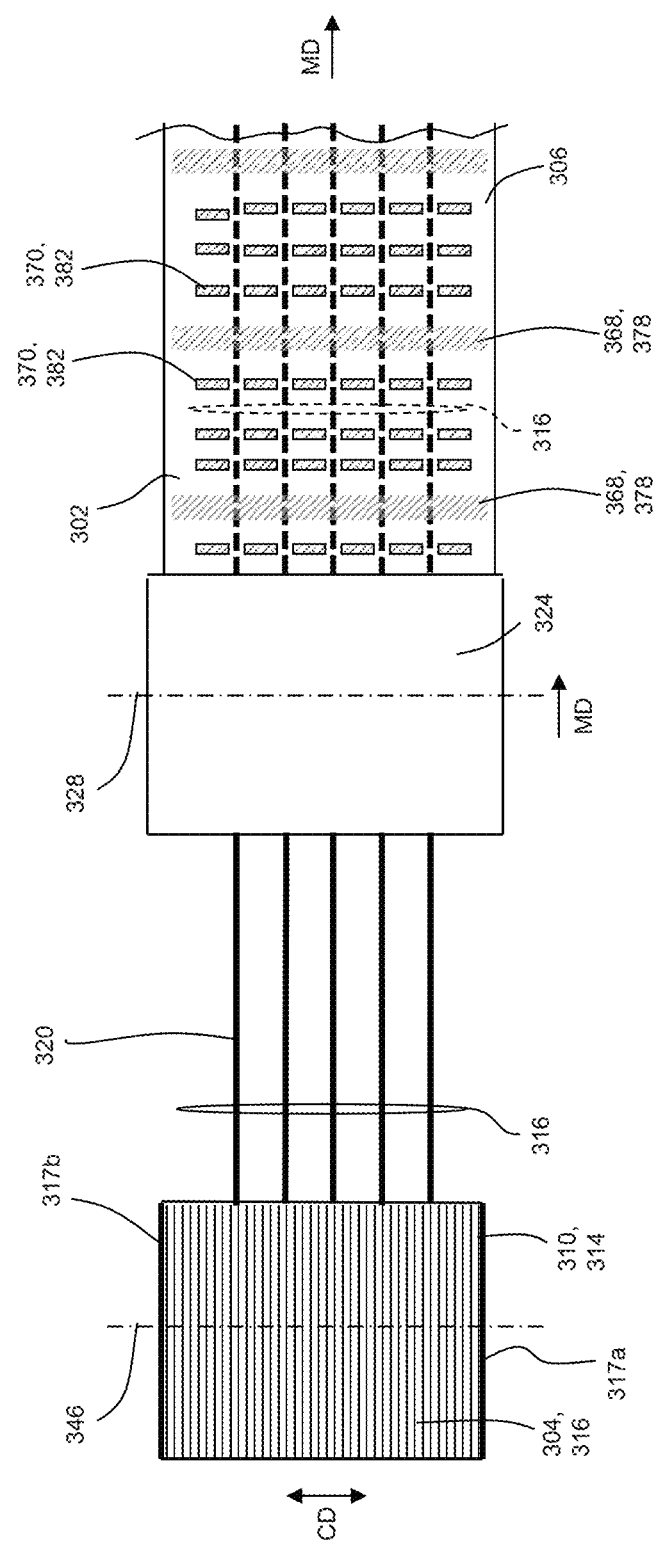
FIG. 13 is a view of the converting apparatus and elastic laminate of FIG. 12 taken along line 13-13.

FIGS. 12 and 13 show an arrangement of first and second rollers 324, 330 and associated features described above with reference to FIGS. 5 and 6 that may be utilized to combine elastic strands 316 and first and second substrates 306, 308 to produce a continuous length of elastomeric laminate 302. Although FIG. 13 shows five elastic strands 316 advancing from the beam 314, it is to be appreciated that the apparatuses herein may be configured such that more or less than five elastic strands 316 advance from the beam 314.

As discussed above, one or more of the elastic strands 316 advancing from the beam 314 may include a spin finish 320. In turn, the advancing elastic strands 316 may be joined with the first substrate 306 and the second substrate 308 to form the elastomeric laminate 302 with first bonds 368 and second bonds 370. The first bonds 368 and second bonds 370 may be configured to secure the elastic strands 316 between the first and second substrates 306, 308 without having to remove the spin finish 320 from the elastic strands 316. It is also to be appreciated that the methods and apparatuses herein may also be configured to remove the spin finish 320 from the elastic strands 316. Examples of spin finish removal processes and apparatuses are discussed above and are disclosed in U.S. Provisional Patent Application No. 62/483,965, which is incorporated by reference herein. As shown in FIGS. 12 and 14, the first substrate 306 may advance past a first bond applicator 372 configured to apply the first bonds 368 to the first substrate 306. And as shown in FIGS. 12 and 15, the first substrate 306 may advance from the first bond applicator 372 to a second bond applicator 374 configured to apply the second bonds 370 to the first substrate 306. In turn, the first substrate 306 may advance from the second bond applicator 374 to be combined with the elastic strands 316 and the second substrate 308.

As shown in FIGS. 12-14, the first bonds 368 extend for discrete lengths along the machine direction MD and may be intermittently arranged along the machine direction of the first substrate 306. When the first substrate 306 is combined with the second substrate 308 and the elastic strands 316 to form the elastomeric laminate 302, the first bonds 368 are positioned to bond discrete lengths of the spin finish 320 on the stretched elastic strands 316 with and between the first substrate 306 and the second substrate 308, such as shown in FIG. 13. It is to be appreciated the first bonds 368 may extend contiguously for various lengths in the cross direction CD and may extend across one or more elastic strands 316. In some configurations, the first bonds 368 may be defined by one or more regions of first adhesive 378 arranged to extend in the cross direction CD. Because the first bonds 368 act to adhere the spin finish 320 of the elastic strands 316 with the first and second substrates 306, 308, the first bonds 368 may be formed with relatively large basis weights of the first adhesive 378. For example, in some configurations, the first bonds 368 may include first adhesive 378 having average basis weights from about 10 gsm to about 50 gsm specifically reciting all 1 gsm increments within the above-recited range and all ranges formed therein or thereby.

Figure 13A:
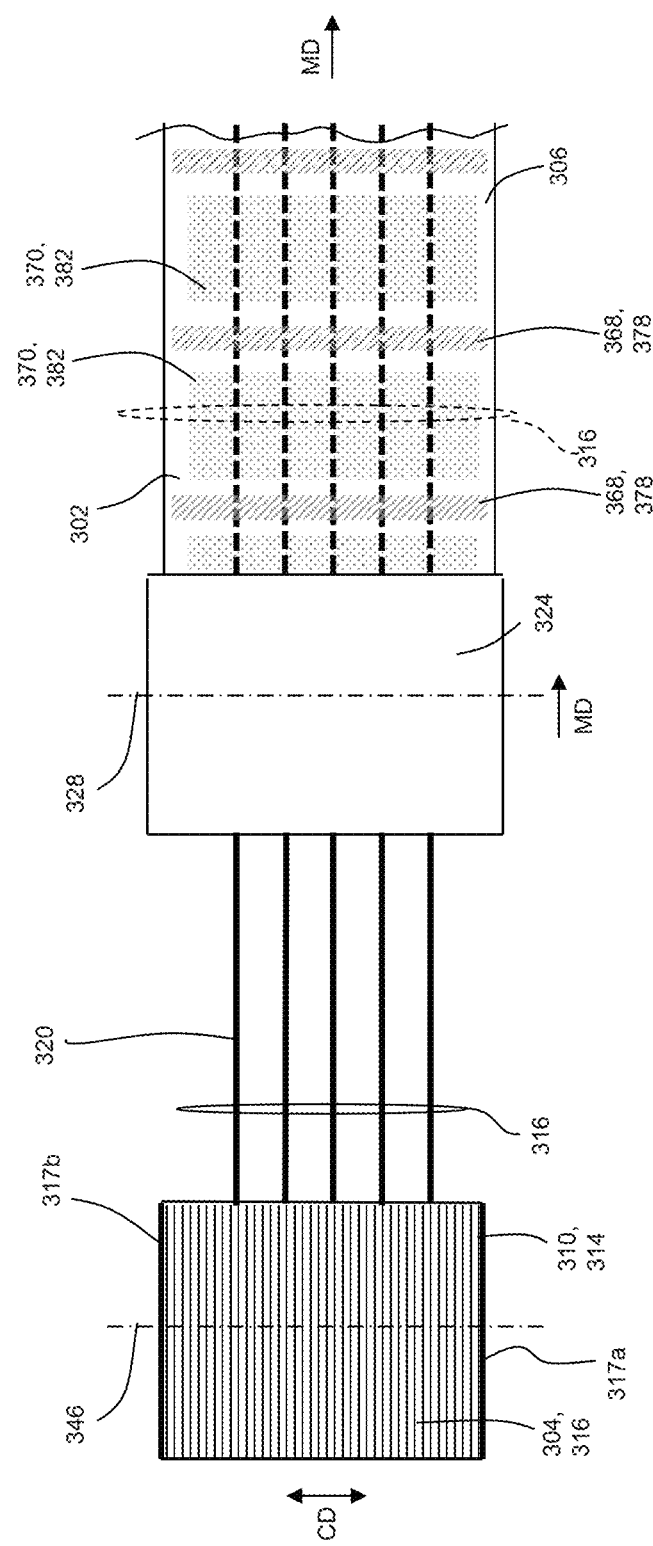
FIG. 13A is a view of the converting apparatus of FIG. 13 showing an alternative configuration of second bonds extending contiguously in the cross direction CD between and across elastic strands.

With continued reference to FIGS. 12, 13, and 15, the second bonds 370 extend for discrete lengths along the machine direction MD and may be intermittently arranged along the machine direction MD of the first substrate 306 positioned between consecutive first bonds 368. The second bonds 370 may also be separated from each other in a cross direction CD by at least one elastic strand 316. Thus, when the first substrate 306 is combined with the second substrate 308 and the elastic strands 316 to form the elastomeric laminate 302, the second bonds 370 are positioned to bond discrete regions of the first substrate 306 directly with the second substrate 308 without adhering the elastic strands 316 to either the first substrate 306 or the second substrate 308, such as shown in FIG. 13. It is to be appreciated that the second bonds 370 may extend contiguously for various lengths in the cross direction CD between elastic strands 316. In some configurations, the second bonds 370 may extend contiguously in the cross direction CD between and across one or more elastic strands 316, such as shown in FIG. 13A, and as such, may also bond the elastics strands 316 together with the first and second substrates 306, 308. In some configurations, the second bonds 370 may be defined by one or more discrete regions of second adhesive 382 arranged to extend in the cross direction CD and the machine direction MD between consecutive first bonds 368. In some configurations, the second bonds 370 may be defined by one or more regions of second adhesive 382 arranged to extend continuously and contiguously in the machine direction MD across and/or through consecutive first bonds 368. The second bonds 370 may be formed with relatively low basis weights of the second adhesive 382. For example, in some configurations, the second bonds 370 may include second adhesive 382 having average basis weights from about 0.5 gsm to about 10 gsm specifically reciting all 1 gsm increments within the above-recited range and all ranges formed therein or thereby. It is to be appreciated that the first bonds 368 and/or second bonds 370 may define various shapes and/or sizes and may correspond with contours of the first substrate 306 and/or second substrate 308.

Figure 16A:
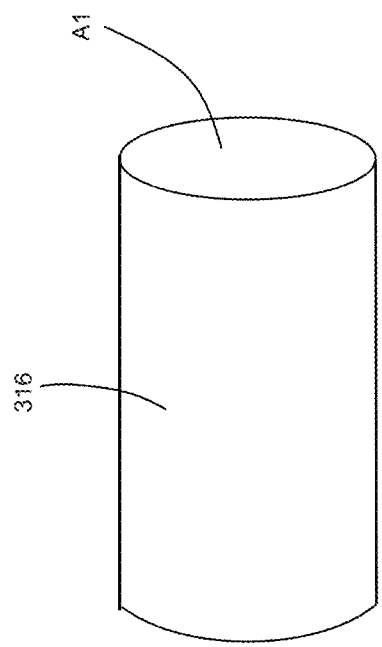
FIG. 16A shows a length of an elastic strand in a relaxed state with a first cross sectional area.
Figure 16B:
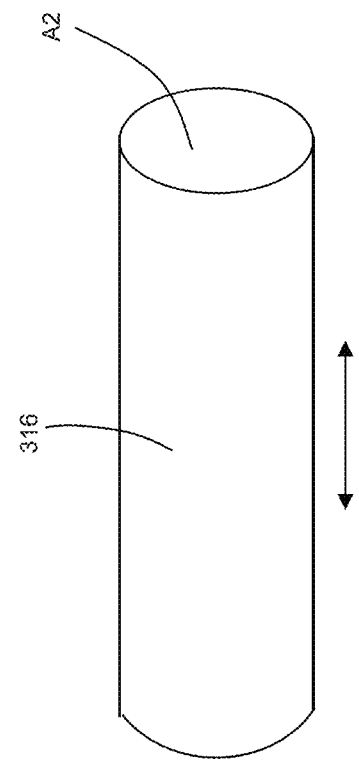
FIG. 16B shows a length of the elastic strand of FIG. 16A in a stretched state with a second cross sectional area that is less than the first cross sectional area.
Figure 17A:
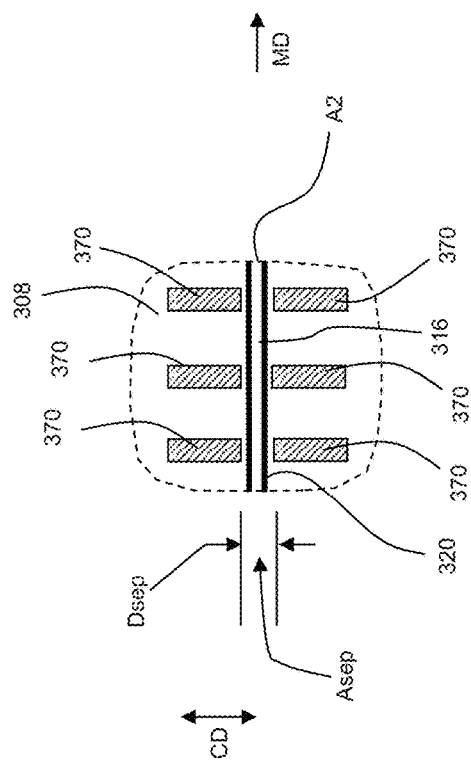
FIG. 17A is a detailed view of a stretched elastic strand positioned between the second bonds.
Figure 17B:
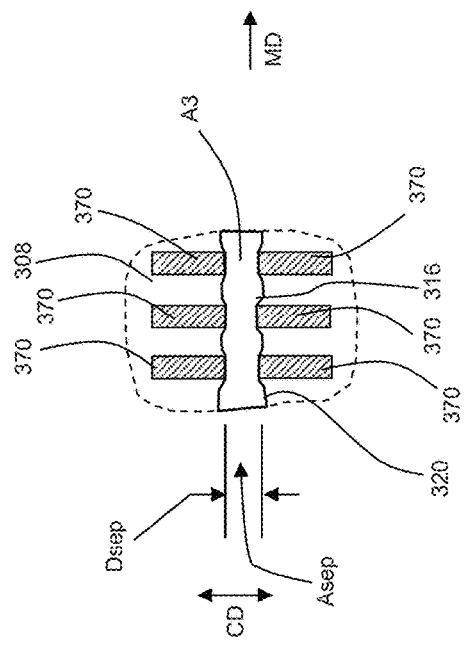
FIG. 17B is a detailed view of a contracted elastic strand having portions immobilized between the second bonds.

As discussed above, the second bonds 370 may be arranged to bond the first and second substrates 306, 308 directly together without adhering the elastic strands 316 to either substrate. As such, the second bonds 370 may be configured to trap and immobilize discrete lengths of the elastic strands 316 between the second bonds 370 after the elastic strands 316 have contracted, such as disclosed for example, in U.S. Pat. No. 6,291,039 and European Patent Publication No. EP 3 092 997 B1. For the purposes of a general explanation, FIG. 16A shows a length of an elastic strand 316 in a unstretched or relaxed state, wherein the elastic strand 316 defines a first cross sectional area A1. And FIG. 16B shows a length of the elastic strand 316 from FIG. 16A in a stretched state, wherein the elastic strand 316 defines a second cross sectional area A2 that is less than the first cross sectional area A1. Thus, the cross sectional area of the stretched elastic strand 316 expands when tension is partially or fully released from the elastic strand 316. Referring now to FIG. 17A, a stretched elastic strand 316 is shown extending between adjacent second bonds 370. As shown in FIG. 17A, the second bonds 370 may be separated from the each other in the cross direction CD by a distance Dsep and defining a cross sectional area Asep. The elastic strand 316 shown in FIG. 17A is stretched and changes the first cross sectional area A1 of the elastic strand 316 in an unstretched state to the second cross sectional area A2 of the elastic strand in a stretched state, wherein the second cross sectional area A2 is less than the cross sectional area Asep. FIG. 17B shows a detailed view of the elastic strand 316 from FIG. 17A having contracted in the machine direction MD. As shown in FIG. 17B, as the elastic strand 316 contracts, the cross sectional area may increase from the second cross sectional area A2 to a third cross sectional area A3, wherein the A3 is greater than A2. However, the discrete lengths of the contracted elastic strand 316 positioned in the cross direction between the second bonds 370 can only expand to Asep and help prevent the cross sectional area of the elastic strand 316 from expanding when tension on elastic strand 316 has been reduced. As such, the second bonds 370 that are separated from each other in the cross direction CD on opposing sides of the elastic strand 316 act to trap or immobilize discrete lengths of the contracted elastic strand 316 positioned between the second bonds 370.

The first bond applicator 372 and the second bond applicator 374 may be arranged in various ways. For example, the apparatus 300 may be configured such that the first substrate 306 advances past the second bond applicator 374 before advancing to the first bond applicator 372. In some configurations, the first bond applicator 372 and the second bond applicator 374 may be arranged to apply the first bonds 368 and the second bonds 370 to different substrates. For example, the first bond applicator 372 may be arranged to apply first bonds 368 to the first substrate 306, and the second bond applicator 374 may be arranged to apply second bonds 370 to the second substrate 308. The first bond applicator 372 may also be arranged to apply first bonds 368 to the second substrate 308, and the second bond applicator 374 may be arranged to apply second bonds 370 to the first substrate 306. Some configurations may include a plurality of first bond applicators 372, for example, wherein one first bond applicator 372 may be arranged to apply first bonds 368 to the first substrate 306 and another first bond applicator 372 may be arranged to apply first bonds 368 to the second substrate 308.

The first bond applicator 372 and the second bond applicator 374 may be also be configured in various ways. For example, as shown in FIG. 12, the first bond applicator 372 may be configured as a first adhesive applicator device 376 that applies a first adhesive 378 to the second surface 340 of the first substrate 306 to form the first bonds 368. In addition, the second bond applicator 374 may be configured as a second adhesive applicator device 380 that applies a second adhesive 382 to the second surface 340 of the first substrate 306 to form the second bonds 370. It is to be appreciated that the first adhesive applicator device 376 and/or the second adhesive applicator device 380 be configured as a spray nozzle and/or a slot coating device. In some configurations, the first adhesive applicator device 376 and/or the second adhesive applicator device 380 may be configured in accordance with the apparatuses and/or methods disclosed in U.S. Pat. Nos. 8,186,296; 9,265,672; 9,248,054; and 9,295,590 and U.S. Patent Publication No. 2014/0148773 A1.

Figure 18:
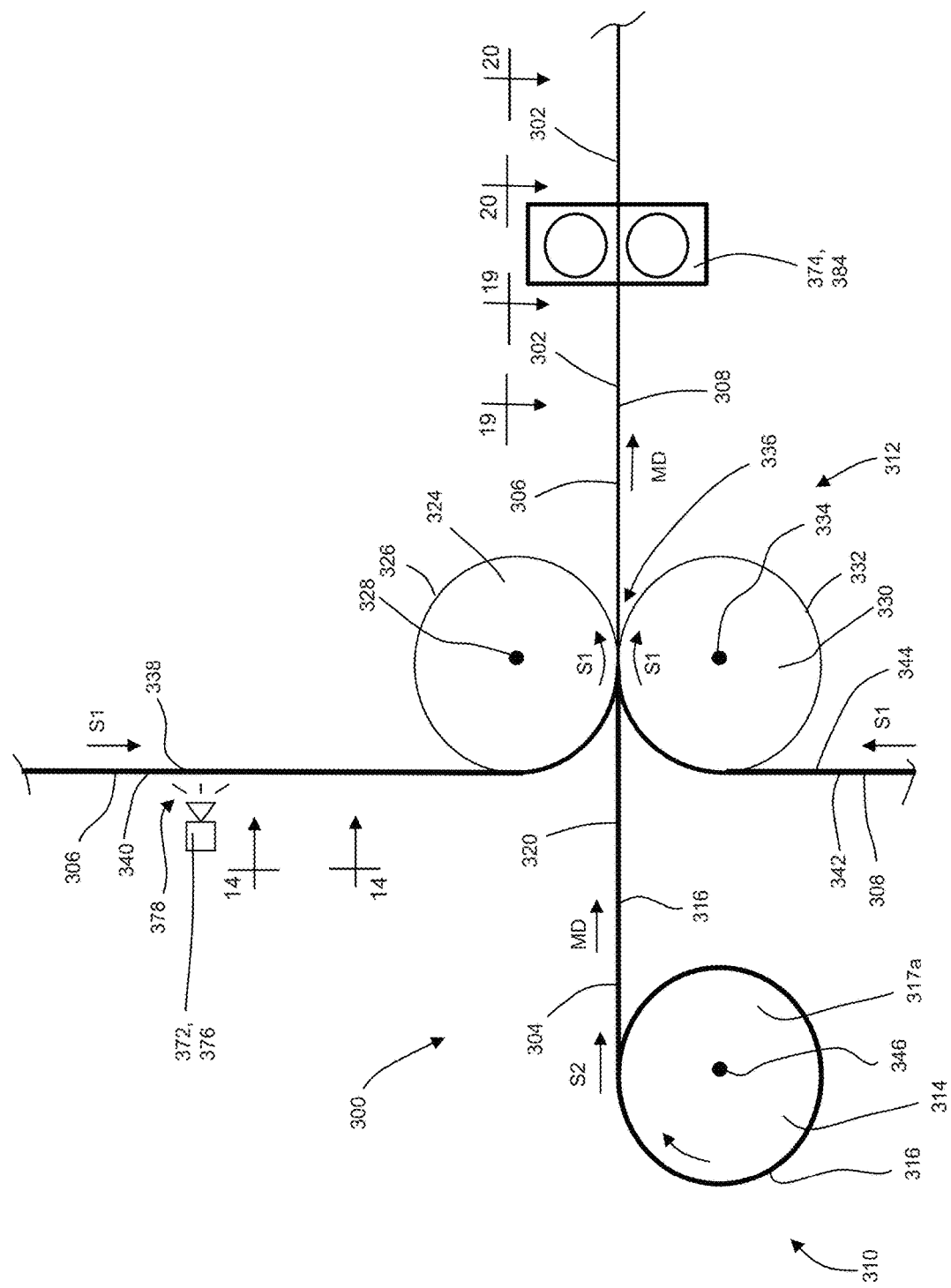
FIG. 18 is a schematic side view of another configuration of a converting apparatus joining elastic strands having a spin finish between a first substrate and a second substrate, wherein first bonds are applied before joining the strands with the first and second substrates and second bonds are applied after joining the strands with the first and second substrates.
Figure 20:
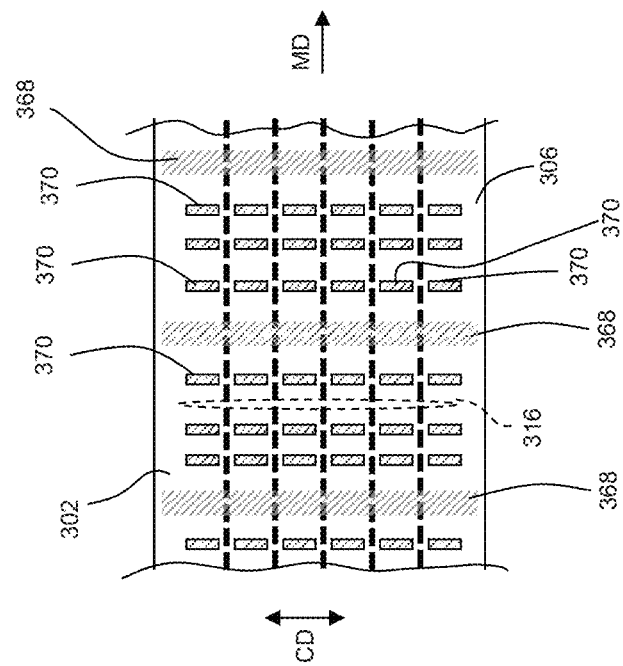
FIG. 20 is a view of the elastic laminate of FIG. 18 taken along line 20-20.
Figure 19:
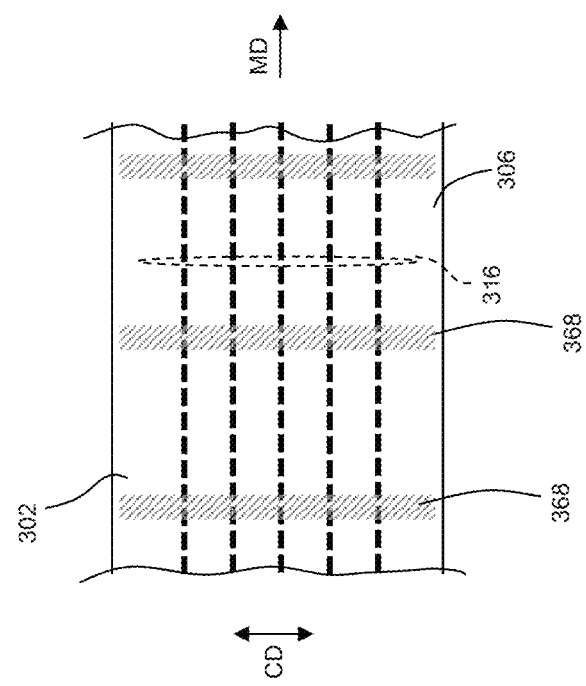
FIG. 19 is a view of the elastic laminate of FIG. 18 taken along line 19-19.

In some configurations, the apparatus 300 may be configured such that the first bond applicator 372 applies the first bonds 368 to either the first and/or second substrates 306, 308 before the first and second substrates 306, 308 are combined with the elastic strands 316. And the second bond applicator 374 may be configured to apply the second bonds 370 to the first and second substrates 306, 308 after being combined with the elastic strands 316. For example, as shown in FIGS. 18-20, the first substrate 306 may advance past the first bond applicator 372 that applies the first bonds 368 to the first substrate 306. As discussed above, the first bond applicator 372 may be configured as a first adhesive applicator device 376 that applies a first adhesive 378 to the second surface 340 of the first substrate 306 to form the first bonds 368, as shown in FIGS. 14 and 18. The first substrate 306 may then advance from the first bond applicator 372 to be combined with the elastic strands 316 and the second substrate 308 to form and elastomeric laminate 302, as shown in FIGS. 18 and 19. As discussed above, the first bonds 368 extend for discrete lengths along the machine direction MD and may be intermittently arranged along the machine direction MD. And the first bonds 368 are positioned to bond discrete lengths of the spin finish 320 on the stretched elastic strands 316 with and between the first substrate 306 and the second substrate 308, such as shown in FIGS. 19 and 20. Referring now to FIGS. 18 and 20, the second bond applicator 374 applies the second bonds 370 to the combined first substrate 306, second substrate 308, and elastic strands 316.

As shown in FIG. 18, the second bond applicator 374 may be configured as a mechanical bonding device 384 that applies the second bonds 370 in the form of mechanical bonds, such as for example, bonds that may be applied with heat, pressure, and/or ultrasonic devices. It is also to be appreciated that the first bond applicator 372 may be configured to apply the first bonds 368 in the form of mechanical bonds, such as for example, bonds that may be applied with heat, pressure, and/or ultrasonic devices. Examples of such mechanical bonding devices and methods are disclosed in U.S. Pat. Nos. 4,854,984; 6,291,039; 6,248,195; 8,778,127; and 9,005,392; and U.S. Patent Publication Nos. 2014/0377513 A1; and 2014/0377506 A1. In addition, it is to be appreciated that the first bond applicator 372 and/or the second bond applicator 374 may be configured to operate in accordance with other bonding methods and apparatuses discussed herein and/or disclosed in the U.S. Provisional Patent Application No. 62/553,171, filed on Sep. 1, 2017, which is incorporated by reference herein. The second bonds 370 applied with a mechanical bonder 384 also extend for discrete lengths along the machine direction MD and may be intermittently arranged along the machine direction MD positioned between consecutive first bonds 368. In addition, the second bonds 370 are also separated from each other in a cross direction CD by at least one elastic strand 316. Thus, the second bonds 370 are positioned to bond discrete regions of the first substrate 306 directly with the second substrate 308 without bonding the elastic strands 316 to either the first substrate 306 or the second substrate 308. The second bonds also act to trap or immobilize discrete lengths of the contracted elastic strand 316 positioned between the second bonds 370 as discussed above with reference to FIGS. 16A-17B.

Figure 21:
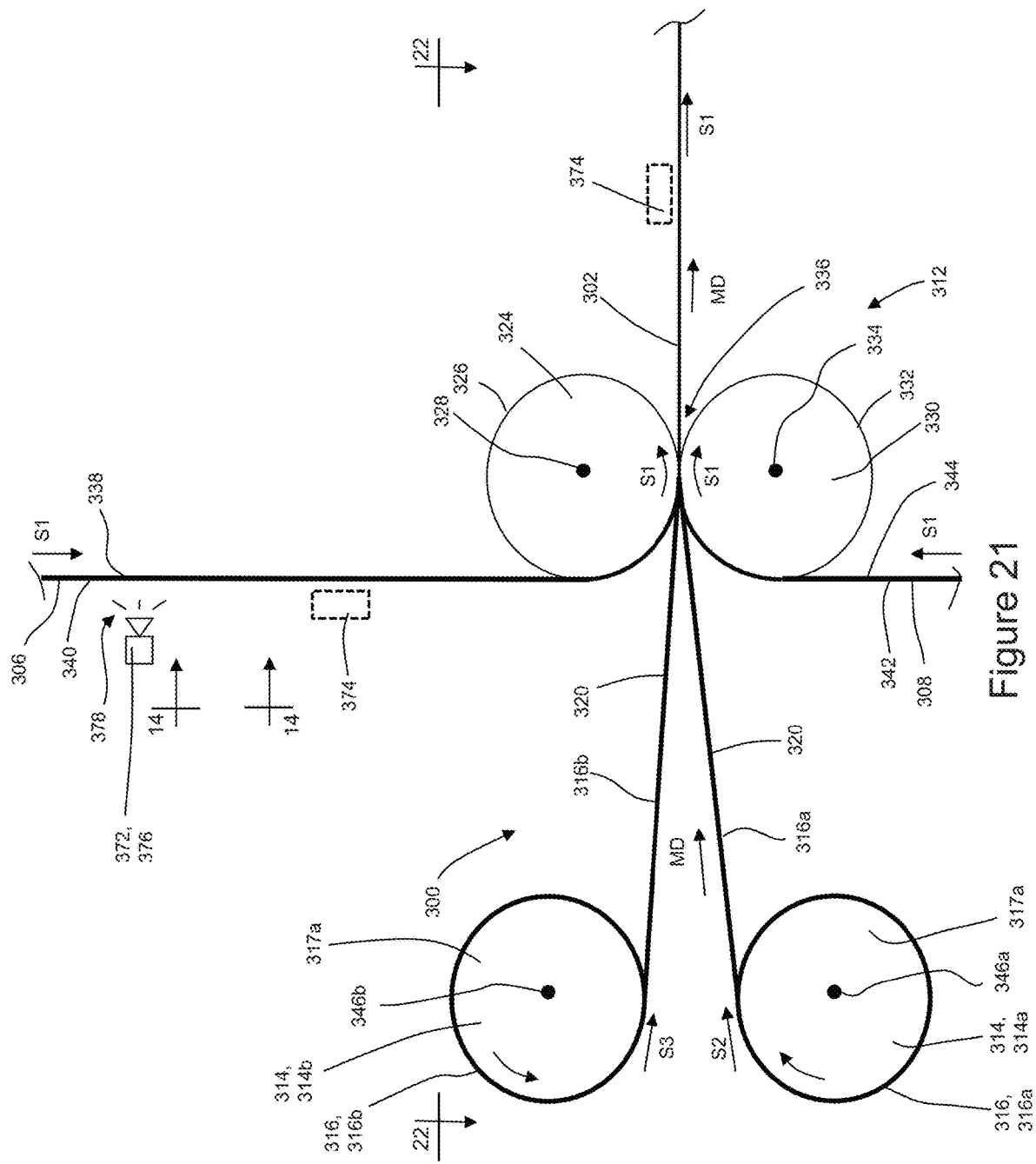
FIG. 21 is a schematic side view of another configuration of a converting apparatus joining elastic strands having a spin finish between a first substrate and a second substrate, wherein the elastic strands are drawn from different beams.
Figure 22:
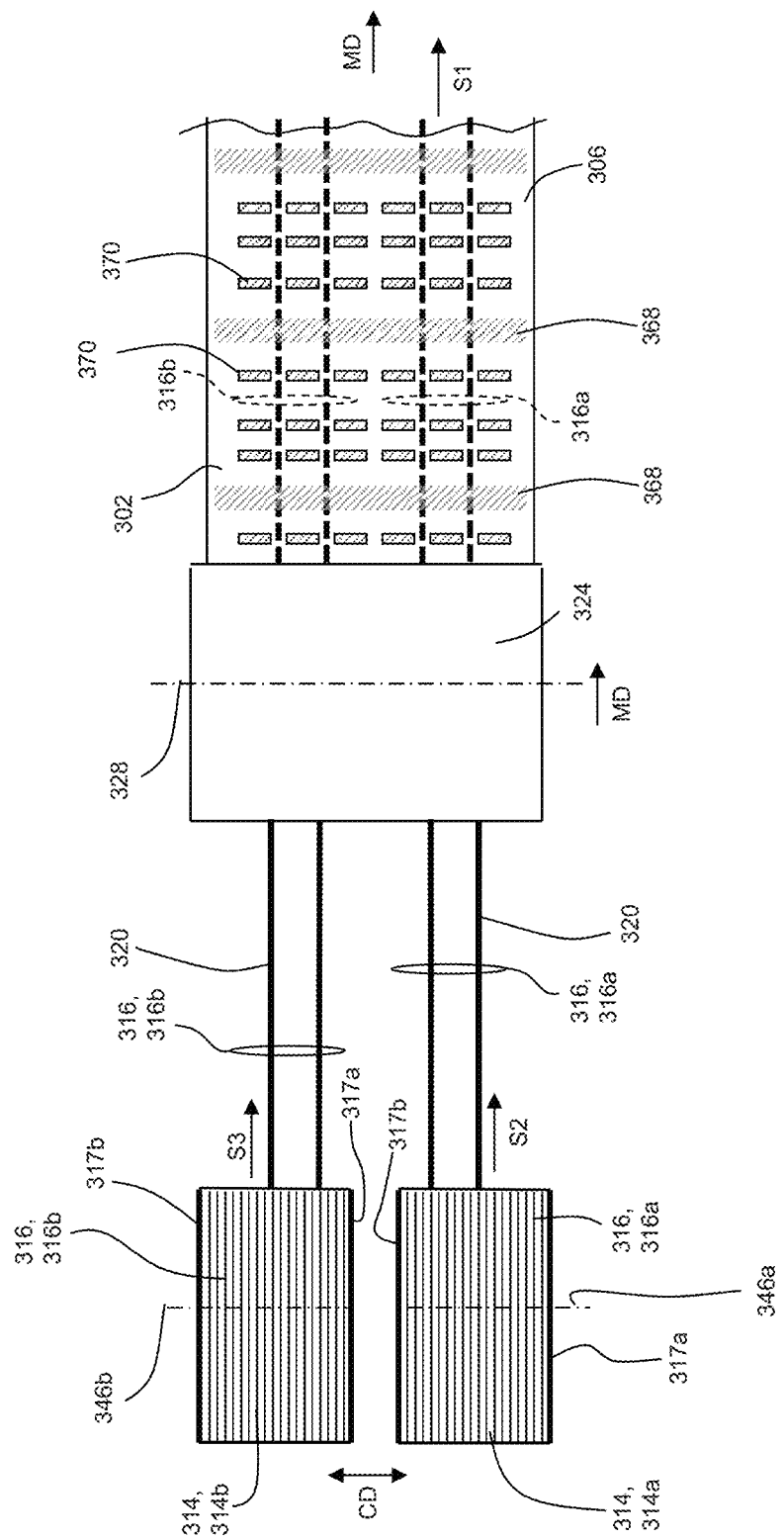
FIG. 22 is a view of the converting apparatus of FIG. 21 taken along line 22-22.

It is to be appreciated that the apparatuses 300 herein may be configured in various ways with various features described herein to assemble elastomeric laminates 302 having various stretch characteristics. For example, the apparatus 300 may be configured to assemble elastomeric laminates 302 with elastic strands 316 unwound from more than one beam. For example, FIGS. 21 and 22 illustrate the apparatus 300 configured to assemble elastomeric laminates 302 with elastic strands 316 unwound from more than one beam 314. In particular, the apparatus 300 may include a first beam 314a with first elastic strands 316a wound thereon and a second beam 314b with second elastic strands 316b wound thereon. The first beam 314a is rotatable about a first beam rotation axis 346a, and the second beam 314b is rotatable about a second beam rotation axis 346b. During operation, as the first beam 314a rotates, the first elastic strands 316a advance in the machine direction MD from the first beam 314a at a speed S2 with the first elastic strands 316a being spaced apart from each other in the cross direction CD. From the first beam 314a, the first elastic strands 316a advance in the machine direction MD and are joined with the first substrate 306 and the second substrate 308 as discussed above. Similarly, as the second beam 314b rotates, the second elastic strands 316b advance in the machine direction MD from the second beam 314b at a speed S3 with the second elastic strands 316b being spaced apart from each other in the cross direction CD. From the second beam 314b, the second elastic strands 316b advance in the machine direction MD and are joined with the first substrate 306 and the second substrate 308 as discussed above. It is also to be appreciated that the apparatuses herein 300 may be configured to assemble elastomeric laminates 302 with elastic strands 316 unwound from one or more beams and in combination with elastic stands supplied from various types of elastic unwinder configurations, such as an overend unwinder or surface driven unwinder and unwinders such as disclosed in U.S. Pat. Nos. 6,676,054; 7,878,447; 7,905,446; and 9,156,648. For example, the configuration shown in FIGS. 21 and 22 and other figures and configurations herein may also include elastic strands 316 supplied from surface and/or surface driven unwinders. It is to be appreciated that the apparatus configurations shown in FIGS. 21 and 22 may also include the first bond applicator 372 and the second bond applicator 374 arranged to apply the first bonds 368 and the second bonds 370 as discussed above. The second bond applicator 374 is generically represented by a dashed-line rectangle in FIG. 21, and it is to be appreciated that the second bond applicator 374 may be configured as an adhesive applicator device 376 or a mechanical bonding device 384 and may be positioned to apply the second bonds 370 before or after the first substrate 306, second substrate 308, and elastic strands 316a, 316b are combined as discussed above.

As previously mentioned, the elastic strands 316 may be joined with the first and second substrates 306, 308 such that the elastomeric laminate 302 may have different stretch characteristics in different regions. For example, with continued reference to FIGS. 21 and 22, the elastic strands 316a, 316b may be joined with the first and second substrates 306, 308 such that the elastomeric laminate 302 may have different stretch characteristics in different regions along the cross direction CD. For example, when the elastomeric laminate 302 is elongated, the first elastic strands 316a may exert contraction forces in the machine direction MD that are different from contraction forces exerted by the second elastic strands 316b. Such differential stretch characteristics can be achieved by stretching the first elastic strands 316a more or less than the second elastic strands 316b before joining the elastic strands 316a, 316b with the first and second substrates 306, 308. For example, as previously discussed, the first substrate 306 and the second substrate 308 may each advance at a speed S1. In some configurations, the first elastic strands 316a may advance from the first beam 314a at speed S2 that is less than the speed S1, and second elastic strands 316b may advance from the second beam 314b at the speed S3 that is less than the speed S1. As such, the first elastic strands 316a and the second elastic strands 316b are stretched in the machine direction MD when combined with the first and second substrates 306, 308. In addition, the speed S2 may be less than or greater than different than the speed S3. Thus, the first elastic strands 316a may be stretched more or less than the second elastic strands 316b when combined with the first and second substrates 306, 308. It is also appreciated that the first and second elastic strands 316a, 316b may have various different material constructions and/or decitex values to create elastomeric laminates 302 having different stretch characteristics in different regions. In some configurations, the elastic laminate may have regions where the elastic strands 316 are spaced relatively close to one another in the cross direction CD and other regions where the elastic strands 316 are spaced relatively farther apart from each other in the cross direction CD to create different stretch characteristics in different regions. In some configurations, the elastic strands 316 may be supplied on the beam 314 in a stretched state, and as such, may not require additional stretching (or may require relatively less additional stretching) before being combined with the first substrate 306 and/or the second substrate 308. Thus, in some configurations, the first elastic strands 316a may be supplied on the first beam 314a at a first tension, and the second elastic strands 316b may be supplied on the second beam 314b at a second tension, wherein the first tension is not equal to the second tension. In some configurations, differential stretch characteristics in an elastomeric laminate may be created by bonding another elastomeric laminate and/or an elastic film to a particular region of an elastomeric laminate. In some configurations, differential stretch characteristics in an elastomeric laminate may be created by folding a portion of an elastomeric laminate onto itself in a particular region of the elastomeric laminate.

Figure 23:
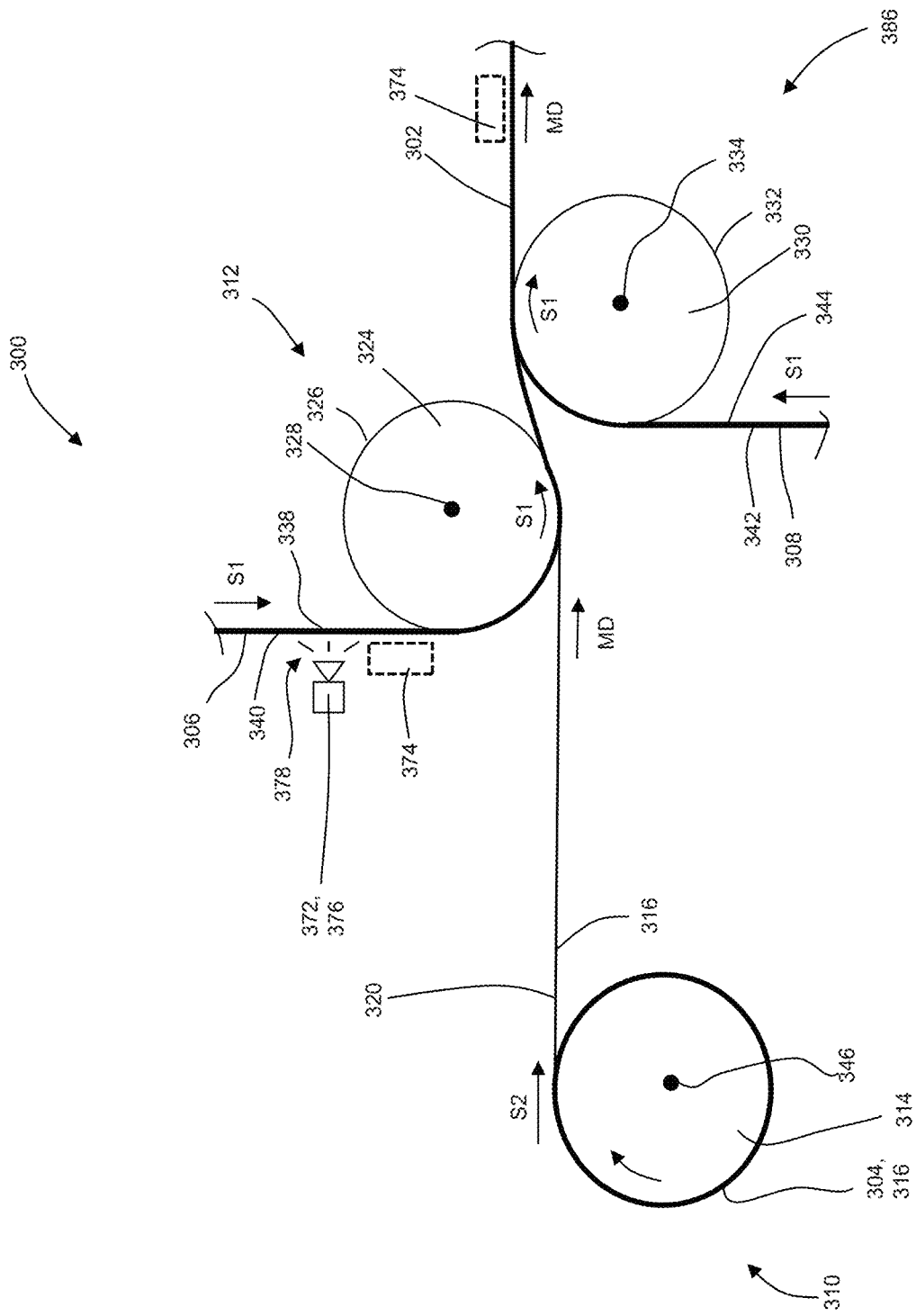
FIG. 23 is a schematic side view of another configuration of a converting apparatus adapted to manufacture an elastomeric laminate including first and second bonds.

FIG. 23 shows an arrangement of first and second rollers 324, 330 and associated features described above with reference to FIG. 9 configured with the first bond applicator 372 and the second bond applicator 374 arranged to apply the first bonds 368 and the second bonds 370 that may be utilized to combine elastic strands 316, with or without a spin finish 320, and first and second substrates 306, 308 to produce a continuous length of elastomeric laminate 302.

Figure 24:
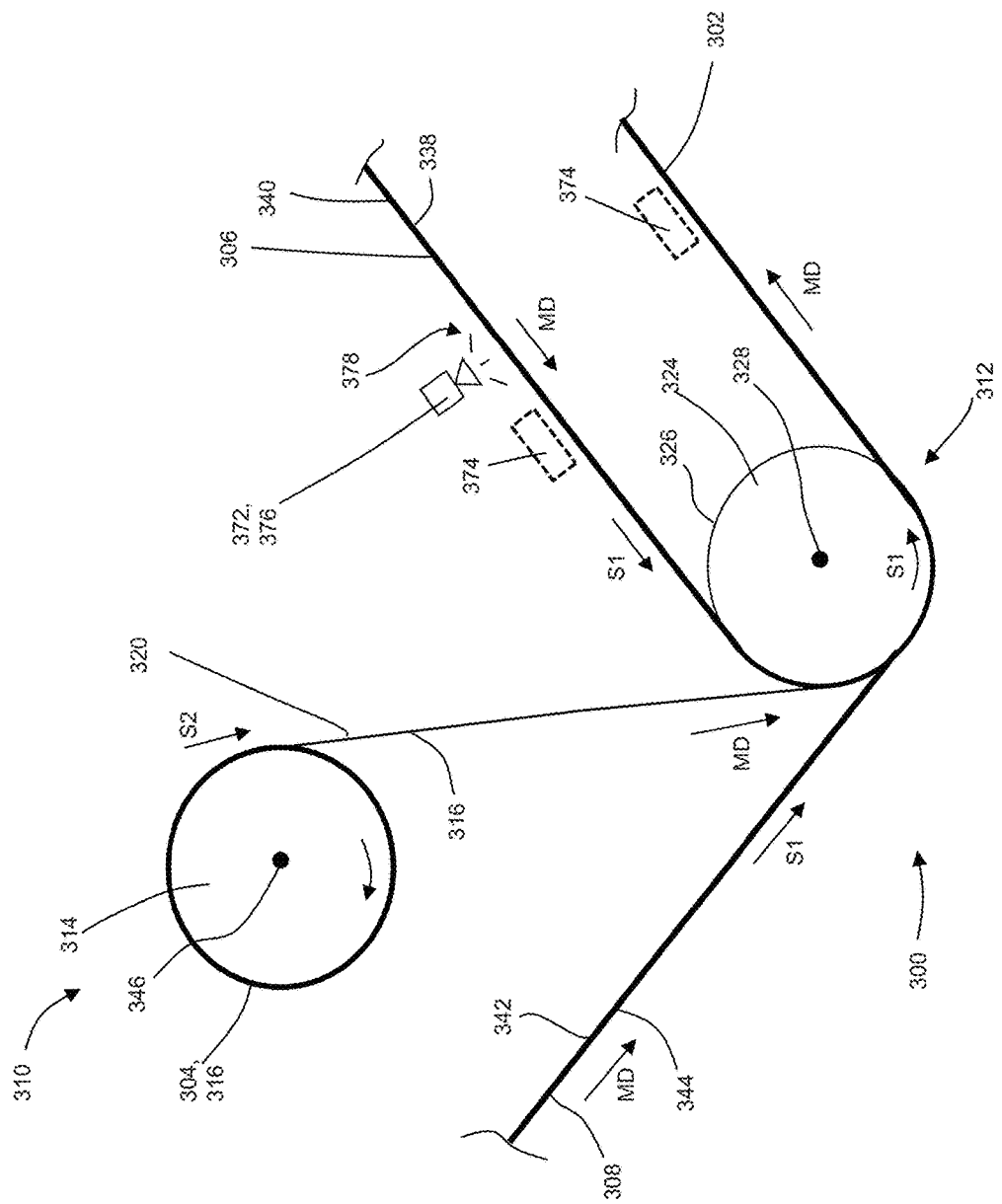
FIG. 24 is a schematic side view of another configuration of a converting apparatus adapted to manufacture an elastomeric laminate including first and second bonds.

In another configuration shown in FIG. 24, the apparatus 300 may be configured with only the first roller 324 and without a second roller 330, such as described above with reference to FIG. 10. As such, the first roller 324 may be configured as the second metering device 312. As shown in FIG. 24, the first substrate 306 advances at speed S1 to the first roller 324 where the first substrate 306 partially wraps around the outer circumferential surface 326 of the first roller 324. While partially wrapped around the outer circumferential surface 326 of the first roller 324, the first substrate 306 is combined with the elastic strands 316 and the second substrate 308. As the beam 314 rotates, the elastic strands 316 advance from the beam 314 at a speed S2 with the elastic strands 316 being spaced apart from each other in the cross direction CD. From the beam 314, elastic strands 316 having a spin finish 320 advance to the first roller 324 and are positioned on the second surface 340 of the first substrate 306. In some configurations, the speed S2 is less than the speed S1, and as such, the elastic strands 316 are stretched in the machine direction MD.

With continued reference to FIG. 24, the second substrate 308 advances at speed S1 to the first roller 324 and partially wraps around the outer circumferential surface 326 of the first roller 324. In turn, the second substrate 308 is combined with the first substrate 306 and the stretched elastic strands 316 while on the first roller 324 such that the elastic strands 316 are joined with the second surface 340 of the first substrate 306 and the first surface 342 of the second substrate 308 to produce a continuous length of elastomeric laminate 302.

It is to be appreciated that the apparatus configurations shown in FIGS. 23 and 24 may also include the first bond applicator 372 and the second bond applicator 374 arranged to apply the first bonds 368 and the second bonds 370 as discussed above. It is also to be appreciated that the second bond applicator 374 may be configured as an adhesive applicator device 376 or a mechanical bonding device 384 and may be positioned to apply the second bonds 370 before or after the first substrate 306, second substrate 308, and elastic strands 316 are combined as discussed above.

As previously mentioned, the elastomeric laminates 302 herein may be used to construct various types of absorbent article components such as discussed above with reference to FIGS. 1-3B. For example, the elastomeric laminates may be used to construct various types of leg cuff and/or topsheet configurations. In other examples, the elastomeric laminates may be used to construct waistbands and/or side panels in taped diaper configurations.

Figure 25:
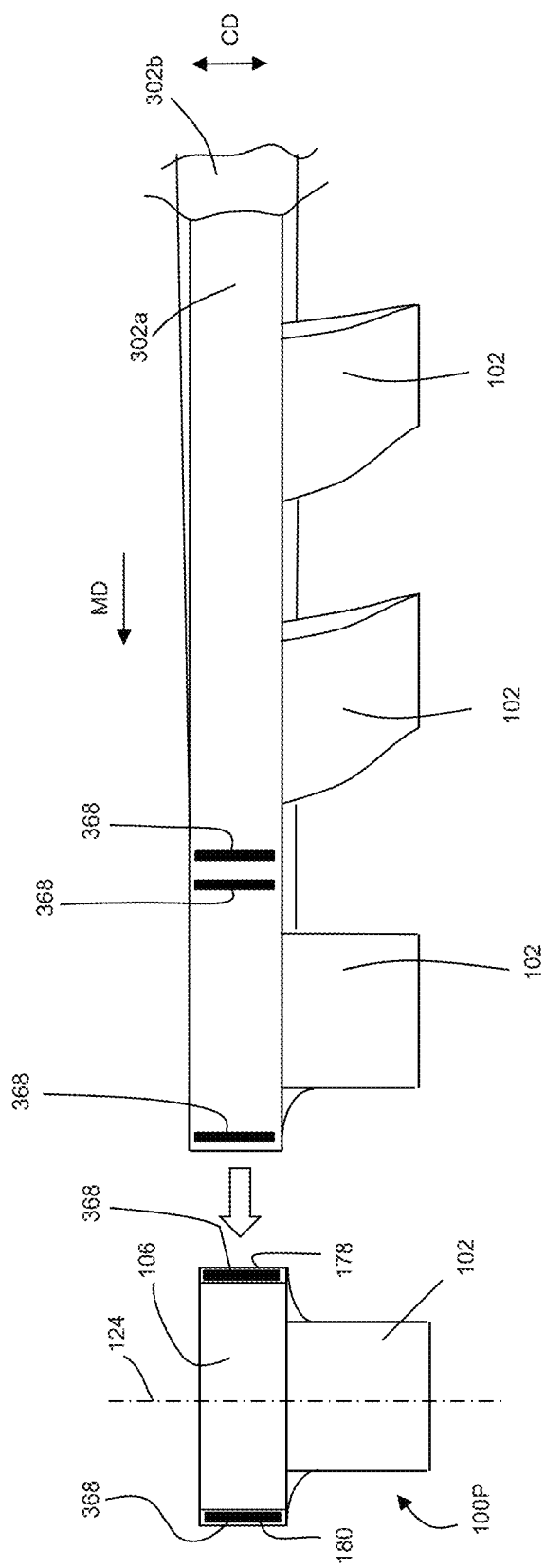
FIG. 25 is a schematic illustration of a diaper pant assembly process with elastomeric laminates.

In yet other examples, the elastomeric laminates 302 herein may be configured as continuous lengths of elastomeric belt material that may be converted into the first and second elastic belts 106, 108 discussed above with reference to FIGS. 1-3B. As previously mentioned, the elastic material 304 may correspond with the belt elastic material 168 interposed between the outer layer 162 and the inner layer 164, which in turn, may correspond with either the first and/or second substrates 306, 308. For example, a first continuous elastomeric laminate 302a and a second continuous elastomeric laminate 302b may be combined with absorbent chassis 102 to form diaper pants 100P. In some converting configurations, such as shown in FIG. 25, discrete absorbent chassis 102 are spaced apart from each other in a machine direction MD and opposing waist regions of discrete absorbent chassis 102 are connected with continuous lengths of first and second continuous elastomeric laminate 302a, 302b. The absorbent chassis 102 may be folded to place the first elastomeric laminate 302a and the second elastomeric laminate 302b into a facing relationship with the each other. Next, first bonds 368 may be applied to the first elastomeric laminate 302a and the second elastomeric laminate 302b, forming a continuous length of absorbent articles. Subsequently, the first and second elastomeric laminates 302a, 302b may be cut along the cross direction CD between adjacent first bonds 368 to form discrete diaper pants 100P. Thus, in the configuration shown in FIG. 25, the second bonds 370 discussed above may be applied during the construction of the first and second elastomeric laminates 302a, 302b to bond the elastic strands 316 and first and second substrates 306, 308 together. And the first bonds 368 may be applied subsequently to the second bonds 370 to bond the first and second elastomeric laminates 302a, 302b to each other. As such, the first bonds 368 may be used to create the side seams 178, 180.

In some method and apparatus configurations discussed below, discrete mechanical bonds may be applied to the first substrate and the second substrate to secure elastic strands therebetween, wherein the discrete bonds are arranged intermittently along the machine direction. As discussed in more detail below, when combining elastic strands having relatively low decitex values with substrates to create bonds having certain ranges of thicknesses, the mechanical bonds can be applied to secure the elastic strands between substrates without severing the elastics strands and without the need for nesting grooves in a mechanical bonding device. It is to be appreciated that various types of mechanical bonding devices can be utilized with the apparatuses and methods herein, such as for example, heated or unheated patterned and anvil rolls and/or ultrasonic bonding devices.

During the bonding process, heat and pressure are applied to the first substrate and the second substrate such that malleable materials of the first and second substrates deform to completely surround an outer perimeter of a discrete length of the stretched elastic strand. After removing the heat and pressure from the first and second substrates, the malleable materials harden to define a bond conforming with a cross sectional shape defined by the outer perimeter of the stretched elastic strand. When the elastic strand is in a stretched state, the stretched elastic strand defines a cross sectional area that is less than a cross sectional area of the elastic strand when in a relaxed state. Thus, when tension is released from the elastic strand, the cross sectional area of the elastic strand is prevented from expanding in the bond by the hardened materials of the first and second substrates, which in turn, creates forces between the elastic strand and the hardened materials. The forces between the elastic strand and the hardened materials increases the friction between the elastic strand and the hardened materials. Thus, a frictional lock may be created between the elastic strand and the hardened materials in the bond region by releasing the tension from the stretched elastic strands. The frictional lock holds the discrete length of the elastic strand in a fixed position in the bond region with the first and second substrates.

As previously mentioned, apparatuses and methods according to the present disclosure may be utilized to produce elastomeric laminates that may be used to construct various components of diapers, such as elastic belts, leg cuffs, and the like. For example, FIGS. 26-37 show various aspects of converting apparatuses 300 adapted to manufacture elastomeric laminates 302. As described in more detail below, the converting apparatuses 300 operate to advance a continuous length of elastic material 304, a continuous length of a first substrate 306, and a continuous length of a second substrate 308 along a machine direction MD. The apparatus 300 stretches the elastic material 304 and joins the stretched elastic material 304 with the first and second substrates 306, 308 to produce an elastomeric laminate 302. Although the elastic material 304 is illustrated and referred to herein as strands, it is to be appreciated that elastic material 304 may include one or more continuous lengths of elastic strands, ribbons, and/or films.

As discussed in more detail below, the converting apparatuses 300 may include metering devices arranged along a process machine direction MD, wherein the metering devices may be configured to stretch the advancing elastic material and/or join stretch elastic material with one or more advancing substrates. In some configurations, a metering device may comprise a beam of elastic strands wound thereon. During operation, elastic material may advance in a machine direction from a rotating beam to a downstream metering device to be joined with one or more advancing substrates. The elastic material advancing from the rotating beam may include a spin finish, and as such, the apparatuses herein may be configured to bond the elastic material with the substrates without having to remove the spin finish before joining the elastic material with the substrates. Bonds are applied to the first substrate and the second substrate to secure discrete lengths of the stretched elastic strands between the first and second substrates. The discrete bonds may be arranged intermittently along the machine direction. In some configurations, the bonds extend in the machine direction and may extend in a cross direction across one or more elastic strands. In some configurations, bonds may be separated from each other in a cross direction. It is to be appreciated that the apparatuses and methods of assembly of elastomeric laminates and absorbent articles described herein and illustrated in the accompanying drawings are non-limiting example configurations. The features illustrated or described in connection with one non-limiting configuration may be combined with the features of other non-limiting configurations. Such modifications and variations are intended to be included within the scope of the present disclosure.

Figure 26:
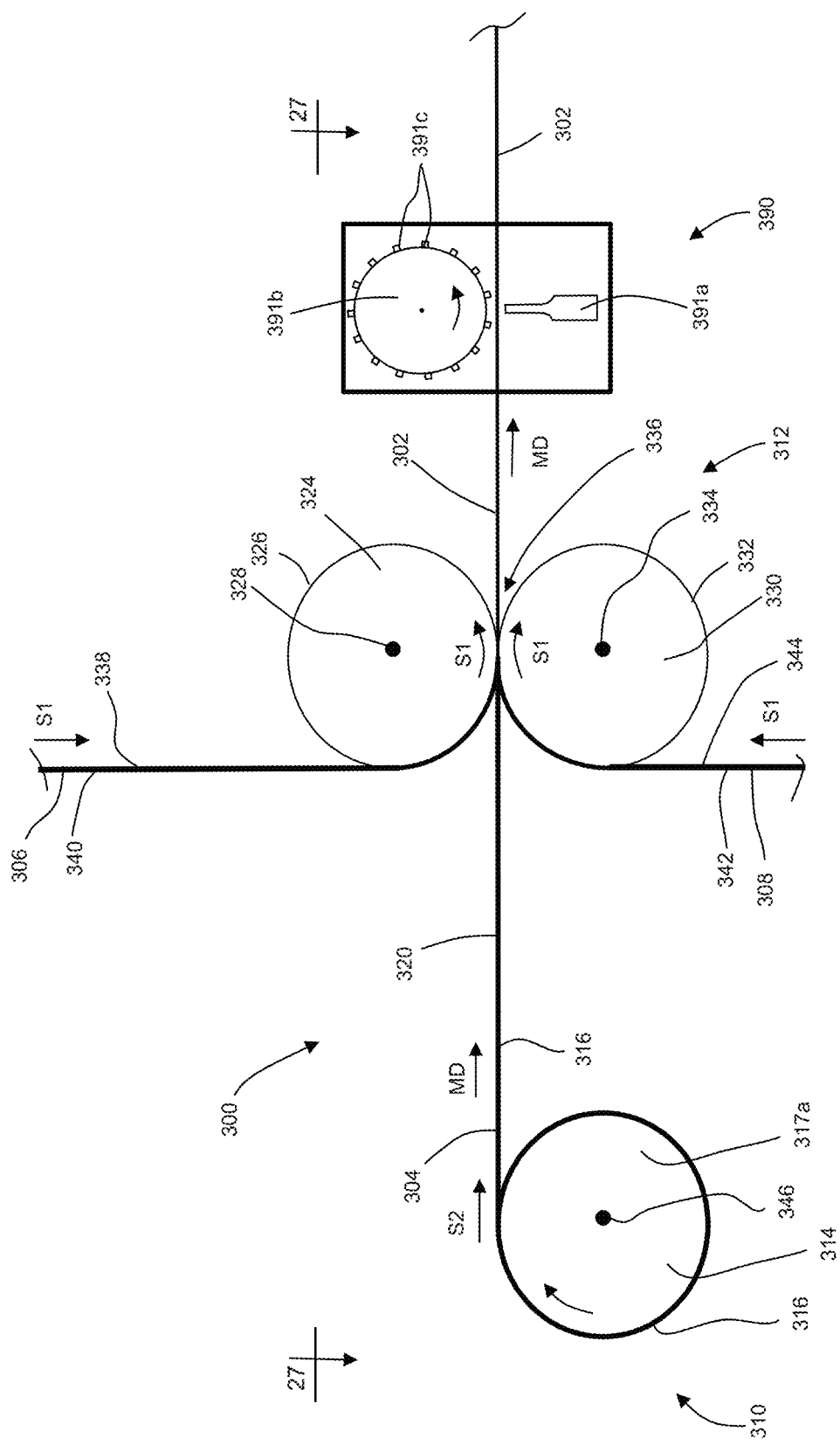
FIG. 26 is a schematic side view of a converting apparatus joining stretched elastic strands between a first substrate and a second substrate.
Figure 27:
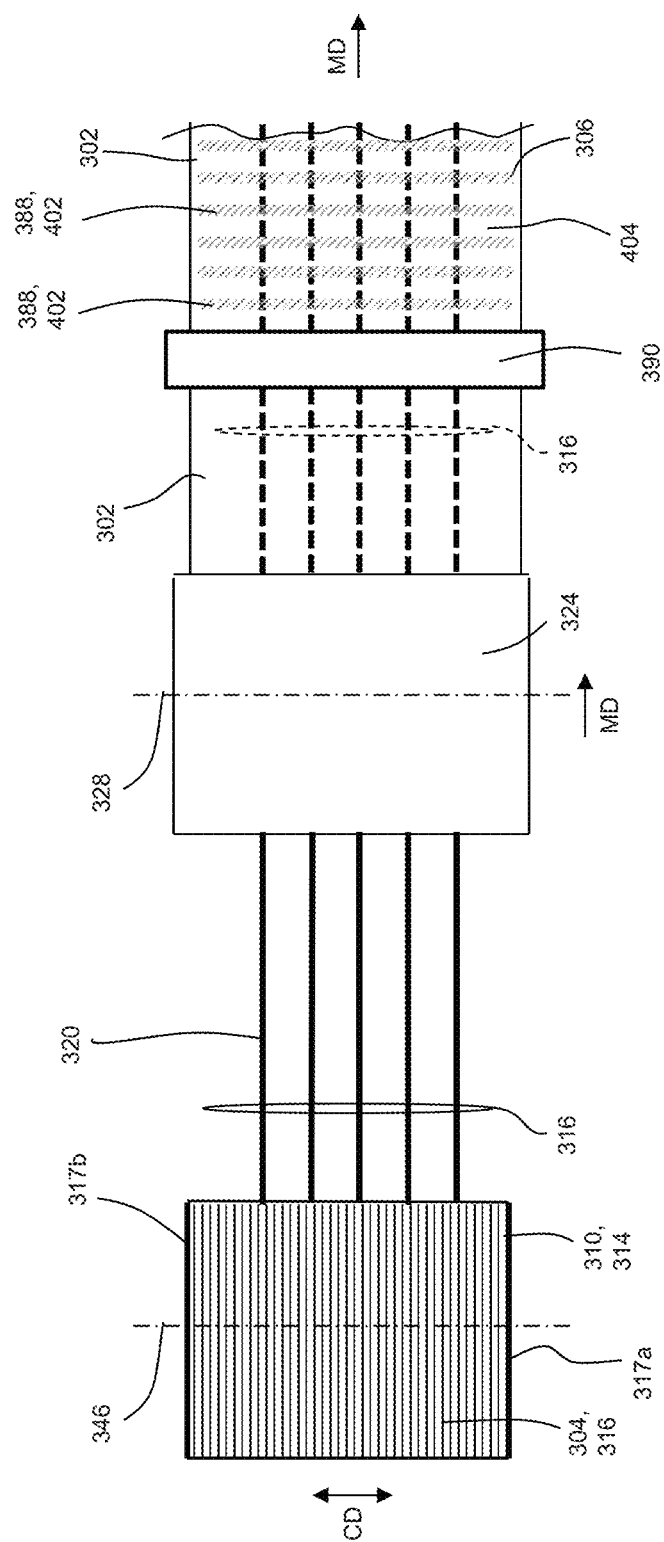
FIG. 27 is a view of the converting apparatus of FIG. 26 taken along line 27-27.

As shown in FIGS. 26 and 27, a converting apparatus 300 for producing an elastomeric laminate 302 may include a first metering device 310 and a second metering device 312. The first metering device 310 may be configured as a beam 314 with a plurality of elastic strands 316 wound thereon. During operation, the plurality of elastic strands 316 advance in the machine direction MD from the beam 314 to the second metering device 312. In addition, the plurality of elastic strands 316 may be stretched along the machine direction MD between the beam 314 and the second metering device 312. The stretched elastic strands 316 are also joined with a first substrate 306 and a second substrate 308 at the second metering device 312 to produce an elastomeric laminate 302. In some configurations, one or more of the elastic strands 316 advancing from the beam 314 may also include a spin finish 320 located on outer surfaces of the elastics strands. In turn, stretched elastic strands 316 may be connected between the first substrate 306 and the second substrate 308 with bonds 388. The bonds 388 may be configured as discrete mechanical bonds 388 applied to the first substrate 306 and the second substrate 308 to secure the elastic strands 316. The discrete bonds 388 may be arranged intermittently along the machine direction. In some configurations, the bonds 388 extend in the machine direction MD and may extend in the cross direction CD across one or more elastic strands 316. In some configurations, discrete bonds 388 may also be separated from each other in the cross direction CD.

FIGS. 26 and 27 show an arrangement of first and second rollers 324, 330 and associated features described above with reference to FIGS. 5 and 6 that may be utilized to combine elastic strands 316 and first and second substrates 306, 308 to produce a continuous length of elastomeric laminate 302. Although FIG. 27 shows five elastic strands 316 advancing from the beam 314, it is to be appreciated that the apparatuses herein may be configured such that more or less than five elastic strands 316 advance from the beam 314.

With continued reference to FIGS. 26 and 27, the advancing elastic strands 316 may be joined with the first substrate 306 and the second substrate 308 to form the elastomeric laminate 302. The elastic laminate 302 may also advance past a bond applicator 390 configured to apply bonds 388 that secure the elastic strands 316 between the first substrate 306 and the second substrate 308. One or more of the elastic strands 316 advancing from the beam 314 may include a spin finish 320. As such, the bonds 388 may be configured to secure the elastic strands 316 between the first and second substrates 306, 308 without having to remove the spin finish 320 from the elastic strands 316. It is also to be appreciated that the methods and apparatuses herein may also be configured to remove the spin finish 320 from the elastic strands 316. Examples of spin finish removal processes and apparatuses are described herein and disclosed in U.S. Provisional Patent Application No. 62/483,965, which is incorporated by reference herein. In addition, the elastic laminates 302 herein may be constructed with or without adhesives between the first and second substrates 306, 308. In addition, it is to be appreciated that the bonding methods and apparatuses herein may be utilized in conjunction with other bonding methods and apparatuses, such as disclosed in U.S. Patent Application No. 62/553,149, filed on Sep. 1, 2017, which is incorporated by reference herein.

As shown in FIG. 27, the bonds 388 may extend for discrete lengths along the machine direction MD and may be intermittently arranged along the machine direction of the elastic laminate 302. Thus, the elastic strands 316 may extend in the machine direction MD between intermittently spaced bond regions 402 and unbonded regions 404. It is to be appreciated that the bonds 388 may extend contiguously for various lengths in the cross direction CD and may extend across one or more elastic strands 316. The bonds 388 may also be separated from each other in the cross direction CD, such as shown for example in FIG. 32.

Figure 28A:
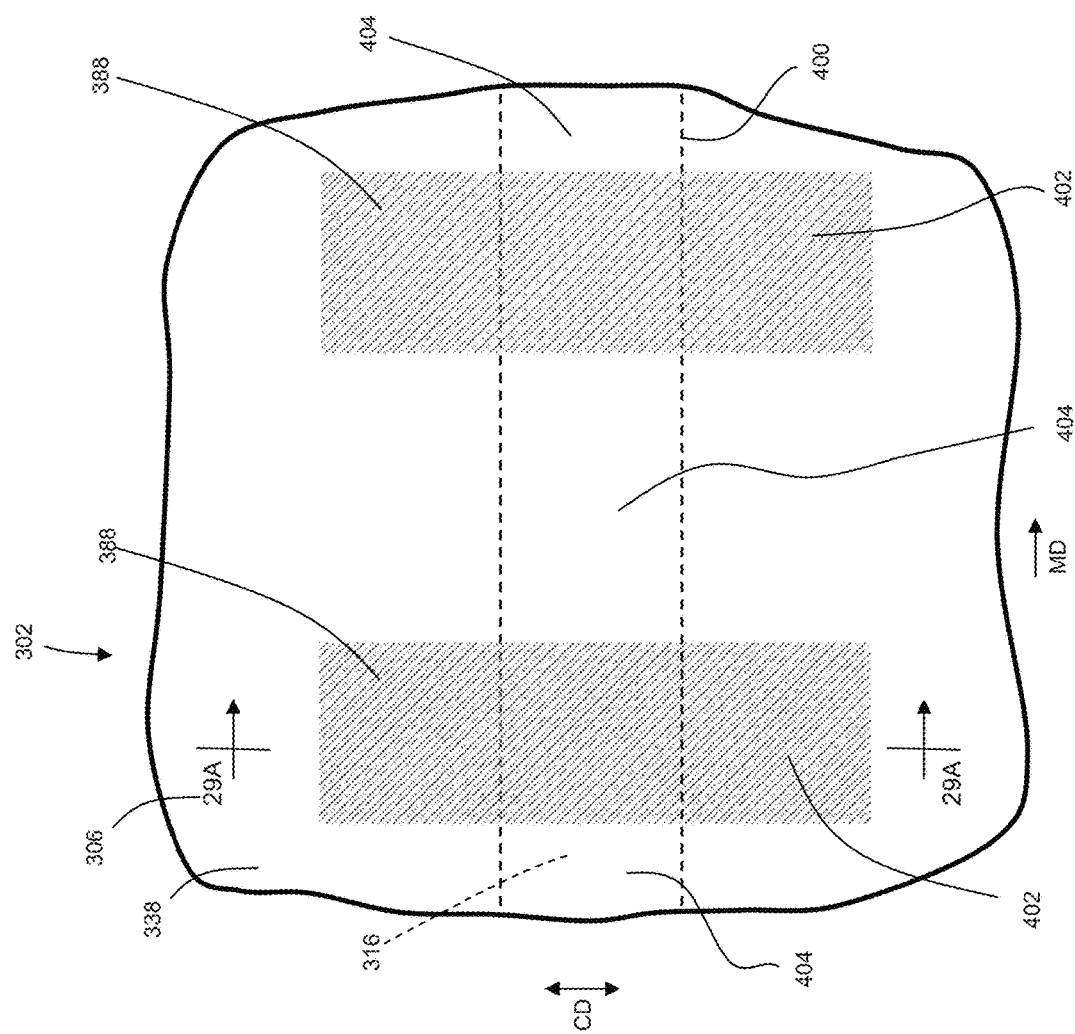
FIG. 28A is a detailed view of an elastic strand in a stretched state bonded between the first and second substrates.
Figure 29A:
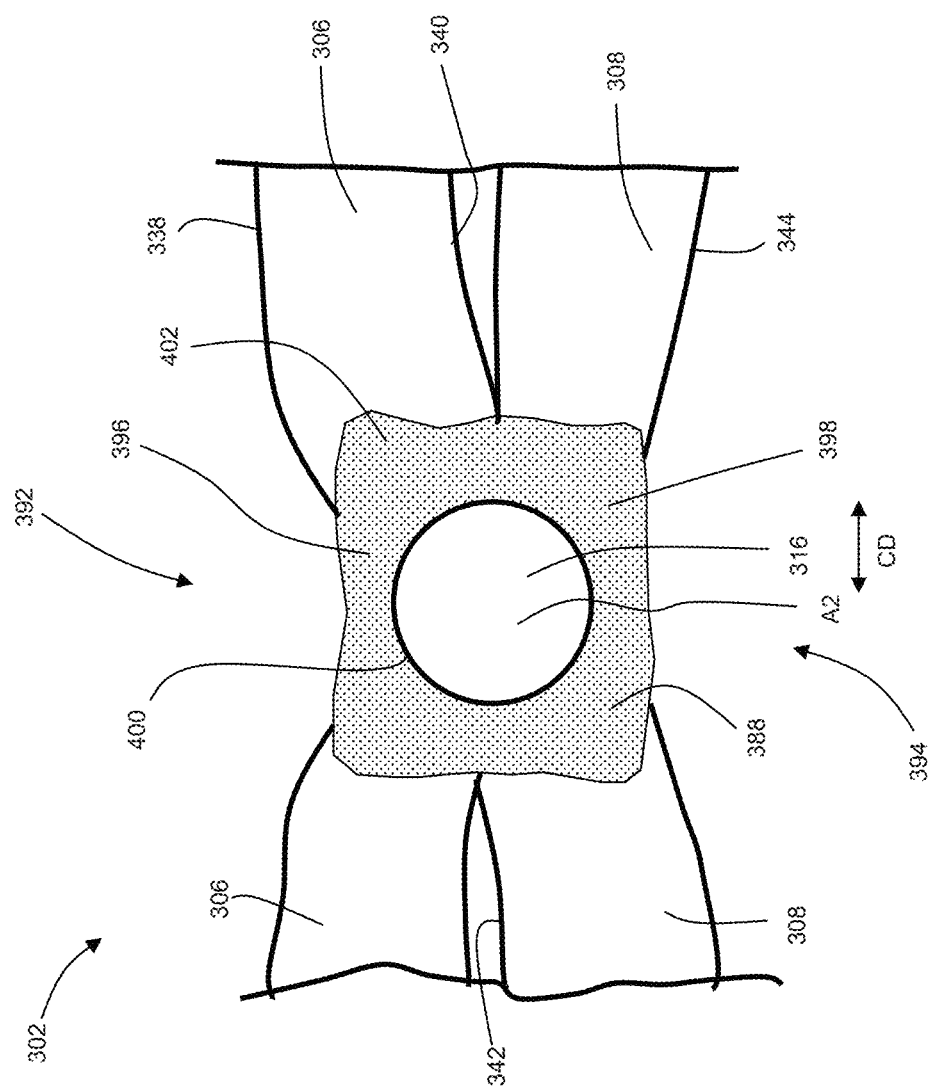
FIG. 29A is a sectional view of the elastic strand, bond, first substrate, and second substrate of FIG. 28A taken along line 29A-29A.

FIGS. 28A and 29A are detailed views of an elastic strand 316 in a stretched state secured with bonds 388 between the first and second substrates 306, 308. During the bonding process, the bond applicator 390 may apply heat and pressure to a first region 392 of the first substrate 306 and a second region 394 of the second substrate 308 such that first material 396 of the first substrate 306 and second material 398 of the second substrate 308 become malleable. In turn, the malleable first and second materials 396, 398 deform and completely surround an outer perimeter 400 of a discrete length of the stretched elastic strand 316 in a bond region 402. The heat and pressure are removed from the first region 392 of the first substrate 306 and the second region 394 of the second substrate 308 as the elastic laminate 302 advances from the bond applicator 390, and as such, the malleable first and second materials 396, 398 harden in a bond 388 that conforms with a cross sectional shape defined by the outer perimeter 400 of the stretched elastic strand 316. In some configurations, an external heat source may be used to generate the heat used in the bonding process, such as with a heated anvil. It is also to be appreciated that heat may be generated solely by the bonding process, such as for example, heat generated by an ultrasonic horn vibration or heat generated by a fusion bonding process, wherein no external heat source is required. In some configurations, tooling used in the bonding process may also be chilled to help provide and/or control the process temperatures at desired levels.

Figure 26A:
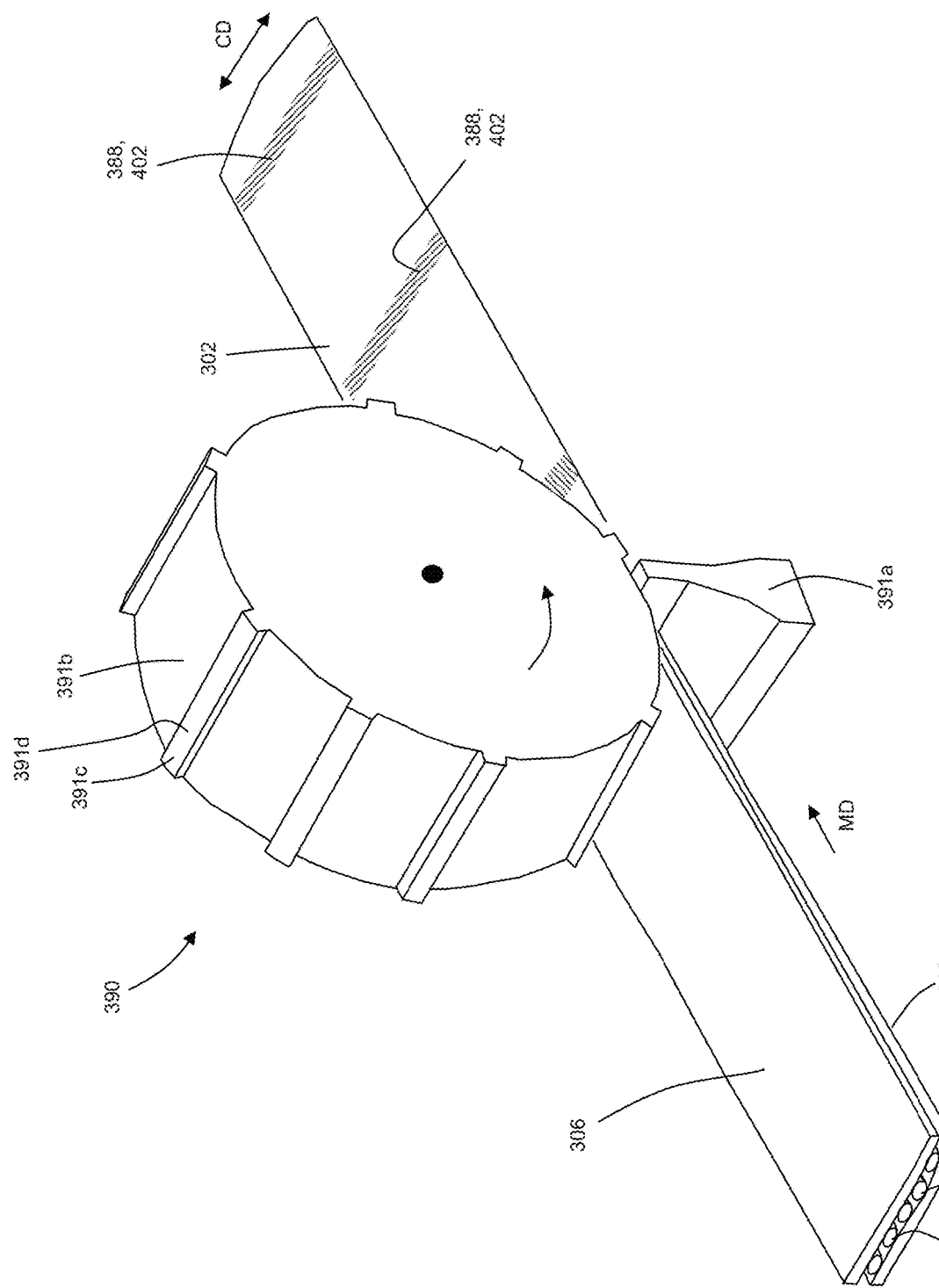
FIG. 26A is a detailed view of an example bonding apparatus configured with an anvil and ultrasonic horn.

It is to be appreciated that the bond applicator 390 may be configured in various ways, such as for example, heated or unheated patterned and anvil rolls and/or ultrasonic bonding devices. When configured as an ultrasonic bonding device such as schematically shown in FIGS. 26 and 26A, the bond applicator 390 may include a horn 391a and may be configured to impart ultrasonic energy to the combined substrates 306, 308 and elastic strands 316 on an anvil 391b. In turn, the anvil 391b may include a plurality of pattern elements 391c protruding radially outward from the anvil 391b, wherein each pattern element includes a pattern surface 391d. It is to be appreciated that the number, size, and shape of some or all the pattern surfaces and/or pattern elements may be different. In some embodiments, the shape and size of the pattern surface 391d of each pattern element 391c may be identical or substantially identical to each other. In some configurations, the pattern elements 391c and/or pattern surfaces 391d may have a perimeter that defines circular, square, rectangular, elliptical, and various types of other shapes. In some configurations, the anvil 391b may include a pattern element 391c with a pattern surface 391d that defines a continuous crossing line pattern and/or various other shapes, such as disclosed in U.S. Pat. No. 9,265,672, which is incorporated by reference herein. It is to be appreciated that the pattern surface 391d, such as discussed above, may be flat and/or may also include regions defined by relatively high and relatively low elevations. Thus, such pattern surfaces may create bonds 388 having varying thicknesses across the bond region 402. In addition, it is to be appreciated that an elastic strand 316 may extend across such relatively high and low elevations during the bonding process. It is to be appreciated that the choice of pattern surface shape may enable the creation of unique textures and patterns where the location and size of the bonding sites impact local buckling resistance of a nonwoven laminate and may create desired homogeneous textures upon relaxation of the elastics and the resulting nonwoven corrugation.

With continued reference to FIGS. 26 and 26A, the ultrasonic bonding device may apply energy to the horn 391a to create resonance of the horn at frequencies and amplitudes so the horn vibrates rapidly in a direction generally perpendicular to the substrates 306, 308 and elastic strands 316 being advanced past the horn 391a on the anvil 391b. Vibration of the horn 391a generates heat to melt and bond the substrates 306, 308 together in areas supported by the pattern elements 391c on the anvil 391b. Thus, the bonds 388 and/or bond regions 402 may have shapes that correspond with and may mirror shapes of the pattern surfaces 391d. As shown in FIG. 26A, the pattern surface 391d may extend contiguously across one or more elastic strands 316 positioned between the first substrate 306, and the second substrate 308. It is to be appreciated that aspects of the ultrasonic bonding devices may be configured in various ways, such as for example linear or rotary type configurations, and such as disclosed for example in U.S. Pat. Nos. 3,113,225; 3,562,041; 3,733,238; 5,110,403; 6,036,796; 6,508,641; and 6,645,330. In some configurations, the ultrasonic bonding device may be configured as a linear oscillating type sonotrode, such as for example, available from Herrmann Ultrasonic, Inc. In some configurations, the sonotrode may include a plurality of sonotrodes nested together in the cross direction CD. The bond applicator 390 may also be configured in various other ways, such as for example, the mechanical bonding devices and methods disclosed in U.S. Pat. Nos. 4,854,984; 6,248,195; 8,778,127; and 9,005,392; and U.S. Patent Publication Nos. 2014/0377513 A1; and 2014/0377506 A1. Although the bond applicator 390 is shown in FIGS. 26 and 27 as a separate device that is positioned downstream of the second metering device 312, it is to be appreciated the second metering device 312 may also be configured as the bond applicator 390. As such, the first substrate 306, second substrate 308, and elastic strands 316 may be combined and bonded together at the bond applicator 390 to form the elastic laminate 302.

As previously mentioned, a frictional lock may be applied between a portion of the elastic strand 316 and the hardened first and second materials 396, 398 by releasing tension from the stretched elastic strand 316. The frictional lock acts to hold and/or secure the elastic strand 316 in a fixed position in the bond region 402. For the purposes of a general explanation, FIG. 16A shows a length of an elastic strand 316 in a unstretched or relaxed state, wherein the elastic strand 316 defines a first cross sectional area A1. And FIG. 16B shows a length of the elastic strand 316 from FIG. 16A in a stretched state, wherein the elastic strand 316 defines a second cross sectional area A2 that is less than the first cross sectional area A1. Thus, the cross sectional area of the stretched elastic strand 316 expands when tension is partially or fully released from the elastic strand 316. As discussed in more detail below, the tendency of the cross sectional area of the elastic strand 316 to expand helps create the frictional lock.

Figure 28B:
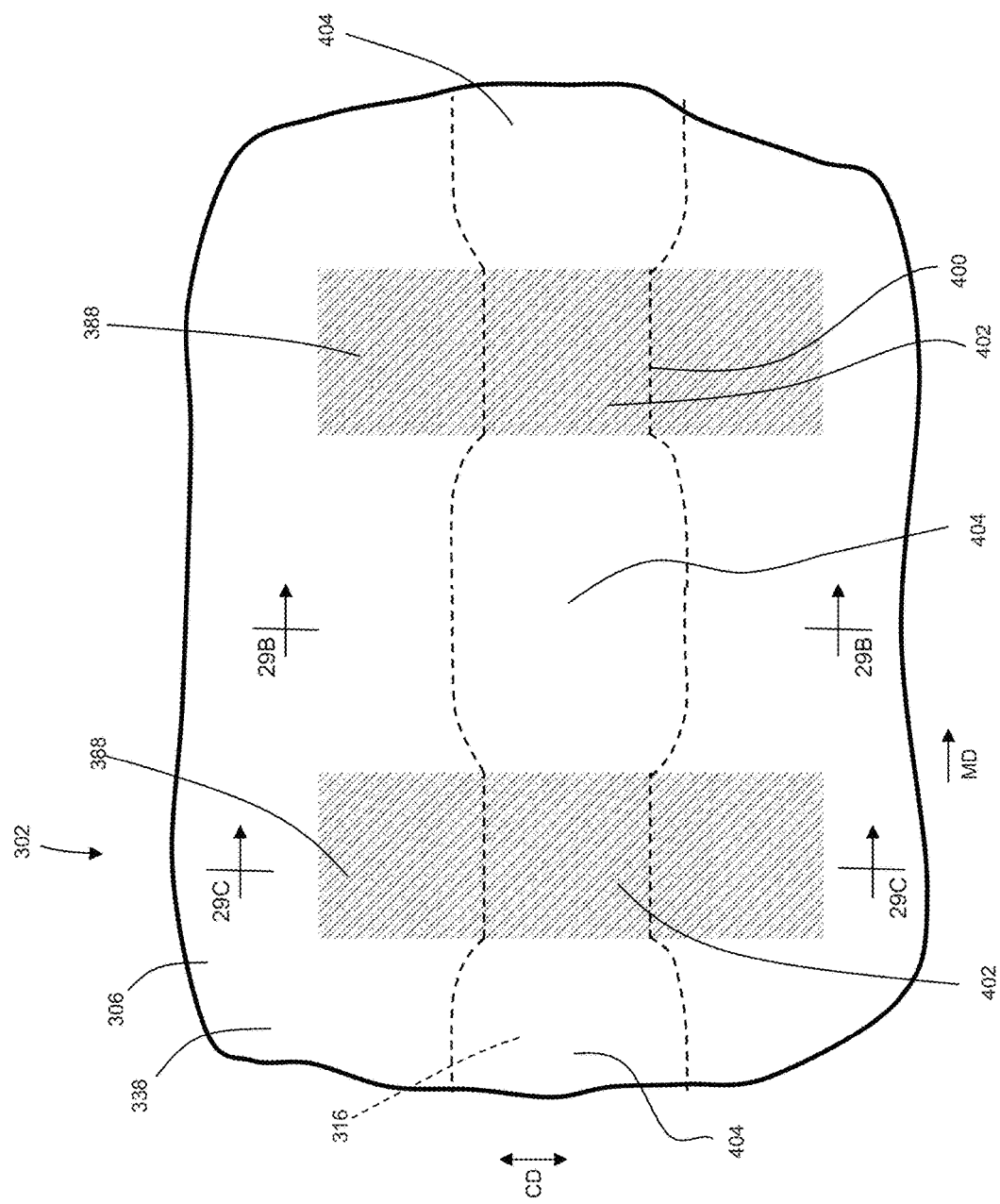
FIG. 28B is a detailed view of an elastic strand in a relaxed state bonded between the first and second substrates.
Figure 29B:
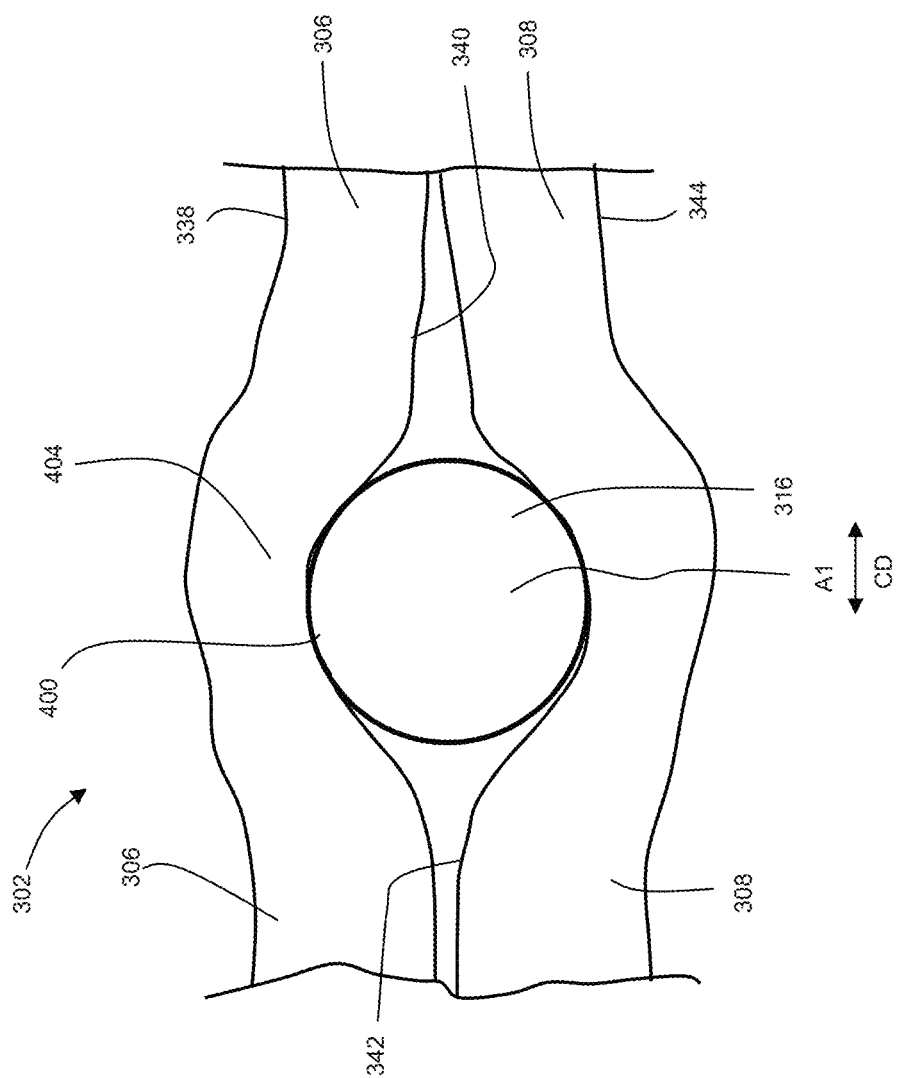
FIG. 29B is a sectional view of the elastic strand in a bonded region of FIG. 28B taken along line 29B-29B, wherein the elastic strand is in a relaxed state.

Turning next to FIG. 28B, a detailed view of an elastic strand 316, such as shown in FIG. 28A, is provided wherein tension has been released (or reduced) on the elastic strand 316 and showing how the tendency of the elastic strand 316 to expand creates a frictional lock in the bonded region 402. FIGS. 28B and 29B show the elastic strand 316 as having a first cross sectional area A1 in an unbonded region 404 of the elastic laminate 302, wherein the first cross sectional area A1 is greater than the second cross sectional area A2 of the stretched elastic strand 316 shown in FIGS. 28A and 29A. And FIGS. 28D and 29C show the elastic strand 316 as having a third cross sectional area A3 in the bond region 402 of the elastic laminate 302, wherein the third cross sectional area A3 is the same or about the same as the second cross sectional area A2 of the stretched elastic strand 316 shown in FIGS. 28A and 29A. As shown in FIG. 29C, the hardened first and second materials 396, 398 in the bond region 402 help prevent the cross sectional area of the elastic strand 316 from expanding when tension has on elastic strand 316 has been reduced. The tendency of the elastic strand 316 to expand creates forces F (represented by dashed double arrow lines in FIG. 29C) exerted between the hardened first and second materials 396, 398 in the bond region 402. In turn, the forces F between the elastic strand 316 and the hardened first and second materials 396, 398 creates a frictional lock by increasing the friction forces between the elastic strand 316 and the hardened materials 396, 398. The increased friction forces in the machine direction MD along the length of the elastic strand 316 in the bond region 402 holds the discrete length of the elastic strand 316 in a fixed position in the bond region 402 together with the first and second substrates 306, 308. As such, in some configurations, no adhesive may be applied to and/or present between the elastic strand 316 and the hardened materials 396, 398. It is also to be appreciated that in some configurations, adhesive may be applied to and/or present between the elastic strand 316 and the hardened materials 396, 398 to help the frictional lock hold the discrete length of the elastic strand 316 in a fixed position in the bond region 402 together with the first and second substrates 306, 308. In some configurations, adhesive and the frictional lock in the bond regions 402 may share the load exerted by elastic strand 316. In some configurations, adhesive positioned on the elastic strand 316 may increase the coefficient of friction between the elastic strand 316 and the hardened materials 396, 398 in the bond region 402. It is to be appreciated that various quantities of adhesive may be present in the bond regions 402, such as for example, about 10 gsm or less.

Figure 30A:
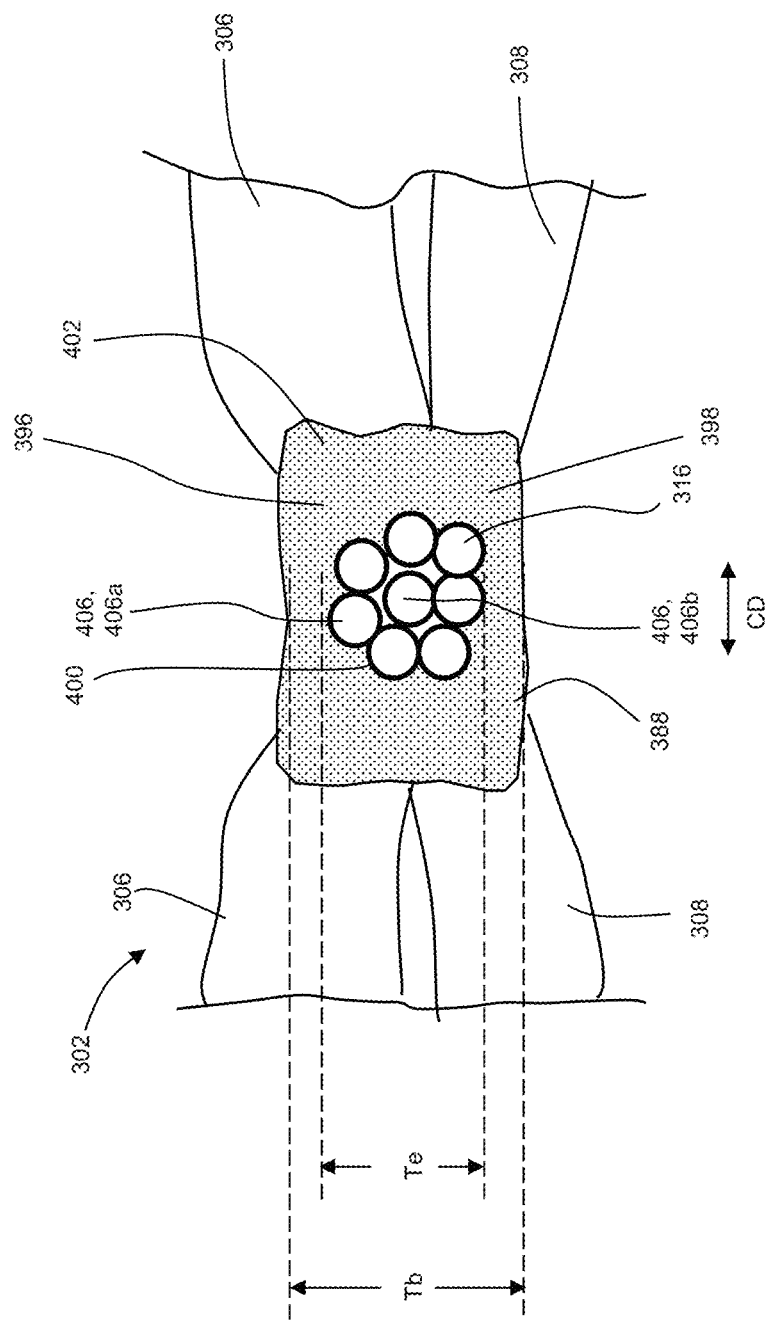
FIG. 30A is a sectional view of an elastic strand, bond, first substrate, and second substrate of FIG. 28A taken along line 29A-29A, wherein a plurality of filaments of the elastic strand are bonded in a first configuration.

It is also to be appreciated that the elastic strands 316 herein bonded in accordance with the methods described herein may also be constructed from one or more filaments 406. For example, FIG. 30A shows a cross sectional view of an elastic strand 316 in a bond region 402 wherein the elastic strand 316 comprises a plurality of individual filaments 406. As shown in FIG. 30A, the elastics strand 316 includes outer filaments 406a surrounding an inner filament 406b. The outer filaments 406a define the outer perimeter 400 of the elastic strand 316, and the outer filaments 406a may surround the inner filament 406b such that the inner filament 406b is not in contact with the hardened first material 396 and the hardened second material 398 in the bond 388. It is to be appreciated that the filaments 406 may be arranged in various positions within the bond region 402. For example, FIG. 30B shows a cross sectional view of an elastic strand 316 in a bond region 402 wherein the plurality of individual filaments 406 together define a perimeter 400 that is elongated along the cross direction CD, and wherein all of the plurality of filaments 406 are in contact with hardened first material 396 and hardened second material 398. In another example, FIG. 30C shows a cross sectional view of an elastic strand 316 in a bond region 402 wherein at least two of the filaments 406 are separated from each other by at least one of hardened first material 396 and hardened second material 398. It is to be appreciated that the elastic strand 316 may be constructed to allow for more or less separation of filaments 406 during the bonding operations herein. For example, in some elastic strand assembly configurations, a cooling operation, such as a manipulating twisting jet of air, may be utilized to modify adhesion properties of the filaments to desired levels. It is also to be appreciated that the strands 316 and/or filaments 406 herein may define various different cross-sectional shapes. For example, in some configurations, strands 316 or filaments 406 may define circular, oval, or elliptical cross sectional shapes or irregular shapes, such as dog bone and hourglass shapes.

As previously mentioned, substrates 306, 308 with elastic strands 316 positioned therebetween can be bonded in accordance with methods herein without severing the elastics strands and without the need for nesting grooves in bond applicator 390. For example, as shown in FIGS. 29C and 30A-30C, heat and pressure may be applied to the substrates 306, 308 to create bonds 388 surrounding the elastic strand 316. The bond 388 is defined by hardened first material 396 and hardened second material 398 and has a minimum thickness Tb. In addition, the elastic strand 316 may have a thickness Te in the bond region 402. In some configurations, substrates 306, 308 that are bonded together to create a bond thickness Tb having a certain size relative to the elastic strand thickness Te, the elastic strand 316 may not be severed during the bonding process. In addition, the forces F exerted between the elastic strand 316 and the hardened first and second materials 396, 398 in the bond region 402 may be prevented from breaking the bond 388. Such a relationship between Te and Tb may be characterized by the decitex of elastic strands 316 and the bond thickness Tb. For example, substrates 306, 308 may be bonded together with an elastic strand having a decitex value less than or equal to about 70 positioned therebetween to create a bond 388 having a thickness Tb of at least about 100 μm ("microns") without severing the elastic strand 316. In another example, substrates 306, 308 may be bonded together with an elastic strand having a decitex value less than or equal to about 250 positioned therebetween to create a bond 388 having a thickness Tb of at least about 200 μm ("microns") without severing the elastic strand 316. In some configurations, such as shown in FIG. 30C, the bond thickness Tb may be at least 50% larger than the minimum cross sectional thickness Tf a filament 406. For example, as shown in FIG. 30C, the minimum cross sectional thickness Tf of a filament 406 having a circular cross section may be defined the diameter of such a filament.

Figure 30E:
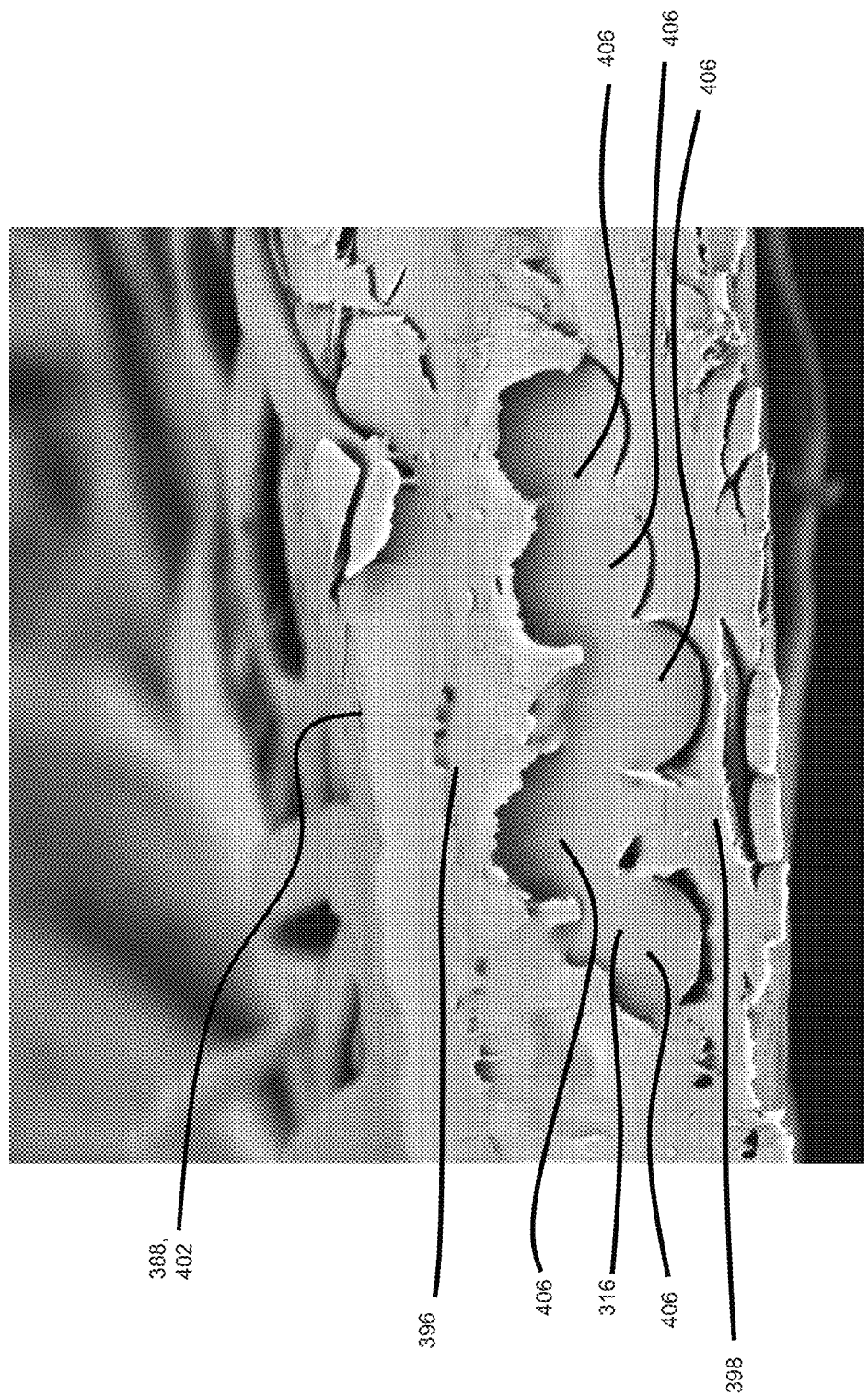
FIG. 30E is a scanning electron microscope ("SEM") photograph of a cross sectional view of an elastic strand including five filaments in a bonded region and surrounded by hardened first and second materials.
Figure 30F:
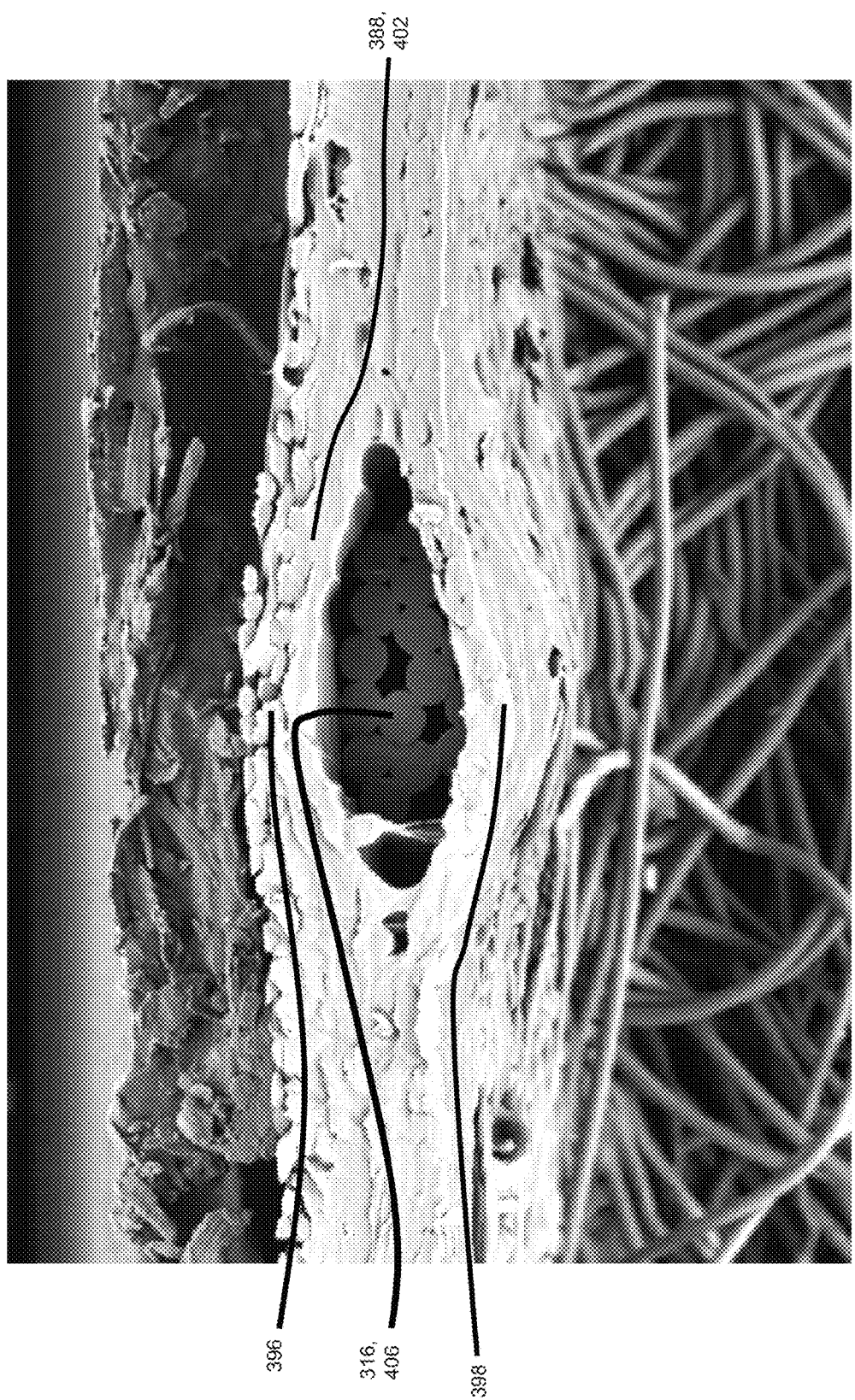
FIG. 30F is a scanning electron microscope ("SEM") photograph of a cross sectional view of an elastic strand including fifteen filaments in a bonded region and surrounded by hardened first and second materials.

FIGS. 30D-30F are electron microscope photographs ("SEM") showing cross sectional views of an elastic strand 316 in a bond region 402 surrounded by hardened first and second materials 396, 398 from two nonwovens. In FIGS. 30D and 30E, the elastic strand 316 is a 70 decitex elastic strand including five filaments 406, wherein each filament 406 has a diameter of about 43 μm ("microns"). And the bond 388 defines a thickness Tb of about 80 μm ("microns"). In FIG. 30F, the elastic strand 316 is a 235 decitex elastic strand including fifteen filaments 406, wherein each filament 406 has a diameter of about 43 μm ("microns"). And the bond 388 defines a thickness Tb of about 200 μm ("microns").

Figure 31:
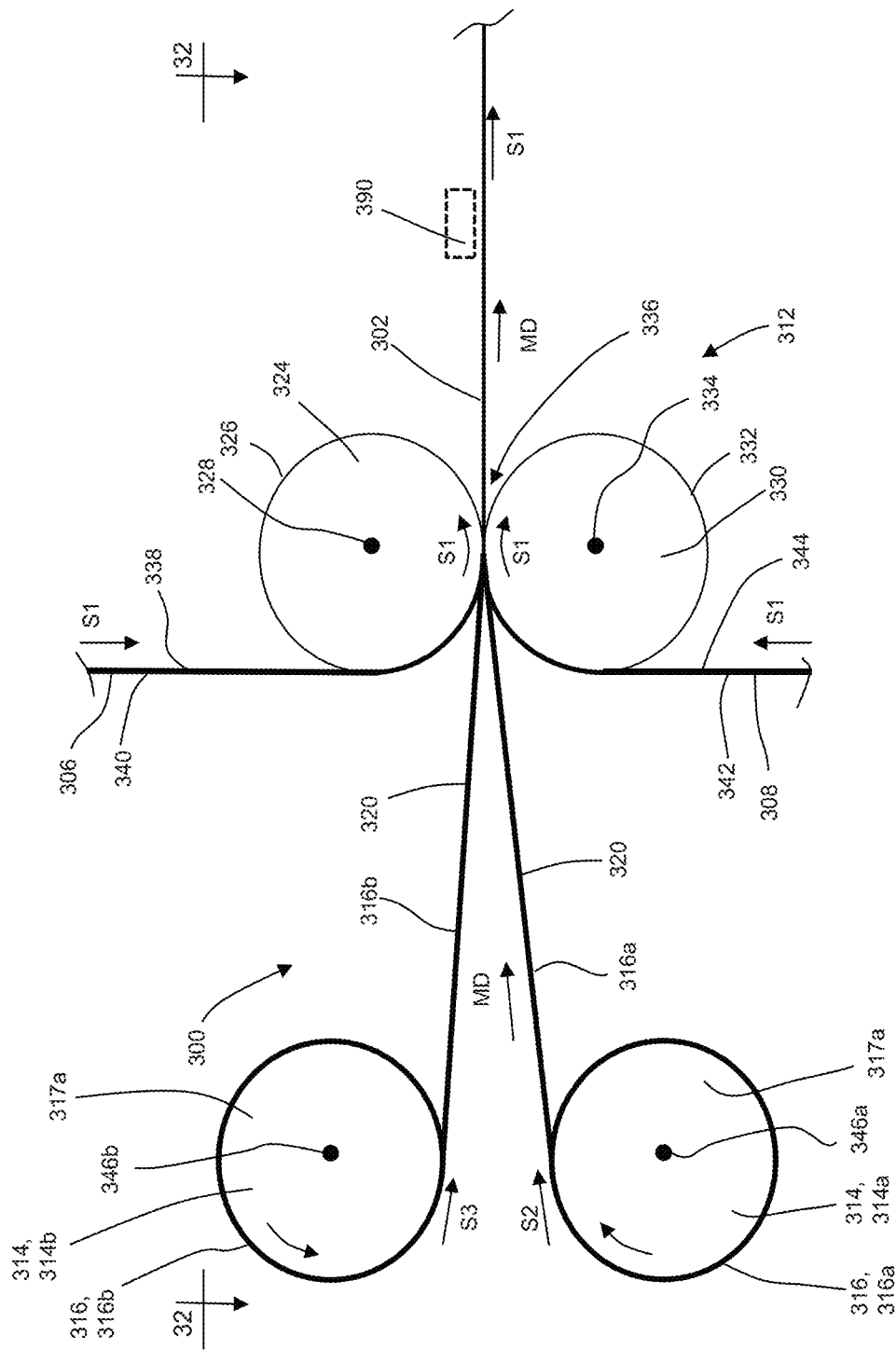
FIG. 31 is a schematic side view of another configuration of a converting apparatus joining elastic strands between a first substrate and a second substrate, wherein the elastic strands drawn from different beams are stretched to have different elongations.
Figure 32:
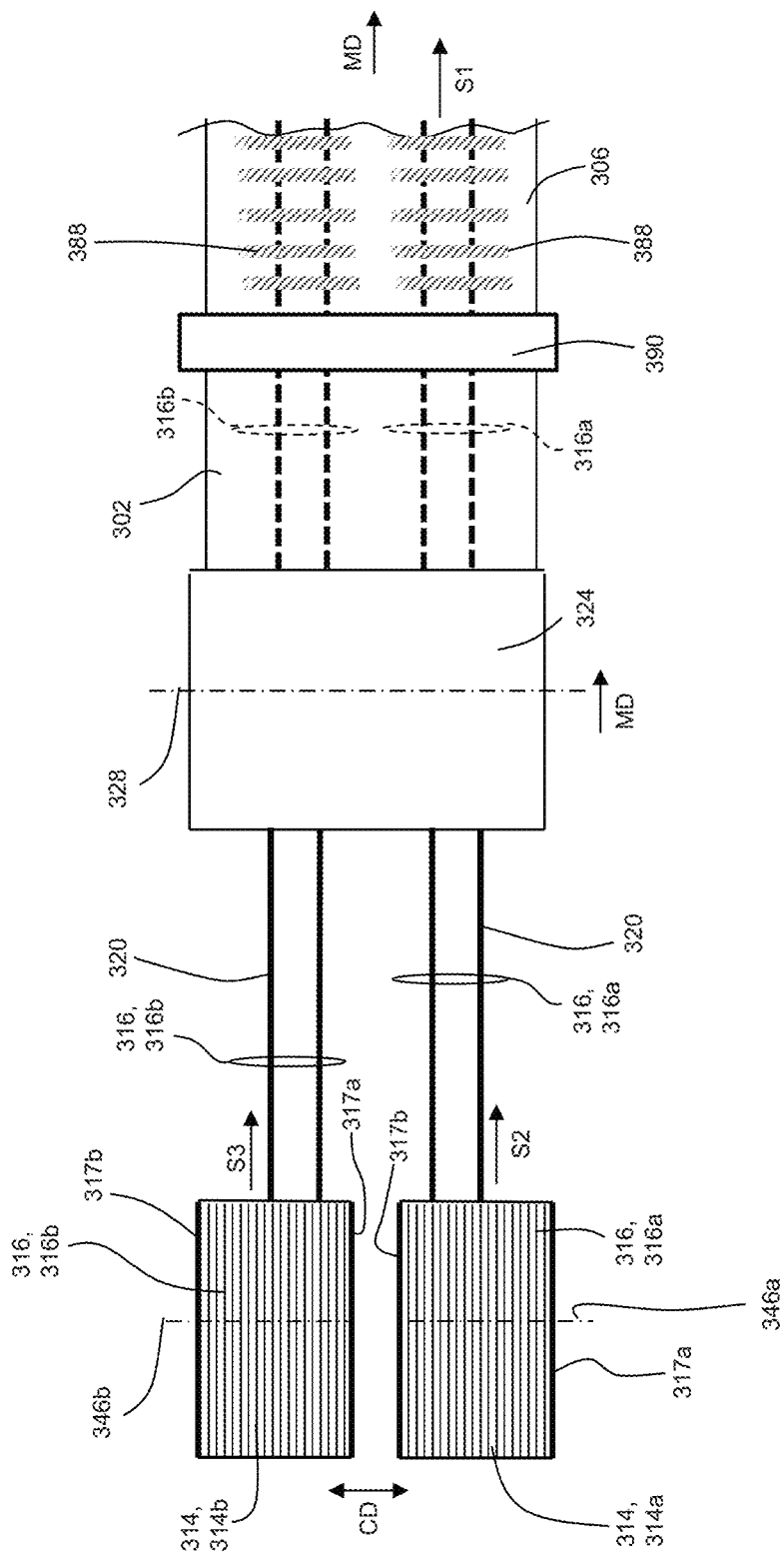
FIG. 32 is a view of the converting apparatus of FIG. 31 taken along line 32-32.

As previously mentioned, it is to be appreciated that the apparatuses 300 herein may be configured in various ways with various features described herein to assemble elastomeric laminates 302 having various stretch characteristics. In addition, the apparatuses 300 herein may be configured in various ways with various features described herein to assemble elastomeric laminates 302 having various stretch characteristics. For example, the apparatus 300 may be configured to assemble elastomeric laminates 302 with elastic strands 316 unwound from more than one beam and/or in combination with elastic stands supplied from various types of elastic unwinder configurations, such as an overend unwinder or surface driven unwinder and unwinders such as disclosed in U.S. Pat. Nos. 6,676,054; 7,878,447; 7,905,446; and 9,156,648. For example, FIGS. 31 and 32 illustrate the apparatus 300 configured to assemble elastomeric laminates 302 with elastic strands 316 unwound from more than one beam 314. In particular, the apparatus 300 may include a first beam 314a with first elastic strands 316a wound thereon and a second beam 314b with second elastic strands 316b wound thereon. The first beam 314a is rotatable about a first beam rotation axis 346a, and the second beam 314b is rotatable about a second beam rotation axis 346b. During operation, as the first beam 314a rotates, the first elastic strands 316a advance in the machine direction MD from the first beam 314a at a speed S2 with the first elastic strands 316a being spaced apart from each other in the cross direction CD. From the first beam 314a, the first elastic strands 316a advance in the machine direction MD and are joined with the first substrate 306 and the second substrate 308 as discussed above. Similarly, as the second beam 314b rotates, the second elastic strands 316b advance in the machine direction MD from the second beam 314b at a speed S3 with the second elastic strands 316b being spaced apart from each other in the cross direction CD. From the second beam 314b, the second elastic strands 316b advance in the machine direction MD and are joined with the first substrate 306 and the second substrate 308 as discussed above. It is also to be appreciated that the apparatus configuration shown in FIGS. 31 and 32 may also include the bond applicator 390 arranged to apply the bonds 388 as discussed above. The bond applicator 390 is generically represented by a dashed-line rectangle in FIG. 31.

As previously mentioned, the elastic strands 316 may be joined with the first and second substrates 306, 308 such that the elastomeric laminate 302 may have different stretch characteristics in different regions. For example, with continued reference to FIGS. 31 and 32, the elastic strands 316a, 316b may be joined with the first and second substrates 306, 308 such that the elastomeric laminate 302 may have different stretch characteristics in different regions along the cross direction CD, such as discussed above with reference to FIGS. 21 and 22.

Figure 33:
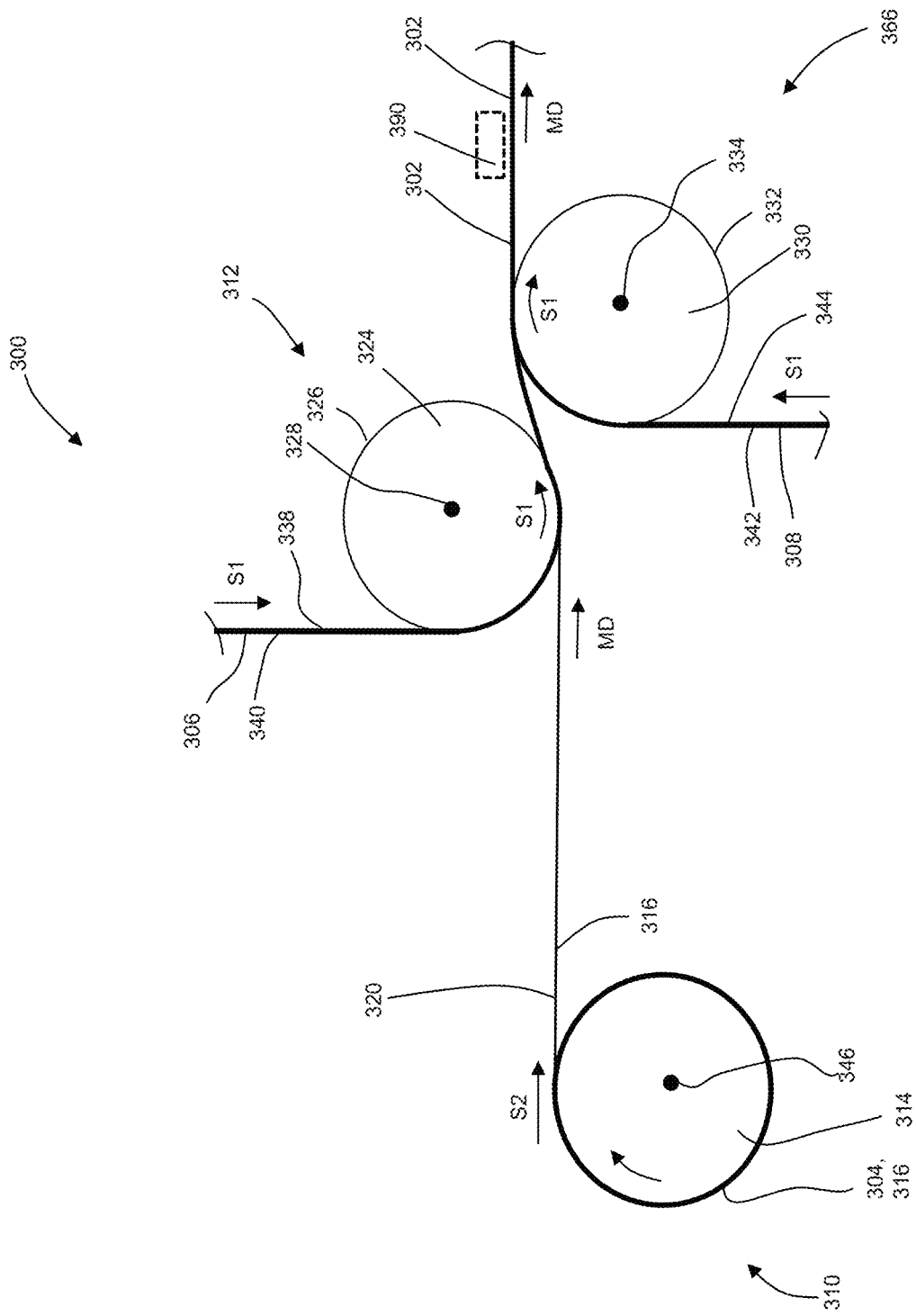
FIG. 33 is a schematic side view of another configuration of a converting apparatus adapted to manufacture an elastomeric laminate.

FIG. 33 shows an arrangement of first and second rollers 324, 330 and associated features described above with reference to FIG. 9 configured with the bond applicator 390 arranged to apply the bonds 388 that may be utilized to combine elastic strands 316 and first and second substrates 306, 308 to produce a continuous length of elastomeric laminate 302.

Figure 34:
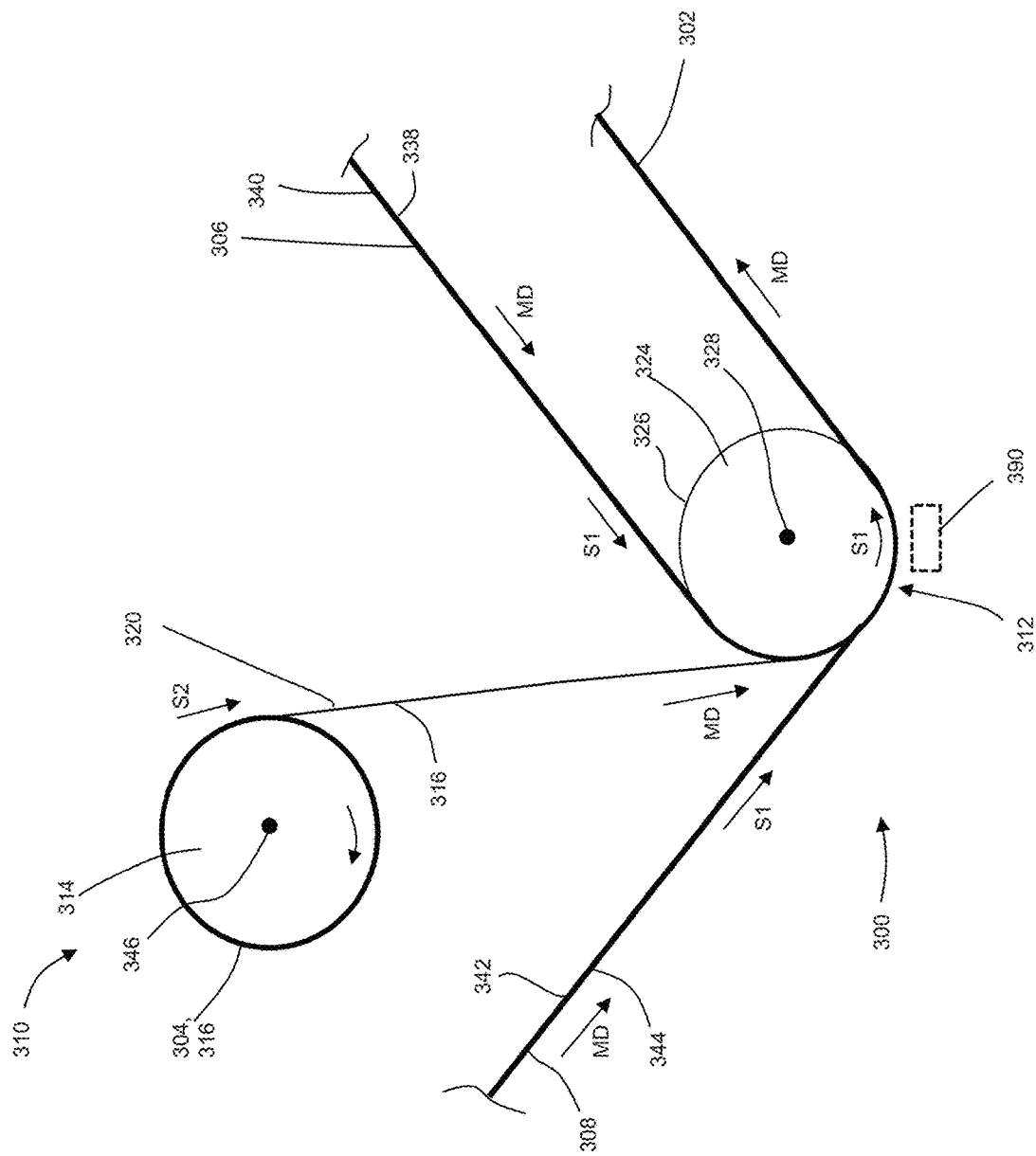
FIG. 34 is a schematic side view of another configuration of a converting apparatus adapted to manufacture an elastomeric laminate.

In another configuration shown in FIG. 34, the apparatus 300 may be configured with only the first roller 324 and without a second roller 330, such as described above with reference to FIG. 10. As such, the first roller 324 may be configured as the second metering device 312. In addition, the first roller 324 may also be configured as a component of the bond applicator 390. As shown in FIG. 34, the first substrate 306 advances at speed S1 to the first roller 324 where the first substrate 306 partially wraps around the outer circumferential surface 326 of the first roller 324. While partially wrapped around the outer circumferential surface 326 of the first roller 324, the first substrate 306 is combined with the elastic strands 316 and the second substrate 308. As the beam 314 rotates, the elastic strands 316 advance from the beam 314 at a speed S2 with the elastic strands 316 being spaced apart from each other in the cross direction CD. From the beam 314, elastic strands 316 advance to the first roller 324 and are positioned on the second surface 340 of the first substrate 306. In some configurations, the speed S2 is less than the speed S1, and as such, the elastic strands 316 are stretched in the machine direction MD. With continued reference to FIG. 34, the second substrate 308 advances at speed S1 to the first roller 324 and partially wraps around the outer circumferential surface 326 of the first roller 324. In turn, the second substrate 308 is combined with the first substrate 306 and the stretched elastic strands 316 while on the first roller 324 such that the elastic strands 316 are joined with the second surface 340 of the first substrate 306 and the first surface 342 of the second substrate 308 to produce a continuous length of elastomeric laminate 302. In addition, the bond applicator 390 may be configured to apply the bonds 388 before elastic laminate 302 advances from the first roller 324.

In some configurations, the speed S2 is less than the speed S1, and as such, the elastic strands 316 are stretched in the machine direction MD. With continued reference to FIG. 34, the second substrate 308 advances at speed S1 to the first roller 324 and partially wraps around the outer circumferential surface 326 of the first roller 324. In turn, the second substrate 308 is combined with the first substrate 306 and the stretched elastic strands 316 while on the first roller 324 such that the elastic strands 316 are joined with the second surface 340 of the first substrate 306 and the first surface 342 of the second substrate 308 to produce a continuous length of elastomeric laminate 302. In addition, the bond applicator 390 may be configured to apply the bonds 388 before elastic laminate 302 advances from the first roller 324.

As previously mentioned, it is also to be appreciated that in some configurations, the first substrate and second substrate 306, 308 herein may be defined by two discrete substrates or may be defined by folded portions of a single substrate. For example, as shown in FIG. 35, the first substrate 306 advances at speed S1 to the first roller 324 where the first substrate 306 partially wraps around the outer circumferential surface 326 of the first roller 324. While partially wrapped around the outer circumferential surface 326 of the first roller 324, the first substrate 306 is combined with the elastic strands 316. As the beam 314 rotates, the elastic strands 316 advance from the beam 314 at a speed S2 with the elastic strands 316 being spaced apart from each other in the cross direction CD. From the beam 314, elastic strands 316 advance to the first roller 324 and are positioned on the second surface 340 of the first substrate 306. As shown in FIGS. 35 and 36, a folding device 368 may operate to fold a first portion 306a onto a second portion 306b of the first substrate with the elastic strands 316 positioned between the first and second portions 306a, 306b to create the elastic laminate 302. As shown in FIGS. 35 and 37, the bond applicator 390 may be configured to apply the bonds 388 before elastic laminate 302 advances from the first roller 324.

In some configurations discussed below, methods and apparatuses may be configured to make elastomeric laminates with deactivated regions that may be used as components of absorbent articles. The methods and apparatuses according to the present disclosure may be configured with a pattern roll and a pressing surface adjacent the pattern roll. The pattern roll may be adapted to rotate about an axis of rotation extending axially in a cross direction, and the pressing surface may be configured as an energy transfer surface of an ultrasonic horn. The pattern roll may include a bonding surface and discrete first channels in the bonding surface, wherein the discrete first channels are circumferentially spaced apart from each other. The pattern roll may also include a protuberance extending axially in the cross direction between two of the discrete first channels. As discussed in more detail below, the assembly process utilizes elastic strands that define a first cross sectional area in an unstretched state, and the elastic strands are stretched to define a second cross sectional area that is less than the first cross sectional area. The first and second substrates with the stretched elastic strands therebetween advance in a machine direction on the pattern roll, wherein stretched elastic strands extend through the discrete first channels. As the pattern roll rotates, the first substrate and the second substrate are welded together between the bonding surface and the pressing surface to create bonds between the first and second substrates. The bonds are separated from each other in the cross direction by the stretched elastic strands positioned in respective discrete first channels to form first sleeves surrounding the stretched elastic strands. The first sleeves may each define a cross sectional area that is less than the first cross sectional area and equal to or greater than the second cross sectional area. As the pattern roll continues to rotate, the first substrate, the second substrate, and one or more stretched elastic strands are compressed between the pressing surface and the protuberance to sever the one or more stretched elastic strands to create deactivated regions in the elastomeric laminate. In turn, the one or more severed elastic strands retract and expand to create a frictional lock between the first sleeves and the one or more severed elastic strands.

As such, the frictional lock prevents the severed elastic strand from continuing to retract.

As discussed in more detail below, the processes and apparatuses herein may also be configured to help prevent ends of the severed elastic strands from snapping back or retracting in an uncontrolled fashion. For example, during the assembly process, the first substrate, the second substrate, and the stretched elastic strands may be wrapped on the rotating pattern roll. In turn, tension exerted on the first and second substrates force the substrates against the pattern roll, and thus, may help to press and hold the stretched elastic strands in position between the first and second substrates. Thus, as the stretched elastic strands are severed, the ends of the severed elastic strands may tend to retract or snap back at a relatively slower and/or controlled rate. In some configurations, the pattern roll may include second discrete channels that may be circumferentially positioned between first discrete channels and/or between first discrete channels and the protuberance. The discrete second channels may also be wider and and/or deeper than the first discrete channels. As the pattern roll rotates, the first substrate and the second substrate are welded together between the bonding surface and the pressing surface to create bonds between the first and second substrates, wherein the bonds are separated from each other in the cross direction by the stretched elastic strands positioned in respective second channels to form second sleeves surrounding the stretched elastic strands. The second sleeves may each define a cross sectional area that is greater than the cross sectional area of a first sleeve. Thus, the ends of the severed elastic strands may retract through the second sleeves while at the same time being guided along the machine direction by the second sleeves while retracting.

As previously mentioned, apparatuses and methods according to the present disclosure may be utilized to produce elastomeric laminates that may be used to construct various types of absorbent article components, such as elastic belts, leg cuffs, and the like. For example, FIGS. 38-49 show various aspects of converting apparatuses 300 adapted to manufacture elastomeric laminates 302. As described in more detail below, the converting apparatuses 300 operate to advance a continuous length of elastic material 304, a continuous length of a first substrate 306, and a continuous length of a second substrate 308 along a machine direction MD. It is also to be appreciated that in some configurations, the first substrate and second substrate 306, 308 herein may be defined by two discrete substrates or may be defined by folded portions of a single substrate. The apparatus 300 stretches the elastic material 304 and joins the stretched elastic material 304 with the first and second substrates 306, 308 to produce an elastomeric laminate 302. Although the elastic material 304 is illustrated and referred to herein as strands 316, it is to be appreciated that elastic material 304 may include one or more continuous lengths of elastic strands, ribbons, and/or films.

As discussed in more detail below, the converting apparatuses 300 may include metering devices arranged along a process machine direction MD, wherein the metering devices may be configured to stretch the advancing elastic material and/or join stretch elastic material with one or more advancing substrates. In some configurations, an upstream metering device may comprise an overend unwind device and/or a beam of elastic strands wound thereon. During operation, elastic material may advance in a machine direction from an upstream metering device to a downstream metering device to be joined with one or more advancing substrates to form an elastomeric laminate. The elastomeric laminate is partially wrapped onto a pattern roll adjacent a pressing surface. The pattern roll rotates and advances the elastomeric laminate between the pattern roll and the pressing surface, wherein bonds are applied to the first substrate and the second substrate to secure discrete lengths of the stretched elastic strands between the first and second substrates. The discrete bonds may be arranged intermittently along the machine direction. In some configurations, bonds may be separated from each other in a cross direction by an elastic strand. The pattern roll and pressing surface also operate to remove the elasticity of discrete regions of the elastomeric laminate by cutting one or more elastic strands in the discrete regions. It is to be appreciated that the apparatuses and methods of assembly of elastomeric laminates and absorbent articles described herein and illustrated in the accompanying drawings are non-limiting example configurations. The features illustrated or described in connection with one non-limiting configuration may be combined with the features of other non-limiting configurations. Such modifications and variations are intended to be included within the scope of the present disclosure.

Figure 38:
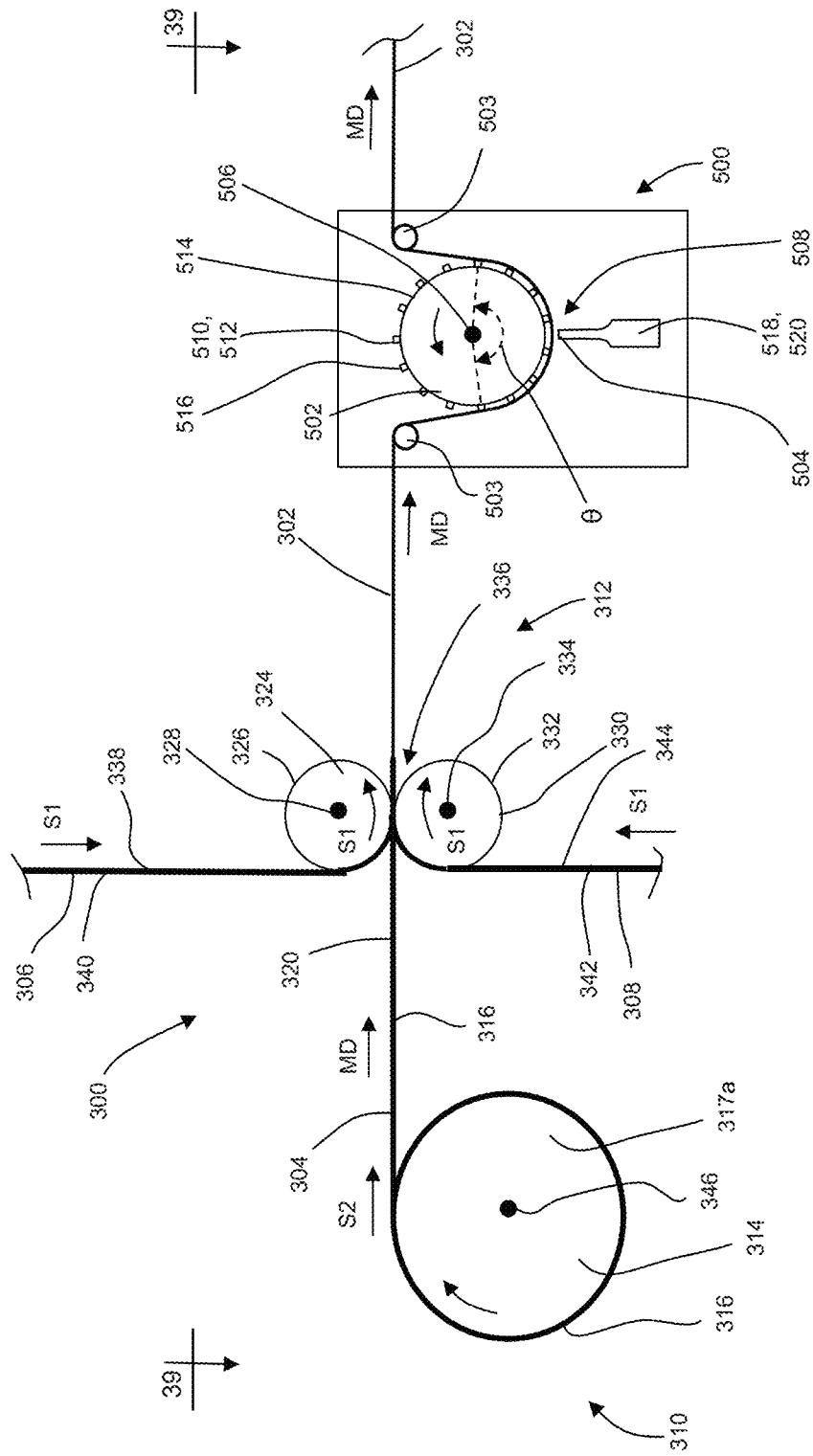
FIG. 38 is a schematic side view of a converting apparatus joining stretched elastic strands between a first substrate and a second substrate.
Figure 39:
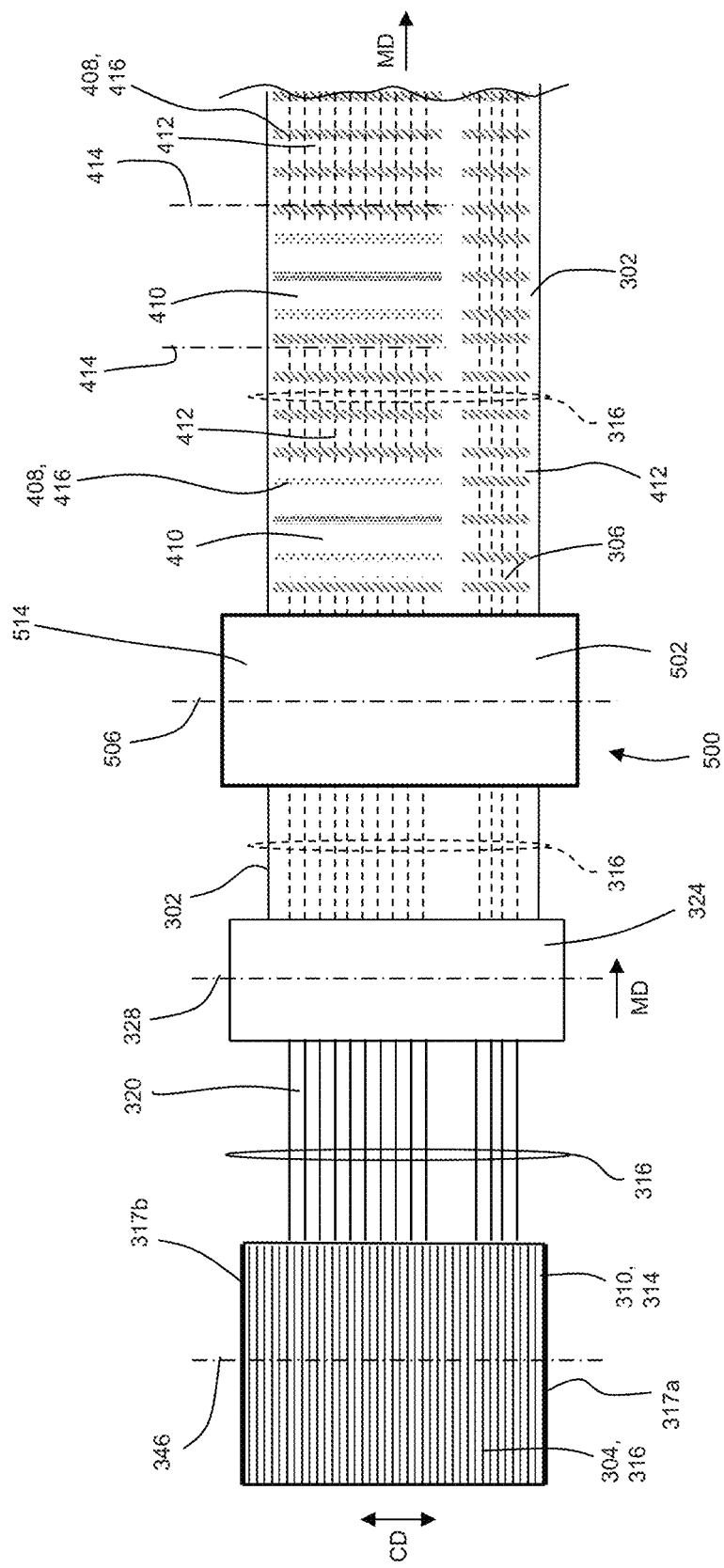
FIG. 39 is a view of the converting apparatus of FIG. 38 taken along line 39-39.

As shown in FIGS. 38 and 39, a converting apparatus 300 for producing an elastomeric laminate 302 may include a first metering device 310 and a second metering device 312. The first metering device 310 may be configured as a beam 314 with a plurality of elastic strands 316 wound thereon. During operation, the plurality of elastic strands 316 advance in the machine direction MD from the beam 314 to the second metering device 312. In addition, the plurality of elastic strands 316 may be stretched along the machine direction MD between the beam 314 and the second metering device 312. The stretched elastic strands 316 are also joined with a first substrate 306 and a second substrate 308 at the second metering device 312 to produce an elastomeric laminate 302. In some configurations, one or more of the elastic strands 316 advancing from the beam 314 may also include a spin finish 320 located on outer surfaces of the elastics strands.

As discussed above, the elastic strands 316 advancing from the rotating beam 314 may also include a spin finish 320, and as such, the apparatuses herein may be configured to bond the elastic strands 316 between the substrates 306, 308 without having to remove the spin finish 320 before joining the elastic strands 316 with the substrates 306, 308. It is also to be appreciated that the methods and apparatuses herein may also be configured to remove the spin finish 320 from the elastic strands 316. Examples of spin finish removal processes and apparatuses are discussed herein and are disclosed in U.S. Provisional Patent Application No. 62/483,965, which is incorporated by reference herein. In addition, the elastomeric laminates 302 herein may be constructed with or without adhesives between the first and second substrates 306, 308. In addition, it is to be appreciated that the bonding methods and apparatuses herein may be utilized in conjunction with other bonding methods and apparatuses disclosed here and as disclosed in U.S. Patent Application Nos. 62/436,589; 62/553,149; and 62/553,171, which are incorporated by reference herein. Although the elastomeric laminate assembly process may utilize elastic strands supplied from a beam, it is to be appreciated that elastic strands may also be supplied with various types of elastic unwinder configurations, such as disclosed in U.S. Pat. Nos. 6,676,054; 7,878,447; 7,905,446; and 9,156,648, all of which are incorporated by reference herein.

FIGS. 38 and 39 show an arrangement of first and second rollers 324, 330 and associated features described above with reference to FIGS. 5 and 6 that may be utilized to combine elastic strands 316 and first and second substrates 306, 308 to produce a continuous length of elastomeric laminate 302. Although FIG. 39 shows fourteen elastic strands 316 advancing from the beam 314, it is to be appreciated that the apparatuses herein may be configured such that more or less than fourteen elastic strands 316 advance from the beam 314.

With continued reference to FIGS. 38 and 39, the advancing elastic strands 316 may be joined with the first substrate 306 and the second substrate 308 to form the elastomeric laminate 302. The elastomeric laminate 302 may also advance to a bond applicator 500 configured to apply bonds 408 that secure the elastic strands 316 between the first substrate 306 and the second substrate 308. The bond applicator 500 may also be configured to intermittently sever one or more stretched elastic strands 316 to create deactivated regions 410 in the elastomeric laminate 302. As shown in FIG. 39, the deactivated regions 410 may be intermittently spaced between elastomeric regions 412 along the machine direction MD. For the purposes of clarity, dashed lines 414 are shown in FIG. 39 to represent example boundaries between the deactivated regions 410 and the elastomeric regions 412. It is to be appreciated that such boundaries between the deactivated regions 410 and the elastomeric regions 412 can also be curved, angled, and/or straight.

It is to be appreciated that the bond applicator 500 may be configured in various ways, such as with heated or unheated patterned and anvil rolls and/or ultrasonic bonding devices. For example, the bond applicator 500 schematically shown in FIGS. 38 and 39 may include a pattern roll 502 and pressing surface 504 adjacent the pattern roll 502. The pattern roll 502 may be adapted to rotate about an axis of rotation 506 extending axially in the cross direction CD. During operation, the elastomeric laminate 302 may be partially wrapped onto the pattern roll 502. And the pattern roll 502 rotates about the axis of rotation 506 to advance the elastomeric laminate 302 through a nip 508 between the pattern roll 502 and the pressing surface 504. As shown in FIG. 38, the bond applicator 500 may also include one or more rolls 503 that help guide the elastomeric laminate to and from the pattern roll 502. The pattern roll 502 may also comprise one or more bonding surfaces 510 defined by one or more bonding elements 512 extending radially outward from an outer circumferential surface 514. The pattern roll 502 may also comprise a protuberance 516 extending radially outward from the outer circumferential surface 514. As discussed in more detail below, the elastomeric laminate 302 is advanced between the bonding surface 510 and the pressing surface 504 to weld the first substrate 306 and the second substrate 308 together to create bonds 408 between the first substrate 306 and the second substrate 308. And the elastomeric laminate 302 is advanced between the protuberance 516 and the pressing surface 504 to sever one or more elastic strands 316. Thus, as the elastomeric laminate 302 advances through the nip 508, the first substrate 306 and the second substrate 308 are welded together and one or more elastic strands 316 are intermittently severed to create deactivated regions 410 in the elastomeric laminate 302.

As discussed above, during the assembly operation, the elastomeric laminate 302 may be partially wrapped onto the pattern roll 502. As shown in FIG. 38, the extent that the elastomeric laminate 302 wraps around the pattern roll 502 is referred to herein as the wrap angle, θ, and may be expressed in units of degrees. In some configurations, the wrap angle, θ, may be greater than zero degrees and less than or equal to 180 degrees, specifically reciting all 1 degree increments within the above-recited range and all ranges formed therein or thereby. In some configurations, the wrap angle, θ, may be greater 180 degrees.

It is to be appreciated that the pressing surface 504 may be configured in various ways. For example, as shown in FIG. 38, the pressing surface 504 may comprise an energy transfer surface of an ultrasonic bonding device 518. As such, the bond applicator 500 may include a horn 520 and may be configured to impart ultrasonic energy to the combined substrates 306, 308 and elastic strands 316 on the pattern roll 502. The ultrasonic bonding device 518 may apply energy to the horn 520 to create resonance of the horn 520 at frequencies and amplitudes so the horn vibrates rapidly in a direction generally perpendicular to the substrates 306, 308 and elastic strands 316 being advanced past the horn 520 on the pattern roll 502. Vibration of the horn 520 creates bonds 408 and/or bond regions 416 by generating heat to melt and bond the substrates 306, 308 together in areas supported by the bonding surface 510 on the pattern roll 502. Thus, the bonds 408 and/or bond regions 416 may have shapes that correspond with and may mirror shape of the bonding surfaces 510.

It is to be appreciated that aspects of the ultrasonic bonding devices 518 may be configured in various ways, such as for example linear or rotary type configurations, and such as disclosed for example in U.S. Pat. Nos. 3,113,225; 3,562,041; 3,733,238; 5,110,403; 6,036,796; 6,508,641; and 6,645,330. In some configurations, the ultrasonic bonding device 518 may be configured as a linear oscillating type sonotrode, such as for example, available from Herrmann Ultrasonic, Inc. In some configurations, the sonotrode may include a plurality of sonotrodes nested together in the cross direction CD.

Although the bond applicator 500 is shown in FIGS. 38 and 39 as a separate device that is positioned downstream of the second metering device 312, it is to be appreciated that the second metering device 312 may also be configured as the bond applicator 500. As such, the first substrate 306, second substrate 308, and elastic strands 316 may be combined and bonded together at the bond applicator 500 to form the elastomeric laminate 302.

It is to be appreciated that the apparatuses and methods herein may be configured to create various configurations of bonds 408 in the elastomeric laminate 302. For example, as previously mentioned, the pattern roll 502 may include one or more bonding elements 512 protruding radially outward from the pattern roll 502, wherein each bonding element 512 includes a bonding surface 510, such as shown for example in FIGS. 40 and 41. It is to be appreciated that the number, size, and shape of some or all the bonding surfaces 510 and/or bonding elements 512 may be different. In some embodiments, the shape and size of the bonding surface 510 of each bonding element 512 may be identical or substantially identical to each other. In some configurations, the bonding elements 512 and/or bonding surfaces 510 may have a perimeter that defines circular, square, rectangular, elliptical, and various types of other shapes. In some configurations, the pattern roll 502 may include a bonding element 512 with a bonding surface 510 that defines a continuous crossing line pattern and/or various other shapes, such as disclosed in U.S. Pat. No. 9,265,672, which is incorporated by reference herein. It is to be appreciated that the bonding surface 510, such as discussed above, may be flat and/or may also include regions defined by relatively high and relatively low elevations. Thus, such bonding surfaces 510 may create bonds 408 having varying thicknesses across the bond region 416.

Figure 39A:
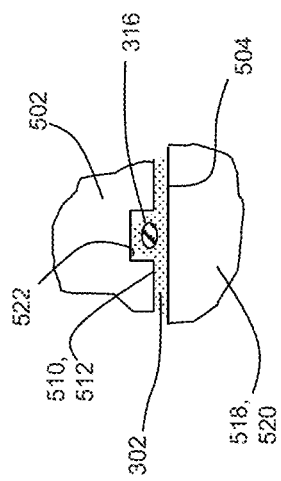
FIG. 39A is a detailed cross sectional view of the elastomeric laminate advancing through the nip between the pattern roll and the pressing surface showing an elastic strand extending through a channel.
Figure 40:
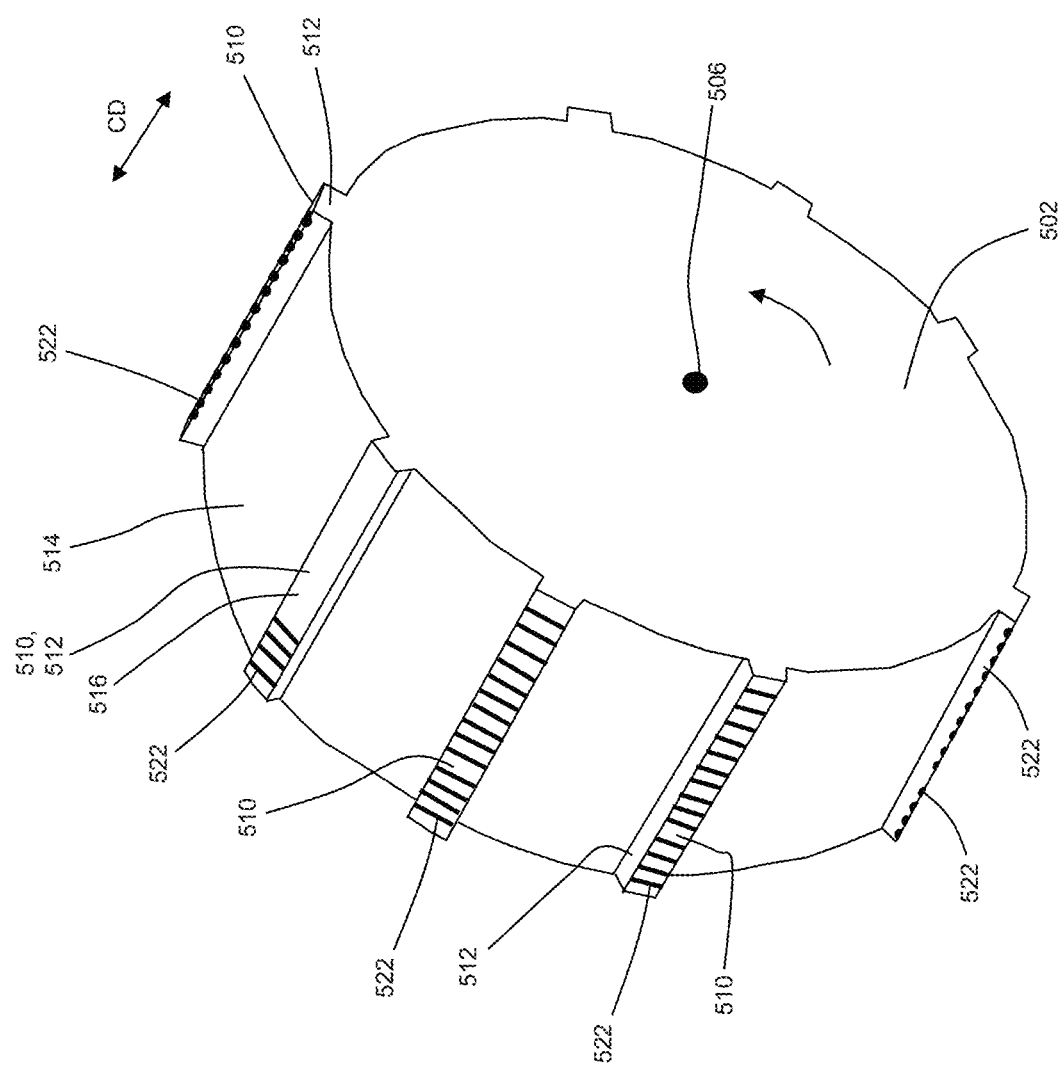
FIG. 40 is a detailed view of an example pattern roll with pluralities of bonding surfaces and a protuberance.
Figure 41:
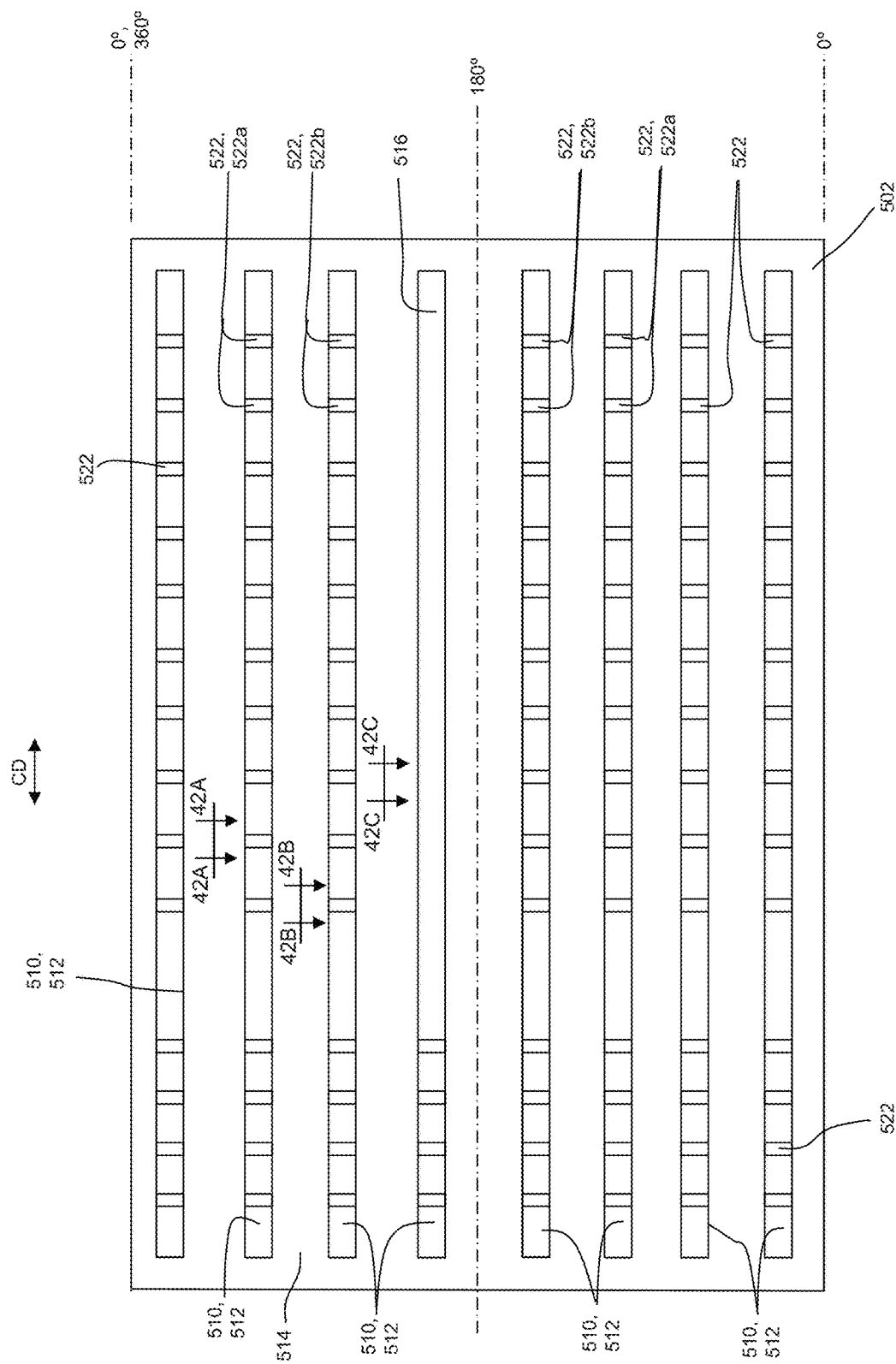
FIG. 41 is a view of an outer circumferential surface of a pattern roll laid out flat and showing pluralities of bonding surfaces and a protuberance.

With continued reference to FIGS. 40 and 41, the pattern roll 502 may also include discrete channels 522 in the bonding surfaces 510. During operation, the first substrate 306 and the second substrate 308 with the stretched elastic strands 316 therebetween may be advanced onto the pattern roll 502, wherein the stretched elastic strands 316 are aligned with and extend through respective channels 522, such as shown in FIG. 39A. As the pattern roll 502 rotates, the first substrate 306 and the second substrate 308 are welded together between the bonding surfaces 510 and the pressing surface 504 to create bonds 408 between the first substrate 306 and the second substrate 308. As discussed below in more detail with reference to FIGS. 43A-43B, the bonds 408 are separated from each other in the cross direction CD by the stretched elastic strands 316 positioned in the channels 522 to form sleeves 418 that surround the stretched elastic strands 316. The inner perimeter of the sleeves 418 may be defined by the first substrate 306, the second substrate 308, and the bonds 408 on opposing sides of the elastic strand 316.

Figure 41A:
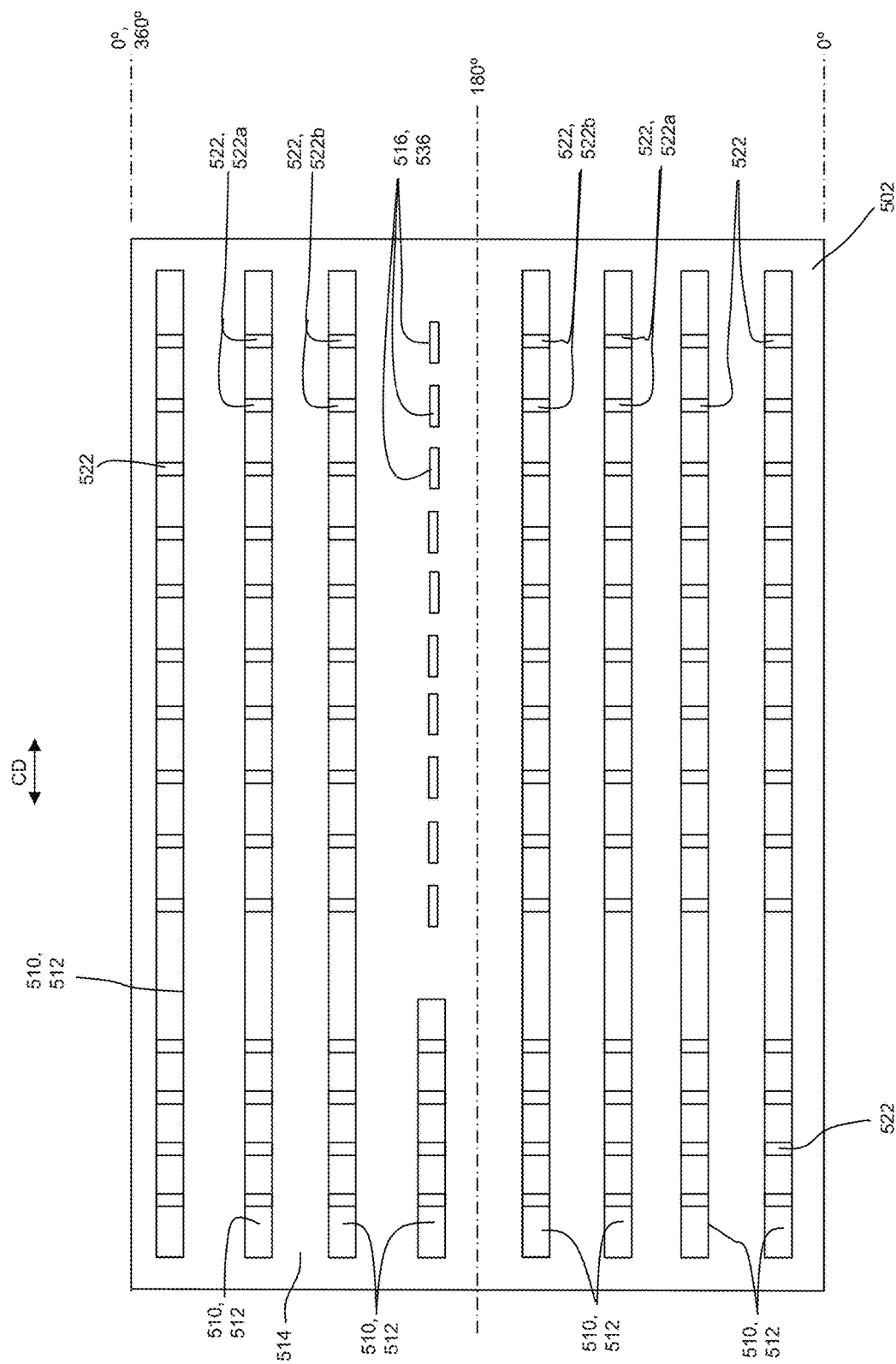
FIG. 41A is a view of an outer circumferential surface of a pattern roll laid out flat and showing a protuberance configured as a plurality of discrete members.

As shown in FIGS. 41, 41A, and 41B, the pattern roll 502 may include first channels 522a and second channels 522b, wherein the first and second channels 522a, 522b may be configured to create sleeves 418 having different sizes. As shown in FIGS. 42A and 42B, the bonding surfaces 510 may be positioned at a first radial distance R1 from the axis of rotation 506. Discrete first channels 522a may be positioned in the bonding surfaces 510 so as to be spaced apart from each other circumferentially and in the cross direction CD. In addition, the first channels 522a may comprise a first width W1 extending axially along the axis of rotation 506 and may comprise a first depth D1 extending radially inward from the bonding surface 510. Discrete second channels 522b may also be positioned in the bonding surfaces 510 so as to be spaced apart from each other circumferentially and in the cross direction CD. The second channels 522b may comprise a second width W2 extending axially along the axis of rotation 506 and may comprise a second depth D2 extending radially inward from the bonding surface 510. In some configurations, the second width W2 may be greater than the first width W1 and/or the second depth D2 may be greater than the first depth D1. In turn, the first channels 522a may be configured to create first sleeves 418a that are sized to secure discrete lengths of the elastic strands 316 in fixed positions with a frictional lock between the first and second substrates 306, 308. In addition, the second channels 522b may be configured to create second sleeves 418b that are sized to allow the elastic strands 316 to move relative to the first and second substrates 306, 308 as the elastic strands 316 stretch and contract along machine direction MD while at the same time holding and/or guiding the elastic strands 316 in desired positions along the cross direction CD.

As previously mentioned, the pattern roll 502 may include first channels 522a that are sized to create first sleeves 418a that surround discrete lengths of stretched elastic strands 316. In turn, a frictional lock may be applied between a portion of the elastic strand 316 and the first sleeves 418a by releasing tension from the stretched elastic strand 316. The frictional lock acts to hold and/or secure a portion of the elastic strand 316 in a fixed position relative to the first and second substrates 306, 308. For the purposes of a general explanation, FIG. 16A shows a length of an elastic strand 316 in a unstretched or relaxed state, wherein the elastic strand 316 defines a first cross sectional area A1. And FIG. 16B shows a length of the elastic strand 316 from FIG. 16A in a stretched state, wherein the elastic strand 316 defines a second cross sectional area A2 that is less than the first cross sectional area A1. Thus, the cross sectional area of the stretched elastic strand 316 expands when tension is partially or fully released from the stretched elastic strand 316. As discussed in more detail below, the tendency of the cross sectional area of the elastic strand 316 to expand helps create the frictional lock.

Figure 43A:
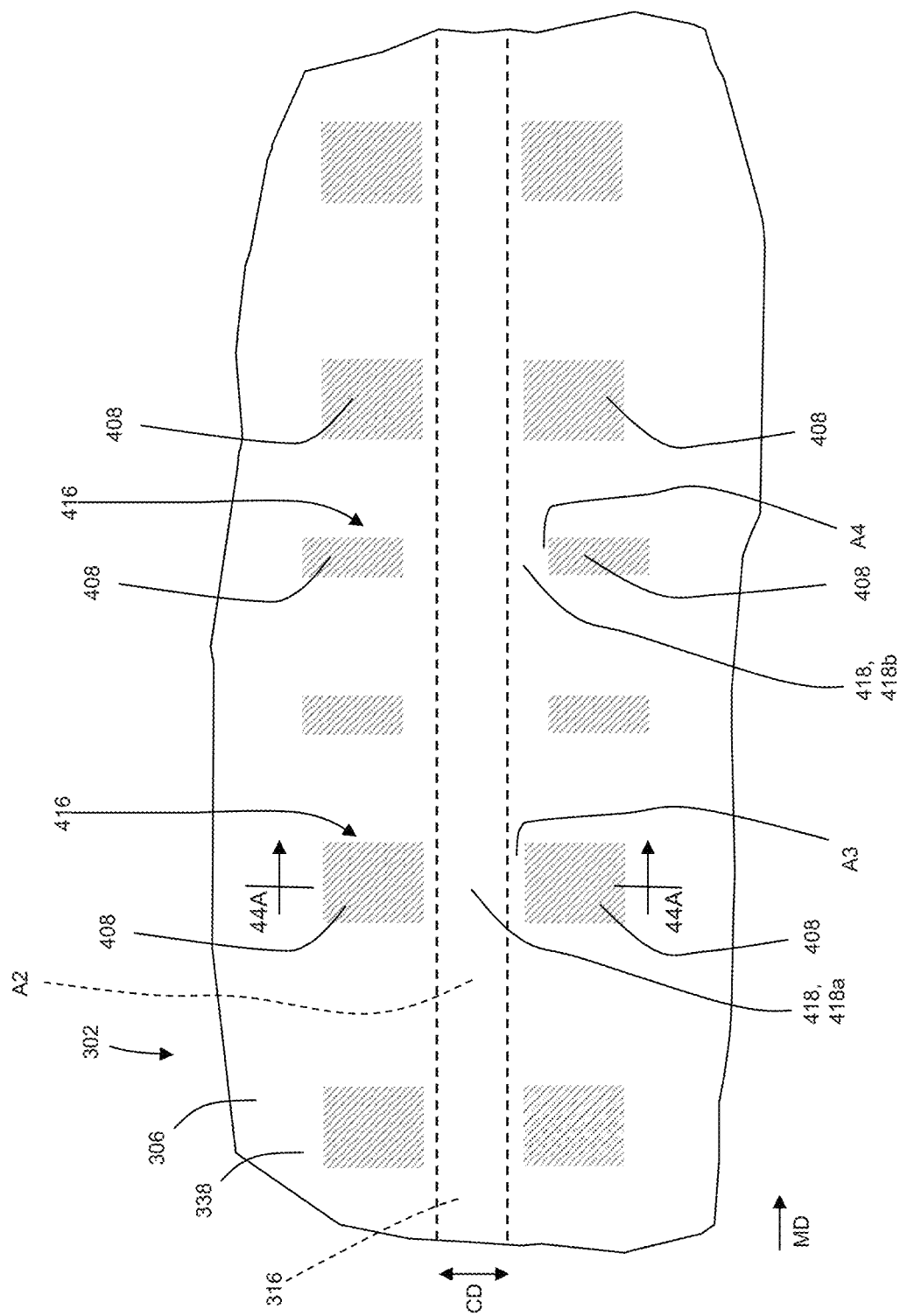
FIG. 43A is a detailed view of an elastic strand in a stretched state bonded between the first and second substrates.
Figure 44A:
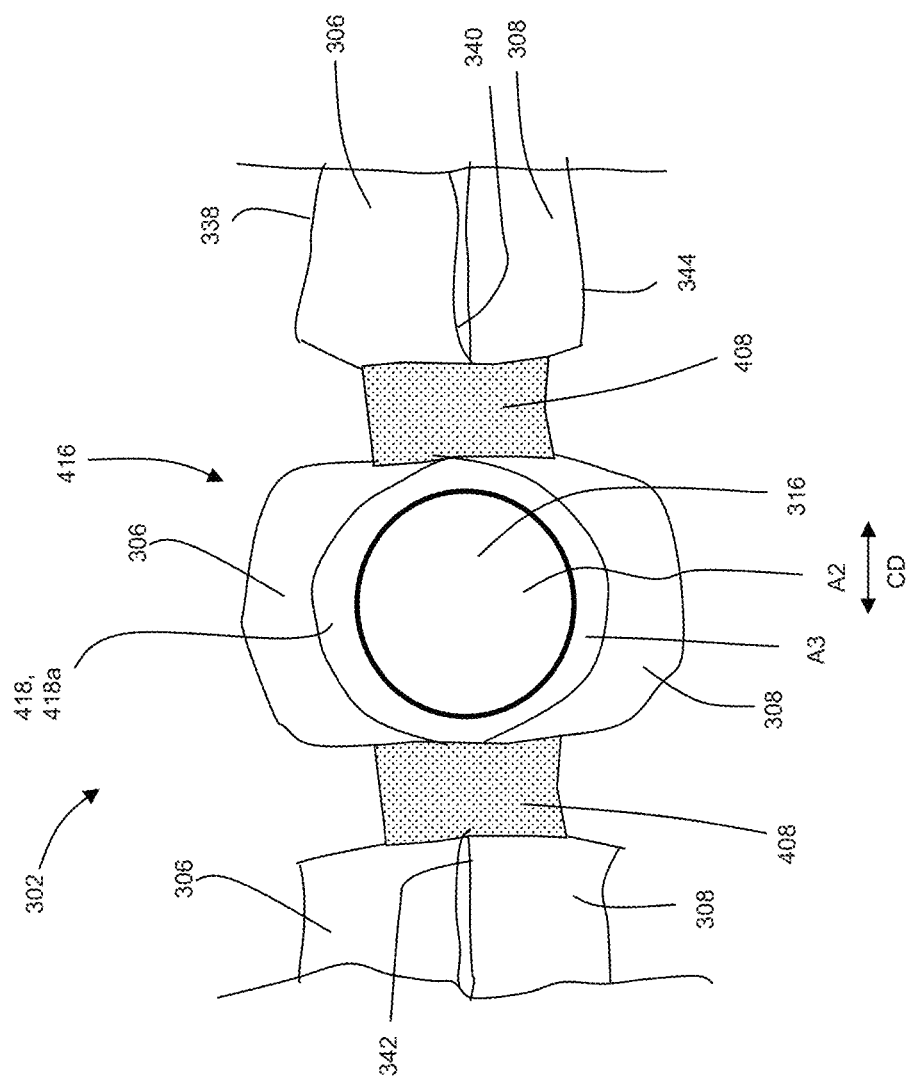
FIG. 44A is a sectional view of the elastic strand, bonds, first substrate, and second substrate of FIG. 43A taken along line 44A-44A.

FIGS. 43A and 44A are detailed views of an elastic strand 316, such as shown in FIG. 39, in a stretched state extending in the machine direction between the first and second substrates 306, 308. During the bonding process, the bond applicator 500 may apply heat and pressure to regions of the first substrate 306 and the second substrate 308 to weld the first and second substrates 306, 308 together with bonds 408. The bonds 408 may be separated from each other in the cross direction CD by the stretched elastic strand 316. In turn, the bonds 408 form sleeves 418 that surround the stretched elastic strands 316. As shown in FIG. 44A, the inner perimeter of the sleeves 418 may be defined by the first substrate 306, the second substrate 308, and the bonds 408 on opposing sides of the elastic strand 316. As discussed above, the first channels 522a in the pattern roll 502 may be configured to create first sleeves 418a to secure discrete lengths of the elastic strands 316 in fixed positions with a frictional lock between the first and second substrates 306, 308. For example, the elastic strand 316 shown in FIGS. 43A and 44A may define a second cross sectional area A2 in a stretched state. The elastic strand 316 may also define a first cross sectional area A1 in a relaxed state, wherein A2 is less than A1. In turn, the first sleeves 418a may define a third cross sectional area A3 that may be greater than or equal to A2, and wherein A3 may be less than A1.

Figure 43B:
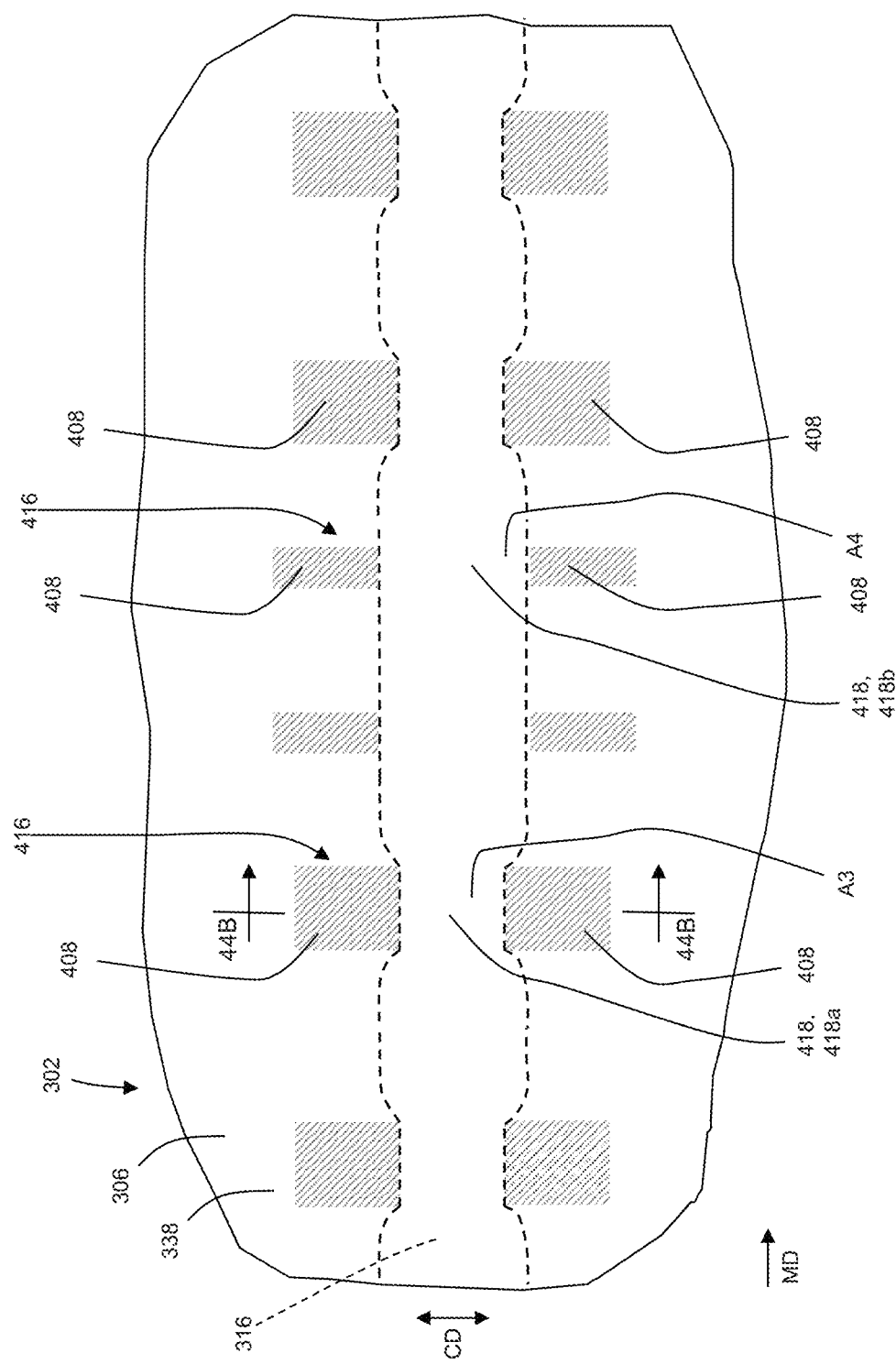
FIG. 43B is a detailed view of an elastic strand in a relaxed state bonded between the first and second substrates.

Turning next to FIGS. 43B and 44B, a detailed view of an elastic strand 316, such as shown in FIGS. 43A and 44A, is provided wherein tension has been released (or reduced) on the elastic strand 316 and showing how the tendency of the elastic strand 316 to expand creates a frictional lock in the bonded region 416. As shown in FIG. 44B, the first sleeve 418a helps prevent the cross sectional area of the elastic strand 316 from expanding beyond the third cross sectional area A3 of the first sleeve 418a when tension has on elastic strand 316 has been reduced. The tendency of the elastic strand 316 to expand creates forces F (represented by dashed double arrow lines in FIG. 44B) exerted between elastic strand 316 and the inner perimeter of the first sleeve 418a. In turn, the forces F between the elastic strand 316 and the first sleeve 418a creates a frictional lock by increasing the friction forces between the elastic strand 316 and the bonds 408 and portions of the first substrate 306 and the second substrate 308 that define the inner perimeter of the first sleeve 418a. The increased friction forces in the machine direction MD along the length of the elastic strand 316 in the first sleeve 418a holds or secures the discrete length of the elastic strand 316 in a fixed position in the first sleeve 418a together with the first and second substrates 306, 308.

In some configurations, no adhesive may be applied to and/or present between the elastic strand 316 and the first sleeves 418a. It is also to be appreciated that in some configurations, adhesive may be applied to and/or present between the elastic strand 316 and the first sleeves 418a to help the frictional lock hold the discrete length of the elastic strand 316 in a fixed position with the first and second substrates 306, 308. In some configurations, adhesive and the frictional lock in the first sleeves 418a may share the load exerted by elastic strand 316. In some configurations, adhesive positioned on the elastic strand 316 may increase the coefficient of friction between the elastic strand 316 and the first sleeve 418a. It is to be appreciated that various quantities of adhesive may be present in the first sleeve 418a, such as for example, about 10 gsm or less.

As discussed above, second channels 522b in the pattern roll 502 may be configured to create second sleeves 418b configured to create second sleeves 418b that are sized to allow the elastic strands 316 to move relative to the first and second substrates 306, 308 as the elastic strands 316 stretch and contract along machine direction MD. The second sleeve 418b may also help hold or guide the elastic strands 316 in desired positions along the cross direction CD as the elastic strands 316 stretch and contract along machine direction MD. For example, the elastic strand 316 shown in FIG. 43A may define a second cross sectional area A2 in a stretched state. The elastic strand 316 may also define a first cross sectional area A1 in a relaxed state, wherein A2 is less than A1. In turn, the second sleeves 418b may define a fourth cross sectional area A4 that may be greater than the third cross sectional area A3 of the first sleeves 418a. In some configurations, A4 may be greater than A1. As such, when the elastic strand 316 contracts and expands, no frictional bond is formed between the elastic strand and the second sleeves 418b. Thus, the elastic strand 316 is allowed to move relative to the first and second substrates 306, 308 along the machine direction MD while also being held in a fixed cross directional position.

Figure 44C:
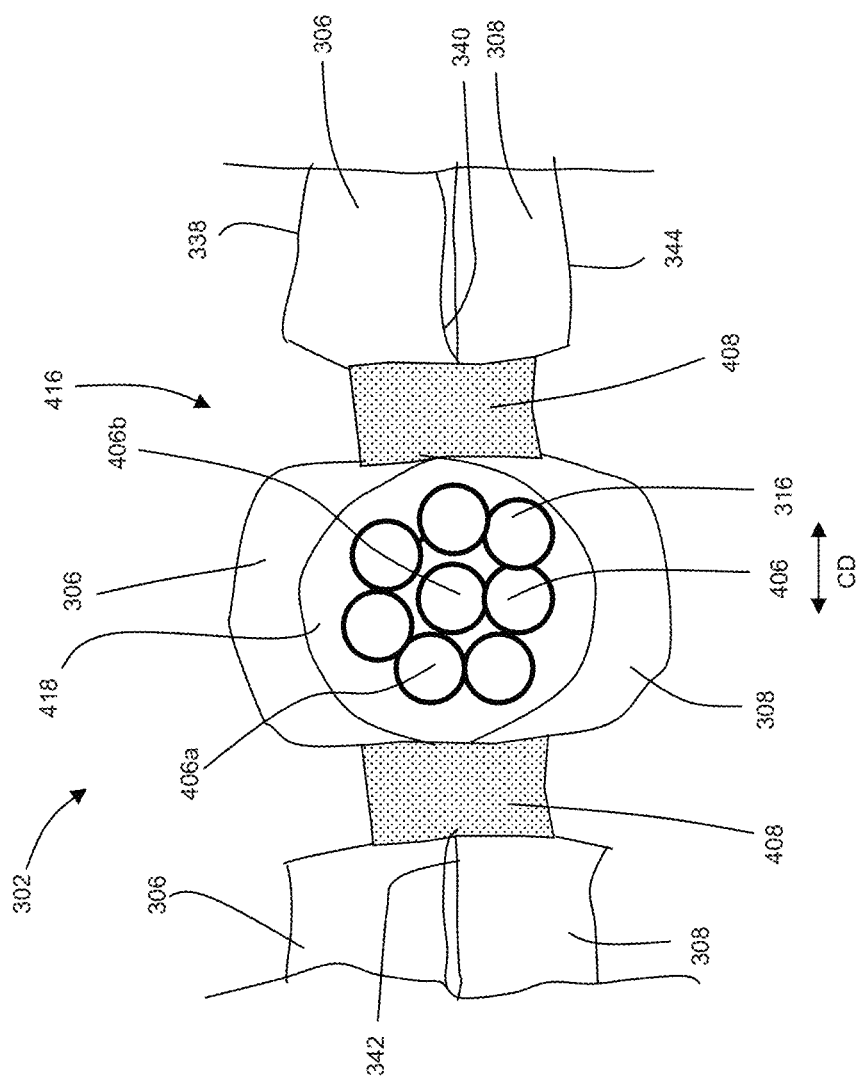
FIG. 44C is a sectional view of an elastic strand, bond, first substrate, and second substrate, wherein a plurality of filaments of the elastic strand are bonded in a first configuration.
Figure 44D:
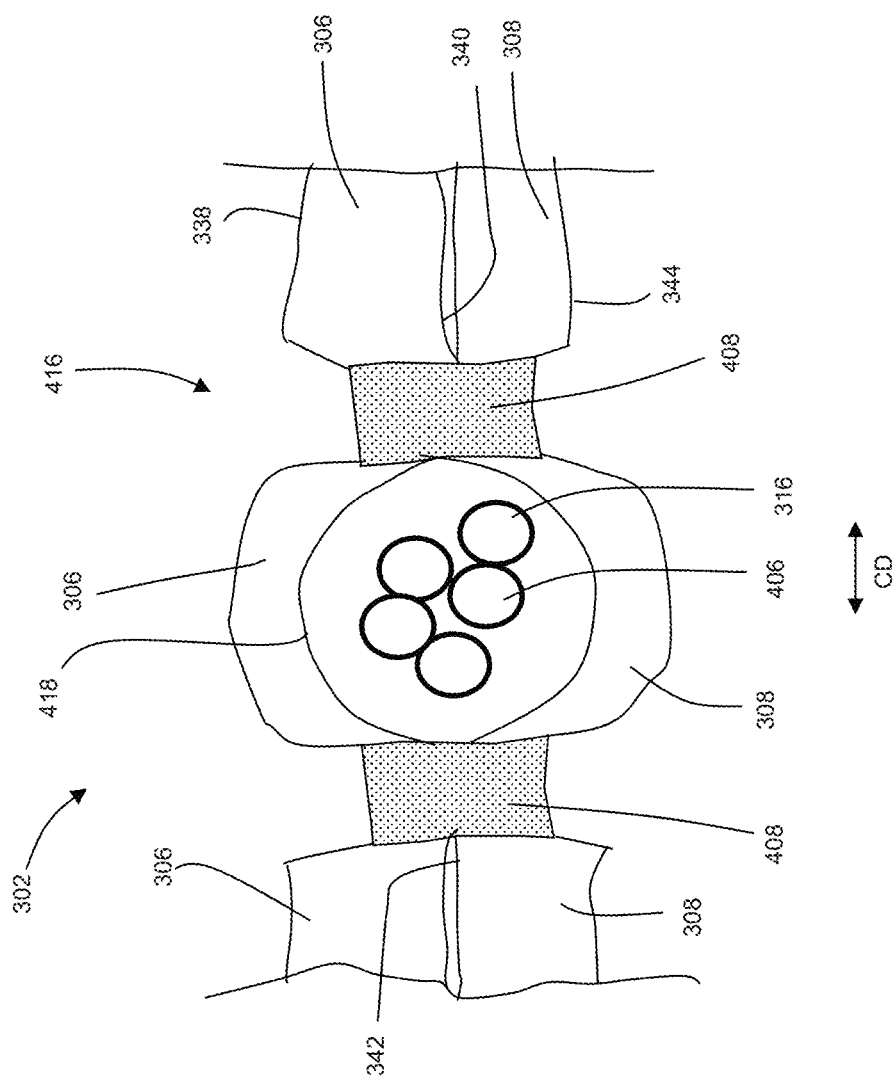
FIG. 44D is a sectional view of an elastic strand, bond, first substrate, and second substrate, wherein a plurality of filaments of the elastic strand are bonded in a second configuration.

It is also to be appreciated that the elastic strands 316 herein bonded in accordance with the methods described herein may also be constructed from one or more filaments 406. For example, FIG. 44C shows a cross sectional view of a stretched elastic strand 316 in a sleeve 418 wherein the elastic strand 316 comprises a plurality of individual filaments 406. As shown in FIG. 44C, the elastic strand 316 may include outer filaments 406a surrounding an inner filament 406b. The outer filaments 406a may define an outer perimeter of the elastic strand 316, and the outer filaments 406a may surround the inner filament 406b such that the inner filament 406b is not in contact with the sleeve 418 when the elastic strand 316 is in a relaxed state. It is to be appreciated that the filaments 406 may be arranged in various positions within the sleeve 418. For example, FIG. 44D shows a cross sectional view of an elastic strand 316 in a sleeve 418 wherein the plurality of individual filaments 406 together define a perimeter that is elongated along the cross direction CD.

As previously mentioned with reference to FIG. 38, the pattern roll 502 includes a protuberance 516 that operates to intermittently sever one or more elastic strands 316 to create deactivated regions 410 in the elastomeric laminate 302. As shown in FIGS. 41 and 42A-42C, the protuberance 516 may extend axially along the axis of rotation 506 and may extend radially outward from the axis of rotation 506 to a second radial distance R2. In some configurations, R1 may be equal to or substantially equal to R1. And in some configurations, R2>(R1–D1) and/or R2>(R1–D2). It is to be appreciated that the pattern roll 502 may include one or more protuberances 516 that may be configured in various ways with various different sizes and/or shapes. In some examples, the protuberance 516 may be configured as a discrete member that is separate from the bonding elements 512 and/or bonding surfaces 510. In some examples, the protuberance may comprise a portion of a bonding element 512 and/or bonding surface 510. In some examples, the protuberance may extend axially along the axis of rotation 506 for a distance that is equal to or less than the axial length of the pattern roll 502. The protuberance may also be positioned circumferentially between two discrete first channels 418a and/or two discrete second channels 418b.

As discussed above with reference to FIGS. 38 and 39, advancing elastic strands 316 may be joined with the first substrate 306 and the second substrate 308 to form the elastomeric laminate 302. In turn, the bond applicator 500, comprising the pattern roll 502 and the pressing surface 504, applies bonds 408 that secure the elastic strands 316 between the first substrate 306 and the second substrate 308. In addition, the bond applicator 500 severs one or more stretched elastic strands 316 to create deactivated regions 410 in the elastomeric laminate 302.

Figure 45B:
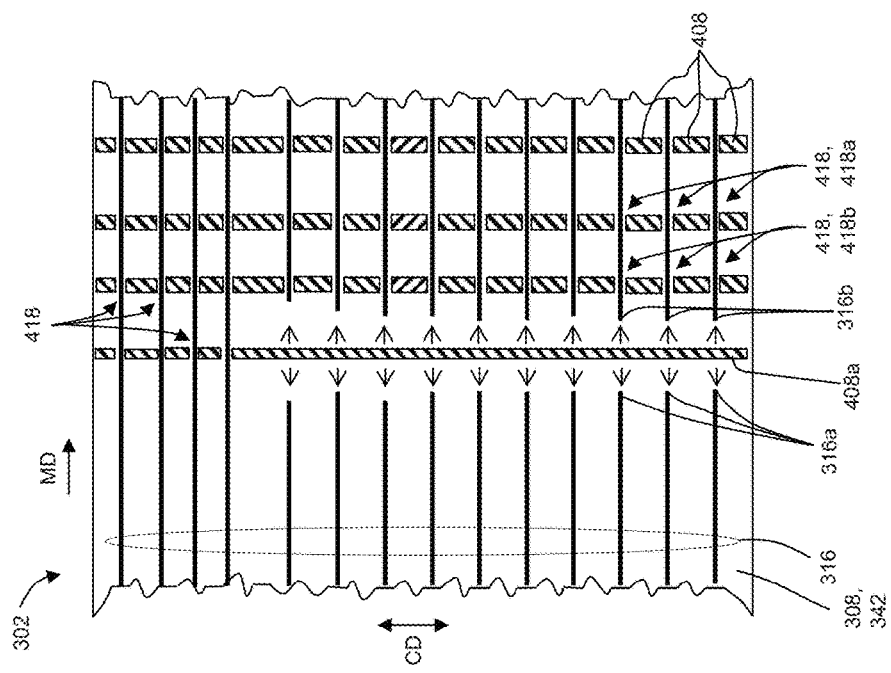
FIG. 45B shows a detailed view of an elastomeric laminate from FIG. 45A continuing to advance from the nip between the pattern roll and pressing surface to illustrate stretched elastic strands having been severed between the protuberance and the pressing surface.
Figure 45A:
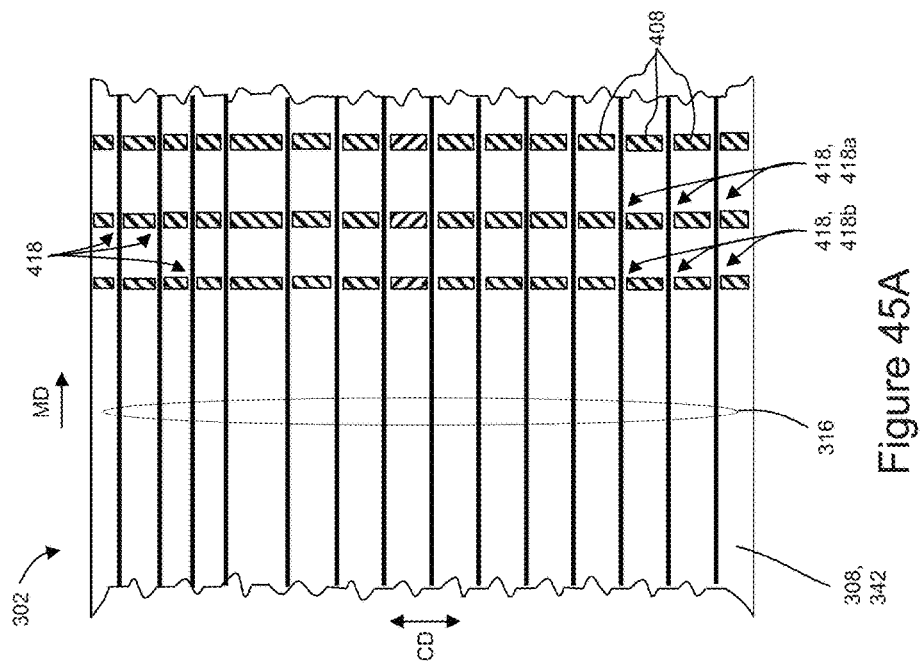
FIG. 45A shows a detailed view of an elastomeric laminate from FIGS. 38 and 39 advancing from the nip between the pattern roll and pressing surface with the first substrate cut-away to illustrate example bond configurations and stretched elastic strands.

FIGS. 45A-45E provide detailed example illustrations of the elastomeric laminate 302 advancing from the nip 508 between the rotating pattern roll 502 and the pressing surface 504. For the purposes of clarity, the first substrate 306 is not shown in the views of elastomeric laminate 302 in FIGS. 45A-45E. With reference to FIGS. 38 and 45A, the first and second substrates 306, 308 with the stretched elastic strands 316 therebetween form an elastomeric laminate 302 advancing in a machine direction MD. The elastomeric laminate 302 is partially wrapped around the pattern roll 502, wherein the stretched elastic strands 316 extend through discrete channels 522 in the pattern surfaces 510, such as discussed above with reference to FIGS. 39A, 40, and 41. As the pattern roll 502 rotates, the first substrate 306 and the second substrate 308 are welded together between the bonding surfaces 510 and the pressing surface 504 to create bonds 408 between the first and second substrates 306, 308. The bonds 408 are separated from each other in the cross direction CD by the stretched elastic strands 316 positioned in respective discrete channels 522 to form sleeves 418 surrounding the stretched elastic strands 316. As discussed above with reference to FIGS. 41-43B, the pattern roll 502 may include first channels 522a configured to create first sleeves 418a that are sized to secure discrete lengths of the elastic strands 316 in fixed positions relative to the first and second substrates 306, 308 with a frictional lock. And the second channels 522b may be configured to create second sleeves 418b that are sized to allow the elastic strands 316 to move relative to the first and second substrates 306, 308 as the elastic strands 316 stretch and contract along machine direction MD while at the same time holding and/or guiding the elastic strands 316 in desired positions along the cross direction CD. FIG. 45A illustrates an example arrangement of first and second sleeves 418a, 418b along the machine direction MD of the elastomeric laminate 302.

As discussed above with reference to FIGS. 41 and 42C, the pattern roll 502 also includes one or more protuberances 516 that sever one or more stretched elastic strands 316 to create deactivated regions 410 in the elastomeric laminate 302. With reference to FIG. 45B, as the pattern roll 502 continues to rotate, the first substrate 306, the second substrate 308, and one or more stretched elastic strands 316 are compressed between the pressing surface 504 and the protuberance 516 to sever the one or more stretched elastic strands 316. As shown in FIG. 45B, the protuberance 516 may also comprise a bonding surface 510 that also welds the first and second substrates 306, 308 together with a bond 408a while also operating to sever the elastic strands 316.

As shown in FIG. 45B, upstream ends 316a and downstream ends 316b of the severed elastic strands 316 may begin to retract in opposing directions. As previously mentioned, the first substrate 306, the second substrate 308, and the stretched elastic strands 316 may be partially wrapped onto the rotating pattern roll 502. And tension exerted on the first and second substrates 306, 308 and the stretched elastic strands 316 forces the elastomeric laminate 302 against a portion of the pattern roll 502 upon which the elastomeric laminate 302 is wrapped. As such, the tension and resulting forces causes the first and second substrates 306, 308 to press against each other and against the stretched elastic strands 316 therebetween. Thus, as the stretched elastic strands 316 are severed, pressure exerted by the substrates 306, 308 on the elastic strands 316 therebetween may help the ends 316a, 316b of the severed elastic strands 316 retract or snap back at a relatively slower and/or controlled rate.

Figure 45D:
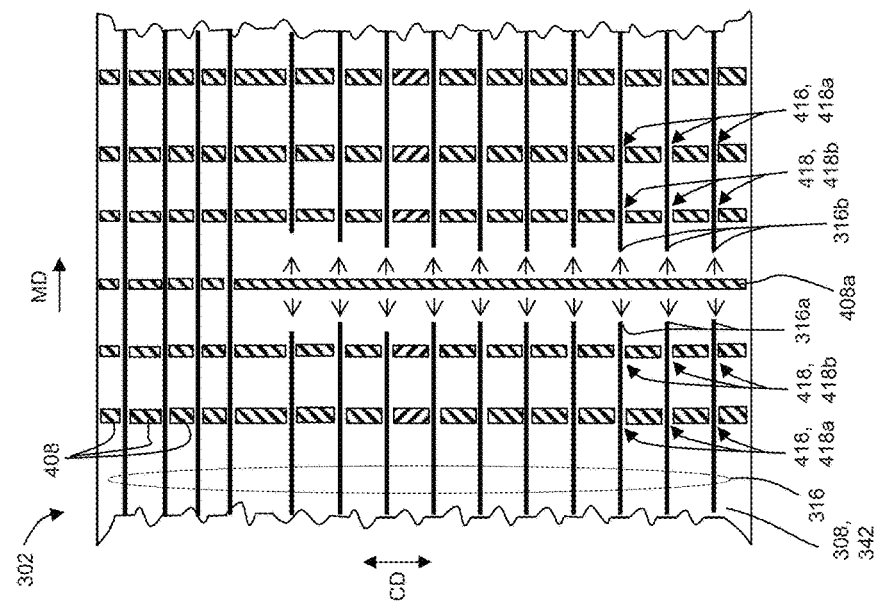
FIG. 45D shows a detailed view of an elastomeric laminate from FIG. 45C continuing to advance from the nip between the pattern roll and pressing surface to illustrate additional bonds having been applied.
Figure 45C:
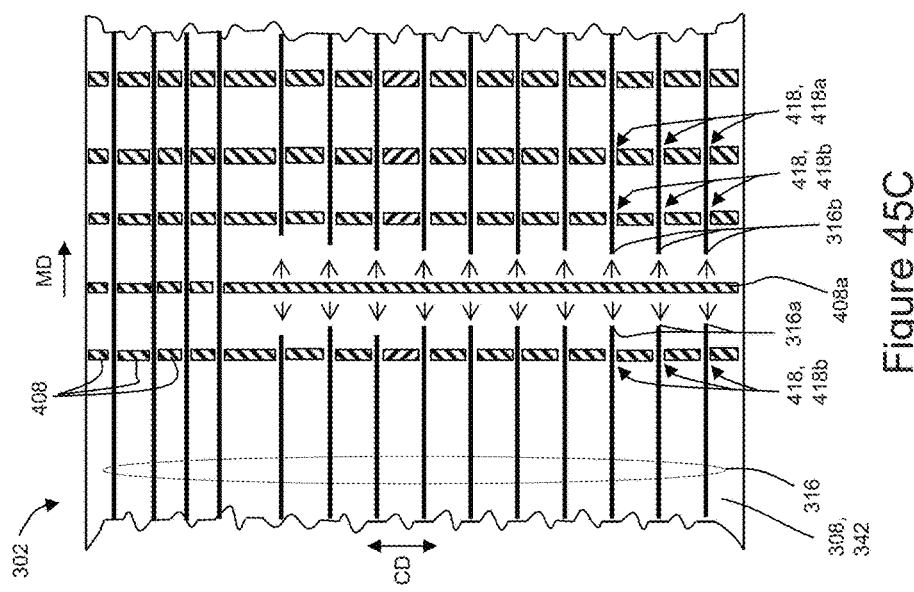
FIG. 45C shows a detailed view of an elastomeric laminate from FIG. 45B continuing to advance from the nip between the pattern roll and pressing surface to illustrate retracting elastic strands after having been severed.
Figure 45E:
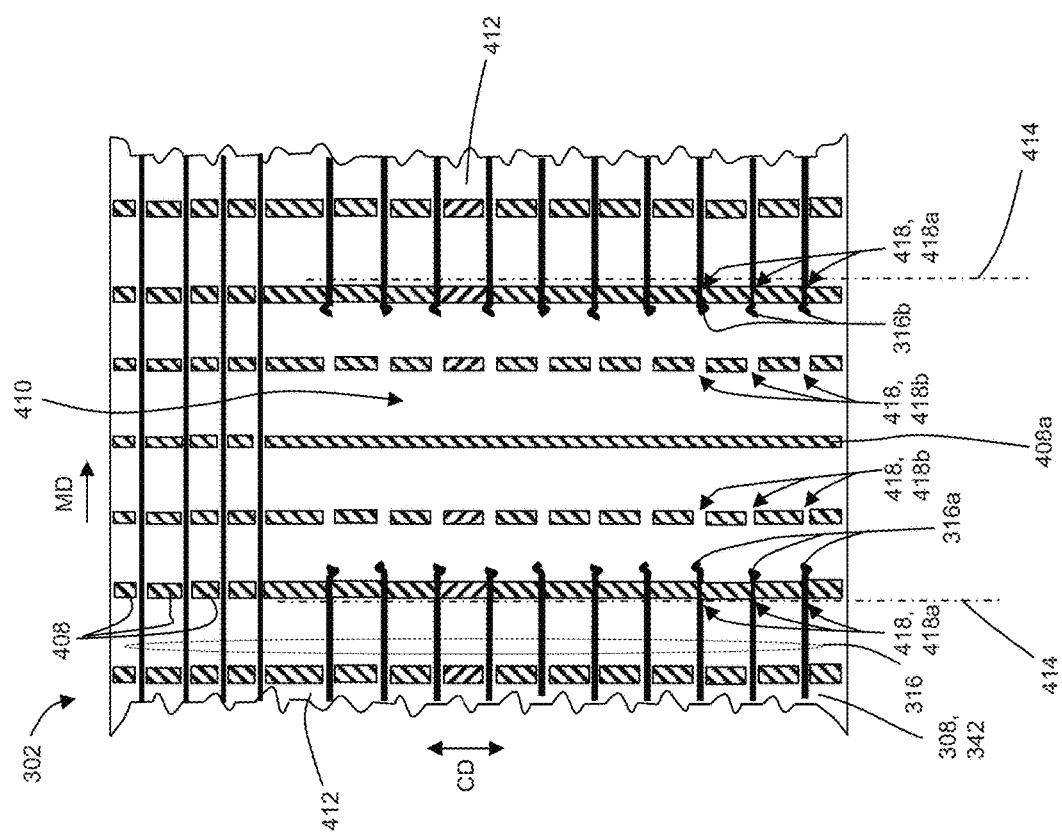
FIG. 45E shows a detailed view of an elastomeric laminate from FIG. 45D continuing to advance from the nip between the pattern roll and pressing surface to illustrate severed elastic strands having retracted to bond regions to define a deactivated region of the elastomeric laminate.

As shown in FIGS. 45C and 45D, as the pattern roll 502 continues to rotate, additional bonds 408 may be applied to the elastomeric laminate 302 upstream of retracting upstream ends 316a of the severed elastic strands 316. As shown in FIG. 45E, the ends 316a, 316b of the elastic strands 316 may retract to first sleeves 418a until a frictional lock is created between the elastic strands 316 and the first sleeves 418a. In turn, the frictional lock prevents the ends 316a, 316b of the elastic strands 316 from further retraction relative to the first and second substrates 306, 308. Retraction of the severed elastic strands 316 creates a deactivated region 410 in the elastomeric laminate 302. For the purposes of clarity, dashed lines 414 are shown in FIG. 45E to represent example boundaries between the deactivated regions 410 and the elastomeric regions 412 of the elastomeric laminate 302. Also, as shown in FIGS. 45C and 45D, the ends 316a, 316b of the severed elastic strands 316 retract through the second sleeves 316b while at the same time being guided along the machine direction MD by the second sleeves 418b while retracting.

It is also to be appreciated that the strands 316 and/or filaments 406 herein may define various different cross-sectional shapes. For example, in some configurations, strands 316 or filaments 406 may define circular, oval, or elliptical cross sectional shapes or irregular shapes, such as dog bone and hourglass shapes.

Figure 38A:
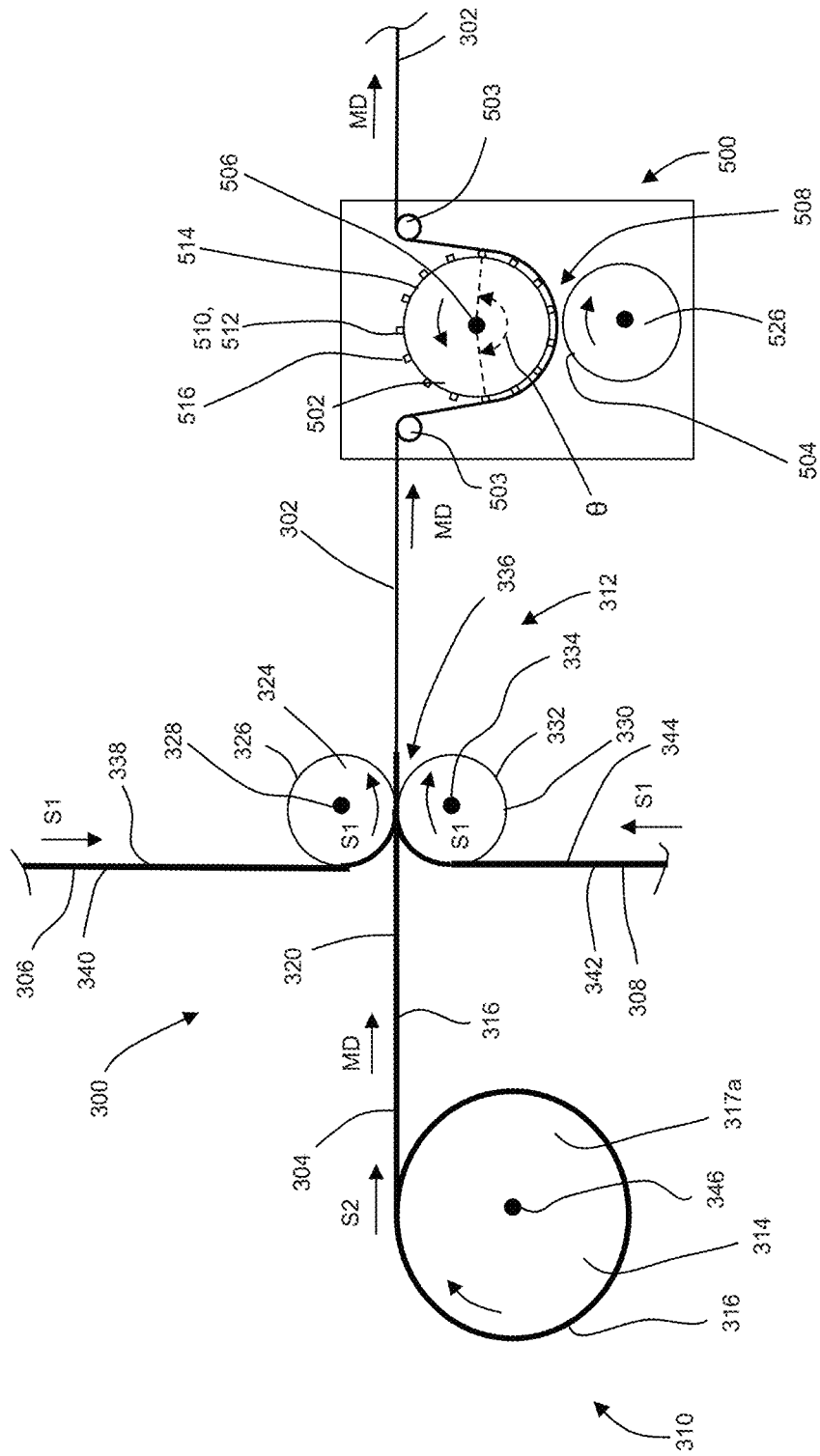
FIG. 38A is a schematic side view of a converting apparatus with a bonding apparatus configured with an anvil.

It is to be appreciated that the bond applicator 500 herein may be configured in various ways with various features described herein to assemble elastomeric laminates 302. For example, as shown in FIG. 38A, the bond applicator 500 may be configured as a mechanical bonding device that includes an anvil 526 that defines the pressing surface 504 operating in conjunction with the pattern roll 502. As such, the pattern roll 502 and/or anvil 526 may be configured to apply heat and pressure in various other ways to perform the bonding and cutting operations described above, such as for example, the mechanical bonding devices and methods disclosed in U.S. Pat. Nos. 4,854,984; 6,248,195; 8,778,127; and 9,005,392; and U.S. Patent Publication Nos. 2014/0377513 A1; and 2014/0377506 A1.

Figure 38B:
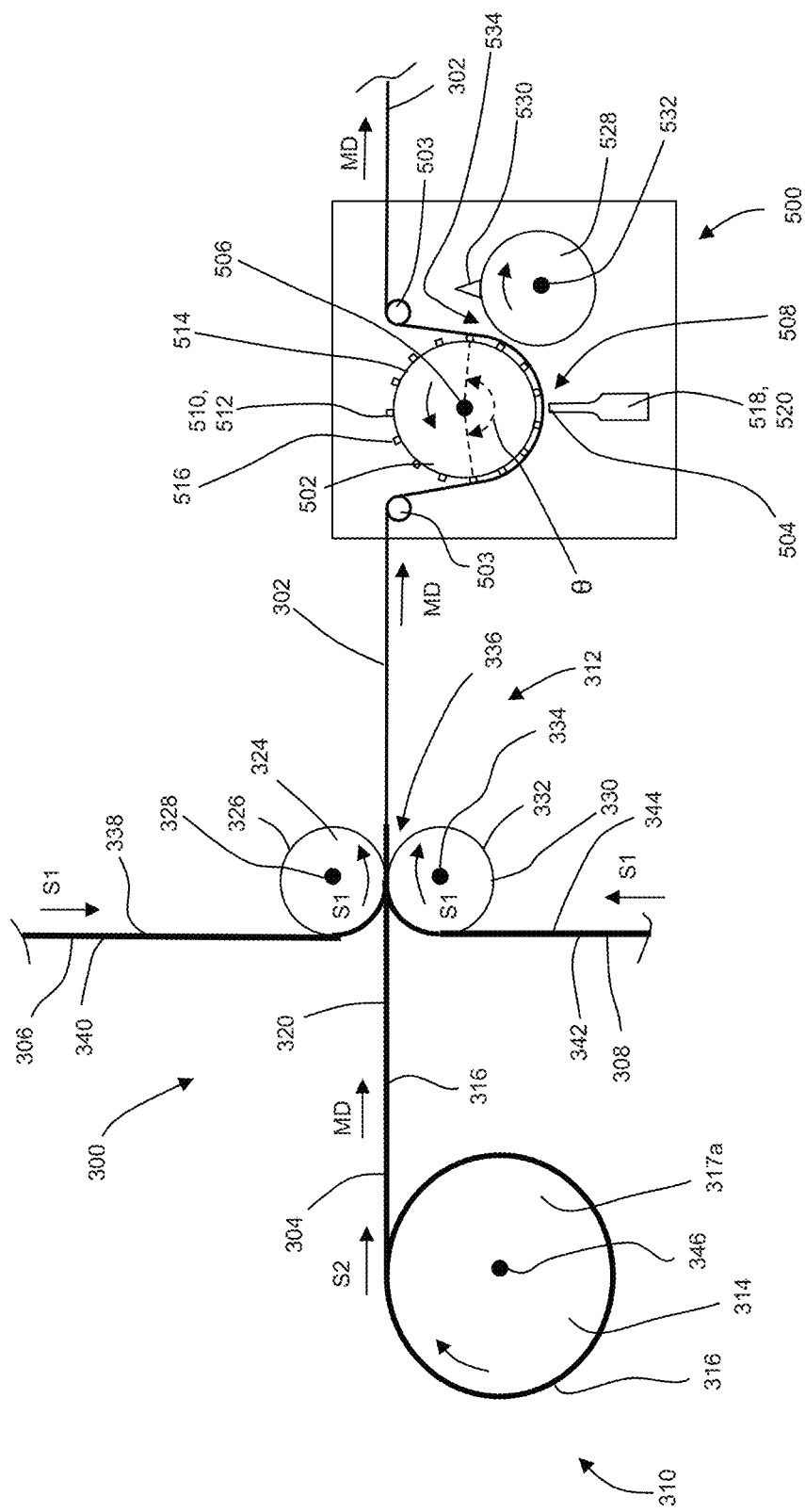
FIG. 38B is a schematic side view of a converting apparatus with a bonding apparatus configured with a cutting roll adapted to engage the pattern roll.
Figure 50:
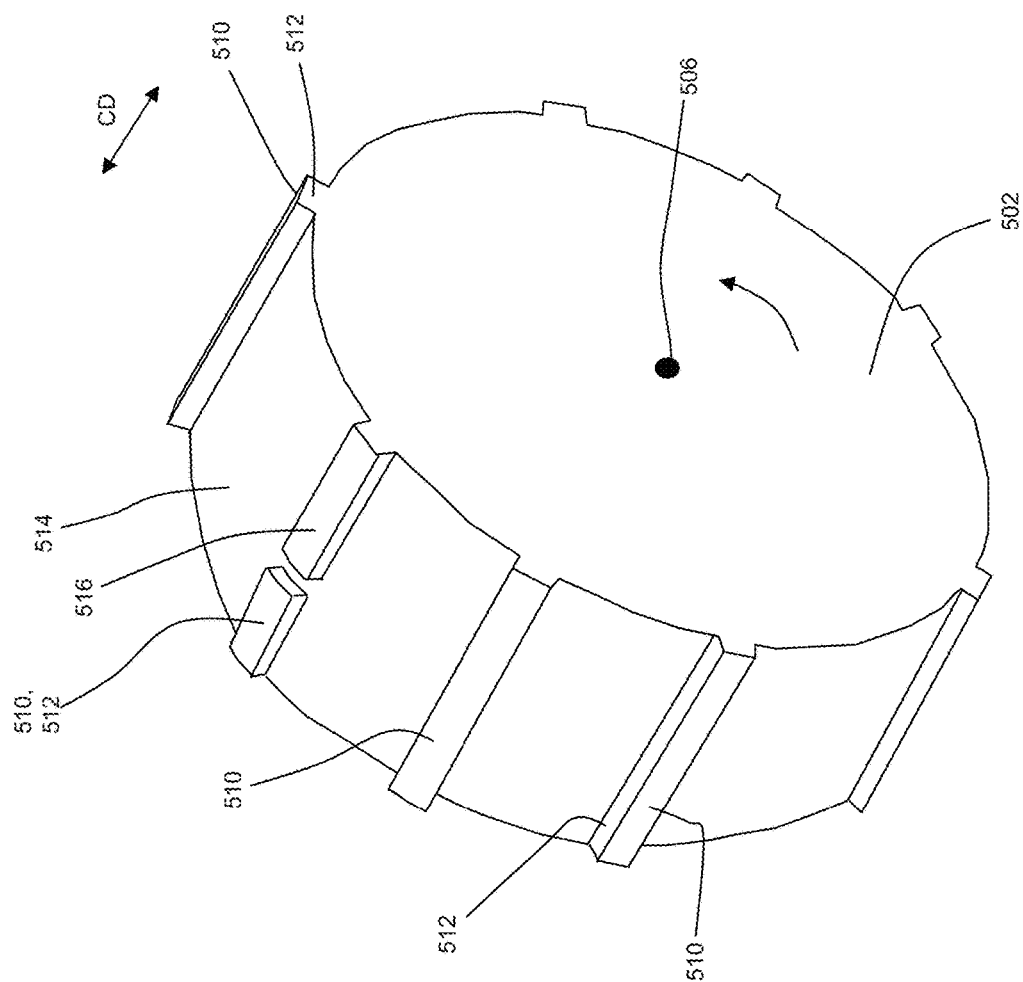
FIG. 50 is a detailed view of an example pattern roll with pluralities of bonding surfaces and a protuberance.
Figure 51:
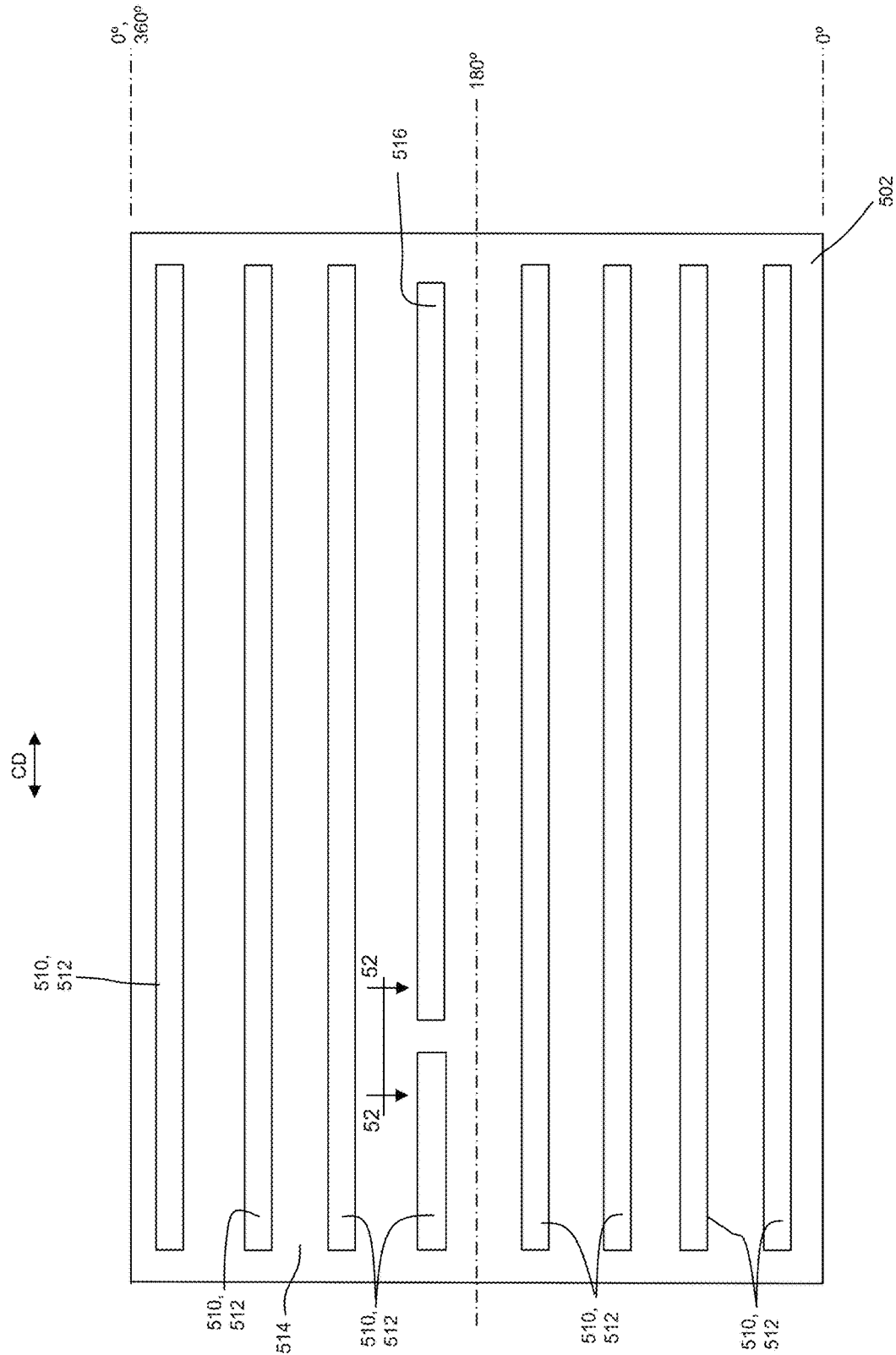
FIG. 51 is a view of an outer circumferential surface of a pattern roll laid out flat and showing pluralities of bonding surfaces and a protuberance.
Figure 52:
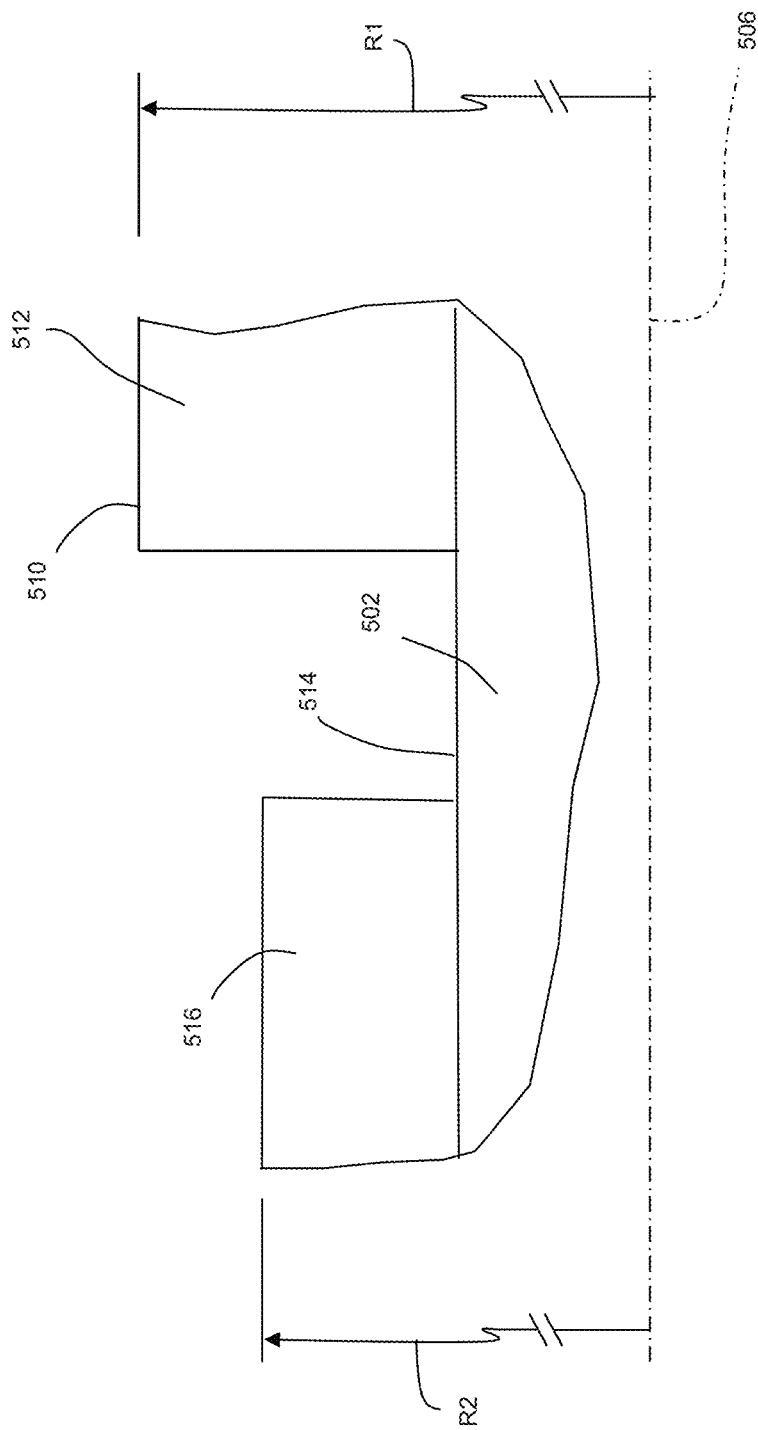
FIG. 52 is a sectional view of a pattern surface and a protuberance on the pattern roll of FIG. 51 taken along line 52-52.

As discussed above, the pattern roll 502 includes a protuberance 516 that engages the pressing surface 504 to intermittently sever one or more elastic strands 316 to create deactivated regions 410 in the elastomeric laminate 302. In some configurations, the one or more elastic strands 316 may be severed downstream of the pressing surface 504. For example, as shown in FIG. 38B, the bond applicator 500 may be configured to include a cutting roll 528 that may include one or more blades 530 and adapted to rotate around an axis of rotation 532. The cutting roll 528 may also be positioned adjacent the pattern roll 502 to define a nip 534 therebetween positioned downstream of the nip 508 between the pattern roll 502 and the pressing surface 504. In operation, the elastomeric laminate 302 advances through the nip 508 between the pattern roll 502 and the pressing surface 504 to apply the bonds 408 that secure the elastic strands 316 between the first substrate 306 and the second substrate 308. However, the protuberance 516 on the pattern roll 502 may be configured such that the elastomeric laminate 302 advances between the protuberance 516 and the pressing surface 504 without severing elastic strands 316. As such, the method and apparatus of FIG. 38B may also be adapted to create deactivated regions 410 in the elastomeric laminate 302 by severing elastic strands 316 that have been bonded in accordance with the methods and apparatuses described above with reference to FIGS. 26-37 as well as other bonding methods described herein. For example, FIGS. 50 and 51 show a pattern roll 502 with bonding surfaces 510 positioned at a first radial distance R1 from the axis of rotation 506. The pattern roll 502 also includes a protuberance 516 extending axially along the axis of rotation 506 and extending radially outward from the axis of rotation 506 to a second radial distance R2. As shown in FIG. 52, the second radial distance R2 may be less than the first radial distance R1 such that the elastic strands 316 are not severed between the protuberance 516 and the pressing surface 504. In turn, the elastomeric laminate 302 advances from the nip 508 to the nip 534 between the cutting roll 528 and the pattern roll 502 wherein the blade 530 engages the protuberance 516 to sever one or more elastic strands 316 to create deactivated regions 410 in the elastomeric laminate 302.

It is to be appreciated that various configurations of cutting rolls 528 can be used with the apparatuses and methods herein. Such cutting roll configurations may include features of the cutting blades/units disclosed, for example, in U.S. Pat. Nos. 5,393,360; 7,708,849; 7,861,756; 7,777,094; and 8,440,043; and U.S. Patent Publication No. 2013/0261589 A1, which are all incorporated by reference herein. As such, the cutting rolls may be configured with die knife, flexible blade, and/or compression roll features, and may also include additional features to control knife-anvil gaps and/or force. In some configurations, a laser device may be utilized to cut the elastic strands 316.

Figure 46A:
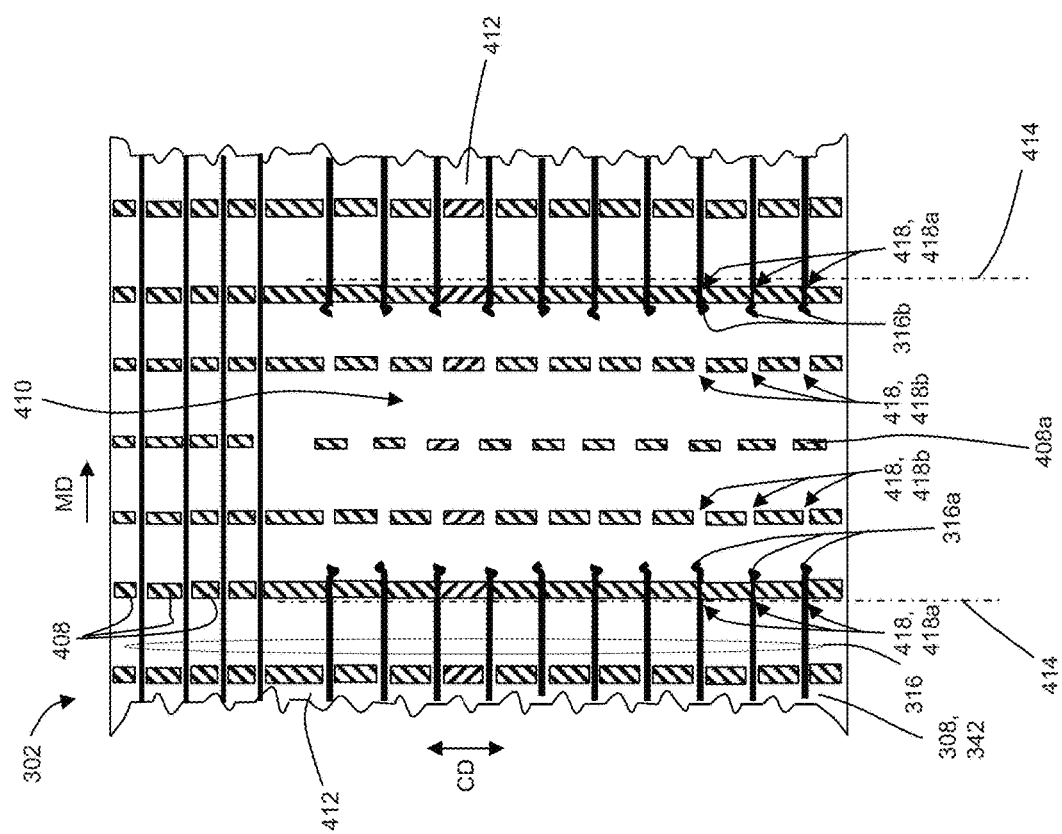
FIG. 46A shows a detailed view of an elastomeric laminate illustrating severed elastic strands having retracted to bond regions and showing examples of discrete bonds created by the protuberance in the deactivated region of the elastomeric laminate.
Figure 46B:
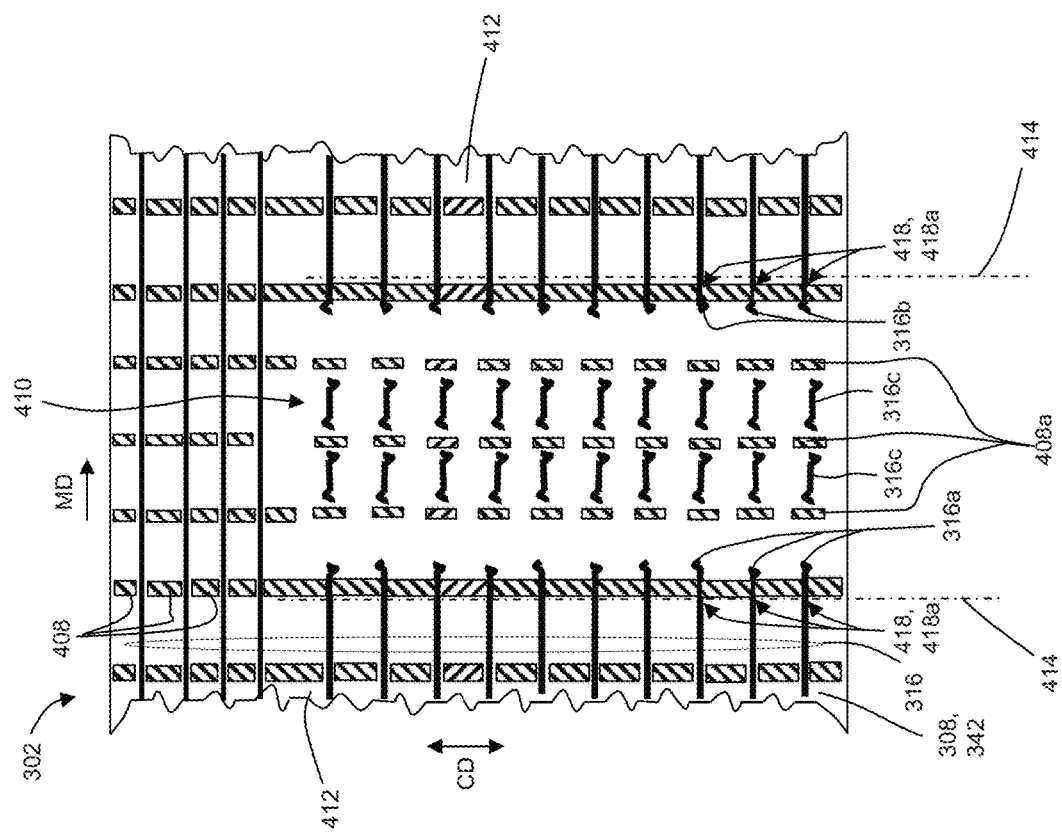
FIG. 46B shows a detailed view of an elastomeric laminate illustrating severed elastic strands having been cut into discrete pieces in the deactivated region of the elastomeric laminate.

As discussed above, the pattern roll 502 may include one or more protuberances 516 that may be configured in various ways with various different sizes and/or shapes. For example as shown in FIG. 41A, the protuberance 516 may be configured as one or more discrete members 536 that are separate from the bonding elements 512 and/or bonding surfaces 510. The discrete members 536 may also be axially offset with respect to the channels 522, and as such, may also be configured to the bond the first and second substrates 306, 308 together while simultaneously severing the elastic strands 316. As shown in FIG. 46A, the discrete members 536 may create discrete bonds 408a shaped and arranged in a pattern corresponding with the shapes of the discrete members 536. In another configuration shown in FIG. 46B, the protuberance 516 and/or the discrete members 536 may be configured to cut the elastic strands 316 into one or more discrete lengths or pieces 316c in the deactivated region 410.

As previously mentioned, the first substrate and second substrate 306, 308 herein may be defined by two discrete substrates or may be defined by folded portions of a single substrate. In addition, the second metering device 312 may also be configured as the bond applicator 500. For example, as shown in FIG. 47, the first substrate 306 may advance at speed S1 to the first roller 324 where the first substrate 306 partially wraps around the pattern roll 502. While partially wrapped around the pattern roll 502, the first substrate 306 is combined with the elastic strands 316. As the beam 314 rotates, the elastic strands 316 advance from the beam 314 at a speed S2 with the elastic strands 316 being spaced apart from each other in the cross direction CD. From the beam 314, elastic strands 316 advance to the pattern roll 502 and are positioned on the second surface 340 of the first substrate

306. As shown in FIGS. 47 and 48, a folding device 538 may operate to fold a first portion 306*a* onto a second portion 306*b* of the first substrate 306 with the elastic strands 316 positioned between the first and second portions 306*a*, 306*b* to create the elastomeric laminate 302. As shown in FIGS. 47 and 49, the pressing surface 504 may be configured to apply the bonds 408 and intermittently sever one or more elastic strands 316 before elastomeric laminate 302 advances from the pattern roll 502.

Some methods and apparatuses according to the present disclosure may be configured with a first plurality of elastic strands wound onto a first beam and a second plurality of elastic strands wound onto a second beam. During assembly of an elastomeric laminate, a first substrate is advanced onto the outer circumferential surface of the roller that is rotating about a first axis of rotation extending in a cross direction. The first beam is rotated to unwind the first plurality of elastic strands from the first beam in the machine direction. The first plurality of elastic strands may be stretched in the machine direction while advancing from the first beam onto the first substrate. A second substrate advances onto the first substrate such that the first plurality of elastic strands are positioned between the first substrate and the second substrate to form the elastomeric laminate. Before the first plurality of elastic strands are completely unwound from the first beam, the second beam is rotated to unwind the second plurality of elastic strands from the second beam in the machine direction, wherein the second plurality of elastic strands are separated from each other in the cross direction. The second plurality of elastic strands are advanced in the machine direction from the second beam to between the first substrate and the second substrate such that the first and plurality of elastic strands are positioned between the first and second substrates. Subsequently, the advancement of the first plurality of elastic strands from the first beam is discontinued. As such, the elastomeric laminate assembly process may continue uninterrupted while switching from an initially utilized elastic material drawn from the first beam to a subsequently utilized elastic material drawn from the second beam.

For example, FIGS. 53-70 show schematic views of converting apparatuses 300 adapted to manufacture elastomeric laminates 302. As described in more detail below, the converting apparatuses 300 shown in FIGS. 53-70 operate to advance a continuous length of elastic material 304, a continuous length of a first substrate 306, and a continuous length of a second substrate 308 along a machine direction MD. It is also to be appreciated that in some configurations, the first substrate and second substrate 306, 308 herein may be defined by two discrete substrates or may be defined by folded portions of a single substrate. The apparatus 300 stretches the elastic material 304 and joins the stretched elastic material 304 with the first and second substrates 306, 308 to produce an elastomeric laminate 302. Although the elastic material 304 is illustrated and referred to herein as strands, it is to be appreciated that elastic material 304 may include one or more continuous lengths of elastic strands, ribbons, and/or films.

As discussed in more detail below, the converting apparatuses 300 may include metering devices arranged along a process machine direction MD, wherein the metering devices may be configured to stretch the advancing elastic material and/or join stretch elastic material with one or more advancing substrates. In some configurations, a metering device may comprise a beam of elastic strands wound thereon. During operation, elastic material may advance in a machine direction from a first rotating beam to a downstream metering device to be joined with one or more advancing substrates. Before the elastic material is completely drawn from or removed from the first beam, elastic material may also be advanced in the machine direction from a second rotating beam to the downstream metering device to be joined with one or more advancing substrates. Subsequently, advancement of the elastic material from the first beam to the downstream metering device may be discontinued. As such, the elastomeric laminate assembly process continues uninterrupted while replacing elastic material unwound from the first beam with elastic material unwound from the second beam. Thus, the empty first beam may be replaced with another beam with elastic material wound thereon without interrupting and/or stopping the assembly of the elastomeric laminate.

Figure 53:
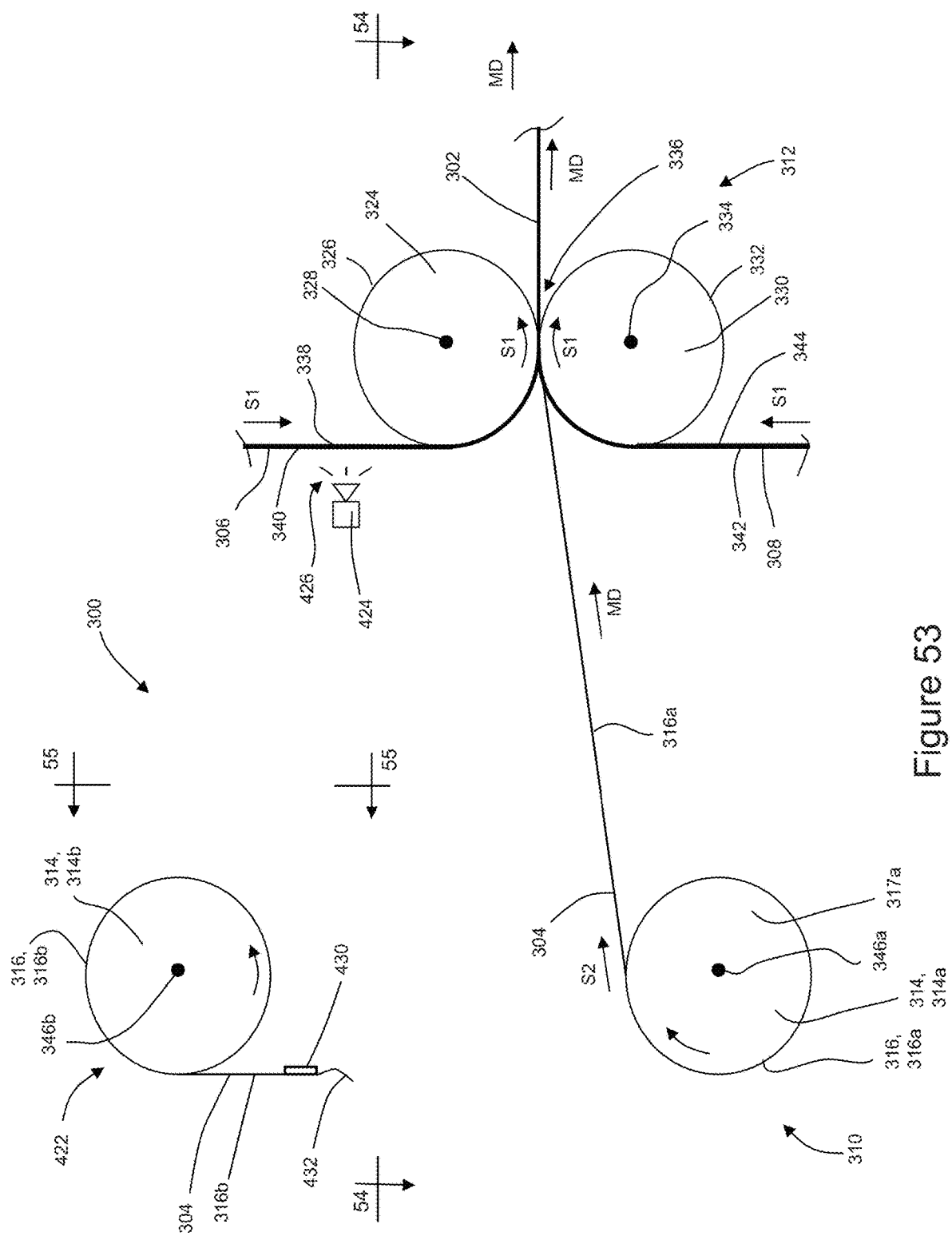
FIG. 53 is a schematic side view of a converting apparatus adapted to manufacture an elastomeric laminate including a first plurality of elastic strands positioned between a first substrate and a second substrate.
Figure 55:
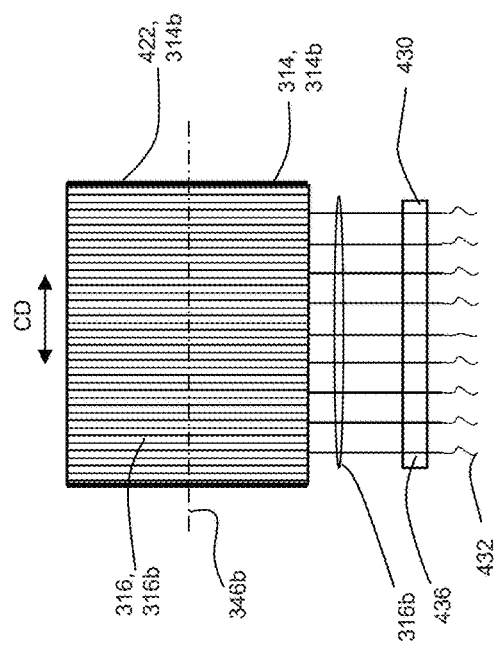
FIG. 55 is a view of the converting apparatus of FIG. 53 taken along line 55-55.
Figure 54:
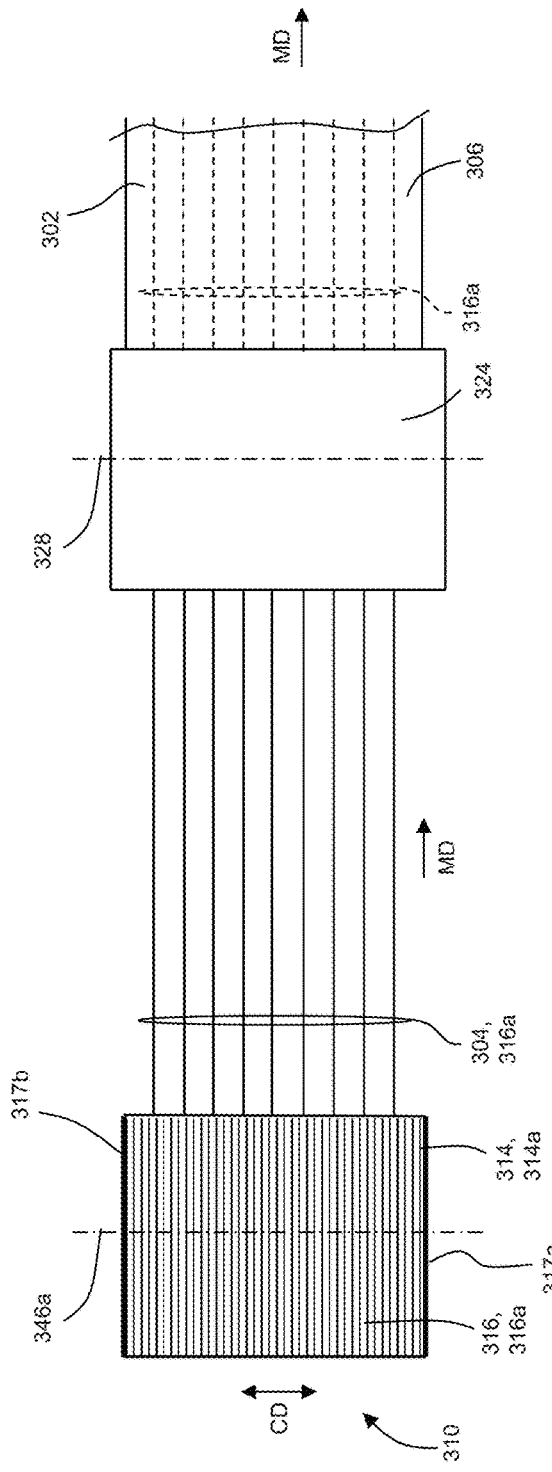
FIG. 54 is a view of the converting apparatus of FIG. 53 taken along line 54-54.

As shown in FIGS. 53 and 55, a converting apparatus 300 for producing an elastomeric laminate 302 may include a first metering device 310, a second metering device 312, and a third metering device 422. The first metering device may be configured as a first beam 314*a* with a first plurality of elastic strands 316*a* wound thereon, and the third metering device is configured as a second beam 314*b* with a second plurality of elastic strands 316*b* wound thereon. During operation, the first plurality of elastic strands 316*a* advance in the machine direction MD from the first beam 314*a* to the second metering device 312. In addition, the first plurality of elastic strands 316*a* may be stretched along the machine direction MD between the first beam 314*a* and the second metering device 312. The stretched first elastic strands 316*a* are also joined with a first substrate 306 and a second substrate 308 at the second metering device 312 to produce an elastomeric laminate 302. As discussed in more detail below, once the first beam 314*a* is empty or nearly depleted of first elastic strands 316*a*, the second plurality of elastic strands 316*b* can be introduced into the assembly operation as replacements for the first plurality of elastic stands 316*a* without having to stop the assembly operation. FIGS. 53 and 54 show an arrangement of first and second rollers 324, 330 and associated features described above with reference to FIGS. 5 and 6 that may be utilized to combine elastic strands 316 and first and second substrates 306, 308 to produce a continuous length of elastomeric laminate 302.

With continued reference to FIGS. 53 and 54, the first beam 314*a* includes the first plurality of elastic strands 316*a* wound thereon, and the first beam 314*a* is rotatable about a first beam rotation axis 346*a*. In some configurations, the first beam rotation axis 346*a* may extend in the cross direction CD. As the first beam 314*a* rotates, the first plurality of elastic strands 316*a* advance from the first beam 314*a* at a speed S2 with the first elastic strands 316*a* being spaced apart from each other in the cross direction CD. From the first beam 314*a*, the first plurality of elastic strands 316*a* advances in the machine direction MD to the nip 336. In some configurations, the speed S2 is less than the speed S1, and as such, the first plurality of elastic strands 316*a* are stretched in the machine direction MD. In turn, the stretched first elastic strands 316*a* advance through the nip 336 between the first and second substrates 306, 308 such that the first elastic strands 316*a* are joined with the second surface 340 of the first substrate 306 and the first surface 342 of the second substrate 308 to produce a continuous length of elastomeric laminate 302. As shown in FIG. 53, the first substrate 306 may advance past an adhesive applicator device 424 that applies adhesive 426 to the second surface 340 of the first substrate 306 before advancing to the nip 336. It is to be appreciated that the adhesive 426 may be applied to the first substrate 306 upstream of the first roller 324 and/or while the first substrate 306 is partially wrapped around the outer circumferential surface 326 of the first roller 324. It is to be appreciated that adhesive may be applied to the first elastic strands 316a before and/or while being joined with first substrate 306 and second substrate 308. In addition, it is to be appreciated that adhesive may be applied to the first surface 342 of the second substrate 308 before or while being joined with the first elastic strands 316a and the first substrate 306. It is also to be appreciated that the elastic strands 316 may be bonded with the first substrate 306 and/or second substrate 308 with the various methods and apparatuses described herein and combinations thereof.

Figure 56:
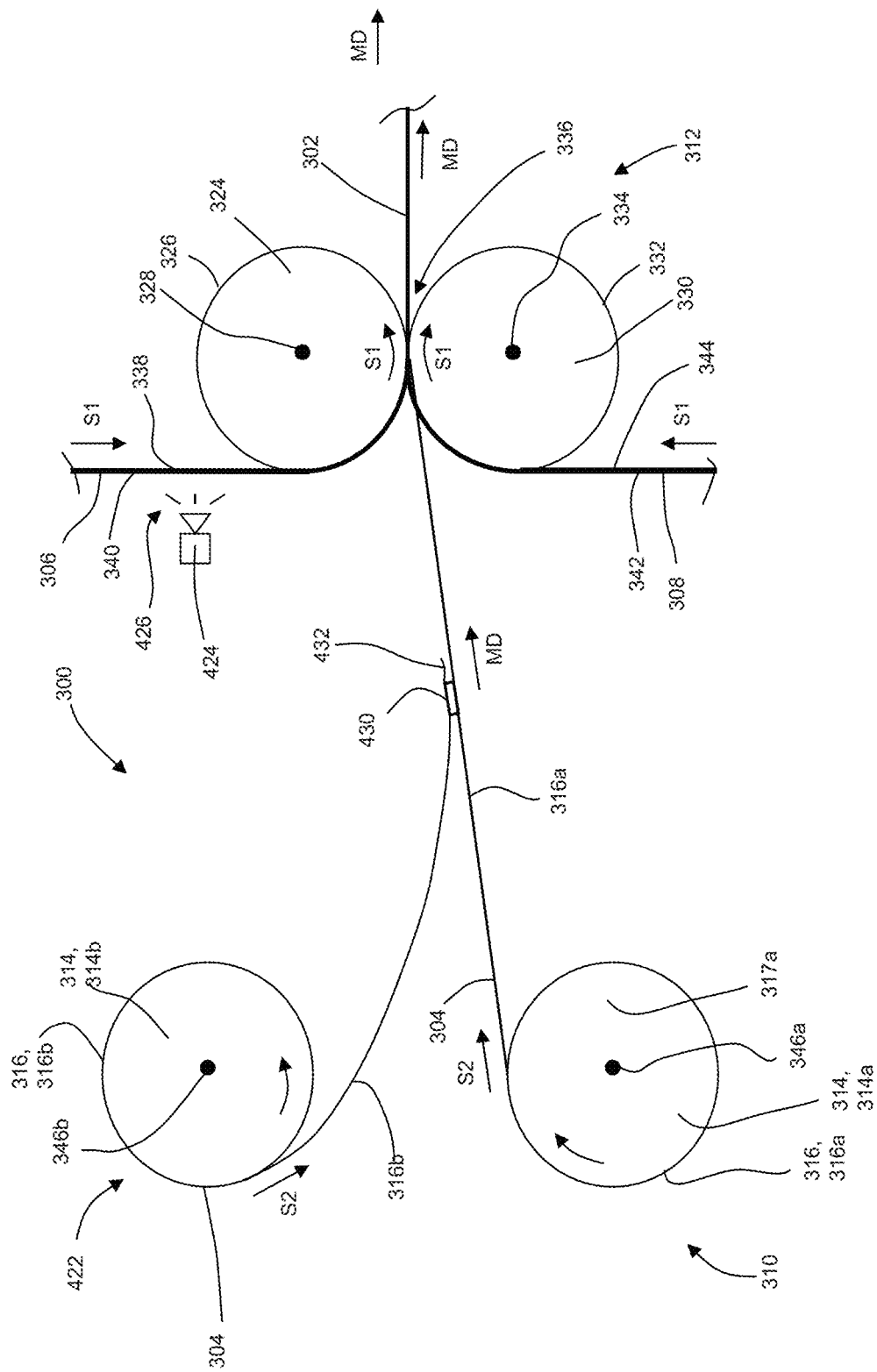
FIG. 56 is a schematic side view of the converting apparatus of FIG. 53 showing a second plurality of elastic strands connected with a first plurality of elastic strands upstream of a nip.
Figure 57:
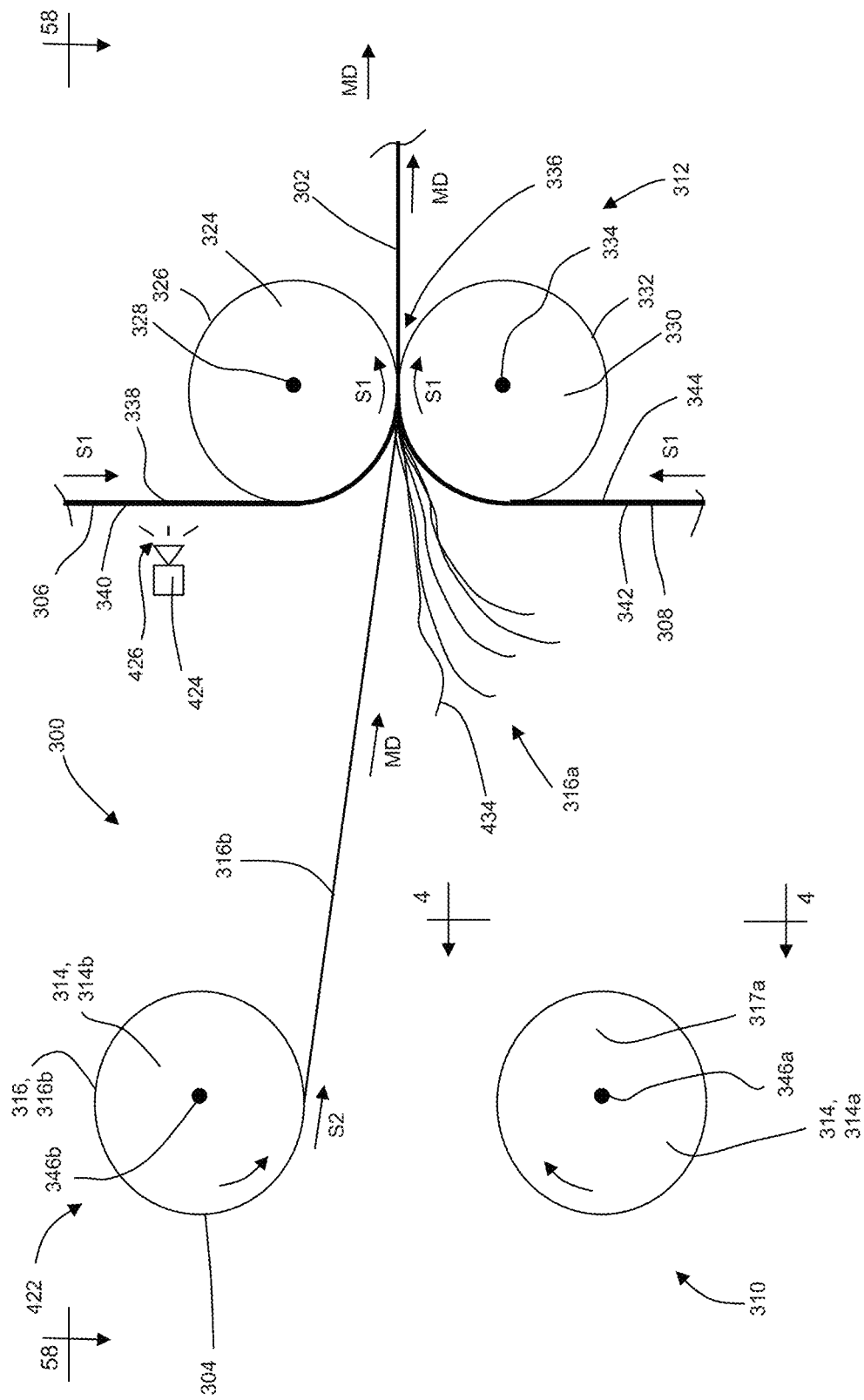
FIG. 57 is a schematic side view of the converting apparatus of FIG. 53 showing the first and second plurality of elastic strands advancing through the nip.
Figure 58:
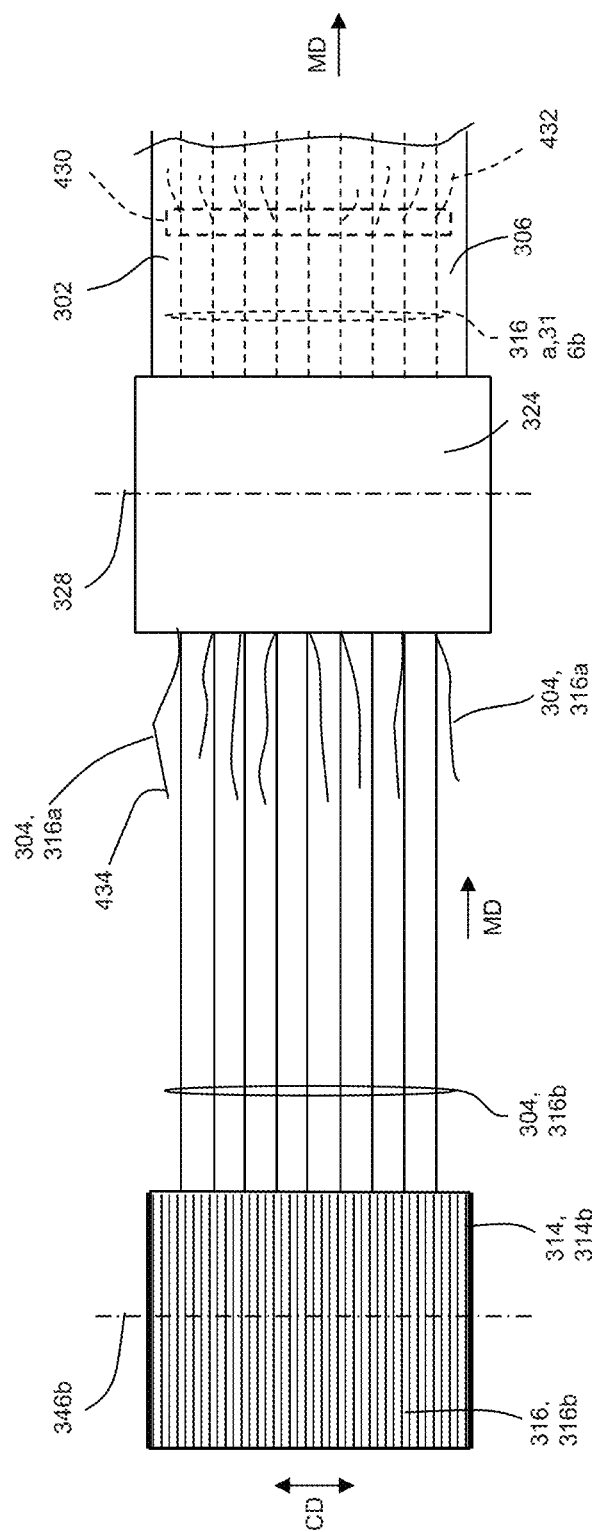
FIG. 58 is a view of the converting apparatus of FIG. 57 taken along line 58-58.

As previously discussed, the apparatus 300 includes the second plurality of elastic strands 316b configured to replace the first plurality of elastic stands 316a once the first beam 314a is completely depleted or nearly depleted of first elastic strands 316a. As shown in FIGS. 53 and 54, the second beam 314b includes the second plurality of elastic strands 316b wound thereon, and the second beam 314b is rotatable about a second beam rotation axis 346b. In some configurations, the second beam rotation axis 346b may extend in the cross direction CD. As the second beam 314b rotates, the second plurality of elastic strands 316b advance from the second beam 314b at a speed S2 with the second elastic strands 316b being spaced apart from each other in the cross direction CD. When introducing the second elastic strands 316b into the assembly operation, the second plurality of elastic strands 316b may first be connected with a splicer member 430. As shown in FIG. 55, the splicer member 430 may be connected adjacent leading ends 432 of the second elastic strands 316b. In turn, the splicer member 430 and the second elastic strands 316b may be connected with the first plurality of elastic strands 316a that are advancing from the first beam 314a to the nip 336 as shown in FIG. 56. As shown in FIGS. 57 and 58, the splicer member 430 and the leading ends 432 of the second plurality of elastic strands 316b advance in the machine direction MD and are positioned between the first and second substrates 306, 308 along with the first plurality of elastic strands 316a. Once the second elastic strands 316b are combined with the first substrate 306 and/or second substrate 308, advancement of the first plurality of elastic strands 316a from the first beam 314a may be discontinued. In some instances, advancement of the first plurality of elastic strands 316a from the first beam 314a may be discontinued as a result of the first elastic strands 316a being completely unwound from the first beam 314a such that trailing ends 434 of the first elastic strands 316a advance through the nip 336 such as shown in FIGS. 57 and 58. In some configurations, the first elastic strands 316a may be cut to discontinue advancement from the first beam 314a.

Figure 59:
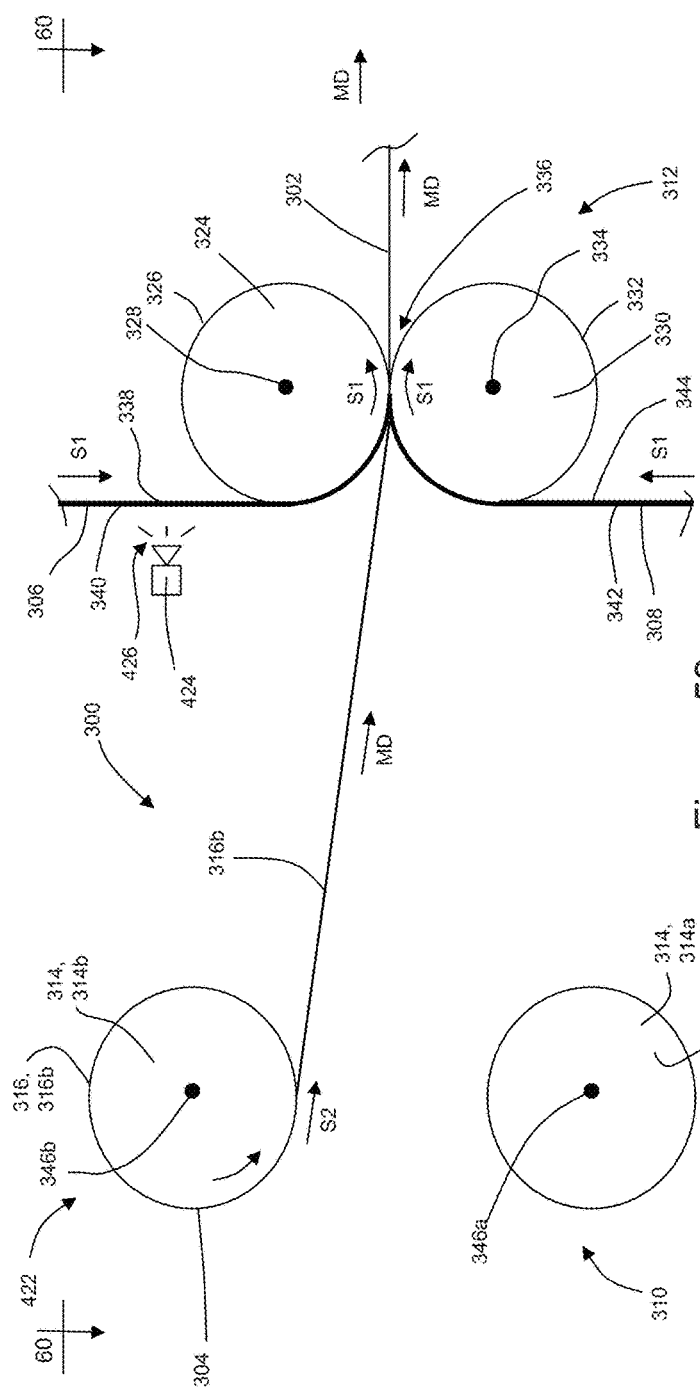
FIG. 59 is a schematic side view of the converting apparatus of FIG. 53 assembling the elastomeric laminate with the second plurality of elastic strands positioned between the first and second substrates.
Figure 60:
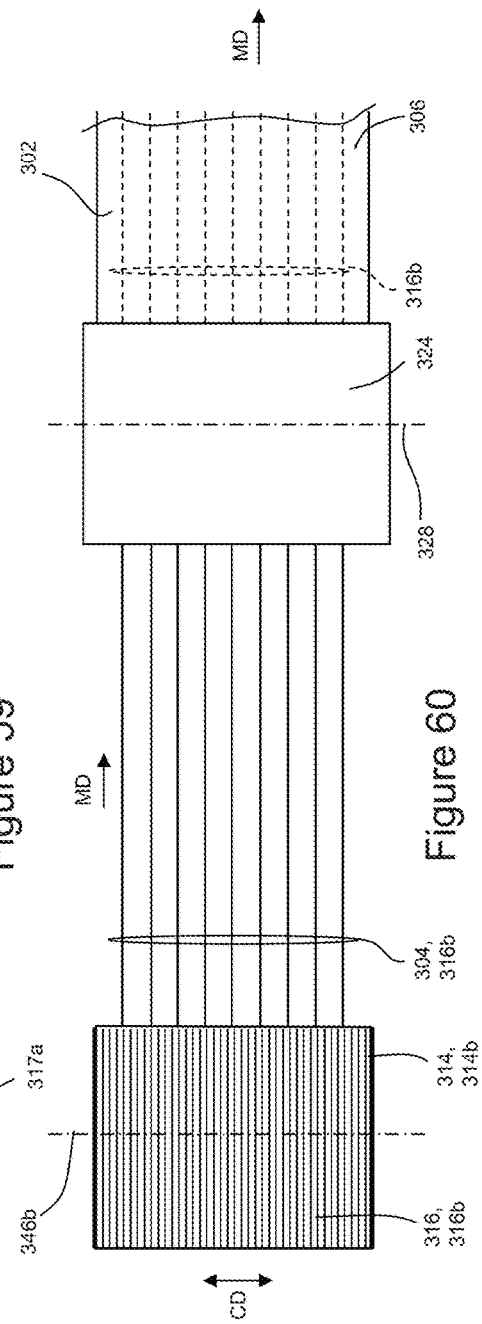
FIG. 60 is a view of the converting apparatus of FIG. 59 taken along line 60-60.

As shown in FIGS. 59 and 60, the apparatus 300 continues to operate to assemble the elastomeric laminate 302 with the second plurality of elastics 316b on the second beam 314b. As the second beam 314b rotates, the second plurality of elastic strands 316b advance from the second beam 314b at a speed S2 with the second elastic strands 316b being spaced apart from each other in the cross direction CD. From the second beam 314b, the second plurality of elastic strands 316b advances in the machine direction MD to the nip 336. In some configurations, the speed S2 is less than the speed S1, and as such, the second plurality of elastic strands 316b are stretched in the machine direction MD. In turn, the stretched second elastic strands 316b advance through the nip 336 between the first and second substrates 306, 308 such that the second elastic strands 316b are joined with the second surface 340 of the first substrate 306 and the first surface 342 of the second substrate 308 to produce the continuous length of elastomeric laminate 302. Thus, the second plurality of elastic strands 316b can be introduced into the assembly operation as replacements for the first plurality of elastic stands 316a without having to stop rotation of the first beam 314a and without having to stop the elastomeric laminate 302 assembly operation. In turn, the empty first beam 314a, such as shown in FIG. 4, can be replaced with a beam having a plurality of elastics wound thereon positioned to replace the second plurality of elastics 316b once depleted from the second beam 314b.

Although FIG. 54 shows nine elastic strands 316a advancing from the first beam 314a, it is to be appreciated that the apparatuses herein may be configured such that more or less than nine elastic strands 316a advance from the first beam 314a. And although FIG. 55 shows nine elastic strands 316b advancing from the second beam 314b, it is to be appreciated that the apparatuses herein may be configured such that more or less than nine elastic strands 316b advance from the second beam 314b.

It is to be appreciated that the apparatus 300 can be configured to operate in various ways to advance the leading ends 432 of the second plurality of elastics 316b between the first and second substrates 306, 308. For example, the splicer member 430 discussed above with reference to FIG. 55 may include one or more tacky surfaces 436 adapted to adhere to the second plurality of elastic strands 316b. In addition, the one or more tacky surfaces 436 also adhere the splicer member 430 with the advancing first plurality of elastic strands 316a as described above with reference to FIGS. 56-58. It is also to be appreciated that the splicer member 430 may be connected with the first elastic strands 316a with adhesive applied to the first elastic strands 316a upstream of the nip 336. It is also to be appreciated that in some configurations of the apparatus 300, the second elastic strands 316b may be introduced into the assembly operation without having to connect the second elastic strands 316b with a splicer member 430.

Figure 61:
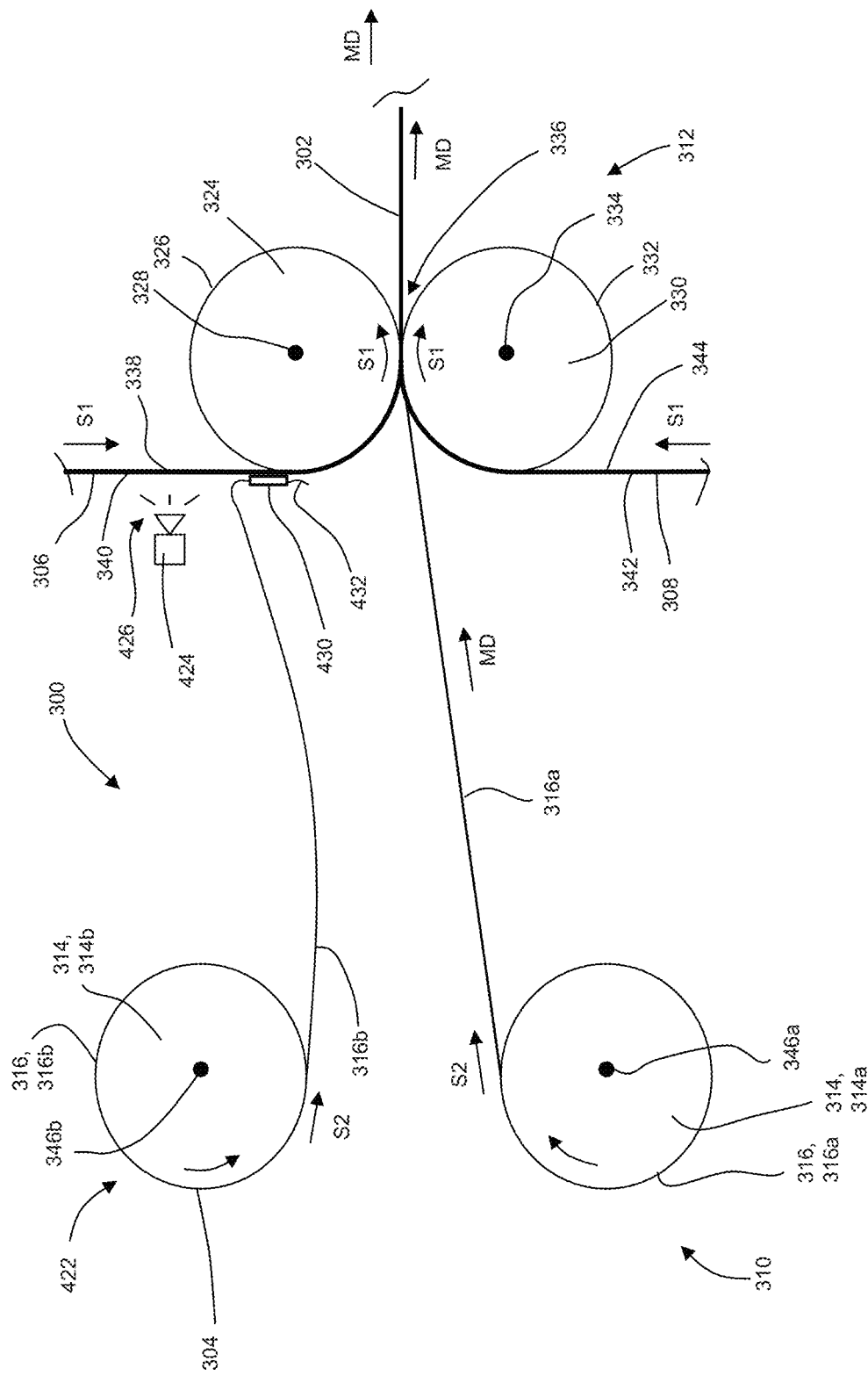
FIG. 61 is a schematic side view of the converting apparatus of FIG. 53 showing the second plurality of elastic strands connected with the first substrate upstream of a nip.

In some configurations, as opposed to being connected with the first elastic strands 316a, the splicer member 430 and/or second elastic strands 316b may be connected with the first substrate 306 or the second substrate 308 upstream of the nip 336. For example, as shown in FIG. 61, after second elastic strands 316b are connected with the splicer member 430, the splicer member 430 may be connected with the second surface 340 of the first substrate 306. As discussed above, the splicer member 430 may include a tacky surface 436 that adheres to the first substrate 306 and/or may be adhered to the first substrate with adhesive 426. Once the splicer member 430 is connected with the first substrate 306, the splicer member 430 and second elastic strands 316b advance along with the first substrate 306 through the nip 336.

Figure 62:
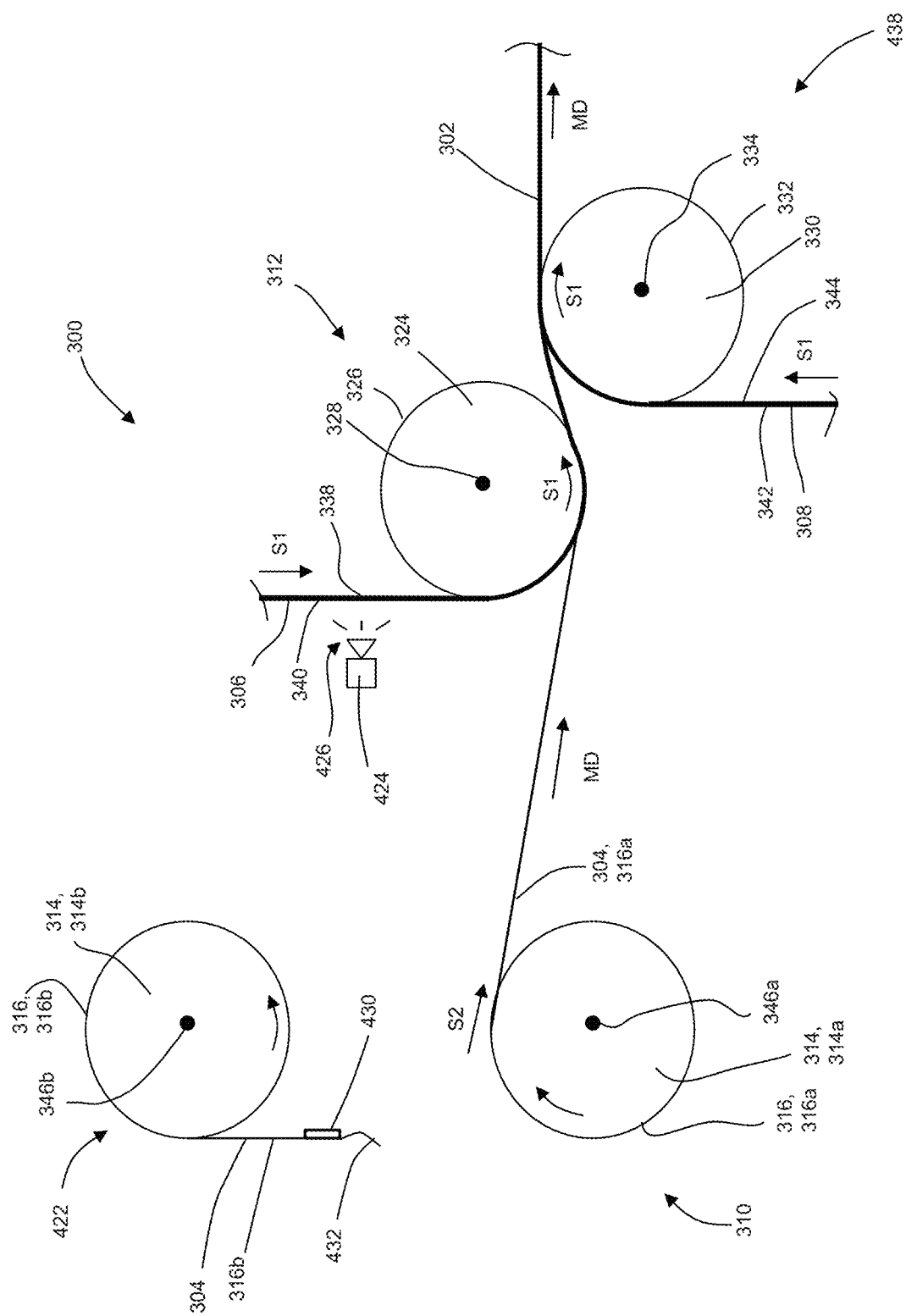
FIG. 62 is a schematic side view of another configuration of a converting apparatus adapted to manufacture an elastomeric laminate including a first plurality of elastic strands positioned between a first substrate and a second substrate.

It is to be appreciated that the apparatuses 300 herein may be configured in various ways. For example, in another configuration of the apparatus 300 shown in FIG. 62, the second roller 330 may be positioned downstream from the first roller 324. As such, the first roller 324 may be configured as the second metering device 312 and the second roller 330 may be configured as a fourth metering device 438. As shown in FIG. 62, the first substrate 306 advances at speed S1 to the first roller 324 where the first substrate 306 partially wraps around the outer circumferential surface 326 of the first roller 324 and advances from the first roller to the second roller 330 to be combined with second substrate 308. As the first beam 314a rotates, the first plurality of elastic strands 316a advance from the first beam 314a at a speed S2 with the first elastic strands 316a being spaced apart from each other in the cross direction CD. From the first beam 314a, the first plurality of elastic strands 316a advances in the machine direction MD to the first roller 324 and are positioned on the second surface 340 of the first substrate 306. In some configurations, the speed S2 is less than the speed S1, and as such, the first plurality of elastic strands 316a are stretched in the machine direction MD.

With continued reference to FIG. 62, the first substrate 306 and the first plurality of elastic strands 316a advance from the outer circumferential surface 326 of the first roller 324 to the second roller 330. In addition, the second substrate 308 advances at speed S1 to the second roller 330 where the second substrate 308 partially wraps around the outer circumferential surface 332 of the second roller 330. In turn, the combined first substrate 306 and the stretched first elastic strands 316a advance from first roller 324 to the second roller 330 and are combined with the second substrate 308 such that the first elastic strands 316a are joined with the second surface 340 of the first substrate 306 and the first surface 342 of the second substrate 308 to produce a continuous length of elastomeric laminate 302. As discussed above, the first substrate 306 may advance past an adhesive applicator device 424 that applies adhesive 426 to the second surface 340 of the first substrate 306 while advancing to the first roller 324. It is to be appreciated that the adhesive 426 may be applied to the first substrate 306 while the first substrate 306 is partially wrapped around the outer circumferential surface 326 of the first roller 324. It is to be appreciated that adhesive may also be applied to the first elastic strands 316a before and/or while being joined with first substrate 306 and second substrate 308. In addition, it is to be appreciated that adhesive may be applied to the first surface 342 of the second substrate 308 before or while being joined with the first elastic strands 316a and first substrate 306.

Figure 63:
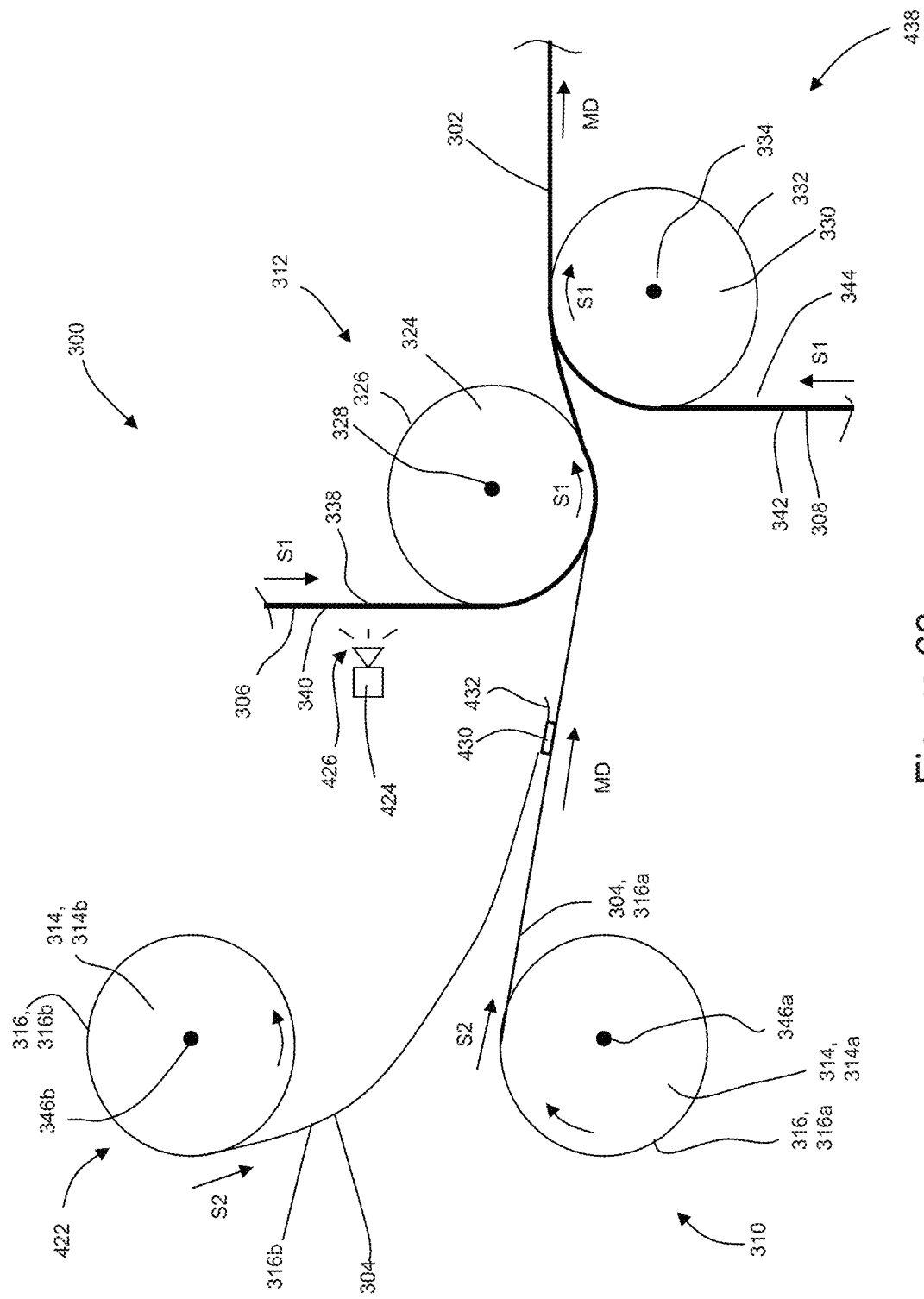
FIG. 63 is a schematic side view of the converting apparatus of FIG. 62 showing a second plurality of elastic strands connected with a first plurality of elastic strands upstream of a first roller.

As previously discussed, the apparatus 300 includes the second plurality of elastic strands 316b configured to replace the first plurality of elastic stands 316a once the first beam 314a is completely depleted or nearly depleted of first elastic strands 316a. As shown in FIGS. 62 and 63, as the second beam 314b rotates, the second plurality of elastic strands 316b advance from the second beam 314b at a speed S2 with the second elastic strands 316b being spaced apart from each other in the cross direction CD. As discussed above, the second plurality of elastic strands 316b may first be connected with a splicer member 430. In turn, the splicer member 430 and the second elastic strands 316b may be connected with the first plurality of elastic strands 316a that are advancing from the first beam 314a to the first roller 324, as shown in FIG. 63. As shown in FIG. 63, the splicer member 430 and the leading ends 432 of the second plurality of elastic strands 316b advance in the machine direction MD and are positioned on the second surface 340 of the first substrate 306 on the first roller 324. From the first roller 324, the combined first substrate 306, first elastic strands 316a, second elastic strands 316b, and splicer member 430 advance to the second roller 330 and are positioned between the first and second substrates 306, 308. Once the second elastic strands 316b are combined with the first substrate 306 and/or second substrate 308, advancement of the first plurality of elastic strands 316a from the first beam 314a may be discontinued wherein trailing ends 434 of the first elastic strands 316a advance downstream to the first and second rollers 324, 330, such as shown in FIG. 64.

Figure 64:
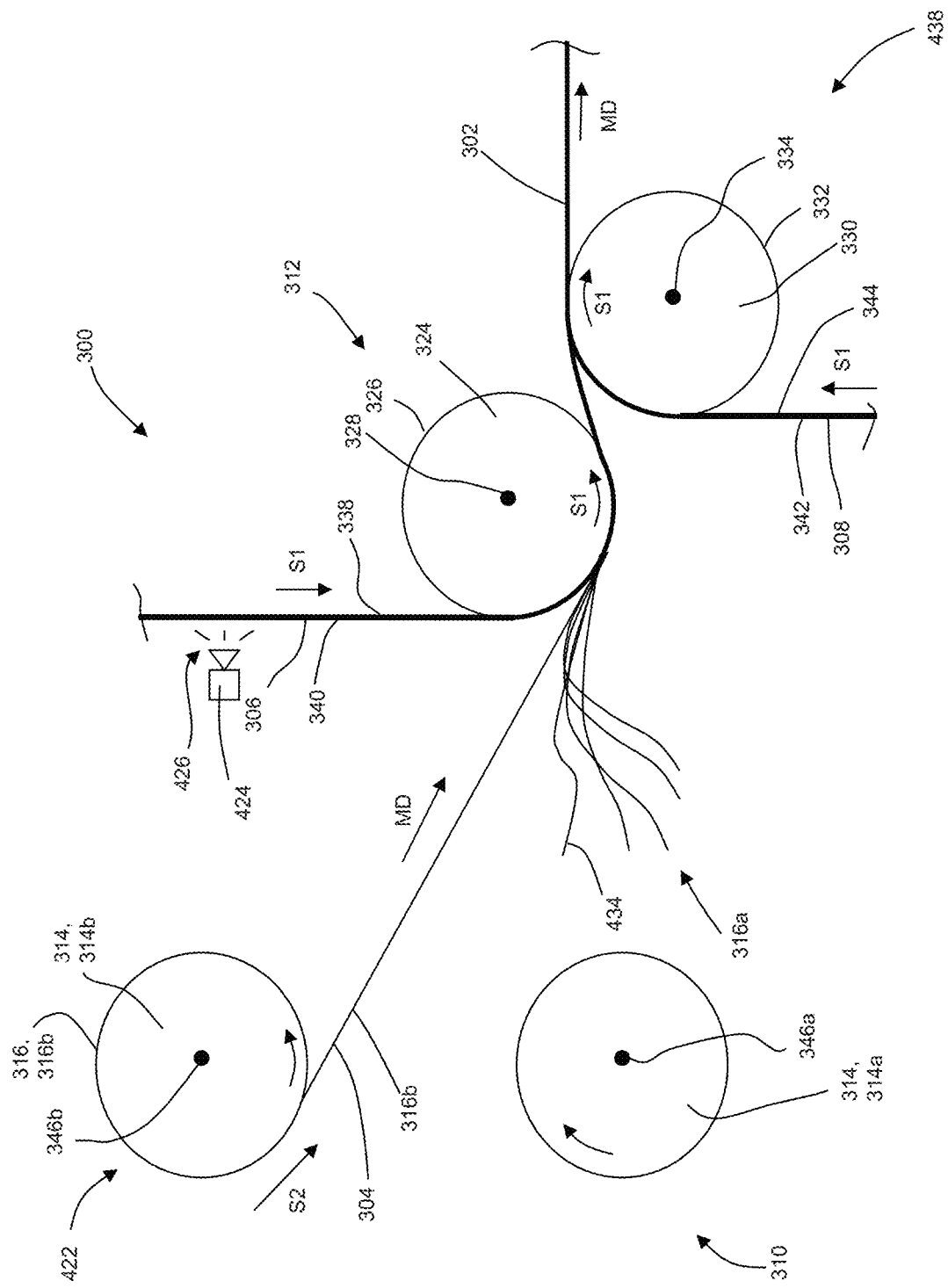
FIG. 64 is a schematic side view of the converting apparatus of FIG. 62 showing the first and second plurality of elastic strands advancing onto the first substrate.
Figure 65:
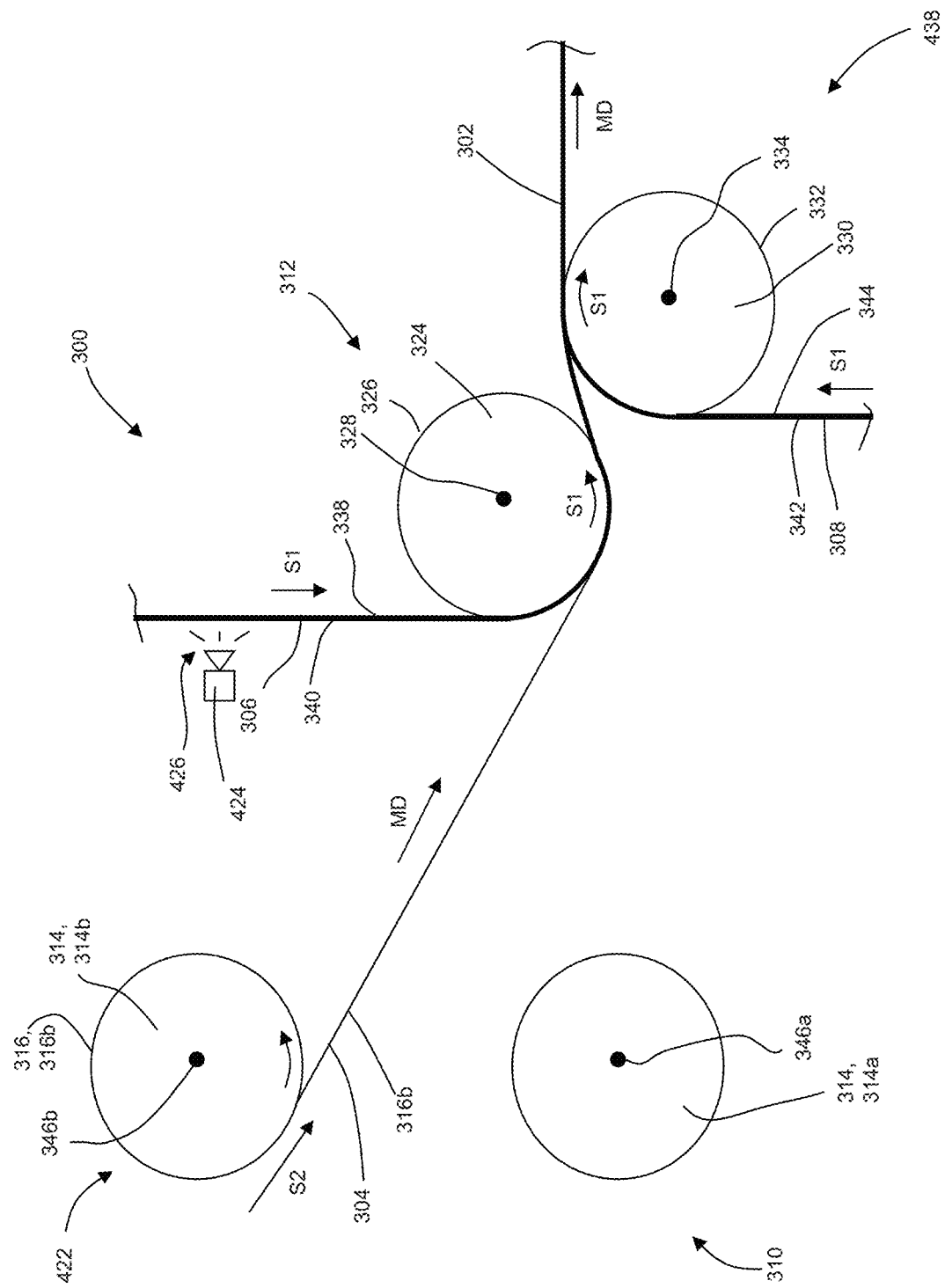
FIG. 65 is a schematic side view of the converting apparatus of FIG. 62 assembling the elastomeric laminate with the second plurality of elastic strands positioned between the first and second substrates.
Figure 66:
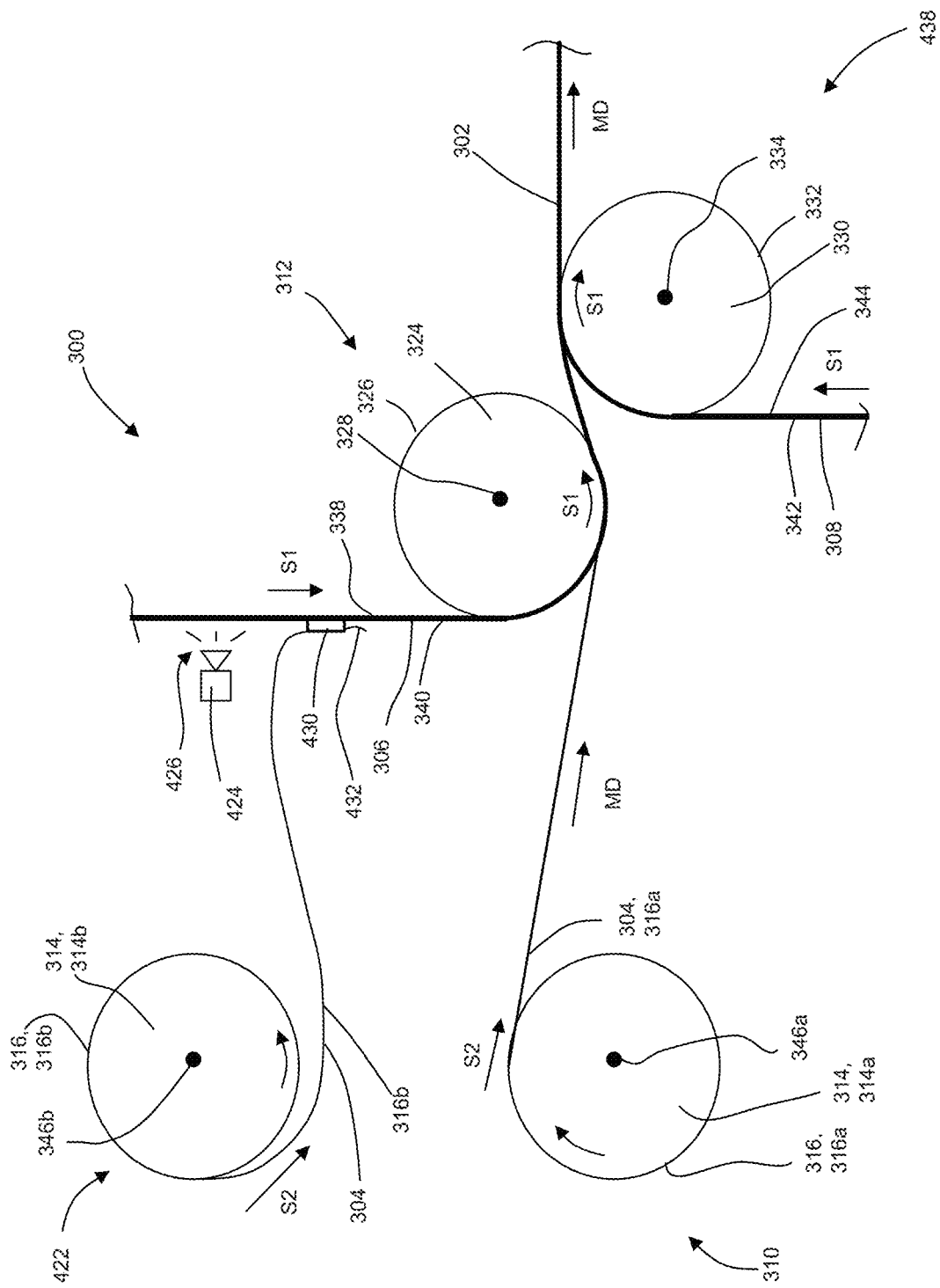
FIG. 66 is a schematic side view of the converting apparatus of FIG. 62 showing the second plurality of elastic strands connected with the first substrate upstream of the first roller.

As shown in FIGS. 64 and 65, the apparatus 300 continues to operate to assemble the elastomeric laminate 302 with the second plurality of elastic strands 316b advancing from the second beam 314b. As the second beam 314b rotates, the second plurality of elastic strands 316b advance from the second beam 314b at a speed S2 with the second elastics strands 316b being spaced apart from each other in the cross direction CD. From the second beam 314b, the second plurality of elastic strands 316b advances in the machine direction MD to the first roller 324 and are positioned on the second surface 340 of the first substrate 306. In some configurations, the speed S2 is less than the speed S1, and as such, the second plurality of elastic strands 316b are stretched in the machine direction MD. In turn, the stretched second elastic strands 316b advance from the first roller 324 to the second roller 330 such that the second elastic strands 316b are joined with the second surface 340 of the first substrate 306 and the first surface 342 of the second substrate 308 to produce the continuous length of elastomeric laminate 302.

As discussed above and as shown in FIG. 66, as opposed to being connected with the first elastic strands 316a, the splicer member 430 and the second elastic strands 316b may be connected with the first substrate 306 upstream of the first roller 306. Once the splicer member 430 is connected with the first substrate 306, the splicer member 430 and second elastic strands 316b advance along with the first substrate 306 to the first roller 306 and the second roller 330 to assemble the elastomeric laminate 302.

As previously mentioned, the second elastic strands 316b may be introduced into the assembly operation without having to connect the second elastic strands 316b with a splicer member 430. Thus, the second elastic strands 316b may be connected directly with the first substrate 306. It is also to be appreciated that the splicer member 430 and/or the second elastic strands 316b may be connected with the first substrate 306 while partially wrapped around the outer circumferential surface 326 of the first roller 306. It is also to be appreciated that the splicer member 430 and/or the second elastic strands 316b may be connected with the second substrate 308 upstream of the second roller 330 or while partially wrapped around the outer circumferential surface 332 of the second roller 330.

Figure 67:
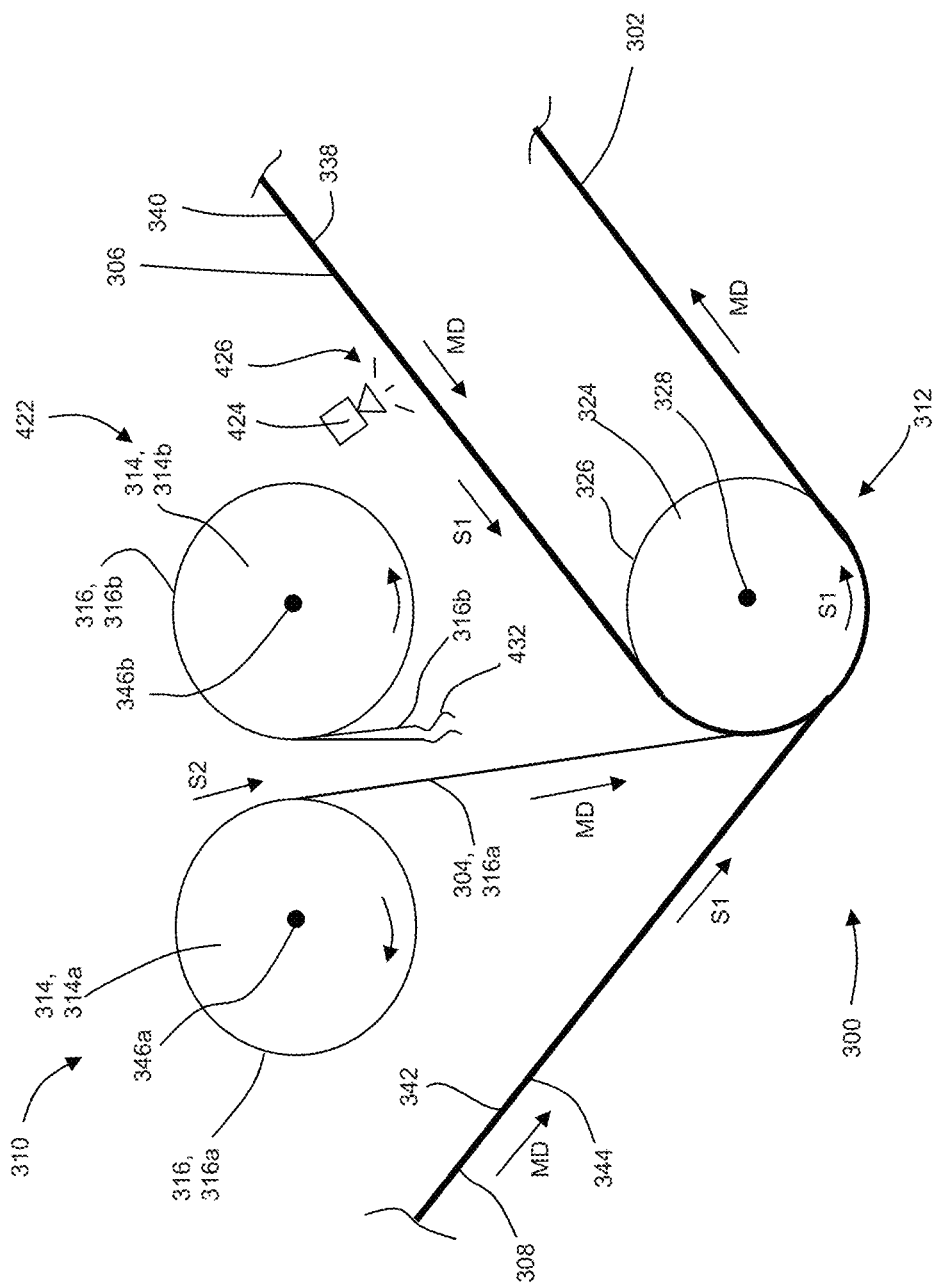
FIG. 67 is a schematic side view of another configuration of a converting apparatus adapted to manufacture an elastomeric laminate including a first plurality of elastic strands positioned between a first substrate and a second substrate.

In another configuration shown in FIG. 67, the apparatus 300 may be configured with only the first roller 324 and without a second roller 330. As such, the first roller 324 may be configured as the second metering device 312. As shown in FIG. 67, the first substrate 306 advances at speed S1 to the first roller 324 where the first substrate 306 partially wraps around the outer circumferential surface 326 of the first roller 324. While partially wrapped around the outer circumferential surface 326 of the first roller 324, the first substrate 306 is combined with the first elastic strands 316a and the second substrate 308. As the first beam 314a rotates, the first plurality of elastic strands 316a advance from the first beam 314a at a speed S2 with the first elastic strands 316a being spaced apart from each other in the cross direction CD. From the first beam 314a, the first plurality of elastic strands 316a advances in the machine direction MD to the first roller 324 and are positioned on the second surface 340 of the first substrate 306. In some configurations, the speed S2 is less than the speed S1, and as such, the first plurality of elastic strands 316a are stretched in the machine direction MD.

With continued reference to FIG. 67, the second substrate 308 advances at speed S1 to the first roller 324 and partially wraps around the outer circumferential surface 326 of the first roller 324. In turn, the second substrate 308 is combined with the first substrate 306 and the stretched first elastic strands 316*a* while on the first roller 324 such that the first elastic strands 316*a* are joined with the second surface 340 of the first substrate 306 and the first surface 342 of the second substrate 308 to produce a continuous length of elastomeric laminate 302. As discussed above, the first substrate 306 may advance past an adhesive applicator device 424 that applies adhesive 426 to the second surface 340 of the first substrate 306 while advancing to the first roller 324. It is to be appreciated that the adhesive 426 may be applied to the first substrate 306 while the first substrate 306 is partially wrapped around the outer circumferential surface 326 of the first roller 324. It is to be appreciated that adhesive may also be applied to the first elastic strands 316*a* before and/or while being joined with first substrate 306 and second substrate 308. In addition, it is to be appreciated that adhesive may be applied to the first surface 342 of the second substrate 308 before or while being joined with the first elastic strands 316*a* and first substrate 306.

Figure 68:
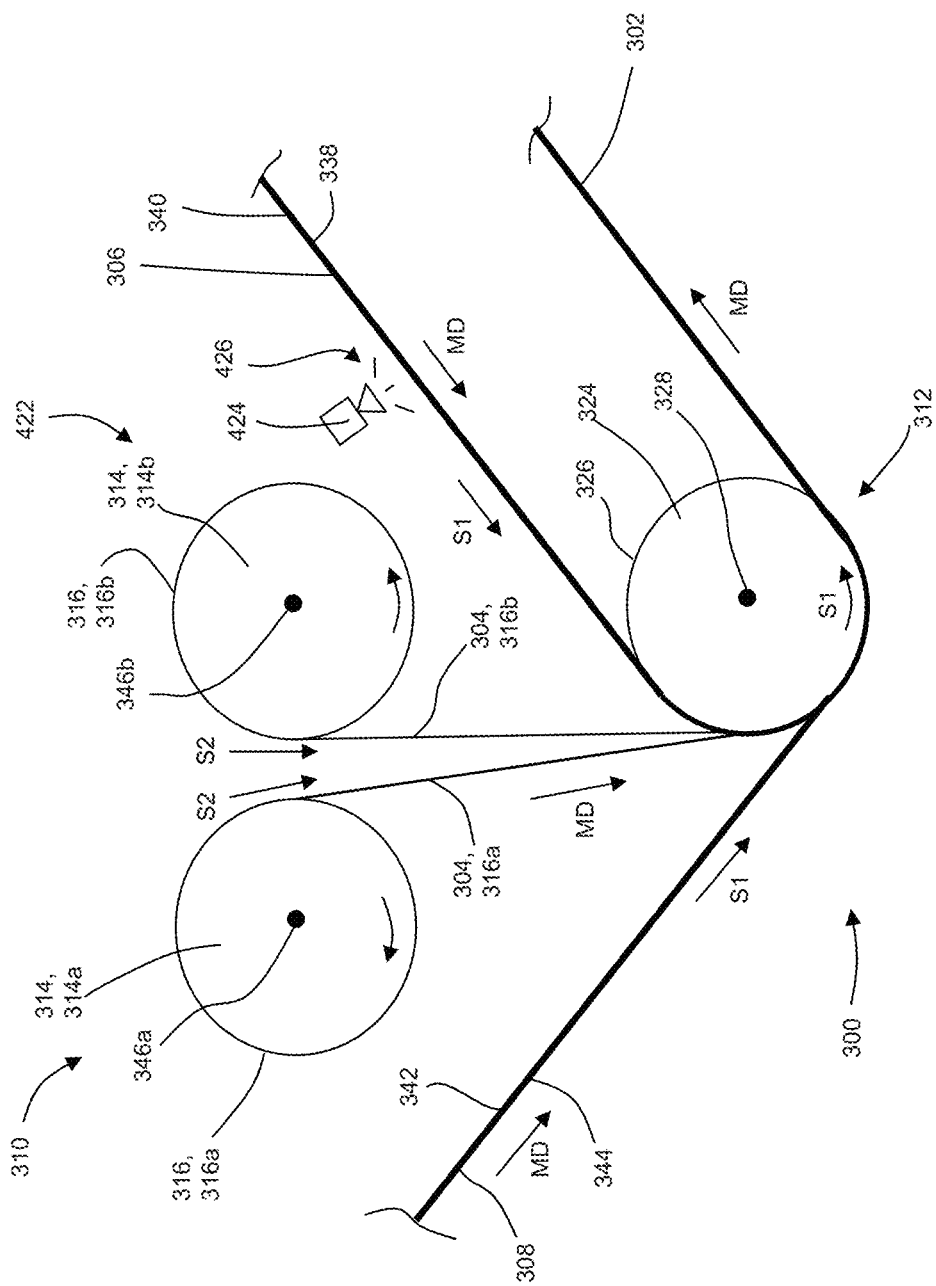
FIG. 68 is a schematic side view of the converting apparatus of FIG. 67 assembling the elastomeric laminate with the first and second plurality of elastic strands advancing between the first and second substrates.

As previously discussed, the apparatus 300 includes the second plurality of elastic strands 316*b* configured to replace the first plurality of elastic stands 316*a* once the first beam 314*a* is completely depleted or nearly depleted of first elastic strands 316*a*. As shown in FIGS. 67 and 68, as the second beam 314*b* rotates, the second plurality of elastic strands 316*b* advance from the second beam 314*b* at a speed S2 with the second elastic strands 316*b* being spaced apart from each other in the cross direction CD. In turn, leading ends 432 of the second plurality of elastic strands 316*b* may be advanced onto the first roller 324 and between first substrate 306 and the second substrate 308. As such, the second plurality of elastic strands 316*b* are positioned in between the second surface 340 of the first substrate 306 and the first surface 342 of the second substrate 308 such that the first plurality of elastic strands 316*a*, the second plurality of elastic strands 316*b*, and the first substrate 306 are positioned between the second substrate 308 and the outer circumferential surface 326 of the first roller 324. As discussed above, the second plurality of elastic strands 316*b* may also be first connected with a splicer member 430. Thus, it is to be appreciated that the splicer member 430 and/or the second elastic strands 316*b* may be connected with the first plurality of elastic strands 316*a*, the first substrate 306, or second substrate 308. As shown in FIGS. 67 and 68, the leading ends 432 of the second plurality of elastic strands 316*b* advance in the machine direction MD and are positioned on the second surface 340 of the first substrate 306 on the first roller 324. And the second substrate 306 advances to the first roller 324 to be combined with first substrate 306, first elastic strands 316*a*, and second elastic strands 316*b* to form the elastomeric laminate 302. Once the second elastic strands 316*b* are combined with the first substrate 306 and/or second substrate 308, advancement of the first plurality of elastic strands 316*a* from the first beam 314*a* may be discontinued wherein trailing ends 434 of the first elastic strands 316*a* advance downstream to the first roller 324, such as shown in FIG. 69.

Figure 69:
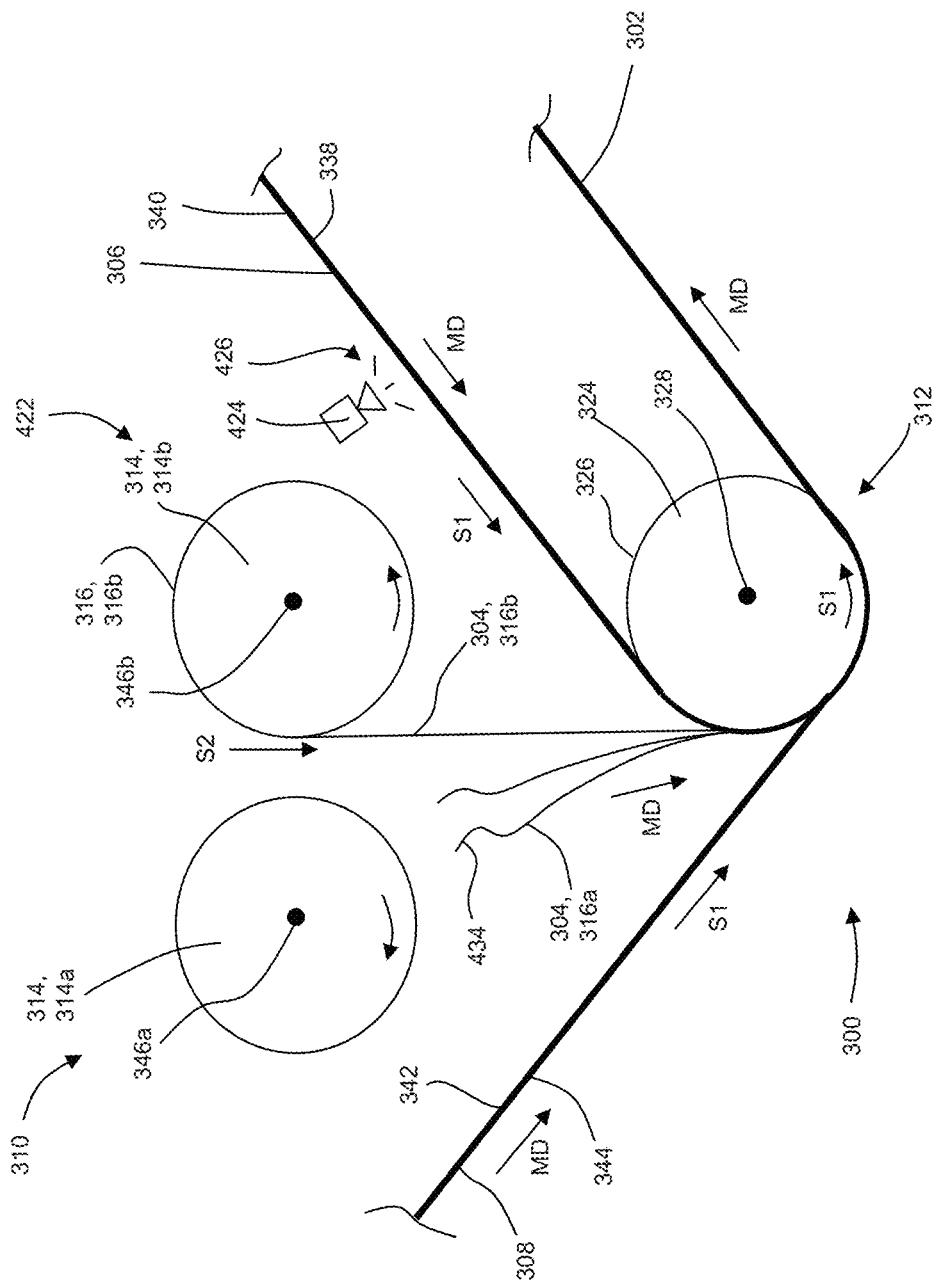
FIG. 69 is a schematic side view of the converting apparatus of FIG. 67 assembling the elastomeric laminate showing the trailing ends of the first plurality of elastic strands advancing between the first and second substrates.
Figure 70:
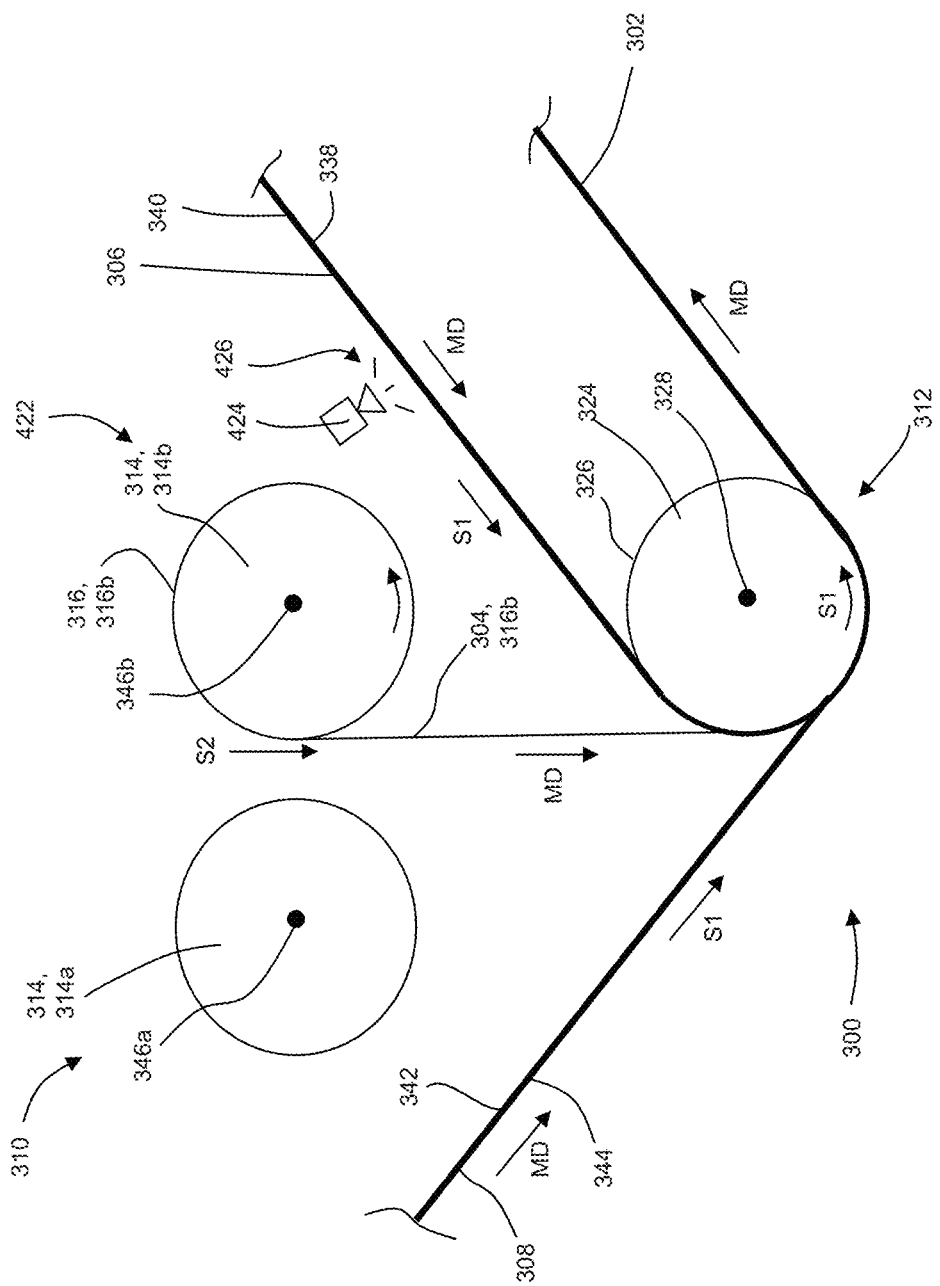
FIG. 70 is a schematic side view of the converting apparatus of FIG. 67 assembling the elastomeric laminate with the second plurality of elastic strands positioned between the first and second substrates.

As shown in FIGS. 69 and 70, the apparatus 300 continues to operate to assemble the elastomeric laminate 302 with the second plurality of elastics 316*b* advancing from the second beam 314*b*. As the second beam 314*b* rotates, the second plurality of elastic strands 316*b* advance from the second beam 314*b* at a speed S2 with the second elastic strands 316*b* being spaced apart from each other in the cross direction CD. From the second beam 314*b*, the second plurality of elastic strands 316*b* advances in the machine direction MD to the first roller 324 and are positioned on the second surface 340 of the first substrate 306. In some configurations, the speed S2 is less than the speed S1, and as such, the second plurality of elastic strands 316*b* are stretched in the machine direction MD. In turn, the stretched second elastic strands 316*b* are joined with the second surface 340 of the first substrate 306 and the first surface 342 of the second substrate 308 to produce the continuous length of elastomeric laminate 302 that advances from the first roller 324.

It is to be appreciated that in the various process configurations discussed above, the second plurality of elastic strands 316*b* may be first connected with a splicer member 430 before advancing the elastic strands 316*b* in the assembly process. It is also to be appreciated that in the various process configurations discussed above, the second plurality of elastic strands 316*b* may be advanced directly into the assembly process without connecting the stands 316*b* to a splicer member. In some configurations, the second plurality of elastic strands 316*b* may be connected or tied to each other with a knot before advancing into the assembly process. In some configurations, the first and/or second substrate may have an electrostatic charge that attracts the strands 316*b* to the substrates before advancing into assembly process. Further, in some configurations, strands 316*b* may be directed into the assembly process by air flow, such as provided from a fan and/or a vacuum system.

It is to be appreciated that a control system and/or an inspection system may be utilized to control various aspects of the splicing operations discussed herein. For example, as previously mentioned, the first beam 314*a* and the second beam 314*b* may be connected with one or more motors, such as servo motors, to drive and control the rotation of the beams 314*a*, 314*b*. As such, a control system may operate to control the acceleration and/or deceleration of the first and/or second beams 314*a*, 314*b* during the splicing operation to achieve and/or maintain the desired tension in the elastic strands. In some configurations, the elastic strands may be advanced from the beams 314*a*, 314*b* through a series of dancer rolls to help maintain desired tensions in the elastic strands during splicing operations. As previously mentioned, the elastomeric laminate 302 may also be subject to additional converting processes. Such additional converting processes may incorporate the elastomeric laminate 302 into discrete absorbent articles 100. As such, in some embodiments, an inspection system may be configured to detect and/or track a defective length of the elastomeric laminate 302. With reference to FIG. 58, a defective length of elastomeric laminate 302 may be defined by a length of elastomeric laminate 302 that includes both the first elastic strands 316*a* and the second elastic strands 316*b* positioned together between the first and second substrates 306, 308. A defective length of elastomeric laminate 302 may also be defined by a length of elastomeric laminate 302 that includes the splicer member 430, leading ends 432 of the second elastic strands 316*b*, and/or the trailing ends 434 of the first elastic strands 316*a*. The inspection system may also correlate inspection results and measurements from the defect length of the elastomeric laminate 302 with absorbent articles 100 made therefrom. In turn, the inspection system may be used to control a reject system on a converting process of absorbent articles, wherein absorbent articles manufactured with portions of the defective length of elastomeric laminate 302 are rejected. In some configurations, defective articles may be subject to the rejection system and removed from the assembly process. Absorbent articles 100 that are not deemed to be defective may be subject to further processing steps, such as folding and packaging. In some configurations, an inspection system may be configured to detect a broken elastic strand advancing from a first beam 314a. Upon detection of a broken elastic strand, the inspection system may activate a splicing operation, such as described above, to place a second beam 314b into service and remove the first beam 314a from service. In some configurations, an inspection and/or a control system may operate to control the timing and placement of the splicer member 430 into the assembly operation, such as in the nip 336 shown in FIG. 54, which may help an inspection system to more accurately track a splicing event. It is to be appreciated that such an inspection system may be configured in various ways, such as disclosed in U.S. Patent Publication No. 2013/0199696 A1.

It is to be appreciated that various operational abnormalities may result while elastic strands 316 are advancing from a beam 314 during assembly operations disclosed herein. For example, breakouts may occur during assembly operations, wherein one or more elastic strands 316 unintentionally breaks while advancing from the beam 314 during assembly of the elastomeric laminate 302. As such, the methods and apparatuses herein may include various devices to help isolate broken elastic strands, such as disclosed in U.S. Patent Publication Nos. 2014/0209652 A1 and 2014/0224855 A1. In some instances, the methods and apparatuses may include a snare member adjacent the beam 314 or other assembly components to help isolate broken elastics strands, such as disclosed in U.S. Patent Publication No. 2015/0090393 A1. The apparatuses and methods herein may also be configured with a two-step elastic strand 316 straining process, wherein the elastic strands 316 advance from the beam 314 and through a nip and drive roll before advancing in the machine direction to be combined with the first and second substrates 306, 308. Such a nip and drive roll arrangement may help isolate broken elastic strands from the beam 314. The apparatuses and methods herein may also be configured with devices and other arrangements to help automatically rethread broken elastic strands 316, such as disclosed in U.S. Patent Publication Nos. 2013/0199707 A1 and 2013/0199696 A1. In some configurations, beams 314 may be wound with elastic strands 316 having pieces of tape extending across the strands, wherein the tape pieces are intermittently spaced apart along the machine direction. As such, the tape pieces may help in locating the end of a broken strand in the event of a breakout.

It is to be appreciated that the elastomeric laminates 302 assembled with the methods and apparatuses herein may be subjected to various other manufacturing transformations, such as cutting and slitting, depending on a particular absorbent article assembly process. For example, a continuous elastomeric laminate 302 may advance to a slitting operation, wherein the elastomeric laminate 302 is slit and separated along the machine direction MD into a first continuous elastomeric laminate and a second continuous elastomeric laminate. It is to be appreciated that the elastomeric laminate 302 may be slit with a shear slitting operation or a crush slit operation. In a crush slit operation, the first substrate 306 and the second substrate 308 may be bonded together during the slitting operation. In some operations, the first and second substrates 306, 308 of an elastomeric laminate 302 may be bonded together along edges of the elastomeric laminate 302. For example, in some operations, edges of the first substrate 306 may be folded over opposing edge portions of the second substrate 308 to create sealed edges of the elastomeric laminate 302. It is to be appreciated that heat, pressure, adhesive, and/or ultrasonic bonding processes may be used to fixate such folded portions of the substrates. In some configurations, the locations of elastic strands 316 relative to side edges of elastic laminates 302 may be adjusted to change corrugation patterns along the side edges in desired manners. The elastomeric laminates 302 herein may be subject to additional operations to help provide aesthetic benefits, such as relatively more homogenous and/or consistent widths along the machine direction. For example, the elastomeric laminates 302 may be subject to cross directional spreading operations that may be executed after the elastomeric laminate has at least partially relaxed.

Every document cited herein, including any cross referenced or related patent or application and any patent application or patent to which this application claims priority or benefit thereof, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A method for making absorbent articles, the method comprising steps of:
   providing first elastic strands wound onto a beam, wherein the first elastic strands comprise a first decitex;
   rotating the beam to unwind the first elastic strands from the beam;
   advancing the first elastic strands from the rotating beam;
   stretching the first elastic strands; and
   providing second elastic strands, wherein the second elastic strands comprise a second decitex, and wherein the second decitex is greater than the first decitex;
   unwinding the second elastic strands from an overend unwinding device;
   stretching the second elastic strands;
   bonding the stretched first and second elastic strands between a first substrate and a second substrate to form an elastomeric laminate comprising different stretch characteristics in different regions in the elastomeric laminate, wherein the first elastic strands are bonded with a first bond applicator configured to apply adhesive or mechanical bonds and wherein the second elastic strands are bonded with a second bond applicator configured to apply adhesive bonds; and
   cutting the first elastic strands to create deactivated regions in the elastomeric laminate.

2. The method of claim 1, wherein the first substrate and the second substrate comprise nonwovens.

3. The method of claim 1, further comprising a step of converting the elastomeric laminate into an elastic belt for a diaper.

4. The method of claim 1, further comprising a step of converting the elastomeric laminate into an elastic leg cuff for a diaper.

5. The method of claim 1, wherein the first elastic strands comprise a spin finish.

6. The method of claim 5, further comprising a step of removing a portion of the spin finish.

7. The method of claim 1, further comprising a step of applying adhesive to at least one of the first elastic strands, the first substrate, and the second substrate.

8. The method of claim 1, further comprising a step of advancing the first substrate, the second substrate, and the first elastic strands between an ultrasonic horn and an anvil.

9. The method of claim 1, further comprising a step of bonding absorbent chassis with the deactivated regions.

* * * * *